US008440854B2

(12) United States Patent
Anderson et al.

(10) Patent No.: US 8,440,854 B2
(45) Date of Patent: May 14, 2013

(54) ANTIOXIDANT INFLAMMATION MODULATORS: OLEANOLIC ACID DERIVATIVES WITH AMINO ACID AND OTHER MODIFICATIONS AT C-17

(75) Inventors: Eric Anderson, Southlake, TX (US); Xin Jiang, Dallas, TX (US); Melean Visnick, Irving, TX (US)

(73) Assignee: Reata Pharmaceuticals, Inc., Irving, TX (US)

( * ) Notice: Subject to any disclaimer, the term of this patent is extended or adjusted under 35 U.S.C. 154(b) by 0 days.

(21) Appl. No.: 13/356,455

(22) Filed: Jan. 23, 2012

(65) Prior Publication Data
US 2012/0214814 A1    Aug. 23, 2012

Related U.S. Application Data

(63) Continuation of application No. 12/426,778, filed on Apr. 20, 2009, now Pat. No. 8,124,799.

(60) Provisional application No. 61/046,342, filed on Apr. 18, 2008, provisional application No. 61/111,269, filed on Nov. 4, 2008.

(51) Int. Cl.
C07D 333/32    (2006.01)
C07D 307/02    (2006.01)
C07D 231/00    (2006.01)
C07D 211/06    (2006.01)
C07D 265/30    (2006.01)
C07C 255/47    (2006.01)
A31K 31/38     (2006.01)
A31K 31/445    (2006.01)
A31K 31/415    (2006.01)
A31K 31/535    (2006.01)
A31K 31/34     (2006.01)
A31K 31/27     (2006.01)

(52) U.S. Cl.
USPC .......... 558/428; 549/65; 549/475; 548/374.1; 546/195; 544/155; 514/445; 514/319; 514/406; 514/237.5; 514/473; 514/478

(58) Field of Classification Search ................ None
See application file for complete search history.

(56) References Cited

U.S. PATENT DOCUMENTS

| 4,395,423 | A | 7/1983 | Neumann ............ 424/304 |
| 4,808,614 | A | 2/1989 | Hertel ................ 514/45 |
| 5,013,649 | A | 5/1991 | Wang et al. ........... 435/69.1 |
| 5,064,823 | A | 11/1991 | Lee et al. ............ 514/198 |
| 5,401,838 | A | 3/1995 | Chou ................ 536/281 |
| 5,426,183 | A | 6/1995 | Kjell ................. 536/285.5 |
| 5,464,826 | A | 11/1995 | Grindey et al. ......... 514/50 |
| 5,521,294 | A | 5/1996 | Wildfeur ............ 536/187 |
| 5,597,124 | A | 1/1997 | Kessel et al. .......... 241/30 |
| 5,603,958 | A | 2/1997 | Morein et al. .......... 424/489 |
| 5,606,048 | A | 2/1997 | Chou et al. ........... 536/271.1 |
| 5,972,703 | A | 10/1999 | Long et al. ............ 435/372 |
| 6,025,395 | A | 2/2000 | Breitner et al. ......... 514/570 |
| 6,303,569 | B1 | 10/2001 | Greenwald et al. ....... 514/2 |
| 6,326,507 | B1 | 12/2001 | Gribble et al. .......... 558/415 |
| 6,369,101 | B1 | 4/2002 | Carlson ............... 514/169 |
| 6,485,756 | B1 | 11/2002 | Aust et al. ............ 424/725 |
| 6,552,075 | B2 | 4/2003 | Gribble et al. .......... 514/522 |
| 6,642,217 | B2 | 11/2003 | Krasutsky et al. ....... 514/169 |
| 6,951,847 | B2 | 10/2005 | Gibson et al. .......... 514/169 |
| 6,974,801 | B2 | 12/2005 | Honda et al. .......... 514/25 |
| 7,144,875 | B2 | 12/2006 | Gibson et al. .......... 514/169 |
| 7,176,237 | B2 | 2/2007 | Honda et al. .......... 514/519 |
| 7,265,096 | B2 | 9/2007 | Gallop et al. .......... 514/49 |
| 7,288,568 | B2 | 10/2007 | Gribble et al. ......... 514/519 |
| 7,410,958 | B2 | 8/2008 | Krasutsky et al. ...... 514/169 |
| 7,435,755 | B2 | 10/2008 | Konopleva et al. ...... 514/510 |
| 7,915,402 | B2 | 3/2011 | Anderson et al. ....... 540/519 |

(Continued)

FOREIGN PATENT DOCUMENTS

DE    10 2005 041613    3/2007
EP        0 272 891 A2    6/1988

(Continued)

OTHER PUBLICATIONS

Liby et al. Mol. Cancer Ther. (2007) 6(7), pp. 2113-2119.*
"CDDO in treating patients with metastatic or unresectable solid tumors or lymphoma," http://www.clinicaltrials.gov/ct2/show/NCT00352040?term=CDDO&rank=1, Dec. 14, 2008.
"FDA mulls drug to slow late-stage Alzheimer's," http://www.cnn.com/2003/HEALTH/conditions/09/24/alzheimers.drug.ap/index.html, Retrieved on Sep. 23, 2003.
"Phase IIa trail to determine the effects of bardoxolone methyl on renal function in patients with diabetic nephropathy," http://www.clinicaltrials.gov/ct2/show/NCT00664027?term=rta&rank=10, Dec. 14, 2008.
"RTA 402 in advanced solid tumors or lymphoid malignancies," http://www.clinicaltrials.gov/ct2/show/NCT00508807?term=rta&rank=2&show_desc=Y, Dec. 14, 2008.
"Study to assess the safety, tolerability, and pharmacodynamics of RTA 402 in patients with hepatic dysfunction," http://www.clinicaltrials.gov/c2/show/NCT00550849?term=rta&rank=4, Dec. 14, 2008.

(Continued)

Primary Examiner — Nyeemah Grazier
(74) Attorney, Agent, or Firm — Parker Highlander PLLC

(57) ABSTRACT

This invention provides, but is not limited to, novel oleanolic acid derivatives having the formula:

wherein the variables are defined herein. Also provided are pharmaceutical compositions, kits and articles of manufacture comprising such compounds, methods and intermediates useful for making the compounds, and methods of using the compounds and compositions.

7 Claims, 55 Drawing Sheets

U.S. PATENT DOCUMENTS

| | | | | |
|---|---|---|---|---|
| 7,943,778 | B2 * | 5/2011 | Jiang et al. | 548/247 |
| 8,071,632 | B2 * | 12/2011 | Jiang et al. | 514/364 |
| 2004/0097436 | A1 | 5/2004 | Krasutsky et al. | 514/169 |
| 2005/0276836 | A1 | 12/2005 | Wilson et al. | 424/434 |
| 2005/0288363 | A1 | 12/2005 | Gribble et al. | 558/303 |
| 2007/0155742 | A1 | 7/2007 | Honda et al. | 514/519 |
| 2007/0232577 | A1 | 10/2007 | Xu et al. | 514/170 |
| 2007/0244081 | A1 | 10/2007 | Krasutsky et al. | 514/169 |
| 2007/0259842 | A1 | 11/2007 | Krasutsky et al. | 514/169 |
| 2008/0220057 | A1 | 9/2008 | Gribble et al. | 514/522 |
| 2008/0233195 | A1 | 9/2008 | Sporn et al. | 514/63 |
| 2008/0261985 | A1 | 10/2008 | Honda et al. | 548/400 |
| 2009/0048204 | A1 | 2/2009 | Walling et al. | 514/49 |
| 2009/0048205 | A1 | 2/2009 | Meyer et al. | 514/49 |
| 2009/0060873 | A1 | 3/2009 | Sporn et al. | 424/85.6 |
| 2009/0093447 | A1 | 4/2009 | Konopleva et al. | 514/510 |
| 2010/0041904 | A1 | 2/2010 | Jiang et al. | 549/456 |
| 2010/0048887 | A1 | 2/2010 | Anderson et al. | 540/8 |
| 2010/0048892 | A1 | 2/2010 | Anderson et al. | 544/154 |
| 2010/0048911 | A1 | 2/2010 | Jiang et al. | 548/250 |
| 2010/0056777 | A1 | 3/2010 | Anderson et al. | 540/520 |
| 2011/0245206 | A1 * | 10/2011 | Jiang et al. | 514/112 |

FOREIGN PATENT DOCUMENTS

| | | |
|---|---|---|
| EP | 0 329 348 B1 | 7/1995 |
| EP | 0 376 518 B1 | 11/1995 |
| EP | 0 576 230 B1 | 4/1996 |
| EP | 0 577 303 B1 | 10/1997 |
| EP | 0 712 860 B1 | 12/2001 |
| WF | WO 02/47611 | 6/2002 |
| WO | WO 91/15498 | 10/1791 |
| WO | WO 98/00173 | 1/1998 |
| WO | WO 98/32762 | 7/1998 |
| WO | WO 99/33483 | 7/1999 |
| WO | WO 99/65478 | 12/1999 |
| WO | WO 00/73253 | 12/2000 |
| WO | WO 01/01135 | 1/2001 |
| WO | WO 02/03996 | 1/2002 |
| WO | WO 02/26761 | 4/2002 |
| WO | WO 02/26762 | 4/2002 |
| WO | WO 03/043631 | 5/2003 |
| WO | WO 03/059339 | 7/2003 |
| WO | WO 03/062260 | 7/2003 |
| WO | WO 2004/064723 | 8/2004 |
| WO | WO 2004/089357 | 10/2004 |
| WO | WO 2005/042002 | 5/2005 |
| WO | WO 2005/046732 | 5/2005 |
| WO | WO 2006/029221 | 3/2006 |
| WO | WO 2007/005879 | 1/2007 |
| WO | WO 2007/069895 | 6/2007 |
| WO | WO 2007/112043 | 10/2007 |
| WO | WO 2008/000068 | 1/2008 |
| WO | WO 2008/000070 | 1/2008 |
| WO | WO 2008/016095 | 2/2008 |
| WO | WO 2008/111497 | 9/2008 |
| WO | WO 2008/136838 | 11/2008 |
| WO | WO 2009/023232 | 2/2009 |
| WO | WO 2009/129545 | 10/2009 |
| WO | WO 2009/129546 | 10/2009 |
| WO | WO 2009/129548 | 10/2009 |
| WO | WO 2009/146216 | 12/2009 |
| WO | WO 2009/146218 | 12/2009 |
| WO | WO 2010/093944 | 8/2010 |

OTHER PUBLICATIONS

Abraham and Kappas, "Heine oxygenase and the cardiovascular-renal system," *Free Radic. Biol. Med.*, 39 (1): 1-25, 2005.

Agarwal and Mehta, "Possible involvement of Bcl-2 pathway in resinoid X receptor alpha-induced apoptosis of HL-60 cells," *Biochem Biophys Res Commun.*, 230(2):251-253, 1997.

Ahmad et al., "Triterpenoid CDDO-Me blocks the NF-κB pathway by direct inhibition of IKKβ on Cys-179", *J Biol. Chem.*, 281: 35764-9, 2006.

Ahmad et al., "Triterpenoid CDDO-methyl ester inhibits the Janus-activated kinase-1 (JAK1)→signal transducer and activator of transcription-3 (STAT3) pathway by direct inhibition of JAK1 and STAT3," *Cancer Res.*, 68 (8): 2920-2926, 2008.

Akrivakis et al., "Prolonged infusion of gemcitabine in stage IV breast cancer: a phase I study," *Anti-Cancer Drugs*, 10 (6): 525-531, 1999.

Al-alami et al., "Divergent effect of taxol on proliferation, apoptosis and nitric oxide production in MHH225 CD34 positive and U937 CD34 negative human leukemia cells," *Leukemia Res.*, 22:939-945, 1998.

Alexander et al., "Synthesis and cytotoxic activity of two novel 1-dodecylthio-2-decyloxypropyl-3-phosphatidic acid conjugates with gemcitabine and cytosine arabinoside," *J. Med. Chem.*, 46 (19): 4205-4208, 2003.

Ambs et al., "p53 and vascular endothelial growth factor regulate tumor growth of NOS2-expressing human carcinoma cells," *Nat. Med.*, 4(12):1371-1376, 1998.

Amstutz et al., "Die position 5 im oxotremorin-gerust: eine zentrale stelle fur die steuerung der aktivitat am muscarinischen rezeptor," *Helv. Chim. Acta.*, 70:2232-2244, 1987.

Andreeff et al., "Expression of bcl-2-related genes in normal and AML progenitors: Changes induced by chemotherapy and cationic acid," *Leukemia*, 13:1881-1892, 1999.

Andreeff et al., "PPARgamma nuclear receptor as a novel molecular target in leukemias," *2002 Keystone Symposia*, Abstract No. 501, 2002.

Andreeff, "Acute myeloid leukemia," In: *Cancer Treatment*, Haskell (Ed.), W. B. Saunders, 911-922, 1995.

Araujo et al., "Systemic rather than local heme oxygenase-1 overexpression improves cardiac allograft outcomes in a new transgenic mouse," *J. Immunol.*, 171 (3): 1572-1580, 2003.

Ardestani et al., "Effects of dexamethasone and betamethasone as COX-2 gene expression inhibitors on rigidity in a rat model of Parkinson's disease," *Indian J. Pharmacol.*, 39:235-9, 2007.

Ariga et al., "Role of sphingolipid-mediated cell death in neurodegenerative diseases," *Journal of Lipid Research*, 39:1-16, 1998.

Bach, "Heine oxygenase-1 and transplantation tolerance," *Hum. Immunol.*, 67 (6): 430-432, 2006.

Baeuerle, "NF-κB: ten years after," *Cell*, 87:13-20, 1996.

Bagasra et al., "Activation of the inducible form of nitric oxide synthase in the brains of patients with multiple sclerosis," *Proc. Natl. Acad. Sci. USA*, 92:12041-12045, 1995.

Baker et al., "2'-Deoxy-2'-methylenecytidine and 2'-deoxy-2',2'-difluorocytidine 5'-diphosphates: potent mechanism-based inhibitors of ribonucleotide reductase," *J Med. Chem.*, 34 (6): 1884, 1991.

Baldwin, Jr., "The NF-κb and IκB proteins: new discoveries and insights," *Annu. Rev. Immunol.*, 14:649-681, 1996.

Balkwill et al., "Smoldering and polarized inflammation in the initiation and promotion of malignant disease," *Cancer Cell*, 7 (3): 211-217, 2005.

Bargou et al., "Constitutive nuclear factor κB-RelA activation is required for proliferation and survival of Hodgkin's disease tumor cells," *J Clin. Invest.*, 100:2961-2969, 1997.

Barkett and Gilmore, "Control of apoptosis by Rel/NF-κB transcription factors," *Oncogene*, 18:6910-6924, 1999.

Barnes and Karin, "Nuclear factor-κB—a pivotal transcription factor in chronic inflammation diseases," *N. Engl. J. Med.*, 336:1066-1071, 1997.

Beal, "Mitochondria, free radicals, and neurodegeneration," *Curr. Opin. Neurobiol.*, 6:661-666, 1996.

Begum et al., "Synthesis of 2β-hydroxyursolic acid and other ursane analogs from ursonic acid," *Australian Journal of Chemistry*, 46 (7): 1067-1071, 1993.

Beran et al., "Topotecan and cytarabine is an active combination regimen in myelodysplastic syndromes and chronic myelomonocytic leukemia," *J. Clinical Oncology*, 17(9):2819-2830, 1999.

Bliard et al., "Glycosylation of acids under phase transfer conditions. Partial synthesis of saponins," *Tetrahedron Lett.*, 35:6107-6108, 1994.

Bogdan and Ding, "Taxol, a microtubule-stabilizing antineoplastic agent, induces expression of tumor necrosis factor α and interleukin-1 in macrophages," *J Leukoc. Biol.*, 52(1):119-121, 1992.

Bogdan et al., "Contrasting mechanisms for suppression of macrophage cytokine release by transforming growth factor-beta and interleukin-10," *J. Biol. Chem.*, 267:23301-23308, 1992.

Bollag and Holdener, "Retinoids in cancer prevention and therapy," *Annals of Oncology*, 3:513-526, 1992.

Boolbol et al., "Cyclooxygenase-2 overexpression and tumor formation are blocked by sulindac in a murine model of familial adenomatous polyposis," *Cancer Res.*, 56(11):2556-2560, 1996.

Bore et al., "The anti-inflammatory triterpenoid methyl 2-cyano-3, 12-dioxoolean 1,9(11)-dien-28-oate methanol solvate hydrate," Acta Crystallorg C., 58(Pt 3):o199-o200, 2002.

Bowden et al., "Constituents of the fruit of *pseudopanax arboreum* (Araliaceae)," *Australian J. of Chemistry*, 28 (1): 91-107, 1975.

Brookes et al., "The triterpenoid 2-cyano-3,12-dioxooleana-1,9-dien-28-oic acid and its derivatives elicit human lymphoid cell apoptosis through a novel pathway involving the unregulated mitochondrial permeability transition pore," *Cancer Res.*, 67:1793-1802, 2007.

Bruder and Caplan, "First bone formation and the dissection of an osteogenic lineage in the embryonic chick tibia is revealed by monoclonal antibodies against osteoblasts," *Bone*, 10:359-375, 1989.

Bruder and Caplan, "A monoclonal antibody against the surface of osteoblasts recognizes alkaline phosphatase isoenzymes in bone, liver, kidney, and intestine," *Bone*, 11:189-198, 1990.

Bruder et al., "Terminal Osteogenic cell differentiation in culture requires beta-glycerol phosphate," *Trans. Ortho. Res. Soc.*, 16:58, 1991.

Bruland et al., "Expression and characteristics of a novel human osteosarcoma-associated cell surface antigen," *Cancer Res.*, 48:5302-5308, 1988.

Buzoni-Gatel et al., "Intraepithelial lymphocytes traffic to the intestine and enhance resistance to Toxoplasma gondii oral infection," *J Immunol.*, 162:5846-5852, 1999.

Buzoni-Gatel et al., "Murine ileitis after intracellular parasite infection is controlled by TGF-beta-producing intraepithelial lymphocytes," *Gastroenterolog*, 120:914-924, 2001.

Cai and Vasella, "A new protecting group for alkynes: orthogonally protected dialkynes," *Helv. Chim. Acta.*, 78:732-757, 1995.

Campbell et al., "Endocyclic α,β-unsaturated ketones. VI. Ultraviolet and infrared absorption spectra and resonance stabalization," *Bioorganic and Medicinal Chemistry Letters*, 7(13): 1623-1628, 1997.

Carter et al., "Expression of survivin, a member of the inhibitor of apoptosis (IAP) family of caspase inhibitors is expressed in AML and regulated by cytokines and ATRA," *Blood*, 94(Suppl 1):479a, Abstract # 2142, 1999.

Cassady and Suffness, In *Anticancer Agents Based on Natural Product Models*; Academic Press, NY, 254-269, 1980.

Castaigne et al., "All-trans retinoic acid as a differentiation therapy for acute promyelocytic leukemia," *Blood*, 76(9):1704-1709, 1990.

Cerwenka and Swain, "TGF-β1: immunosuppressant and viability factor for T lymphocytes," *Microbes and Infection*, 1: 1291-1296, 1999.

Chattopadhyay et al., "Studies on autoxidation: Part IV. Synthesis of isomeric 2,3-diols of olean-12-en-28-oate and isohopane (moretane)," *Indian J. of Chemistry, Section B: Organic Chemistry Including Medicinal Chemistry*, 15 (1): 21-24, 1977.

Chauhan et al., "The bortezomib/proteasome inhibitor PS-341 and triterpenoid CDDO-Im induce synergistic anti-multiple myeloma (MM) activity and overcome bortezomib resistance," *Blood*, 103:3158-3166, 2004.

Chen et al., "Chondrogenesis in chick limb bud mesodermal cells: reciprocal modulation by activin and inhibin," *Exp. Cell. Res.*, 206:119-27, 1993.

Chen et al., "Stimulation of chondrogenesis in limb bud mesoderm cells by recombinant human bone morphogenetic protein 2B (BMP-2B) and modulation by transforming growth factor beta 1 and beta 2," *Exp. Cell. Res.*, 195:509-15, 1991.

Cheng et al., "Differentiation of human bone marrow osteogenic stromal cells in vitro: induction of the osteoblast phenotype by dexamethasone," *Endocrinology*, 134:277-86, 1994.

Chintharlapalli et al., "2-Cyano-3,12-dioxoolean-1,9-dien-28-oic acid and related compounds inhibit growth of colon cancer cells through peroxisome proliferator-activated receptor gamma-dependent and -independent pathways," *Mol. Pharmacol.*, 68:119-128, 2005.

Chintharlapalli et al., "2-Cyano-lup-1-en-3-oxo-20-oic acid, a cyano derivative of betulinic acid, activates peroxisome proliferator-activated receptor [gamma] in colon and pancreatic cancer cells.," *Carcinogenesis*, 28 (11): 2337-2346, 2007.

Chintharlapalli et al., "Structure-dependent activity of glycyrrhetinic acid derivatives as peroxisome proliferator-activated receptor {gamma} agonists in colon cancer cells," *Molecular Cancer Therapeutics*, 6 (5): 1588-1598, 2007.

Cho et al., "The transcription factor NRF2 protects against pulmonary fibrosis," *FASEB Journal*, 18:1-29, 2004.

Chou et al., "Sterospecific Synthesis of 2-Deoxy-2,2-difluororibonolactone and its Use in the Preparation of 2'-Deoxy-2',2'-difluoro-B—D-ribofuranosyl Pyrimidine Nucleosides: The Key Role of Selective Crystallization," *Synthesis*, 565-570, 1992.

Chung and Wasicak, "Synthesis of chiral ∀-acetylenic cyclic amines from ∀-amino acids: App.s to differentially constrained oxotremorine analogues as muscarinic agents," *Tetrahedron Lett.*, 31:3957-3960, 1990.

Cianchi et al., "Cyclooxygenase-2 activation mediates the proangiogenic effect of nitric oxide in colorectal cancer," *Clinical Cancer Research*, 10:2694-2704, 2004.

Clinton et al., "Steroidal[3,2-c]pyrazoles. II. Androstanes, 19-norandrostanes and their unsaturated analogs," *J. Am Chem Soc.*, 83:1478-1491, 1961.

Corey and Ruden, "Stereoselective methods for the synthesis of terminal cis AND trans enyne units," *Tetrahedron Lett.*, 1495-1499, 1973.

Couch et al., "2-cyano-3,12-dioxooleana-1,9(11)-diene-28-oic acid disrupts microtubule polymerization: a possible mechanism contributing to apoptosis," *Molecular Pharmacology*, 69 (4): 1158-1165, 2006.

Couch et al., "Studies on the reactivity of CDDO, a promising new chemopreventive and chemotherapeutic agent: implications for a molecular mechanism of action ," *Bioorganic and Medicinal Chemistry Letters*, 15 (9): 2215-2219, 2005.

Coyle and Puttfarcken, "Oxidative stress, glutamate, and neurodegenerative disorders," *Science*, 262:689-695, 1993.

Cripe, "Adult Acute Leukemia," *Current Problems in Cancer*, 21 (1): 4-64, 1997.

Cui, "A material science perspective of pharmaceutical solids," *Int. J. Pharmceutics*, 339 (1-2): 3-18, 2007.

Dean et al., "Halogenolysis of methyl glycyrrhetate with lithium iodidedimethylformamide," *J. Chem. Soc.*, 6655-6659, 1965.

Deng and Snyder, "Preparation of a 24-Nor-1,4-dien-3-one triterpene derivative from betulin: a new route to 24-nortriterpene analogues," *J of Organic Chemistry*, 67 (9): 2864-2873, 2002.

Devi et al., "Constituents of black dammar resin and some transformation products of α- and and β-amyrins," *Indian J. of Chemistry*, 7 (12): 1279-1280, 1969.

Dezube et al., "Interim results of a phase I trial with a novel orally administered synthetic triterpenoid RTA 402 (CDDO-Me) in patients with solid tumors and lymphoid malignancies," *J. Clin. Oncol.*, 2007 ASCO Annual Meeting Proceedings, 25(18S):14101, 2007.

Di Stefano et al., "Inhibition of [3H]thymidine incorporation into DNA of rat regenerating liver by 2',2'-difluorodeoxycytidine coupled to lactosaminated poly-L-lysine," *Biochem. Pharmacol.*, 57 (7): 793-799, 1999.

Ding et al., "Macrophage deactivating factor and transforming growth factors-$\beta_1$ $\beta_2$ and $\beta_3$, inhibit induction of macrophage nitrogen oxide synthesis by IFNγ[1]," *J. Immunol.*, 145:940-944, 1990.

Dinkova-Kostova et al., "Extremely potent triterpenoid inducers of the phase 2 response: correlations of protection against oxidant and inflammatory stress," *PNAS*, 102:4584-4589, 2005.

Drach et al., "Induction of differentiation in myeloid leukemia cell lines and acute promyelocytic leukemia cells by liposomal all-trans-retinoic acid," *Cancer Research*, 53:2100-2104, 1993.

Dragnev et al., "Specific chemopreventive agents trigger proteasomal degradation of G1 cyclins: implications for combination therapy," *Clin. Cancer Research*, 10 (7): 2570-2577, 2004.

Dragnev et al., "The retinoids and cancer prevention mechanisms," *The Oncologist*, 5:361-368, 2000.

Drefahl and Huneck, "Nor-olea-12-enol-17-amin und Olea-12-enol-28-amin," *Chem. Ber.*, 91:278-281, 1958.

Duan et al., "Immunosuppressive terpenoids from extracts of *tripterygium wilfordii*," *Tetrahedron*, 57 (40): 8413-8424, 2001.

DuBois et al., "$G_1$ delay in cells overexpressing prostaglandin endoperoxide synthase-$2^1$," *Cancer Res.*, 56(4):733-737, 1996.

DuBois et al., "Increased cyclooxygenase-2 levels in carcinogen-induced rat colonic tumors," *Gastroenterology*, 110:1259-1262, 1996.

Dutcher et al., "Pentacyclic triterpene synthesis. 5. Synthesis of optically pure ring AB precursors," *J. Org. Chem.*, 41:2663-2669, 1976.

Ekmekcioglu et al., "Tumor iNOS predicts poor survival for stage III melanoma patients," *Int. J. Cancer*, 119:861-866, 2006.

Elgamal et al., "Glycyrrhetic acid derivatives with modified ring A," *J of Pharmaceutical Sciences*, 62 (9): 1557-1558, 1973.

Elgamal et al., "The C-2,C-3-glycol derivatives of glycyrrhetic acid," *Tetrahedron*, 30 (23/24): 4083-4087, 1974.

Ellies et al., "Mammary tumor latency is increased in mice lacking the inducible nitric oxide synthase," *Int. J. Cancer*, 106:1-7, 2003.

Elliot et al., "The triterpenoid CDDO inhibits expression of matrix metalloproteinase-1, matrix metalloproteinase-13 and Bcl-3 in primary human chondrocytes," *Arthritis Res. Ther.*, 5:R285-R291, 2003.

Elsawa et al., "Preferential Inhibition of Malignant Cell Growth by CDDO in Waldenstrom Macroglobulinemia," *Blood*, 108(11):2528, 2006.

Elstner et al., "Ligands for peroxisome proliferator-activated receptorgamma and retinoic acid receptor inhibit growth and induce apoptosis of human breast cancer cells in vitro and in BNX mice," *Proc. Natl. Acad. Sci. USA*, 95:8806-8811, 1998.

Embleton et al., "Antitumour reactions of monoclonal antibody against a human osteogenic-sarcoma cell line," *Br. J Cancer*, 43:4801-4805, 1981.

Endová et al., "Preparation of 2,3-secodiacids of the lupane series," *Collection of Czechoslovak Chemical Communications*, 59 (6): 1420-1429, 1994.

Engel et al., "Quantitation of minimal residual disease in acute myelogenous leukemia and myelodysplastic syndromes in complete remission by molecular cytogenetics of progenitor cells," *Leukemia*, 13:568-577, 1999.

Estey et al., "Molecular remissions induced by liposomal-encapsulated all-trans retinoic acid in newly diagnosed acute promyelocytic leukemia," *Blood*, 94:2230-2235, 1999.

Estey et al., "Randomized phase II study of fludarabine + cytosine arabinoside + idarubicin + all-trans retinoic acid + granulocyte-colony stimulating factor in poor prognosis newly diagnosed acute myeloid leukemia and myelodysplastic syndrom," *Blood*, 93(8):2478-2484, 1999.

Evers et al., "Betulinic acid derivatives: a new class of human immunodeficiency virus type 1 specific inhibitors with a new mode of action," *J of Medicinal Chemistry*, 39 (5): 1056-1068, 1996.

Favaloro, Jr. et al., "Design and synthesis of tricyclic compounds with enone functionalities in rings A and C: a novel class of highly active inhibitors of nitric oxide production in mouse macrophages," *J Med Chem*, 45(22):4801-4805, 2002.

Finkbeiner and Stiles, "Chelation as a driving force in organic reactions. IV. Synthesis of a ∀-nitro acids by control of the carboxylation-decarboxylation equilibrum," *J. Am. Chem. Soc.*, 85:616-622, 1963.

Gandhi et al., "Prolonged infusion of gemcitabine: clinical and pharmacodynamic studies during a phase I trial in relapsed acute myelogenous leukemia," *J Clin. Oncol.*, 20 (3): 665-673, 2002.

Ganguly et al., "Oxidation of ring in a lupeol," *Tetrahedron*, 22 (10): 3597-3599, 1966.

Garcia-Granados et al., "Semi-synthesis of triterpene A-ring derivatives from oleanolic and maslinic acids. Theoretical and experimental $^{13}$C chemical shifts," *J. of Chemical Research*, Synopses, 2: 56-57, 2000.

Garcia-Granados et al., "Semi-synthesis of triterpene A-ring derivatives from oleanolic and maslinic acids. Part II. Theoretical and experimental $^{13}$C chemical shifts," *J. of Chemical Research*, Synopses, 5: 211-212, 2000.

Genain and Hauser, "Creation of a model for multiple sclerosis in Callithrix jacchus marmosets," *J. Mol. Med.*, 75:187-197, 1997.

Ghosh et al., "NF-κB and Rel proteins: evolutionarily conserved mediators of immune response," *Annu Rev Immunol.*, 16:225-260, 1998.

Glen et al., "Isolation of a new triterpenoid from rose-bay willow-herb," *Chemistry and Industry*, London, United Kingdom), 46: 1908, 1965.

Godoy et al., "Central and systemic IL-I exacerbates neurodegeneration and motor symptoms in a model of Parkinson's disease," *Brain*, 131:1880-1894, 2008.

Govindachari et al., "Gymnosporol, a new pentacyclic triterpene from *gymnosporia rothiana*," *Indian Journal of Chemistry*, 8 (5): 395-397, 1970.

Green and Long, "Compounds related to the steroid hormones. Part II. The action of hydrogen bromide on 2-bromo-3-oxo-$\delta^1$-5α-steroids," *J. of the Chemical Society*, 2532-2543, 1961.

Grieco and Speake, "Synthetic Studies on Quassinoids: Total Synthesis and Biological Evaluation of (+)-Des-D-chaparrinone," *J. Org. Chem.*, 63:5929-5936, 1998.

Guo et al., "Selective Protection of 2',2'-Diflurodeoxycytidine (Gemcitabine)," *J. Org. Chem.*, 64: 8319-8322, 1999.

Guo et al., "Targeted delivery of a peripheral benzodiazepine receptor ligand-gemcitabine conjugate to brain tumors in a xenograft model," *Cancer Chemother. Pharmacol.*, 48 (2): 169-176, 2001.

Gura et al., "Systems for identifying new drugs are often faulty," *Science*, 278:1041-1042, 1997.

Guttridge et al., "NF-kappaB controls cell growth and differentiation through transcriptional regulation of cyclin D1," *Mol. Cell. Biol.*, 19 (8): 5785-5799, 1999.

Hail et al., "Evidence supporting a role for calcium in apoptosis induction by the synthetic triterpenoid 2-cyano-3,12-dioxooleana-1,9-dien-28-oic acid (CDDO)," *J. Biol. Chem.*, 279:11179-11187, 2004.

Hanna and Ourisson, "Studies of cyclic ketones. VIII. Preparation and properties of polycyclic α-diketones," *Bulletin de la Societe Chimique de France*, 1945-1951, 1961. (French only, but see attached English CAPLUS database summary.).

Hattori et al., "A triterpene from the fruits of *rubus chingii*," *Phytochemistry*, 27 (12): 3975-3976, 1988.

Heiner et al., "Localization of GD2-specific monoclonal antibody 3F8 in human osteosarcoma," *Cancer Res.*, 47:5377-5384, 1987.

Hidvegi et al., "A low temperature method of isolating normal human articular chondrocytes," *Osteoarthr. Cartil.*, 14:89-93, 2006.

Hinz et al., "NF-kappaB function in growth control: regulation of cyclin D1 expression and G0/G1-to-S-phase transition," *Mol. Cell. Biol.*, 19 (4): 2690-2698, 1999.

Hirota et al., "Stereoselective total synthesis of (±)-eperuane-8β,15-diol$^1$," *Bull. Chem. Soc. Jpn.*, 61:4023-4028, 1988.

Hirota et al., "Total synthesis of (±)-amarolide, a quassinoid bitter principle," *J Org. Chem.*, 56:1119-1127, 1991.

Hirota et al.,"Suppression of tumor promoter-induced inflammation of mouse ear by ursolic acid and 4,4-dimethycholestane derivatives " *Agric. Biol. Chem.*, 54:1073-1075, 1990.

Honda et al., "A novel dicyanotriterpenoid, 2-cyano-3,12-dioxooleanan-1,9(11)-dien-28-onitrile, active at picomolar concentrations for inhibition of nitric oxide production," *Bioorganic & Medicinal Chemistry Letters*, 12:1027-1030, 2002.

Honda et al., "An efficient synthesis of tricyclic compounds (±)-(4aβ, 8aβ, 10aβ)-1,2,3,4,4a,6,7,8,8a,9,1-,10a-Dodecahydro-1,1,4a-Trimethyl-2-Oxophenanthrene-8a-Carboxolic acid, its methyl ester, and (±)-(4aβ,8aβ,10aβ)-3,4,4a,6,7,8,8a,9,10,10a-Decahydro-8a-Hydroxymethy1-1,1,4a-Trimethylphenanthren-2(1H)-one," *Org. Prep. Proced. Int.*, 37 (6):546-550, 2005.

Honda et al., "Design and synthesis of 23,24-dinoroleanolic acid derivatives, novel triterpenoid—steroid hybrid molecules," *J Org. Chem.*, 63:4846-4849, 1998.

Honda et al., "Design and synthesis of 2-cyano-3,12-dioxoolean-1,9-dien-28-oic acid, a novel and highly active inhibitor of nitric oxide production in mouse macrophages," *Bioorg Med Chem Lett.*, 8(19):2711-2714, 1998.

Honda et al., "Design and synthesis of 2-cyano-3,12-dioxoolean-1,9-dien-28-oic acid, a novel and highly active inhibitor of nitric oxide production in mouse macrophages," *Bioorganic & Medicinal Chemistry Letters*, 8:2711-2714, 1998.

Honda et al., "Design, synthesis, and biological evaluation of biotin conjugates of 2-cyano-3,12- dioxooleana-1,9(11)-dien-28-oic acid for the isolation of the protein targets," *J. Med. Chem.*, 47 (20): 4923-4932, 2004.

Honda et al., "Efficient synthesis of (−)- and (+)-tricyclic compounds with enome functionalities in rings A and C. A novel class of orally active anti-inflammatory and cancer chemopreventive agents," *Org Biomol Chem.*, 1:4384-4391, 2003.

Honda et al., "New enone derivatives of oleanolic acid and ursolic acid as inhibitors of nitric oxide production in mouse macrophages," *Bioorg. Med. Chem. Lett.*, 7:1623-1628, 1997.

Honda et al., "Novel synthetic oleanane and ursane triterpenoids with various enone functionalities in ring A as inhibitors of nitric oxide production in mouse macrophages," *J Med. Chem.*, 43:1866-1877, 2000.

Honda et al., "Novel synthetic oleanane triterpenoids: a series of highly active inhibitors of nitric oxide production in mouse macrophages," *Bioorg Med Chem Lett*, 9(24):3429-3434, 1999.

Honda et al., "Novel tricyclic compounds having acetylene groups at C-8a and cyano enones in rings A and C: highly potent anti-inflammatory and cytoprotective agents," *J Med. Chem.*, 50:1731-1734, 2007.

Honda et al., "Synthesis of (±)-3,3-ethylenedioxy-14α-hydroxy-5-picrasene-11,16-dione, a 14αH-picrasane derivative," *Chem. Lett.*, 299-302, 1981.

Honda et al., "Synthesis of a novel dicyano abietane analogue: a potential antiinflammatory agent," *J. Org. Chem.*, 71:3314-3316, 2006.

Honda et al., "Synthetic oleanane and ursane triterpenoids with modified rings A and C: A series of highly active inhibitors of nitric oxide production in mouse macrophages," *J. Med. Chem.*, 43:4233-4246, 2000.

Hong et al., "Phase I trial of a novel oral NF-κB/pSTAT3 inhibitor RTA-402 in patients with solid tumors and lymphoid malignancies," 44th Annual Meeting of the American Society of Clinical Oncology, 2008.

Hosoi et al., "Detection of human osteosarcoma-associated antigen(s) by monoclonal antibodies," *Cancer Res.*, 42:654-661, 1982.

Huang et al., "Inhibition of skin tumorigenesis by Rosemary and its constituents carnosol and ursolic acid," *Cancer Res.*, 54:701-708, 1994.

Huang et al., "Inhibitory effects of dietary curcumin on forestomach, duodenal, and colon carcinogenesis in mice," *Cancer. Res.*, 54:5841-5847, 1994.

Huang et al., "Structure of a WW domain containing fragment of dystrophin in complex with β-dystroglycan," *Nat. Struct. Biol.*, 7:634-638, 2000.

Huneck, "Triterpene, XIV: die bromierung von 19β28-epoxy-3-oxo-2-diazo- und -1-oxo-2- diazo- sowie von 19β28-epoxy-1-oxo-18αH-oleanan," *Chemische Berichte*, 98 (9): 2837-2843, 1965. (German only, but see attached English CAPLUS database summary.).

Hyer et al., "Synthetic triterpenoids cooperate with tumor necrosis factor-related apoptosis-inducing ligand to induce apoptosis of breast cancer cells," *Cancer Res.*, 65:4799-4808, 2005.

Iguchi et al., "Lipid peroxidation and disintegration of the cell membrane structure in cultures of rat lung fibroblasts treated with asbestos," *J. Appl. Toxicol.*, 13:269-275, 1993.

Ikeda et al., "Induction of redox imbalance and apoptosis in multiple myeloma cells by the novel triterpenoid 2-cyano-3,12-dioxoolean-1,9-dien-28-oic acid," *Mol. Cancer Ther.*, 3:39-45, 2004.

Ikeda et al., "The novel triterpenoid CDDO and its derivatives induce apoptosis by disruption of intracellular redox balance," *Cancer Res.*, 63:5551-5558, 2003.

Ishikawa et al., "Heme oxygenase-1 inhibits atherogenesis in Watanabe heritable hyperlipidemic rabbits," *Circulation*, 104 (15): 1831-1836, 2001.

Ito et al., "Involvement of caspase-8 in the induction of osteosarcoma cell apoptosis by the novel triterpenoid CDDO," 47th Annual Meeting, Orthopaedic Research Society, Feb. 25-28, 2001, San Francisco, California, p. 0863, Poster Session, 2001.

Ito et al., "The novel triterpenoid 2-cyano-3, 12-dioxoolean-1,9-dien-28-oic acid induces apoptosis of human myeloid leukemia cells by a caspase-8-dependent mechanism," *Cell Growth & Differentiation*, 11(5):261-267, 2000.

Ito et al., "The novel triterpenoid CDDO induces apoptosis and differentiation of human osteosarcoma cells by a caspase-8 dependent mechanism," *Mol. Pharmacol.*, 59:1094-1099, 2001.

Johansen et al., "Pharmacology and preclinical pharmacokinetics of the triterpenoid CDDO methyl ester," *Proc. Amer. Assoc. Cancer Res.*, 44:1728, 2003.

Johnson et al., "A plan for distinguishing between some five- and six-membered ring ketones," *J. Am Chem. Soc.*, 67:1745-1754, 1945.

Johnson et al., "Relationships between drug activity in NCI preclinical in vitro and in vivo models and early clinical trials," *Br. J. Cancer*, 84:1424-1431, 2001.

Joyce et al., "Integration of Rac-dependent regulation of cyclin D1 transcription through a nuclear factor-kappaB-dependent pathway," *J Biol. Chem.*, 274 (236): 25245-25249, 1999.

Kahne and Collum, "Kinetic cyanations of ketone enolates," *Tetrahedron Lett.*, 22:5011-5014, 1981.

Kaltschmidt et al.,"Transcription factor NF-kappaB is activated in primary neurons by amyloid beta peptides and in neurons surrounding early plaques from patients with Alzheimer disease," *Proc. Natl. Acad. Sci. USA*, 94:2642-2647, 1997.

Karin, "Nuclear factor-kappaB in cancer development and progression," *Nature*, 441:431-436.

Kasinski et al., "Inhibition of IkappaB kinase-nuclear factor-kappaB signaling pathway by 3,5-bis(2-flurobenzylidene)piperidin-4-one (EF24), a novel monoketone analog of curcumin," *Mol. Pharmacology*, 74 (3): 654-661, 2008.

Kawamori et al., "Chemopreventive activity of celecoxib, as specific cyclooxygenase-2 inhibitor, against colon carcinogenesis," *Cancer Res.*, 58(3):409-412, 1998.

Kerwin et al., "Quassinoid synthesis. 2. Preparation of a tetracyclic intermediate having the Bruceantin tetrahydrofuran ring," *J Org. Chem.*, 52:1686-1695, 1987.

Khan et al., "A dichotomous role for nitric oxide during acute Toxoplasma gondii infection in mice," *Proc. Natl. Acad. Sci. USA*, 94:13955-13960, 1997.

Khan et al., "α-amyrin derivatives from *corchorus depressus*," *Phytochemistry*, 30 (6): 1989-1992, 1991.

Kim et al., "Capasase-3 activation is involved in apoptosis induced by a synthetic triterpenoid in Non-small cell lung cancer (NSCLC) cells," *Proc. Amer. Assoc. Cancer Res.*, 41:770, Abstract #4894, 2000.

Kim et al., "Identification of a novel synthetic triterpenoid, methyl-2-cyano-3,12-dioxooleana-1,9-dien-28-oate, that potently induces caspace-mediated apoptosis in human lung cancer cells," Molecular Cancer Therapeutics, 1:177-184, 2002.

Kircher, "Triterpenes, in organ pipe cactus," *Phytochemistry*19:2707-2712, 1980; Database CAPLUS on STN AN:1981:550946.

Klinot and Vystrcil, "Triterpenes. VII. Stereochemistry of 2-bromo derivatives of allobetuline and alloheterobetaline," *Collection of Czechoslovak Chemical Communications*, 31 (3): 1079-1092, 1966.

Klinot et al., "Triterpenes. Part LXXXVI. Triterpenoid 2,3-ketolis, diols and their acetates: preparation and conformation of the ring A," *Collection of Czechoslovak Chemical Communications*, 54 (2): 400-412, 1989.

Klotz et al., "Selective expression of inducible nitric oxide synthase in human prostate carcinoma," *Cancer*, 82:1897-1903, 1998.

Konopleva and Andreeff, "Regulatory pathways in programmed cell death," *Cancer Mol Biol*, 6:1229-1260, 1999.

Konopleva et al., "Activation of nuclear transcription factor PPARgamma by the novel triterpenoid CDDO as targeted therapy in breast cancer," *2002 Keystone Symposium*, Abstract No. 539, 2002.

Konopleva et al., "Apoptosis: molecules and mechanisms," *Adv Exp Med Biol*, 457:217-236, 1998.

Konopleva et al., "Engraftment potential of AML progenitors into Nod/scid mice is dependent on baseline CXCR4 expression," *Blood*, 94(Suppl 1):166b, Abstract #3916, 1999.

Konopleva et al., "Mechanisms and Activity of PPARgamma-Active Triterpenoids CDDO and CDDO-Me in Leukemias," *Blood*, 106:2460, 2005.

Konopleva et al., "Novel synthetic triterpenoid CDDO-Me: potent antiproliferative, proapoptotic and differentiating agent in AML," *Blood*, 96(11), Part 1: 121A, abstract # 522, 2000.

Konopleva et al., "Novel synthetic triterpenoid, CDDO, and its methyl ester: Potent antiproliferative, proapoptotic and differentiating agents in AML," *Blood*, 94(Suppl 1):479a, Abstract #2140, 1999.

Konopleva et al., "Novel triterpenoid CDDO-Me is a potent inducer of apoptosis and differentiation in acute myelogenous leukemia," *Blood*, 99(1):326-335, 2002.

Konopleva et al., "Peroxisome proliferator-activated receptor gamma and retinoid X receptor ligands are potent inducers of differentiation and apoptosis in leukemias," *Mol. Cancer Ther.*, 3:1249-1262, 2004.

Konopleva et al., "PPARγ nuclear receptor as a novel therapeutic target in AML," *Blood*, 96(11):460a, Abstract #1982, 2000.

Konopleva et al., "PPARgamma Ligand CDDO Induces Apoptosis in Leukemias Via Multiple Apoptosis Pathways," *Abstracts of the 44th Annual Meeting of the American Society of Hematology*, Abstract No. 2209, 2002.

Konopleva et al., "PPARgamma Ligands Are Potent Inducers of Apoptosis in Leukemias and Lymphomas," *American Society of Hematology 43rd Annual Meeting and Exposition*, Abstract No. 501, 2001.

Konopleva et al., "PPARgamma Nuclear Receptor as a Novel Molecular Target in Leukemia Therapy," *Proc. Amer. Assoc. Cancer Res.*, 43:4730, 2002.

Konopleva et al., "Suppression of ERK Activation is Required for Triterpenoid Methyl-CDDO-Induced Apoptosis in AML," *Blood*, 102(11):1404, 2003.

Konopleva et al., "Synthetic triterpenoid 2-cyano-3,12-dioxooleana-1,9-dien-28-oic acid induces growth arrest in HER2-overexpressing breast cancer cells," *Mol. Cancer Ther.*, 5:317328, 2006.

Konopleva et al., "Synthetic triterpenoid CDDO as a novel therapy for resistant breast cancer," *Proc. Amer. Assoc. Cancer Res.*, 44:2726, 2003.

Konopleva et al., "The novel triterpenoid CDDO-Me suppresses MAPK pathways and promotes p38 activation in acute myeloid leukemia cells," *Leukemia*, 19:1350-1354, 2005.

Konopleva et al., "The synthetic triterpenoid 2-cyano-3,12-dioxooleana-1,9-dien-28-oic acid induces caspase-dependent and -independent apoptosis in acute myelogenous leukemia," *Cancer Res.*, 64:7927-7935, 2004.

Konopleva et al., "Triterpenoid methyl-CDDO s a potent inducer of apoptosis in CD34+ AML progenitor cells via activation of SAPK pathways and inhibition of MAPK cascades," *Blood*, 104:2533, 2004.

Kornblau et al., "Apoptosis regulating proteins as targets of therapy for hematological malignancies," *Exp. Opin. Inv. Drugs*, 8:2027-2057, 1999.

Kornblau et al., "Phase I study of mitoxantrone plus etoposide with multidrug blockage by SDZ PSC-833 in relapsed or refractory acute myelogenous leukemia," *J. Clin. Oncol.*, 15(5):1796-1802, 1997.

Korovin and Tkachev, "Synthesis of quinoxalines fused with triterpenes, ursolic acid and betulin derivatives," *Russian Chemical Bulletin*, (Translation of Izvestiya Akademii Nauk, Seriya Khimicheskaya), 20 (2): 304-310, 2001.

Kowalski and Reddy, "Ester homologation revisited: a reliable, higher yielding and better understood procedure," *J. Org. Chem.*, 57:7194-7208, 1992.

Kress et al., "Triterpenoids display single agent activity in a mouse model of CLL/SBL," *Blood*, 108(11):2530, 2006.

Kress et al., "Triterpenoids display single agent anti-tumor activity in a transgenic mouse model of chronic lymphocytic leukemia and small B cell lymphoma," *PLOS ONE*, 6(e559):1-11, 2007.

Kruger et al., "Up-regulation of heme oxygenase provides vascular protection in an animal model of diabetes through its antioxidant and antiapoptotic effects," *J. Pharmacol. Exp. Ther.*,319 (3): 1144-1152, 2006.

Kumar and Seshadri, "Triterpenoids of *pterocarpus santalinus*: constitution of a new lupene diol," *Phytochemistry*, 14 (2): 521-523, 1975.

Kundu et al., "Synthese von 2α-methoxycarbonyl-A-nor-lupa," *Chemische Beerichte*, 101 (9): 3255-3264, 1968. (German only, but see attached English CAPLUS database summary.).

Kurbacher et al., "Ascorbic acid (vitamin C) improves the antineoplastic activity of doxorubicin, cisplatin, and paclitaxel in human breast carcinoma cells in vitro," *Cancer Lett.*, 103:183-189, 1996.

Kurinna et al., "The novel triterpenoid CDDO-Me promotes apoptosis in Gleevec-resistant chronic myeloid leukemia cells by caspase-independent mechanisms," *Proc. Amer. Assoc. Cancer Res.*, 46:2240, 2005.

Lala et al., "Role of nitric oxide in tumor progression: lessons from experimental tumors," *Cancer and Metastasis Reviews*, 17 (1): 91-106, 1998.

Langille et al., "Differential effects of physiological concentrations of retinoic acid in vitro on chondrogenesis and myogenesis in chick craniofacial mesenchyme," *Differentiation*, 40:84, 1989.

Lapillonne et al., "Activation of peroxisome proliferator-activated receptor gamma by a novel synthetic triterpenoid 2-cyano-3,12-dioxooleana-1,9-dien-28-oic acid induces growth arrest and apoptosis in breast cancer cells," *Cancer Res.*, 63:5926-5939, 2003.

Lavie and Shvo, "Constituents of Ecballium elaterium: proposed structure for elatericin A and B," *Chemistry and Industry*, (London, United Kingdom), 429-430, 1959.

Lawrie et al. "Isolation of derivatives of ursolic acid from apple skin," *Chemistry and Industry*, (London, United Kingdom), 41: 1720, 1966.

Lawson et al., "Isolation and preliminary characterization of a monoclonal antibody that interacts preferentially with the liver isoenzyme of human alkaline phosphatase," *Clin. Chem.*, 31:381-385, 1985.

Lee et al., "Functional and quantitative analysis of splenic T cell immune responses following oral toxoplasma gondii infection in mice," *Experimental Parasitology*, 91:212-221, 1999.

Lehn and Ourisson, "Nuclear magnetic response (N.M.R.) of natural products. I. General introduction. Triterpenes of the lupane series. Methyl groups," *Bulletin de la Societe Chimique de France*, 1137-1142, 1962. (French only, but see attached English CAPLUS database summary.).

Lehn and Ourisson, "Syntheses in the lupane series," *Bulletin de la Societe Chimque de France*, 1133-1136, 1962. (French only, but see attached English CAPLUS database summary.).

Lehn and Vystreil, "Resonance magnetique nucleaire de produits naturels—VI: Triterpènes dérivés de la bétuline," *Tetrahedron*, 19 (11): 1733-1745, 1963. (English abstract).

Lemieux, "Acylglycosyl Halides. [55] tetra-O-acetyl-α-D-glucopyranosyl bromide," *Methods Carbohydr. Chem.*, 2:221-222, 1963.

Leonard et al., "Expression of nitric oxide synthase in inflammatory bowel disease is not affected by corticosteroid treatment," *J. Clin. Pathol.*, 51:750-753, 1998.

Li and Nel, "Role of the Nrf2-mediated signaling pathway as a negative regulator of inflammation: implications for the impact of particulate pollutants on asthma," *Antioxidants & Redox Signaling*, 8:88-98, 2006.

Li et al., "Studies on constituents of Rosa multiflora thunb," *Zhongguo Yaoke Daxue Xuebao*, 33 (3): 184-187, 2002. (Chinese only, but see attached English CAPLUS database summary.).

Liby et al., "A novel acetylenic tricyclic bis-(cyano enone) potently induces phase 2 cytoprotective pathways and blocks liver carcinogenesis induced by aflatoxin," *Cancer Res.*, 68:6727-6733, 2008.

Liby et al., "Novel semisynthetic analogues of betulinic acid with diverse cytoprotective, antiproliferative, and proapoptotic activities," *Molecular Cancer Therapeutics*, 6 (7): 2113-2119, 2007.

Liby et al., "The rexinoid LG100268 and the synthetic triterpenoid CDDO-methyl amide are more potent than erlotinib for prevention of mouse lung carcinogenesis," *Mol. Cancer Ther.*, 7:1251-1257, 2008.

Liby et al., "The synthetic triterpenoids, CDDO and CDDO-imidazolide, are potent inducers of heme oxygenase-1 and Nrf2/ARE signaling," *Cancer Res.*, 65:4789-4798, 2005.

Liby et al., "Triterpenoids and rexinoids as multifunctional agents for the prevention and treatment of cancer," *Nature Reviews Cancer*, 7:357-369, 2007.

Lieu et al., "Dual cytotoxic mechanisms of submicromolar taxol on human leukemia HL-60 cells," *Biochem. Pharmacology*, 53:1587-1596, 1997.

Ling et al., "The novel triterpenoid C-28 methyl ester of 2-cyano-3, 12-dioxoolen-1, 9-dien-28-oic acid inhibits metastatic murine breast tumor growth through inactivation of STAT3 signaling," *Cancer Res.*, 67:4210-4218, 2007.

Ling et al., "The novel triterpenoid CDDO-Me inhibits metastatic murine breast tumor through inhibition of Stat3 signaling," 2007 AACR Annual Meeting, Abstract No. 301, 2007.

Liotta et al., "A simple method for the efficient sysnthesis of unsaturated Ǝ-dicarbonyl compunds," *J. Org. Chem.*, 46:2920-2923, 1981.

Liu et al., "Heme oxygenase-1 (HO-1) inhibits postmyocardial infarct remodeling and restores ventricular function," *FASEB J.*, 20 (2): 207-216, 2006.

Long, "Regulation of human bone marrow-derived osteoprogenitor cells by osteogenic growth factors ," *Clin. Invest.*, 95:881-887, 1995.

Lugemwa et al., "A heliothis zea antifeedant from the abundant birchbark triterpene betulin", *Journal of Agricultural and Food Chemistry*, 38 (2): 493-496, 1990.

Luo et al., "IKK/NF-kappaB signaling: balancing life and death—a new approach to cancer therapy," *J. Clin. Invest.*, 115 (10): 2625-2631, 2005.

MacMicking et al., "Altered responses to bacterial infection and endotoxic shock in mice lacking inducible nitric oxide synthase," *Cell*, 81:641-650, 1995.

Mane and Ingle, "Synthesis and biological activity of some new 1,5-benzothiazepines containing thiazole moiety: 2-aryl-4-(4-methyl -2-substituted-aminothiazol-5-y1)-2,3-dihydro-1,5-benzothiazepines," *Indian Journal of Chemistry, Section B: Organic Chemistry Including Medicinal Chemistry*, 21B (10): 973-974, 1982.

Mantovani et al., "Inflammation by remote control," *Nature*, 435:752-753, 2005.

Manzoor-i-Khuda and Habermehl, "Chemical constituents of *Corchorus capsularis* and *C. olitorium* (jute plant). III. Structure of corosin," *Zeitschrift fuer Naturforschung, Teil C: Biochemie, Biophysik, Biologie, Virologie*, 29 (5-6): 209-221, 1974.

Manzoor-i-Khuda, "Isolation techniques for active principles from plants and their composition and structure determination through spectroscopic techniques," *New Trends Nat. Prod.*, 26: 303-323, 1986.

Marnett, "Aspirin and the potential role of prostaglandins in colon cancer," *Cancer Res.*, 52(20):5575-5589, 1992.

Marrogi et al., "Nitric oxide synthase, cyclooxygenase 2, and vascular endothelial growth factor in the angiogenesis of non-small cell lung carcinoma," *Clinical Cancer Research*, 6:4739-4744, 2000.

Maurel et al., "Phase I trial of weekly gemcitabine at 3-h infusion in refractory, heavily pretreated advanced solid tumors," *Anti-Cancer Drugs*, 12 (9): 713-717, 2001.

McGeer and McGeer, "The inflammatory response system of brain: implications for therapy of Alzheimer and other neurodegenerative diseases," *Brain Research Reviews*, 21:195-218, 1995.

Mehta et al., "Activation of retinoid receptors RAR alpha and RXR alpha induces differentiation and apoptosis, respectively, in HL-60 cells," *Cell, Growth Differ*, 7(2): 179-186, 1996.

Melichar et al., "Growth-inhibitory effect of a novel synthetic triterpenoid, 2-cyano-3,12-dioxoolean-1,9-dien-28-oic acid, on ovarian carcinoma cell lines not dependent on peroxisome proliferator-activated receptor-gamma expression," *Gynecologic Oncology*, 93:149-154, 2004.

Melia et al., "1, 2-dideoxy-3, 4:5, 7-bis-o—(1-methylethylidene)—D-gluco- and—D-galacto-hept-l-ynitols : synthesis and conformational studies," *Tetrahedron*, 44:1673-1678, 1988.

Merril and Benveniste, "Cytokines in inflammatory brain lesions: helpful and harmful," *Trends Neurosci.*, 19:331-338, 1996.

Minns et al., "A novel triterpenoid induces transforming growth factor beta production by intraepithelial lymphocytes to prevent ileitis," *Gastroenterology*, 127:119-126, 2004.

Misra et al., "Studies on autoxidation: Part II—synthesis of isomeric 2,3-diols of Δ12- oleanene," *Indian J of Chemistry, Section B: Organic Chemistry Including Medicinal Chemistry*, 14B (6): 411-414, 1976.

Mix et al., "A synthetic triterpenoid selectively inhibits the induction of matrix metalloproteinases 1 and 13 by inflammmatory cytokines," *Arthritis Rheum.*, 44:1096-1104, 2001.

Mix et al., "Peroxisome proliferator-activated receptor-gamma-independent repression of collagenase gene expression by 2-cyano-3,12-dioxooleana-1,9-dien-28-oic acid and prostaglandin 15-deoxy-delta(12,14) J2: a role for Smad signaling," *Mol. Pharmacol.*, 65:309-318, 2004.

Moncada et al., "Nitric oxide: physiology, pathophysiology, and pharmacology," *Pharmacol. Rev.*, 43:109-142, 1991.

Morris et al., "Association of a functional inducible nitric oxide synthase promoter variant with complications in type 2 diabetes," *J Mol. Med.*, 80 (2): 96-104, 2002.

Morse and Choi, "Heme oxygenase-1: from bench to bedside," *Am. J. Respir. Crit. Care Med.*, 172 (6): 660-670, 2005.

Morse and Choi, "Heme oxygenase-1: the 'emerging molecule' has arrived," *Am. J. Respir. Crit. Care Med.*, 27(1):8-16, 2002.

Murphy et al., "Immunomodulatory Effects of the Triterpenoid CDDO after Allogeneic Bone Marrow Transplantation in Mice: Reduction of Acute Graft-Versus-Host Disease Lethality," *Blood*, 106:1316, 2005.

Murray and Zweifel, "Preparation of Phenyl Cyanate and Its Utilization for the Synthesis of α, β-Unsaturated Nitriles," *Synthesis*, 150-151, 1980.*Synthesis*, 150-151, 1980.

Muzart, "Synthesis of unsaturated carbonyl compounds via a chromium-mediated allylic oxidation by 70% tert.butylhydroperoxide," *Tetrahedron Lett.*, 28:4665-4668, 1987.

Na and Surh et al., "Transcriptional regulation via cysteine thiol modification: a novel molecular strategy for chemoprevention and cytoprotection," *Mol. Carcinog.*,45 (6): 368-380, 2006.

Nathan and Xie, "Nitric oxide synthases: roles, tolls, and controls," *Cell*, 78:915-918, 1994.

Nathan et al., "Protection from Alzheimer's-like disease in the mouse by genetic ablation of inducible nitric oxide synthase," *The Journal of Experimental Medicine*, 202:1163-1169, 2005.

Nathan, "Points of control in inflammation," *Nature*, 420:846-852, 2002.

Nicholson et al., "Lethality of endotoxin in mice genetically deficient in the respiratory burst oxidase, inducible nitric oxide synthase, or both," *Shock*, 11:253-258, 1999.

Nishino et al., "Inhibition of the tumor-promoting action of 12-O tetradecanoylphorbol-13-acetate by some oleanane-type triterpenoid compounds," *Cancer Res.*, 48:5210-5215, 1988.

Office Action issued in New Zealand Patent Application No. 588710, mailed Mar. 30, 2011.

Ohshima and Bartsch, "Chronic infections and inflammatory process as cancer risk factors: possible role of nitric oxide in carcinogenesis," *Mutat. Res.*, 305:253-264, 1994.

Omura and Swern, "Oxidation of Alcohols by 'Activated' Dimethyl Sulfoxide. A Preparative, Steric and Mechanistic Study," *Tetrahedron*, 34:1651-1660, 1978.

Ono et al., "A convenient procedure for esterification of carboxylic acids," *Bull. Chem. Soc. Jpn.*, 51:2401-2404, 1978.

Osburn et al., "Genetic of pharmacologic amplification of Nrf2 signaling inhibits acute inflammatory liver injury in mice," *Toxicological Sciences*, 104:218-227, 2008.

Oshima et al., "Suppression of intestinal polyposis in Apc$^{\Delta 716}$ knockout mice by inhibition of cyclooxygenase 2 (COX-2)," *Cell*, 87:803-809, 1996.

Osman et al., "Application of chemical reactions on thin-layer chromatoplates. IV. Triterpene," *Bulletin of the Chemical Society of Japan*, 47 (8): 2056-2058, 1974.

Osman et al., "Chemical studies on pentacyclic triterpenes. I. Benzilic acid rearrangement of ring A in ursolic acid," *Egyptian J. of Chemistry*, 15 (3): 269-272, 1972.

Pahl, "Activators and target genes of Rel/NF-κB transcription factors," *Oncogene*, 18:6853-6866, 1999.

Palcy and Goltzman, "Protein kinase signalling pathways involved in the up-regulation of the rat alpha1 (I) collagen gene by transforming growth factor beta1 and bone morphogenetic protein 2 in osteoblastic cells," *Biochem. J.*, 343:21-27, 1999.

Parra-Delgado et al., "Synthesis and comparative molecular field analysis (CoMFA) of argentatin B derivatives as growth inhibitors of human cancer cell lines," *Bioorganic and Medicinal Chemistry*, 14 (6): 1889-1901, 2006.

Patel et al., "Phase II clinical investigation of gemcitabine in advanced soft tissue sarcomas and window evaluation of dose rate on gemcitabine triphosphate accumulation," *J Clin. Oncol.*, 19 (15): 3483-3489, 2001.

Paul et al., "Design and synthesis of a self-assembled photochemical dyad based on selective imidazole recognition," *Inorg. Chem.*, 41:3699-3704, 2002.

Paul et al., "Effective expression of small interfering RNA in human cells," *Nature Biotechnol.*, 20:505-508, 2002.

PCT International Preliminary Report on Patentability issued in International Application No. PCT/US2009/041172, mailed Oct. 28, 2010.

PCT International Search Report and Written Opinion issued in International Application No. PCT/US2009/041172, mailed Aug. 5, 2009.

Pedersen et al., "The triterpenoid CDDO induces apoptosis in refractory CLL B cells," *Blood*, 100:2965-2972, 2002.

Picard et al., "Structure of the triterpenes," *J. Soc. Chem. Ind.*, 58: 58-59, 1939.

Picard et al., "The triterpene resinols and related acids, part VI," *J. Chem. Soc.*, 1045-108, 1939.

Pitzele, "Synthesis of 2-oxygenated glycyrrhetic acid derivatives," *J. of Medicinal Chemistry*, 117 (2): 191-194, 1974.

Place et al., "The novel synthetic triterpenoid, CDDO-imidazolide, inhibits inflammatory response and tumor growth in vivo," *Clin. Cancer Res.*, 9:2798-2806, 2003.

Pollard, "Tumour-educated macrophages promote tumour progression and metastasis," *Nature Reviews*, 4:71-78, 2004.

Pradhan and De, "Preparation of triterpenoid diosphenol via oximinoketone and structure of baccatin," *Indian J of Chemistry, Section B: Organic Chemistry including Medicinal Chemistry*, 21B (9): 823-828, 1982.

Pradhan and Ghosh, "Studies on reactions of 2-bromo-3-ketotriterpenoids: Part IV. Debromination and dehydrobromination of 2α-bromo and 2,2-dibromo derivatives of lupanone and methyl dihydrobetulonate," *Indian J of Chemistry, Section B: Organic Chemistry including Medicinal Chemistry*, 33B (1): 73-75, 1994.

Prescott and White, "Self-promotion? Intimate connections between APC and prostaglandin H synthase-2," *Cell*, 87:783-786, 1996.

Rangasamy et al., "Disruption of Nrf2 enhances susceptibility to severe airway inflammation and asthma in mice," *Journal of Experimental Medicine*, 202:47-59, 2005.

Rayet and Gelinas, "Aberrant rel/nfkb genes and activity in human cancer," *Oncogene*, 18:6938-6947, 1999.

Reddy et al., "Evaluation of cyclooxygenase-2 inhibitor for potential chemopreventive properties in colon carcinogenesis," *Cancer Res.*, 56(20):4566-4569, 1996.

Richardson et al., "Synthesis and restriction enzyme analysis of oligodeoxyribonucleotides containing the anti-cancer drug 2',2'-difluoro-2'-deoxycytidine," *Nucleic Acid Res.*, 20 (7): 1763-1769, 1992.

Rizzieri et al., "Phase I evaluation of prolonged-infusion gemcitabine with mitoxantrone for relapsed or refractory acute leukemia," *J. Clin. Oncol.*, 20 (3): 674-679, 2002.

Robbins et al., "Inflammation and Repair," In: Basic Pathology 3rd Edition, W.B. Saunders Company, Chapter 2, p. 28, 1981.

Rossi et al., "Anti-inflammatory cyclopentenone prostaglandins are direct inhibitors of IkappaB kinase," *Nature*, 403:103-108, 2000.

Ruvolo et al., "The novel triterpenoid methyl-CDDO inhibits Bcl2 phosphorylation and potently kolls U937 cells," *Blood*, 94(10), Suppl. 1, Part 1: 280A, abstract #1251, 1999.

Sacerdoti et al., "Heme oxygenase overexpression attenuates glucose-mediated oxidative stress in quiescent cell phase: linking heme to hyperglycemia complications," *Curr. Neurovasc. Res.*, 2(2): 103-111, 2005.

Salvemini et al., "Endogenous nitric oxide enhances prostaglandin production in a model of renal inflammation," *J. Clin. Invest.*, 93(5):1940-1947, 1994.

Salvemini et al., "Nitric oxide activates cyclooxygenase enzymes," *Proc. Natl. Acad. Sci. USA*, 90(15):7240-7244, 1993.

Samudio et al., "2,cyano-3,12 dioxoolean-1,9 diene-28-imidazolide induces apoptosis in pancreatic cancer via redox-dependent cytoplasmic stress," *Proc. Amer. Assoc. Cancer Res.*, 46: Abstract No. 5899, 2005.

Samudio et al., "2-Cyano-3,12-dioxooleana-1,9-dien-28-imidazolide (CDDO-Im) directly targets mitochondrial glutathione to induce apoptosis in pancreatic cancer," *J. Biol. Chem.*, 280:36273-36282, 2005.

Samudio et al., "A novel mechanism of action of methyl-2-cyano-3,12 dioxoolean-1,9 diene-28-oate: direct permeabilization of the inner mitochondrial membrane to inhibit electron transport and induce apoptosis," *Mol. Pharmacol.*, 69:1182-1193, 2006.

Samudio et al., "A novel mechanism of action of methyl-2-cyano-3,12 dioxoolean-1,9 diene-28-oate (CDDO-Me): Direct permeabilization of the inner mitochondrial membrane to inhibit electron transport and induce apoptosis," *Proc. Am. Assoc. Cancer Res.*, 47: Abstract No. 4693, 2006.

Samudio et al., "The novel triterpenoid CDDOme potently synergizes with inhibition of bcl-2 function to induce apoptosis in AML via disruption of intracellular redox homeostasis," *Proc. Amer. Assoc. Cancer Res.*, 46: Abstract No. 4955, 2005.

Satoh et al., "Activation of the Keapl/Nrf2 pathway for neuroprotection by electrophilic [correction of electrophillic] phase II inducers," *PNAS*, 103 (3): 768-773, 2006.

Scholz et al., "Sensitive and specific methods for the determination of CDDO methyl ester in mouse, rat, dog, monkey, and human plasma by LC-tandem mass spectrometry," *Proc. Amer. Assoc. Cancer Res.*, 4: Abstract No. 6321, 2003.

Seibert and Masferrer, "Role of inducible cyclooxygenase (COX-2) in inflammation," *Receptor*, 4(1):17-23, 1994.

Sejbal et al., "Triterpenes. Part LXXIII. Reactions of triterpenoid ketones with sulfur and morpholine under Willgerodt-Kindler reaction conditions," *Collection of Czechoslovak Chemical Communications*, 51 (1): 118-127, 1986.

Sejbal et al., "Triterpenes. Part XC. Conversion of betulin into careyagenolide (2α,3β-dihydroxy-18α, 19βH-ursan-28, 20β-olide," *Collection of Czechoslovak Chemical Communications*, 54 (4): 1036-1042, 1989.

Sharpless et al., "Electrophilic and nucleophilic organoselenium reagents. New routes to alpha, beta-unsaturated carbonyl compounds," *J Am. Chem. Soc.*, 95:6137, 1973.

Sheng et al., "A selective cyclooxygenase 2 inhibitor suppresses the growth of H-ras-transformed rat intestinal epithelial cells," *Gastroenterology*, 113(6):1883-18891, 1997.

Sheng et al., "Inhibition of human colon cancer cell growth by selective inhibition of cyclooxygenase-2," *J Clin. Invest.*, 99(9):2254-2259, 1997.

Shimao and Oae, "The Wallach rearrangement of some 4,4'-disubstituted azoxybenzenes," *Bulletin of the Chemical Society of Japan*, 56 (2): 643-644, 1983.

Shishodia et al., "A synthetic triterpenoid, CDDO-Me, inhibits IkappaBalpha kinase and enhances apoptosis induced by TNF and chemotherapeutic agents through down-regulation of expression of nuclear factor kappaB-regulated gene products in human leukemic cells," *Clin. Cancer Res.*, 12:1828-1838, 2006.

Shull et al., "Identification of a vitamin D-responsive protein on the surface of human osteosarcoma cells," *Proc. Natl. Acad. Sci. USA*, 86:5405-5410, 1989.

Shull et al., "Morphologic and biochemical studies of canine mucopolysaccharidosis I," *Am. J. Pathol.*, 114:487-495, 1984.

Simonian and Coyle, "Oxidative stress in neurodegenerative diseases," *Annu. Rev. Pharmacol. Toxicol.*, 36:83-106, 1996.

Simonsen et al., "Tetracyclic hydroxy acids," In *the Terpenes*, Cambridge University, Cambridge, 5:221-285, 1957.

Singh and Evans, "Nitric oxide, the biological mediator of the decade: fact or fiction?" *Eur. Respir. J.*, 10:699-707, 1997.

Singh et al., "Anti-inflammatory activity of oleanolic acid in rats and mice," *J. Pharm.Pharmacol.*, 44:456-458, 1992.

Sive et al., "Expression of chondrocyte markers by cells of normal and degenerate intervertebral discs," *Mol. Pathol.*, 55:91-97, 2002.

Snitman et al., "Synthetic approaches to taxodione synthesis of methyl 12-oxopodocarpa-5,9(11)-diene-8β-carboxylate," *Synth. Comm.*, 8:187-194, 1978.

Sonogashira et al., "A convenient synthesis of acetylenes: catalytic substitutions of acetylenic hydrogen with bromoakenes, iodoarenes, and bromopyridines," *Tetrahedron Lett.*, 4467-4470, 1975.

Sporn and Roberts, "Peptide growth factors and inflammation, tissue repair, and cancer," *J. Clin. Invest.*, 78:329-332, 1986.

Sporn et al., "Prospects for prevention and treatment of cancer with selective PPARγ modulators (SPARMs)," *Trends in Molecular Medicine*, 7(9):395-400, 2001.

Sporn et al., "Transforming growth factor-beta: biological function and chemical structure," *Science*, 233:532-534, 1986.

Stadheim et al., "The novel triterpenoid 2-cyano-3,12-dioxooleana-1,9-dien-28-oic acid (CDDO) potently enhances apoptosis induced by tumor necrosis factor in human leukemia cells," *J. Biol. Chem.*, 277:16448-16455, 2002.

Steadman's Medical Journal 23$^{rd}$ Edition, The Williams & Wilkins Company, p. 401, 1976.

Sterzycki, "Pyrodinium tosylate, a mild catalyst for formation and cleavage of dioxolane-type acetals," *Synthesis*, 724-725, 1979.

Stewart et al., "Risk of Alzheimer's disease and duration of NSAID use" *Neurology*, 48:626-632, 1997.

Strejan et al., "Suppression of chronic-relapsing experimental allergic encephalomyelitis in strain-13 guinea pigs by administration of liposome-associated myelin basic protein," *J. Neuroimmunol.*, 7 (1): 27, 1984.

Suh et al., "A novel synthetic oleanane triterpenoid, 2-cyano-3,12-dioxoolean-1,9-dien-28-oic acid, with potent differentiating, antiproliferative, and anti-inflammatory activity," *Cancer Res.*, 59(2):336-341, 1999.

Suh et al., "A novel synthetic oleanane triterpenoid, 2-cyano-3,12-dioxoolean-1,9-dien-28-oic acid (CDDO), induces cell differentiation in human myeloid leukemias," *Proceedings of the American Association for Cancer Research Annual Meeting*, 40:300, abstract # 1988, 1999.

Suh et al., "New triterpenoids as cancer preventive and anti-inflammatory agents," *Proceedings of the American Association for Cancer Research*, Abstract No. 1457, 38: 216, 1997.

Suh et al., "Novel triterpenoids suppress inducible nitric oxide synthase (iNOS) and inducible cyclooxygenase (COX-2) in mouse macrophages," *Cancer Research*, 58:717-723, 1998.

Suh et al., "Novel triterpenoids suppress inducible nitric oxide synthase (iNOS) and inducible cyclooxygenase (COX-2)," *Proceedings of the American Association for Cancer Research Annual Meeting*, 39: Abstract No. 1821, 1998.

Suh et al., "Synthetic triterpenoids activate a pathway for apoptosis in AML cells involving downregulation of FLIP and sensitization to TRAIL," *Leukemia*, 17:2122-2129, 2003.

Suh et al., "Synthetic triterpenoids enhance transforming growth factor β/Smad signaling," *Cancer Res.*, 63:1371-1376, 2003.

Suh et al., "Triterpenoids CDDO and CDDO-Me Down-Regulate FLIP Expression and Sensitize AML Cells to Trail-Induced Apoptosis," *American Society of Hematology 43$^{rd}$ Annual Meeting and Exposition*, Abstract No. 498, 2001.

Sun et al., "Structure-activity relationships of oleanane- and ursane-type triterpenoids," *Botanical Studies*, 47:339-368, 2006.

Sun et al., "The synthetic triterpenoid, CDDO, suppresses alloreactive T cell responses and reduces murine early acute graft-versus-host disease mortality," *Biology of Blood and Marrow Transplantation*, 13:521-529, 2007.

Sussan et al., "Disruption of Nrf2, a key inducer of antioxidant defenses, attenuates ApoE-mediated atherosclerosis in mice," *PLoS One*, 3 (11): 1-9, 2008.

Syftestad et al., "The in vitro chondrogenic response of limb-bud mesenchyme to a water-soluble fraction prepared from demineralized bone matrix," *Differentiation*, 29:230, 1985.

Tabe et al., "Chromatin-Mediated Transcriptional Activation with Novel Peroxisome Proliferator—Activated Receptor gamma(PPARgamma) Ligand 2-cyano-1,9-dien-28-oic Acid (CDDO) in Acute Promyelocytic Leukemia Cells," *Abstracts of the 44$^{th}$ Annual Meeting of the American Society of Hematology*, Abstract No. 2191, 2002.

Takabe et al., "Synthesis of lycosyl esters of oleanolic," *Carbohydrate Research*, 76:101-108, 1979, Database CAPLUS on STN AN:1980:42278.

Takahashi et al., "Increased expression of inducible and endothelial constitutive nitric oxide synthases in rat colon tumors induced by azoxymethane," *Cancer Res.*, 57:1233-1237, 1997.

Tamir and Tannebaum, "The role of nitric oxide (NO) in the carcinogenic process," *Biochim. Biophys. Acta*, 1288:F31-F36, 1996.

Tamm et al., "Expression and prognostic significance of IAP-family genes in human cancers and leukemias," *Blood*, 94(Suppl. 1):69a, Abstract # 298, 1999.

Tan et al., "Survey on the triterpenoids from rubus 1. and their spectral features," *Huagong Shikan*, 18 (9): 1-4, 2004.

Tempero et al., "Randomized phase II comparison of dose-intense gemcitabine: thirty-minute infusion and fixed dose rate infusion in patients with pancreatic adenocarcinoma," *J. Clin. Oncol.*, 21 (18): 3402-3408, 2003.

Tenenbaum and Heersche, "Differentiation of osteoblasts and formation of mineralized bone in vitro," *Calcif. Tissue Int.*, 34:76, 1982.

Therasse et al., "New guidelines to evaluate the response to treatment in solid tumors. European Organization for Research and Treatment of Cancer, National Cancer Institute of the United States, National Cancer Institute of Canada," *J. Natl. Cancer Instit.*, 92 (3): 205, 2000.

Thimmulappa et al., "Nrf2 is a critical regulator of the innate immune response and survival during experimental sepsis," *J. Clinical Investigation*, 116 (4): 984-995, 2006.

Thimmulappa et al., "Nrf2-dependent protection from LPS induced inflammatory response and mortality by CDDO-imidazolide," *Biochem. Biophys. Res. Commun.*, 351:883-889, 2006.

Thimmulappa et al., "Preclinical evaluation of targeting the Nrf2 pathway by triterpenoids (CDDO-Im and CDDO-Me) for protection from LPS-induced inflammatory response and reactive oxygen species in human peripheral blood mononuclear cells and neutrophils," *Antioxidants & Redox Signaling*, 9:1-8, 2007.

Toriumi et al., "Mandibular reconstruction with a recombinant bone-inducing factor. Functional, histologic, and biomechanical evaluation," *Arch. Otolaryngol. Head Neck Surg.*, 117:1101-1112, 1991.

Tones et al., "Inflammation and nitric oxide production in skeletal muscle of type 2 diabetic patients," *Journal of Endocrinology*, 181:419-427, 2004.

Tran et al., "The synthetic triterpenoid CDDO-methyl ester modulates microglial activities, inhibits TNF production, and provides dopaminergic neuroprotection," *Journal of Neuroinflammation*, 5:1-14, 2008.

Tsai et al., "Monoclonal antibody to human osteosarcoma: a novel Mr 26,000 protein recognized by murine hybridoma TMMR-2," *Cancer Res.*, 50:152-161, 1990.

Tsao et al., "DRIP205 co-activator overexpression enhances PPARgamma-mediated differentiation of leukemia cells by CDDO," *Proc. Amer. Assoc. Cancer Res.*, 46: Abstract No. 1855, 2005.

Tsao et al., "Targeted Induction of Apoptosis in Leukemias by PPARgammma Ligation," *American Society of Hematology 43$^{rd}$ Annual Meeting and Exposition*, Abstract No. 2381, 2001.

Tsujii and DuBois, "Alterations in cellular adhesion and apoptosis in epithelial cells overexpressing prostaglandin endoperoxide synthase 2," *Cell*, 83(3):493-501, 1995.

Tsujii et al., "Cyclooxygenases regulates angiogenesis induced by colon cancer cells," *Cell*, 93:705-716, 1998.

Turksen et al., "Isolation of monoclonal antibodies recognizing rat bone-associated molecules in vitro and in vivo," *J. Histochem. Cytochem.*, 40:1339-1352, 1992.

Urban et al., "Influence of esterification and modification of A-ring in a group of lupane acids on their cytotoxicity," *Bioorganic and Medicinal Chemistry*, 13 (19): 5527-5535, 2005.

Van Muiswinkel and Kuiperij, "The Nrf2-ARE signaling pathway: promising drug target to combat oxidative stress in neurodegenerative disorders," *Current Drug Target—CNS & Neurological Disorders*, 4:267-281, 2005.

Vazquez et al., "Human immunodeficiency virus type 1-induced macrophage gene expression includes the p21 gene, a target for viral regulation," *J. Virol.*, 79:4479-4491, 2005.

Veerman et al., "Antitumor activity of prolonged as compared with bolus administration of 2',2'-difluorodeoxycytidine in vivo against murine colon tumors," *Cancer Chemother. Pharmacol.*, 38 (4): 335-342, 1996.

Vodovotz et al., "Inducible nitric oxide synthase in tangle-bearing neurons of patients with Alzheimer's Disease," *The Journal of Experimental Medicine*, 184:1425-1433, 1996.

Vukicevic et al., "Stimulation of the expression of osteogenic and chondrogenic phenotypes in vitro by osteogenin," *Proc. Natl. Acad. Sci. USA*, 86:8793-7, 1989.

Walczak et al., "Tumoricidal activity of tumor necrosis factor-related apoptosis-inducing ligand in vivo", *Nature Medicine*, 5(2):157-163, 1999.

Walsh et al., "Monoclonal antibodies with selective reactivity against osteoblasts and osteocytes in human bone," *J. Bone Miner Res.*, 9:1687-1696, 1994.

Wang et al., "A novel synthetic triterpenoid, 2-cyano-3,12-dioxoolean-1,9-dien-28-oic acid (CDDO) induces adipocyte differentiation in 3T3-L1 cells," *Proceedings of the American Association for Cancer Research Annual Meeting*, 40:300, abstract # 1989, 1999.

Wang et al., "A synthetic triterpenoid, 2-cyano-3,12-dioxooleana-1,9-dien-28-oic acid (CDDO), is a ligand for the peroxisome proliferator-activated receptor γ," *Mol. Endocrin.*, 14(10):1550-1556, 2000.

Wang et al., "Synthetic triterpenoid CDDO and its derivatives increase ceramides and are cytotoxic to pediatric acute lymphoblastic leukemia cell lines," *Proc. Am. Assoc. Cancer Res.*, 47: 4643, 2006.

Warrell et al., "Differentiation therapy of acute promyelocytic leukemia with tretinoin (all-trans-retinoic acid)," *N. Engl. J. Med.*, 324(20):1385-1393, 1991.

Wen et al., "Pentacyclic triterpenes. Part 2: Synthesis and biological evaluation of maslinic acid derivatives as glycogen phosphorylase inhibitors," *Bioorganic and Medicinal Chemistry Letters*, 16 (3): 722-726, 2006.

Williams et al., "Immunology of multiple sclerosis," *Clin. Neurosci.*, 2(3-4):229-245, 1994.

Witz et al., "Cyclic ketones. XIII. Circular dichroism of steroid and triterpene ketones. Conformation of ring a of 8-methylated 3-oxotriterpenes," *Bull. Soc. China*, France: 1101-1112, 1963. (French only, but see attached English CAPLUS database summary.).

Woodley, "Liposomes for Oral Administration of Drugs," *Crit. Rev. Therapeutic Drug Carrier System*, 2(1):1-18, 1995.

Xie et al., "Differential expression patterns in human myeloblastic leukemia HL-60 and multidrug resistant HL-60/Dox cells analyzed by human cDNA expression array," *Blood*, 92 (Suppl 1):387a, Abstract #1600, 1998.

Yates et al., "Pharmacodynamic characterization of chemopreventive triterpenoids as exceptionally potent inducers of Nrf2-regulated genes," *Mol. Cancer Ther.*, 6:154-162, 2007.

Yates et al., "Potent protection against aflatoxin-induced tumorigenesis through induction of Nrf2-regulated pathways by the triterpenoid 1-[2-cyano-3-,12-dioxooleana-1,9(11)-dien-28-oyl]imidazole," *Cancer Res.*, 66:2488-2494, 2006.

Yore et al., "The synthetic triterpenoid 1[2-cyano-3,12-dioxooleana-1,9(11)-dien-28-oyl]imidazole blocks nuclear factor-kappaB activation through direct inhibition of IkappaB kinase beta," *Mol. Cancer Ther.*, 5 (12): 3232-3239, 2006.

Yu and Kensler, "Nrf2 as a target for cancer chemoprevention," *Mutat. Res.*, 591 (1-2): 93-102, 2005.

Yue et al., "Depletion of intracellular glutathione contributes to JNK-mediated death receptor 5 upregulation and apoptosis induction by the novel synthetic triterpenoid methyl-2-cyano-3, 12-dioxooleana-1,9-dien-28-oate (CDDO-Me).," *Cancer & Biology Therapy*, 5(5):492-497, 2006.

Zapata et al., "CDDO and CDDO-Im Reduce Tumor Burden in a Transgenic Mouse Model of CLL," *Blood*, 104:3477, 2004.

Zapata et al., "Triterpenoids show activity against leukemic cells in a transgenic mouse model of CLL," *Proc. Amer. Assoc. Cancer Res.*, 46: Abstract No. 5179, 2005.

Zhang et al., "Synthetic triterpenoid CDDO as effective therapy for HER2-expressing resistant breast cancer," *Proc. Amer. Assoc. Cancer Res.*, Abstract No. 3799, 2004.

Zhang et al., "The novel synthetic oleanane triterpenoid CDDO (2-cyano-3, 12-dioxoolean-1,9-dien-28-oic acid) induces apoptosis in Mycosis fungoides/Sézary syndrome cells," *J Invest. Dermatol.*, 123:380-387, 2004.

Zhou et al., "Carbon monoxide suppresses bleomycin-induced lung fibrosis," *Am. J. Pathol.*, 166 (1): 27-37, 2005.

Zhou et al., "Physical stability of amorphous pharmaceuticals: Importance of configurational thermodynamic quantities and molecular mobility," *J. Pharmaceutical Sciences*, 91 (8): 1863-1872, 2002.

Zou et al., "c-Jun NH2-terminal kinase-mediated up-regulation of death receptor 5 contributes to induction of apoptosis by the novel synthetic triterpenoid methyl-2-cyano-3,12-dioxooleana-1,9-dien-28-oate in human lung cancer cells," *Cancer Res.*, 64:7570-7578, 2004.

Office Communication issued in Chinese Patent Application No. 200980123340.0, dated Feb. 17, 2012. (English translation).

Office Communication issued in Eurasian Patent Application No. 201001555, dated Dec. 6, 2011. (English translation).

Office Communication issued in Mexican Patent Application No. MX/a/2010/011438, dated May 29, 2012. (English Translation).

Search report and Written Opinion issued in Singapore Patent Application No. 201007610-7, dated Jun. 16, 2012.

Notice of Allowance issued in U.S. Appl. No. 12/426,778, dated May 31, 2011.

Notice of Allowance issued in U.S. Appl. No. 12/426,778, dated Jan. 9, 2012.

* cited by examiner

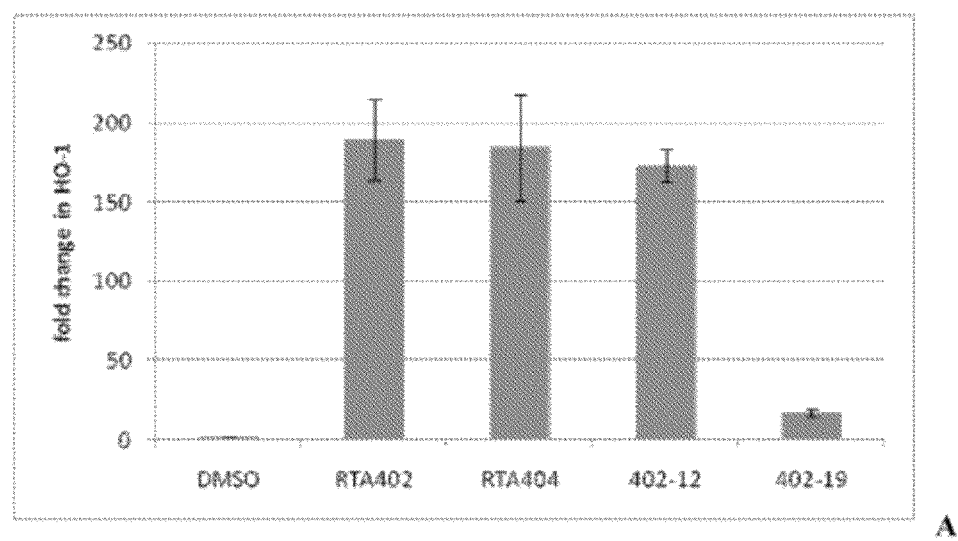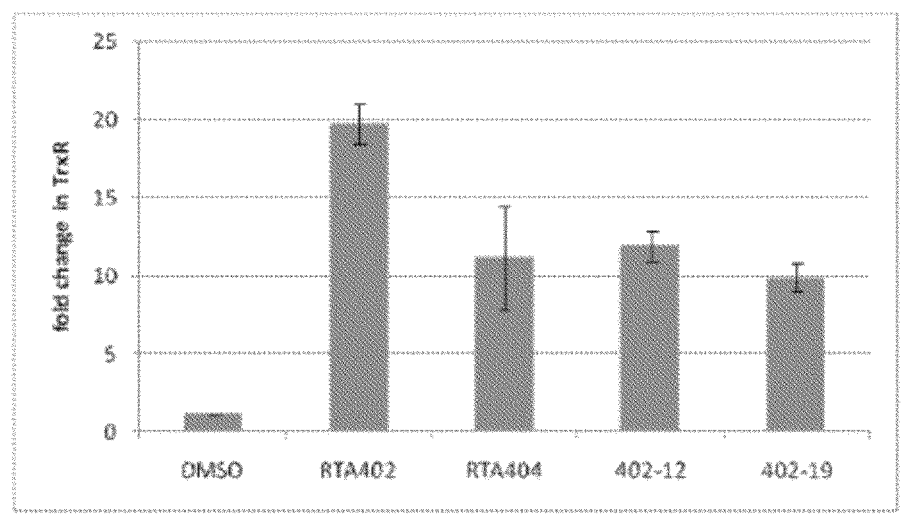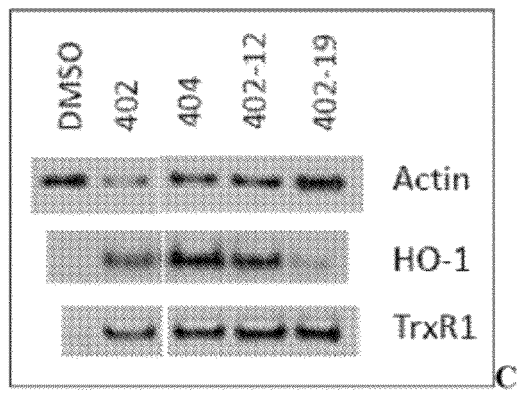
FIGS. 43A-C

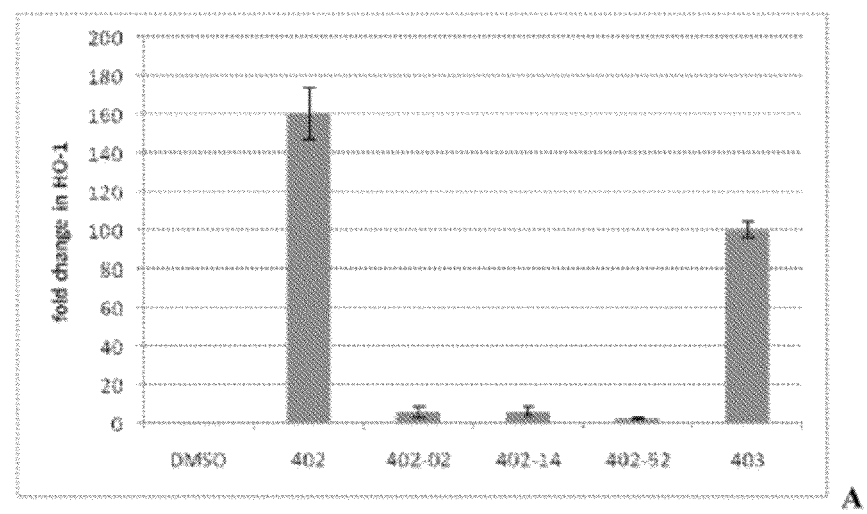
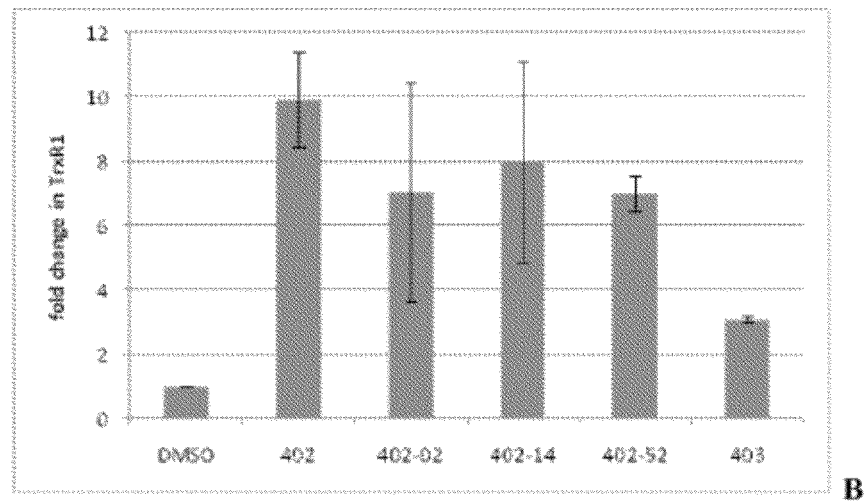
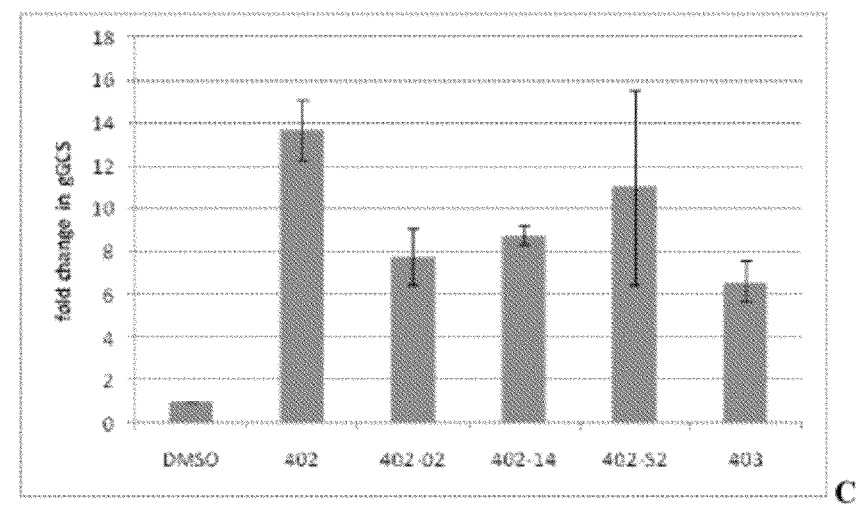
FIGS. 44A-C

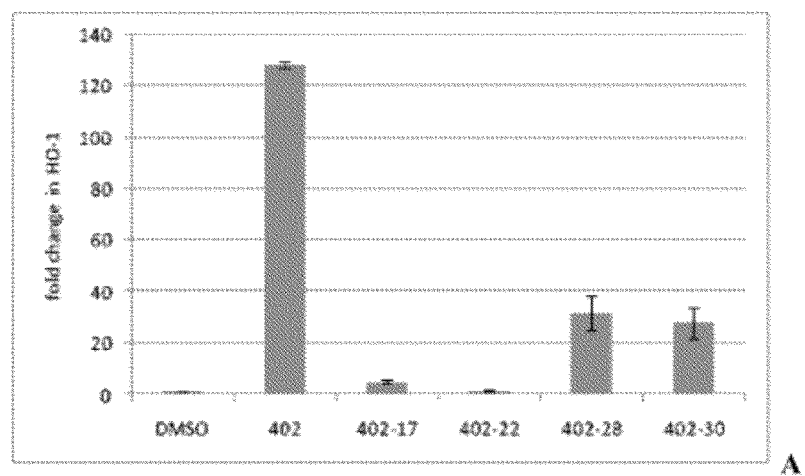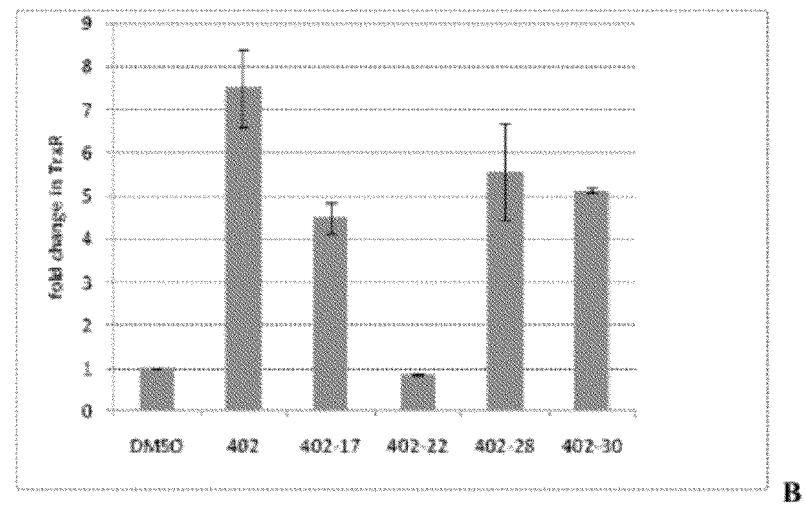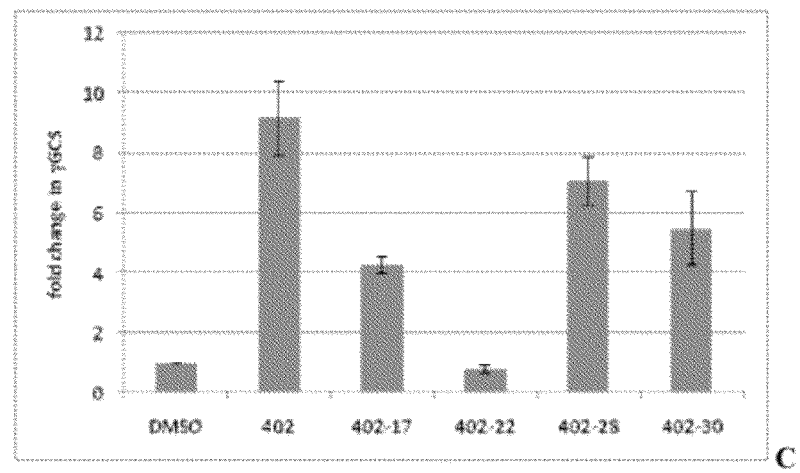
FIGS. 45A-C

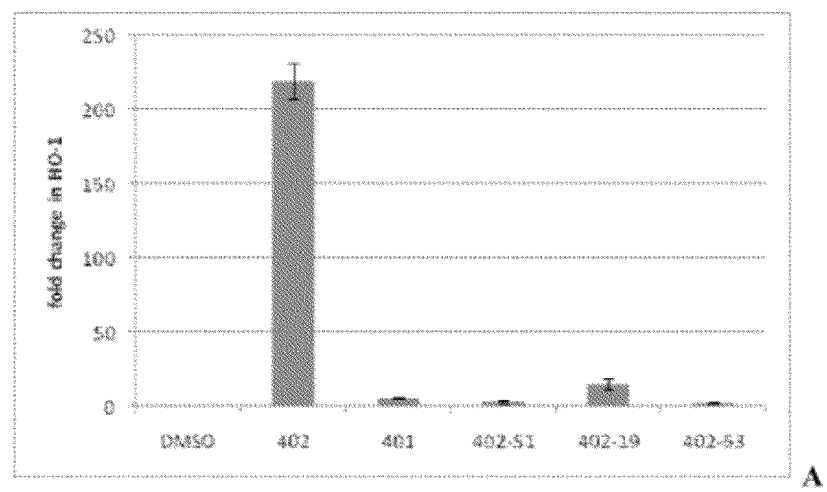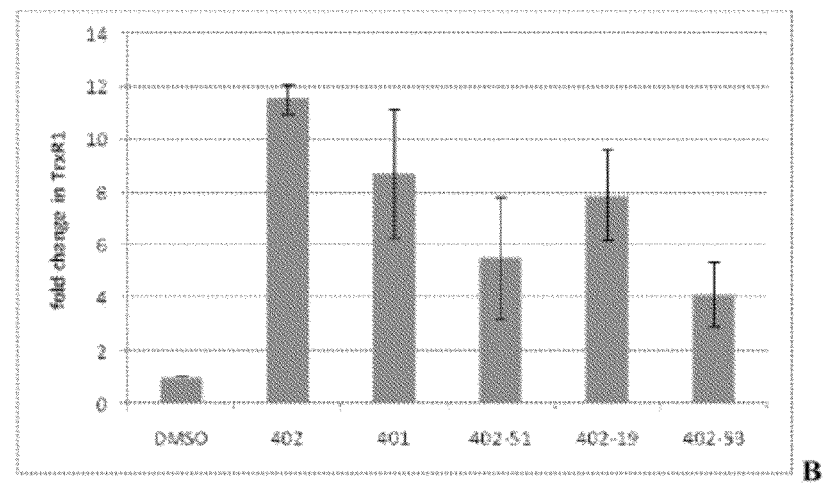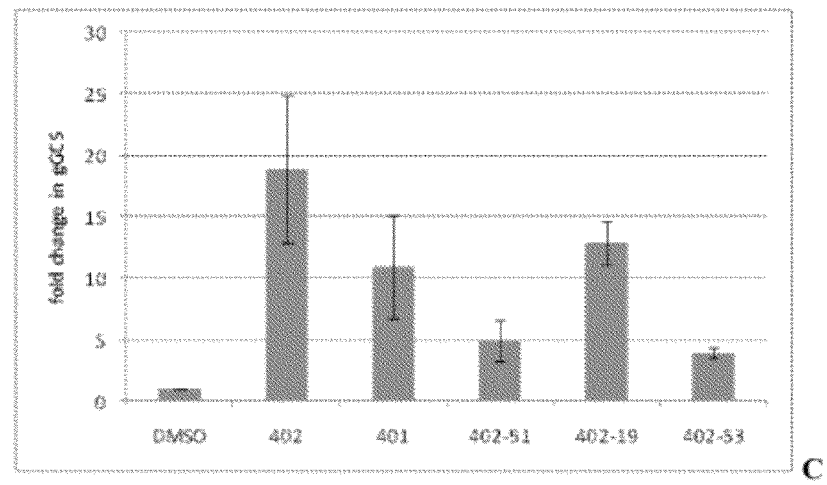
FIGS. 46A-C

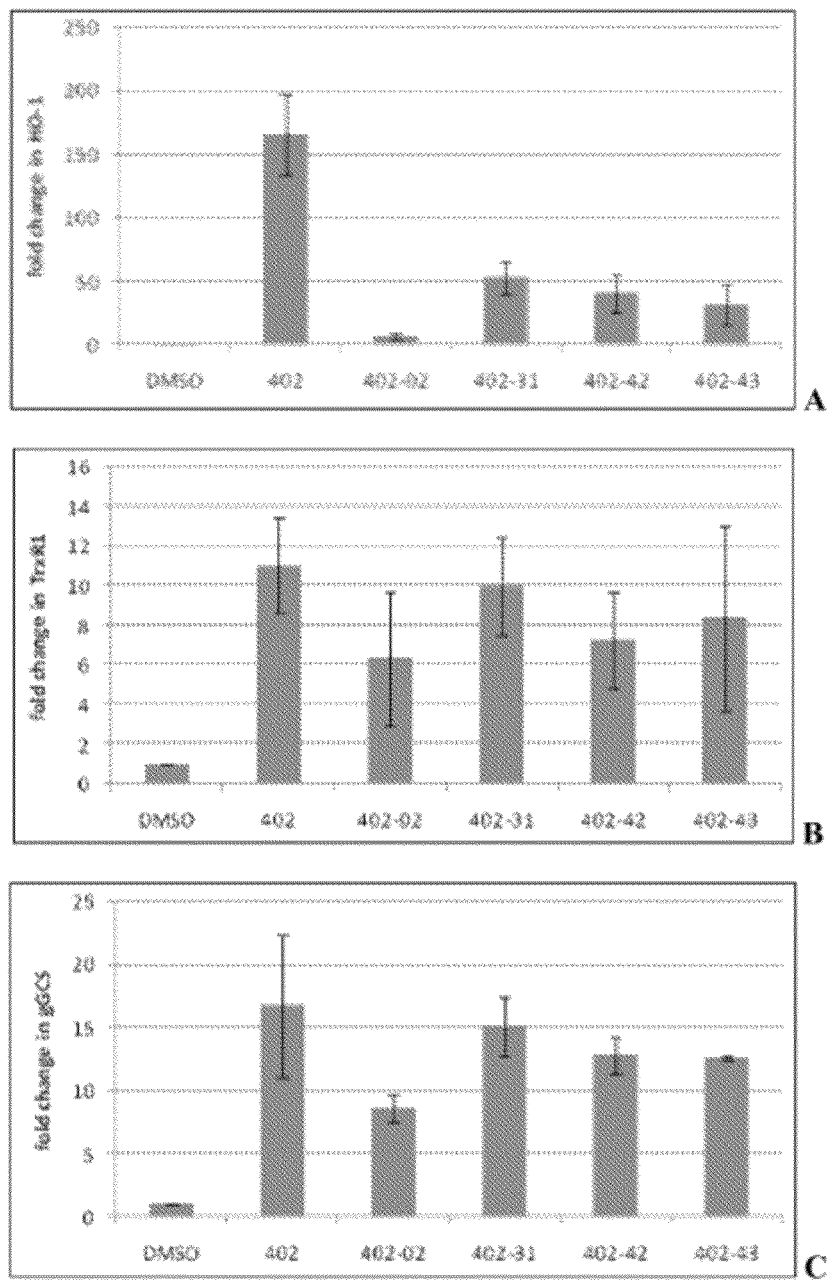
FIGS. 47A-C

ANTIOXIDANT INFLAMMATION MODULATORS: OLEANOLIC ACID DERIVATIVES WITH AMINO ACID AND OTHER MODIFICATIONS AT C-17

The present application claims the benefit of priority to U.S. patent application Ser. No. 12/426,778, filed Apr. 20, 2009, which claims the benefit of priority to U.S. Provisional Application Nos. 61/046,342, filed Apr. 18, 2008, and 61/111,269, filed Nov. 4, 2008, the entire contents of both applications are incorporated herein by reference in their entireties.

BACKGROUND OF THE INVENTION

I. Field of the Invention

The present invention relates generally to the fields of biology and medicine. More particularly, it concerns compounds and methods for the treatment and prevention of diseases such as those associated with oxidative stress and inflammation.

II. Description of Related Art

Many serious and intractable human diseases are associated with dysregulation of inflammatory processes, including diseases such as cancer, atherosclerosis, and diabetes, which were not traditionally viewed as inflammatory conditions. Similarly, autoimmune diseases such as rheumatoid arthritis, lupus, psoriasis, and multiple sclerosis involve inappropriate and chronic activation of inflammatory processes in affected tissues, arising from dysfunction of self vs. non-self recognition and response mechanisms in the immune system. In neurodegenerative diseases such as Alzheimer's and Parkinson's diseases, neural damage is correlated with activation of microglia and elevated levels of pro-inflammatory proteins such as inducible nitric oxide synthase (iNOS).

One aspect of inflammation is the production of inflammatory prostaglandins such as prostaglandin E, whose precursors are produced by the enzyme cyclo-oxygenase (COX-2). High levels of COX-2 are found in inflamed tissues. Consequently, inhibition of COX-2 is known to reduce many symptoms of inflammation and a number of important anti-inflammatory drugs (e.g., ibuprofen and celecoxib) act by inhibiting COX-2 activity. Recent research, however, has demonstrated that a class of cyclopentenone prostaglandins (e.g., 15-deoxy prostaglandin J2, a.k.a. PGJ2) plays a role in stimulating the orchestrated resolution of inflammation. COX-2 is also associated with the production of cyclopentenone prostaglandins. Consequently, inhibition of COX-2 may interfere with the full resolution of inflammation, potentially promoting the persistence of activated immune cells in tissues and leading to chronic, "smoldering" inflammation. This effect may be responsible for the increased incidence of cardiovascular disease in patients using selective COX-2 inhibitors for long periods of time. Corticosteroids, another important class of anti-inflammatory drugs, have many undesirable side effects and frequently are not suitable for chronic use. Newer protein-based drugs, such as anti-TNF monoclonal antibodies, have proven to be effective for the treatment of certain autoimmune diseases such as rheumatoid arthritis. However, these compounds must be administered by injection, are not effective in all patients, and may have severe side effects. In many severe forms of inflammation (e.g., sepsis, acute pancreatitis), existing drugs are ineffective. In addition, currently available drugs do not have significant antioxidant properties, and are not effective in reducing oxidative stress associated with excessive production of reactive oxygen species and related molecules such as peroxynitrite. Accordingly, there is a pressing need for improved therapeutics with antioxidant and anti-inflammatory properties.

A series of synthetic triterpenoid analogs of oleanolic acid have been shown to be inhibitors of cellular inflammatory processes, such as the induction by IFN-γ of inducible nitric oxide synthase (iNOS) and of COX-2 in mouse macrophages. See Honda et al. (2000a); Honda et al. (2000b), and Honda et al. (2002), which are all incorporated herein by reference. For example, one of these, 2-cyano-3,12-dioxooleane-1,9(11)-dien-28-oic acid methyl ester (CDDO-Me), is currently in clinical trials for a variety of disorders related to inflammation, including cancer and diabetic nephropathy. The pharmacology of these molecules is complex, as they have been shown to affect the function of multiple protein targets and thereby modulate the function of several important cellular signaling pathways related to oxidative stress, cell cycle control, and inflammation (e.g., Dinkova-Kostova et al., 2005; Ahmad et al., 2006; Ahmad et al., 2008; Liby et al., 2007). Given that the biological activity profiles of the known oleanolic acid derivatives vary, and in view of the wide variety of diseases that may be treated with compounds having potent antioxidant and anti-inflammatory effects, it is desirable to synthesize new candidates for the treatment or prevention of disease.

SUMMARY OF THE INVENTION

The present disclosure provides new compounds with antioxidant and anti-inflammatory properties, methods for their manufacture, and methods for their use. Compounds covered by the generic or specific formulas below or specifically named are referred to as "compounds of the invention," "compounds of the present disclosure," or "oleanolic acid derivatives" in the present application.

In some aspects, the disclosure provides compounds of the formula:

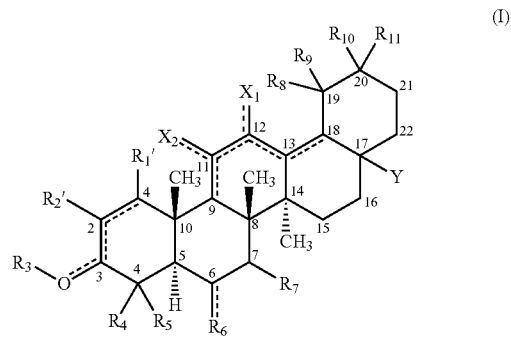

wherein:
  $X_1$ and $X_2$ are independently:
    hydrogen, $OR_b$, $NR_bR_c$, or $SR_b$, wherein $R_b$ and $R_c$ are each independently:
      hydrogen or hydroxy;
      alkyl$_{(C \leq 8)}$, aryl$_{(C \leq 8)}$, aralkyl$_{(C \leq 8)}$, acyl$_{(C \leq 8)}$, alkoxy$_{(C \leq 8)}$, aryloxy$_{(C \leq 8)}$, acyloxy$_{(C \leq 8)}$, alkylamino$_{(C \leq 8)}$, arylamino$_{(C \leq 8)}$, amido$_{(C \leq 8)}$, or a substituted version of any of these groups; or
      a substituent convertible in vivo to hydrogen;
      provided that $R_b$ is absent when the atom to which it is bound is part of a double bond, further provided that when $R_b$ is absent the atom to which it is bound is part of a double bond;

Y is hydroxy, alkoxy$_{(C\leq 8)}$, aryloxy$_{(C\leq 8)}$, acyloxy$_{(C\leq 8)}$, substituted alkoxy$_{(C\leq 8)}$, substituted alkoxy$_{(C\leq 8)}$, substituted aryloxy$_{(C\leq 8)}$, substituted acyloxy$_{(C\leq 8)}$, or NR$_1$R$_2$, wherein R$_1$ and R$_2$ are independently:
  hydrogen or hydroxy; or
  alkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, acyl$_{(C\leq 12)}$, alkoxy$_{(C\leq 12)}$, alkenyloxy$_{(C\leq 12)}$, alkynyloxy$_{(C\leq 12)}$, aryloxy$_{(C\leq 12)}$, aralk-oxy$_{(C\leq 12)}$, heteroaryloxy$_{(C\leq 12)}$, heteroaralkoxy$_{(C\leq 12)}$, thio-acyl$_{(C\leq 12)}$, alkylsulfonyl$_{(C\leq 12)}$, alkenylsulfonyl$_{(C\leq 12)}$, alkynylsulfonyl$_{(C\leq 12)}$, arylsulfonyl$_{(C\leq 12)}$, aralkyl-sulfonyl$_{(C\leq 12)}$, heteroarylsulfonyl$_{(C\leq 12)}$, or heteroaralkyl-sulfonyl$_{(C\leq 12)}$, or a substituted version of any of these groups;
R$_1'$ is:
  hydrogen, cyano, hydroxy, halo, or amino; or
  alkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heteroaralkyl$_{(C\leq 8)}$, acyl$_{(C\leq 8)}$, alkoxy$_{(C\leq 8)}$, aryloxy$_{(C\leq 8)}$, acyloxy$_{(C\leq 8)}$, alkylamino$_{(C\leq 8)}$, arylamino$_{(C\leq 8)}$, amido$_{(C\leq 8)}$, or a substituted version of any of these groups;
R$_2'$ is:
  cyano, hydroxy, halo or amino; or
  fluoroalkyl$_{(C\leq 8)}$, alkenyl$_{(C\leq 8)}$, alkynyl$_{(C\leq 8)}$, aryl$_{(C\leq 8)}$, heteroaryl$_{(C\leq 8)}$, acyl$_{(C\leq 8)}$, alkoxy$_{(C\leq 8)}$, aryloxy$_{(C\leq 8)}$, acyloxy$_{(C\leq 8)}$, alkylamino$_{(C\leq 8)}$, arylamino$_{(C\leq 8)}$, amido$_{(C\leq 8)}$, or a substituted version of any of these groups;
R$_3$ is:
  absent or hydrogen;
  alkyl$_{(C\leq 8)}$, aryl$_{(C\leq 8)}$, aralkyl$_{(C\leq 8)}$, acyl$_{(C\leq 8)}$, or a substituted version of any of these groups; or
  a substituent convertible in vivo to hydrogen;
  provided that R$_3$ is absent when the oxygen atom to which it is bound is part of a double bond, further provided that when R$_3$ is absent the oxygen atom to which it is bound is part of a double bond;
R$_4$ and R$_5$ are each independently alkyl$_{(C\leq 8)}$ or substituted alkyl$_{(C\leq 8)}$;
R$_6$ is hydrogen, hydroxy or oxo;
R$_7$ is hydrogen or hydroxy; and
R$_8$, R$_9$, R$_{10}$ and R$_{11}$ are each independently hydrogen, hydroxy, alkyl$_{(C\leq 8)}$, substituted alkyl$_{(C\leq 8)}$, alkoxy$_{(C\leq 8)}$ or substituted alkoxy$_{(C\leq 8)}$;
or pharmaceutically acceptable salts, esters, hydrates, solvates, tautomers, prodrugs, or optical isomers thereof.

In some embodiments, the compound is further defined as:

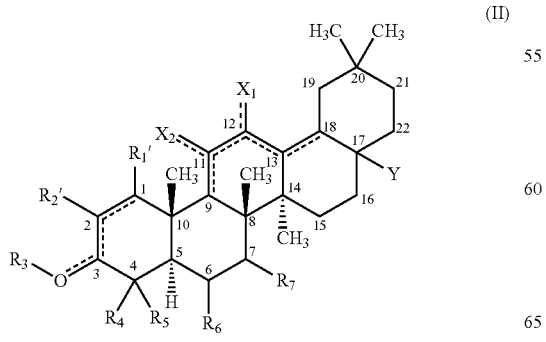

(II)

wherein:
  X$_1$ and X$_2$ are independently:
    hydrogen, OR$_b$, NR$_b$R$_c$, or SR$_b$, wherein R$_b$ and R$_c$ are each independently:
      hydrogen;
      alkyl$_{(C\leq 8)}$, aryl$_{(C\leq 8)}$, aralkyl$_{(C\leq 8)}$, acyl$_{(C\leq 8)}$, or a substituted version of any of these groups; or
      a substituent convertible in vivo to hydrogen;
      provided that R$_b$ is absent when the atom to which it is bound is part of a double bond, further provided that when R$_b$ is absent the atom to which it is bound is part of a double bond;
  Y is hydroxy or NR$_1$R$_2$, wherein:
    R$_1$ and R$_2$ are independently:
      hydrogen or hydroxy; or
      alkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, acyl$_{(C\leq 12)}$, alkoxy$_{(C\leq 12)}$, alkenyloxy$_{(C\leq 12)}$, alkynyloxy$_{(C\leq 12)}$, aryloxy$_{(C\leq 12)}$, aralk-oxy$_{(C\leq 12)}$, heteroaryloxy$_{(C\leq 12)}$, heteroaralkoxy$_{(C\leq 12)}$, thioacyl$_{(C\leq 12)}$, alkylsulfonyl$_{(C\leq 12)}$, alkenylsulfonyl$_{(C\leq 12)}$, alkynylsulfonyl$_{(C\leq 12)}$, arylsulfonyl$_{(C\leq 12)}$, aralkyl-sulfonyl$_{(C\leq 12)}$, heteroarylsulfonyl$_{(C\leq 12)}$, or heteroaralkyl-sulfonyl$_{(C\leq 12)}$, or a substituted version of any of these groups;
  R$_1'$ is:
    hydrogen, cyano, hydroxy, halo, or amino; or
    alkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heteroaralkyl$_{(C\leq 8)}$, acyl$_{(C\leq 8)}$, alkoxy$_{(C\leq 8)}$, aryloxy$_{(C\leq 8)}$, acyloxy$_{(C\leq 8)}$, alkylamino$_{(C\leq 8)}$, arylamino$_{(C\leq 8)}$, amido$_{(C\leq 8)}$, or a substituted version of any of these groups;
  R$_2'$ is:
    cyano, hydroxy, halo or amino; or
    fluoroalkyl$_{(C\leq 8)}$, alkenyl$_{(C\leq 8)}$, alkynyl$_{(C\leq 8)}$, aryl$_{(C\leq 8)}$, heteroaryl$_{(C\leq 8)}$, acyl$_{(C\leq 8)}$, alkoxy$_{(C\leq 8)}$, aryloxy$_{(C\leq 8)}$, acyloxy$_{(C\leq 8)}$, alkylamino$_{(C\leq 8)}$, arylamino$_{(C\leq 8)}$, amido$_{(C\leq 8)}$, or a substituted version of any of these groups;
  R$_3$ is:
    absent or hydrogen;
    alkyl$_{(C\leq 8)}$, aryl$_{(C\leq 8)}$, aralkyl$_{(C\leq 8)}$, acyl$_{(C\leq 8)}$, or a substituted version of any of these groups; or
    a substituent convertible in vivo to hydrogen;
    provided that R$_3$ is absent when the oxygen atom to which it is bound is part of a double bond, further provided that when R$_3$ is absent the oxygen atom to which it is bound is part of a double bond;
  R$_4$ and R$_5$ are each independently alkyl$_{(C\leq 8)}$ or substituted alkyl$_{(C\leq 8)}$; and
  R$_6$ and R$_7$ are each independently hydrogen or hydroxy;
or pharmaceutically acceptable salts, esters, hydrates, solvates, tautomers, prodrugs, or optical isomers thereof.

In some embodiments, the compound is further defined as:

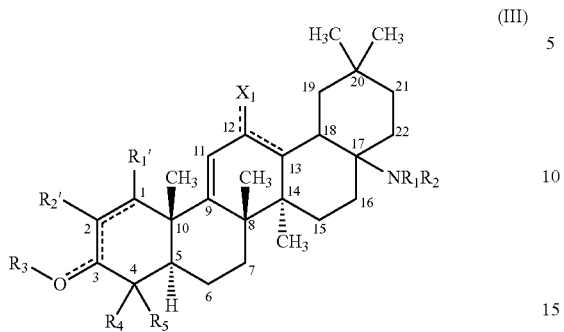

(III)

wherein:
X$_1$ is:
hydrogen, OR$_b$, NR$_b$R$_c$, or SR$_b$, wherein R$_b$ and R$_c$ are each independently: hydrogen;
alkyl$_{(C\leq 8)}$, aryl$_{(C\leq 8)}$, aralkyl$_{(C\leq 8)}$, acyl$_{(C\leq 8)}$, or a substituted version of any of these groups; or
a substituent convertible in vivo to hydrogen;
provided that R$_b$ is absent when the atom to which it is bound is part of a double bond, further provided that when R$_b$ is absent the atom to which it is bound is part of a double bond;
R$_1$ and R$_2$ are independently:
hydrogen or hydroxy; or
alkyl$_{(C\leq 12)}$, alkenyl$_{(C\leq 12)}$, alkylnyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, acyl$_{(C\leq 12)}$, alkoxy$_{(C\leq 12)}$, alkenyloxy$_{(C\leq 12)}$, alkynyloxy$_{(C\leq 12)}$, aryloxy$_{(C\leq 12)}$, aralkoxy$_{(C\leq 12)}$, heteroaryloxy$_{(C\leq 12)}$, heteroaralkoxy$_{(C\leq 12)}$, thioacyl$_{(C\leq 12)}$, alkyl-sulfonyl$_{(C\leq 12)}$, alkenylsulfonyl$_{(C\leq 12)}$, alkynylsulfonyl$_{(C\leq 12)}$, arylsulfonyl$_{(C\leq 12)}$, aralkylsulfonyl$_{(C\leq 12)}$, heteroarylsulfonyl$_{(C\leq 12)}$, or heteroaralkylsulfonyl$_{(C\leq 12)}$, or a substituted version of any of these groups;
R$_1$' is:
hydrogen, cyano, hydroxy, halo, or amino; or
alkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heteroaralkyl$_{(C\leq 8)}$, acyl$_{(C\leq 8)}$, alkoxy$_{(C\leq 8)}$, aryloxy$_{(C\leq 8)}$, acyloxy$_{(C\leq 8)}$, alkylamino$_{(C\leq 8)}$, arylamino$_{(C\leq 8)}$, amido$_{(C\leq 8)}$, or a substituted version of any of these groups;
R$_2$' is:
cyano, hydroxy, halo or amino; or
fluoroalkyl$_{(C\leq 8)}$, alkenyl$_{(C\leq 8)}$, alkynyl$_{(C\leq 8)}$, aryl$_{(C\leq 8)}$, heteroaryl$_{(C\leq 8)}$, acyl$_{(C\leq 8)}$, alkoxy$_{(C\leq 8)}$, aryloxy$_{(C\leq 8)}$, acyloxy$_{(C\leq 8)}$, alkylamino$_{(C\leq 8)}$, arylamino$_{(C\leq 8)}$, amido$_{(C\leq 8)}$, or a substituted version of any of these groups;
R$_3$ is:
absent or hydrogen;
alkyl$_{(C\leq 8)}$, aryl$_{(C\leq 8)}$, aralkyl$_{(C\leq 8)}$, acyl$_{(C\leq 8)}$, or a substituted version of any of these groups; or
a substituent convertible in vivo to hydrogen;
provided that R$_3$ is absent when the oxygen atom to which it is bound is part of a double bond, further provided that when R$_3$ is absent the oxygen atom to which it is bound is part of a double bond; and
R$_4$ and R$_5$ are each independently alkyl$_{(C\leq 8)}$ or substituted alkyl$_{(C\leq 8)}$;
or pharmaceutically acceptable salts, esters, hydrates, solvates, tautomers, prodrugs, or optical isomers thereof.

In some embodiments, the compound is further defined as:

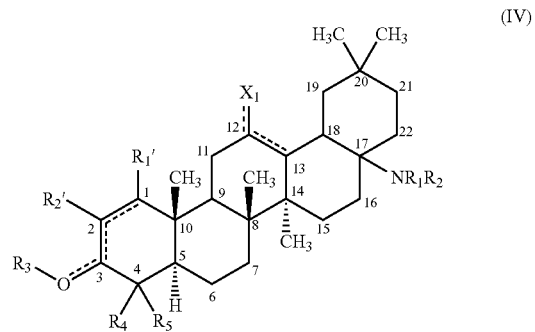

(IV)

wherein:
X$_1$ is:
hydrogen, OR$_b$, NR$_b$R$_c$, or SR$_b$, wherein R$_b$ and R$_c$ are each independently:
hydrogen;
alkyl$_{(C\leq 8)}$, aryl$_{(C\leq 8)}$, aralkyl$_{(C\leq 8)}$, acyl$_{(C\leq 8)}$, or a substituted version of any of these groups; or
a substituent convertible in vivo to hydrogen;
provided that R$_b$ is absent when the atom to which it is bound is part of a double bond, further provided that when R$_b$ is absent the atom to which it is bound is part of a double bond;
R$_1$ and R$_2$ are independently:
hydrogen or hydroxy; or
alkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, acyl$_{(C\leq 12)}$, alkoxy$_{(C\leq 12)}$, alkenyloxy$_{(C\leq 12)}$, alkynyloxy$_{(C\leq 12)}$, aryloxy$_{(C\leq 12)}$, aralkoxy$_{(C\leq 12)}$, heteroaryloxy$_{(C\leq 12)}$, heteroaralkoxy$_{(C\leq 12)}$, thioacyl$_{(C\leq 12)}$, alkyl-sulfonyl$_{(C\leq 12)}$, alkenylsulfonyl$_{(C\leq 12)}$, alkynylsulfonyl$_{(C\leq 12)}$, arylsulfonyl$_{(C\leq 12)}$, aralkylsulfonyl$_{(C\leq 12)}$, heteroarylsulfonyl$_{(C\leq 12)}$, or heteroaralkylsulfonyl$_{(C\leq 12)}$, or a substituted version of any of these groups;
R$_1$' is:
hydrogen, cyano, hydroxy, halo, or amino; or
alkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heteroaralkyl$_{(C\leq 8)}$, acyl$_{(C\leq 8)}$, alkoxy$_{(C\leq 8)}$, aryloxy$_{(C\leq 8)}$, acyloxy$_{(C\leq 8)}$, alkylamino$_{(C\leq 8)}$, arylamino$_{(C\leq 8)}$, amido$_{(C\leq 8)}$, or a substituted version of any of these groups;
R$_2$' is:
cyano, hydroxy, halo or amino; or
fluoroalkyl$_{(C\leq 8)}$, alkenyl$_{(C\leq 8)}$, alkynyl$_{(C\leq 8)}$, aryl$_{(C\leq 8)}$, heteroaryl$_{(C\leq 8)}$, acyl$_{(C\leq 8)}$, alkoxy$_{(C\leq 8)}$, aryloxy$_{(C\leq 8)}$, acyloxy$_{(C\leq 8)}$, alkylamino$_{(C\leq 8)}$, arylamino$_{(C\leq 8)}$, amido$_{(C\leq 8)}$, or a substituted version of any of these groups;
R$_3$ is:
absent or hydrogen;
alkyl$_{(C\leq 8)}$, aryl$_{(C\leq 8)}$, aralkyl$_{(C\leq 8)}$, acyl$_{(C\leq 8)}$, or a substituted version of any of these groups; or
a substituent convertible in vivo to hydrogen;
provided that R$_3$ is absent when the oxygen atom to which it is bound is part of a double bond, further provided that when R$_3$ is absent the oxygen atom to which it is bound is part of a double bond; and $R_4$ and $R_5$ are each independently alkyl$_{(C \leq 8)}$ or substituted alkyl$_{(C \leq 8)}$;

or pharmaceutically acceptable salts, esters, hydrates, solvates, tautomers, prodrugs, or optical isomers thereof.

In some embodiments, the compound is further defined as:

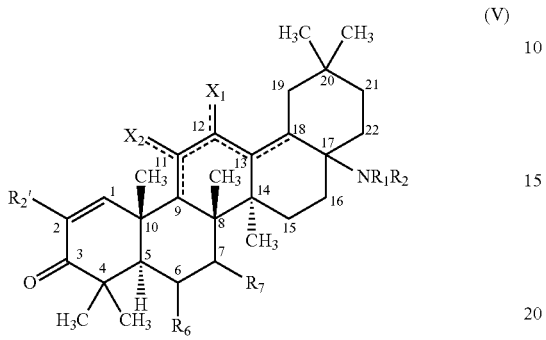

(V)

wherein:

$X_1$ and $X_2$ are independently:
hydrogen, $OR_b$, $NR_bR_c$, or $SR_b$, wherein $R_b$ and $R_c$ are each independently:
hydrogen;
alkyl$_{(C \leq 8)}$, aryl$_{(C \leq 8)}$, aralkyl$_{(C \leq 8)}$, acyl$_{(C \leq 8)}$, or a substituted version of any of these groups; or
a substituent convertible in vivo to hydrogen;
provided that $R_b$ is absent when the atom to which it is bound is part of a double bond, further provided that when $R_b$ is absent the atom to which it is bound is part of a double bond;

$R_1$ and $R_2$ are independently:
hydrogen or hydroxy; or
alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkoxy$_{(C \leq 12)}$, alkenyloxy$_{(C \leq 12)}$, alkynyloxy$_{(C \leq 12)}$, aryloxy$_{(C \leq 12)}$, aralkoxy$_{(C \leq 12)}$, heteroaryloxy$_{(C \leq 12)}$, heteroaralkoxy$_{(C \leq 12)}$, thioacyl$_{(C \leq 12)}$, alkyl-sulfonyl$_{(C \leq 12)}$, alkenylsulfonyl$_{(C \leq 12)}$, alkynylsulfonyl$_{(C \leq 12)}$, arylsulfonyl$_{(C \leq 12)}$, aralkylsulfonyl$_{(C \leq 12)}$, heteroarylsulfonyl$_{(C \leq 12)}$, or heteroaralkylsulfonyl$_{(C \leq 12)}$, or a substituted version of any of these groups;

$R_2'$ is:
cyano, hydroxy, halo or amino; or
fluoroalkyl$_{(C \leq 8)}$, alkenyl$_{(C \leq 8)}$, alkynyl$_{(C \leq 8)}$, aryl$_{(C \leq 8)}$, heteroaryl$_{(C \leq 8)}$, acyl$_{(C \leq 8)}$, alkoxy$_{(C \leq 8)}$, aryloxy$_{(C \leq 8)}$, acyloxy$_{(C \leq 8)}$, alkylamino$_{(C \leq 8)}$, arylamino$_{(C \leq 8)}$, amido$_{(C \leq 8)}$, or a substituted version of any of these groups;

$R_6$ and $R_7$ are each independently hydrogen or hydroxy;
or pharmaceutically acceptable salts, esters, hydrates, solvates, tautomers, prodrugs, or optical isomers thereof.

In some embodiments, the compound is further defined as:

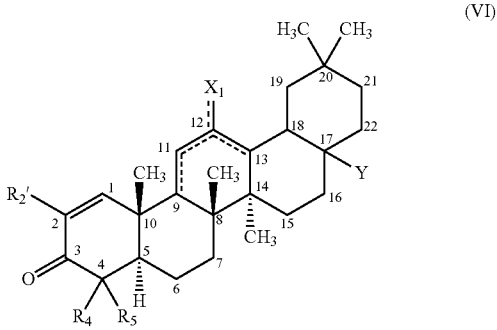

(VI)

wherein:

$X_1$ is:
hydrogen, $OR_b$, $NR_bR_c$, or $SR_b$, wherein $R_b$ and $R_c$ are each independently:
hydrogen;
alkyl$_{(C \leq 8)}$, aryl$_{(C \leq 8)}$, aralkyl$_{(C \leq 8)}$, acyl$_{(C \leq 8)}$, or a substituted version of any of these groups; or
a substituent convertible in vivo to hydrogen;
provided that $R_b$ is absent when the atom to which it is bound is part of a double bond, further provided that when $R_b$ is absent the atom to which it is bound is part of a double bond;

Y is hydroxy or $NR_1R_2$, wherein:
$R_1$ and $R_2$ are independently:
hydrogen or hydroxy; or
alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkoxy$_{(C \leq 12)}$, alkenyloxy$_{(C \leq 12)}$, alkynyloxy$_{(C \leq 12)}$, aryloxy$_{(C \leq 12)}$, aralkoxy$_{(C \leq 12)}$, heteroaryloxy$_{(C \leq 12)}$, heteroaralkoxy$_{(C \leq 12)}$, thioacyl$_{(C \leq 12)}$, alkylsulfonyl$_{(C \leq 12)}$, alkenylsulfonyl$_{(C \leq 12)}$, alkynylsulfonyl$_{(C \leq 12)}$, arylsulfonyl$_{(C \leq 12)}$, aralkylsulfonyl$_{(C \leq 12)}$, heteroarylsulfonyl$_{(C \leq 12)}$, or heteroaralkylsulfonyl$_{(C \leq 12)}$, or a substituted version of any of these groups;

$R_2'$ is:
cyano, hydroxy, halo or amino; or
fluoroalkyl$_{(C \leq 8)}$, alkoxy$_{(C \leq 8)}$, aryloxy$_{(C \leq 8)}$, acyloxy$_{(C \leq 8)}$, alkylamino$_{(C \leq 8)}$, arylamino$_{(C \leq 8)}$, amido$_{(C \leq 8)}$, or a substituted version of any of these groups; and $R_4$ and $R_5$ are each independently alkyl$_{(C \leq 8)}$ or substituted alkyl$_{(C \leq 8)}$;

or pharmaceutically acceptable salts, esters, hydrates, solvates, tautomers, prodrugs, or optical isomers thereof.

In some embodiments, the compound is further defined as:

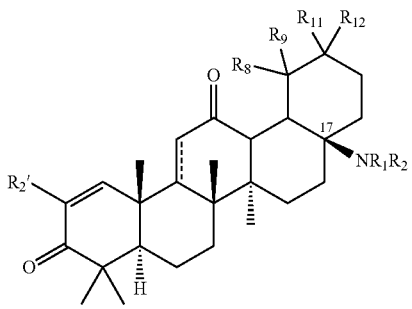

(VII)

wherein:
R$_2$' is:
cyano, hydroxy, halo or amino; or
fluoroalkyl$_{(C \leq 8)}$, alkoxy$_{(C \leq 8)}$, aryloxy$_{(C \leq 8)}$, acyloxy$_{(C \leq 8)}$, alkylamino$_{(C \leq 8)}$, arylamino$_{(C \leq 8)}$, amido$_{(C \leq 8)}$, or a substituted version of any of these groups;
R$_1$ and R$_2$ are independently:
hydrogen; or
alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkylsulphonyl, alkenylsulphonyl$_{(C \leq 12)}$, alkynylsulphonyl$_{(C \leq 12)}$, arylsulphonyl$_{(C \leq 12)}$, aralkylsulphonyl$_{(C \leq 12)}$, heteroarylsulphonyl$_{(C \leq 12)}$, heteroaralkyl-sulphonyl$_{(C \leq 12)}$, or a substituted version of any of these groups; and
R$_8$, R$_9$, R$_{10}$ and R$_{11}$ are each independently hydrogen, hydroxy, alkyl$_{(C \leq 6)}$, substituted alkyl$_{(C \leq 6)}$, alkoxy$_{(C \leq 6)}$ or substituted alkoxy$_{(C \leq 6)}$;
or pharmaceutically acceptable salts, esters, hydrates, solvates, tautomers, prodrugs, or optical isomers thereof.

In some embodiments, the compound is further defined as:

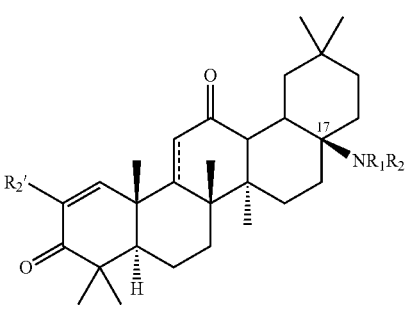

(VIII)

wherein:
R$_2$' is:
cyano, hydroxy, halo or amino; or
fluoroalkyl$_{(C \leq 8)}$, alkoxy$_{(C \leq 8)}$, aryloxy$_{(C \leq 8)}$, acyloxy$_{(C \leq 8)}$, alkylamino$_{(C \leq 8)}$, arylamino$_{(C \leq 8)}$, amido$_{(C \leq 8)}$, or a substituted version of any of these groups; and
R$_1$ and R$_2$ are independently:
hydrogen; or
alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkylsulphonyl, alkenylsulphonyl$_{(C \leq 12)}$, alkynylsulphonyl$_{(C \leq 12)}$, arylsulphonyl$_{(C \leq 12)}$, aralkylsulphonyl$_{(C \leq 12)}$, heteroarylsulphonyl$_{(C \leq 12)}$, heteroaralkyl-sulphonyl$_{(C \leq 12)}$, or a substituted version of any of these groups;
or pharmaceutically acceptable salts, esters, hydrates, solvates, tautomers, prodrugs, or optical isomers thereof.

In some embodiments, the compound is further defined as:

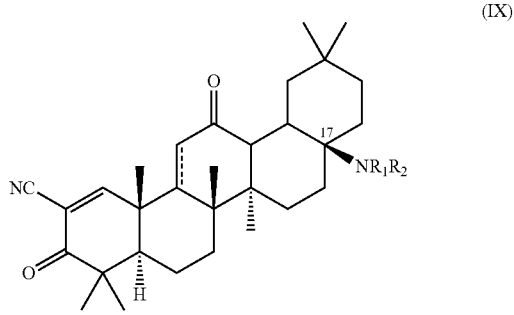

(IX)

wherein:
R$_1$ and R$_2$ are independently:
hydrogen; or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkylsulphonyl, alkenylsulphonyl$_{(C \leq 12)}$, alkynylsulphonyl$_{(C \leq 12)}$, arylsulphonyl$_{(C \leq 12)}$, aralkylsulphonyl$_{(C \leq 12)}$, heteroarylsulphonyl$_{(C \leq 12)}$, heteroaralkyl-sulphonyl$_{(C \leq 12)}$, or a substituted version of any of these groups;
or pharmaceutically acceptable salts, esters, hydrates, solvates, tautomers, prodrugs, or optical isomers thereof.

In some embodiments, the compound is further defined as:

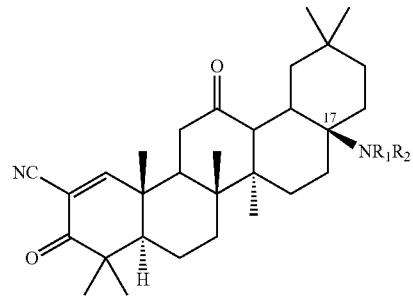

(X)

wherein:
R$_1$ and R$_2$ are independently:
hydrogen; or
alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkylsulphonyl, alkenylsulphonyl$_{(C \leq 12)}$, alkynylsulphonyl$_{(C \leq 12)}$, arylsulphonyl$_{(C \leq 12)}$, aralkylsulphonyl$_{(C \leq 12)}$, heteroarylsulphonyl$_{(C \leq 12)}$, heteroaralkyl-sulphonyl$_{(C \leq 12)}$, or a substituted version of any of these groups;
or pharmaceutically acceptable salts, esters, hydrates, solvates, tautomers, prodrugs, or optical isomers thereof.

In some variations of one or more of the above embodiments, $X_1$ or $X_2$ is $OR_b$, wherein $R_b$ is absent. In some variations of one or more of the above embodiments, $X_1$ is $OR_b$ and $R_b$ is absent. In some variations of one or more of the above embodiments, $X_2$ is hydrogen. In some variations of one or more of the above embodiments, Y is hydroxy. In some variations of one or more of the above embodiments, Y is $NR_1R_2$. In some variations of one or more of the above embodiments, $R_1$ or $R_2$ is hydrogen. In some variations of one or more of the above embodiments, $R_1$ and $R_2$ are each hydrogen. In some variations of one or more of the above embodiments, $R_1$ or $R_2$ comprises a fluoro group. In some variations of one or more of the above embodiments, $R_1$ or $R_2$ comprises a trifluoromethyl group. In some variations of one or more of the above embodiments, $R_1$ and $R_2$ are each independently hydrogen, alkyl$_{(C \leq 8)}$, aryl$_{(C \leq 10)}$, aralkyl$_{(C \leq 10)}$, heteroaryl$_{(C \leq 10)}$, heteroaralkyl$_{(C \leq 10)}$, or a substituted version of any of these groups. In some variations of one or more of the above embodiments, $R_2$ is alkyl$_{(C \leq 8)}$. In some variations of one or more of the above embodiments, $R_2$ is alkyl$_{(C3-12)}$ or substituted alkyl$_{(C3-12)}$. In some variations of one or more of the above embodiments, $R_2$ is alkyl$_{(C \leq 4)}$ or substituted alkyl$_{(C \leq 4)}$. In some variations of one or more of the above embodiments, $R_2$ is alkylsulphonyl$_{(C \leq 8)}$, arylsulphonyl$_{(C \leq 8)}$, aralkylsulphonyl$_{(C \leq 8)}$, heteroaryl-sulphonyl$_{(C \leq 8)}$, heteroaralkylsulphonyl$_{(C \leq 8)}$, or a substituted version of any of these groups. In some variations of one or more of the above embodiments, $R_2$ is alkylsulphonyl$_{(C \leq 8)}$ or substituted alkylsulphonyl$_{(C \leq 8)}$. In some variations of one or more of the above embodiments, $R_2$ is alkylsulphonyl$_{(C \leq 8)}$. In some variations of one or more of the above embodiments, $R_2$ is substituted alkylsulphonyl$_{(C \leq 8)}$. In some variations of one or more of the above embodiments, $R_2$ is arylsulphonyl$_{(C \leq 8)}$. In some variations of one or more of the above embodiments, $R_2$ is heteroarylsulphonyl$_{(C \leq 8)}$. In some variations of one or more of the above embodiments, $R_2$ is acyl$_{(C \leq 10)}$. In some variations of one or more of the above embodiments, $R_2$ is substituted acyl$_{(C \leq 10)}$. In some variations of one or more of the above embodiments, $R_1'$ is hydrogen. In some variations of one or more of the above embodiments, $R_2'$ is cyano. In some variations of one or more of the above embodiments, $R_2'$ is —$CF_3$. In some variations of one or more of the above embodiments, $R_3$ is absent. In some variations of one or more of the above embodiments, $R_4$ and $R_5$ are the same. In some variations of one or more of the above embodiments, $R_4$ and $R_5$ are each alkyl$_{(C \leq 4)}$. In some variations of one or more of the above embodiments, $R_4$ and $R_5$ are each methyl. In some variations of one or more of the above embodiments, $R_6$ and $R_7$ are each hydrogen. In some variations of one or more of the above embodiments, the bond joining carbon 1 and carbon 2 is a double bond. In some variations of one or more of the above embodiments, the bond joining carbon 9 and carbon 11 is a double bond. In some variations of one or more of the above embodiments, the bond joining carbon 9 and carbon 11 is a single bond. In some variations of one or more of the above embodiments, the bond joining carbon 12 and carbon 13 is a single bond. In some variations of one or more of the above embodiments, the bond joining carbon 13 and carbon 18 is a single bond.

Examples of specific compounds provided by the present disclosure include:

(4aR,6aR,6bR,8aS,12aS,12bR,14aR,14bR)-8a-amino-4,4,6a,6b,11,11,14b-heptamethyl-3,13-dioxo-3,4,4a,5,6,6a,6b,7,8,8a,9,10,11,12,12a,12b,13,14,14a,14b-icosahydropicene-2-carbonitrile;

N-((4aS,6aR,6bR,8aR,12aR,12bR,14aR,14bS)-11-cyano-2,2,6a,6b,9,9,12a-heptamethyl-10,14-dioxo-1,2,3,4,4a,5,6,6a,6b,7,8,8a,9,10,12a,12b,13,14,14a,14b-icosahydropicen-4a-yl)methanesulfonamide;

methyl-(4aS,6aR,6bS,8aR,12aS,14aR,14b5)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-ylcarbamate;

ethyl-(4aS,6aR,6bS,8aR,12aS,14aR,14b5)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-ylcarbamate;

(4aR,6aS,6bR,8aS,12aS,12bR,14bS)-8a-amino-4,4,6a,6b,11,11,14b-heptamethyl-3,13-dioxo-3,4,4a,5,6,6a,6b,7,8,8a,9,10,11,12,12a,12b,13,14b-octadecahydropicene-2-carbonitrile;

N-((4aS,6aR,6bS,8aR,12aS,14aR,14b5)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)acetamide;

N-((4aS,6aR,6bS,8aR,12aS,14aR,14bS)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)-2,2,2-trifluoroacetamide;

1-((4aS,6aR,6bS,8aR,12aS,14aR,14bS)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)-3-methylurea;

1-((4aS,6aR,6bS,8aR,12aS,14aR,14bS)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)-3-ethylurea;

N-((4aS,6aR,6bS,8aR,12aS,14aR,14b5)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)methanesulfonamide;

benzyl-(4aS,6aR,6bS,8aR,12aS,14aR,14bS)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-ylcarbamate;

1-((4aS,6aR,6bS,8aR,12aS,14aR,14bS)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)urea;

N-((4aS,6aR,6bS,8aR,12aS,14aR,14b5)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)-1H-pyrazole-1-carboxamide;

N-((4aS,6aR,6bS,8aR,12aS,14aR,14b5)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)-3,3,3-trifluoropropanamide;

3-((4aS,6aR,6bS,8aR,12aS,14aR,14bS)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)-1,1-dimethylurea;

N-((4aS,6aR,6bS,8aR,12aS,14aR,14b5)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)piperidine-1-carboxamide;

N-((4aS,6aR,6bS,8aR,12aS,14aR,14b5)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)benzamide;

N-((4aS,6aR,6bS,8aR,12aS,14aR,14b5)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)acrylamide;

allyl-(4aS,6aR,6bS,8aR,12aS,14aR,14bS)-11-cyano-2,2,6a,
6b,9,9,12a-heptamethyl-10,14-dioxo-1,2,3,4,4a,5,6,6a,
6b,7,8,8a,9,10,12a,14,14a,14b-octadecahydropicen-4a-
ylcarbamate;

N-((4aS,6aR,6bS,8aR,12aS,14aR,14b5)-11-cyano-2,2,6a,
6b,9,9,12a-heptamethyl-10,14-dioxo-1,2,3,4,4a,5,6,6a,
6b,7,8,8a,9,10,12a,14,14a,14b-octadecahydropicen-4a-
yl)cyclopropanesulfonamide;

N-((4aS,6aR,6bS,8aR,12aS,14aR,14bS)-11-cyano-2,2,6a,
6b,9,9,12a-heptamethyl-10,14-dioxo-1,2,3,4,4a,5,6,6a,
6b,7,8,8a,9,10,12a,14,14a,14b-octadecahydropicen-4a-
yl)thiophene-2-sulfonamide;

N-((4aS,6aR,6bS,8aR,12aS,14aR,14b5)-11-cyano-2,2,6a,
6b,9,9,12a-heptamethyl-10,14-dioxo-1,2,3,4,4a,5,6,6a,
6b,7,8,8a,9,10,12a,14,14a,14b-octadecahydropicen-4a-
yl)-4-hydroxypiperidine-1-carboxamide;

N-((4aS,6aR,6bS,8aR,12aS,14aR,14b5)-11-cyano-2,2,6a,
6b,9,9,12a-heptamethyl-10,14-dioxo-1,2,3,4,4a,5,6,6a,
6b,7,8,8a,9,10,12a,14,14a,14b-octadecahydropicen-4a-
yl)morpholine-4-carboxamide;

isopropyl-(4aS,6aR,6bS,8aR,12aS,14aR,14b5)-11-cyano-2,
2,6a,6b,9,9,12a-heptamethyl-10,14-dioxo-1,2,3,4,4a,5,6,
6a,6b,7,8,8a,9,10,12a,14,14a,14b-octadecahydropicen-
4a-ylcarbamate;

N-((4aS,6aR,6bS,8aR,12aS,14aR,14bS)-11-cyano-2,2,6a,
6b,9,9,12a-heptamethyl-10,14-dioxo-1,2,3,4,4a,5,6,6a,
6b,7,8,8a,9,10,12a,14,14a,14b-octadecahydropicen-4a-
yl)ethanesulfonamide;

N-((4aS,6aR,6bS,8aR,12aS,14aR,14b5)-11-cyano-2,2,6a,
6b,9,9,12a-heptamethyl-10,14-dioxo-1,2,3,4,4a,5,6,6a,
6b,7,8,8a,9,10,12a,14,14a,14b-octadecahydropicen-4a-
yl)-2-phenylacetamide;

N-((4aS,6aR,6bS,8aR,12aS,14aR,14b5)-11-cyano-2,2,6a,
6b,9,9,12a-heptamethyl-10,14-dioxo-1,2,3,4,4a,5,6,6a,
6b,7,8,8a,9,10,12a,14,14a,14b-octadecahydropicen-4a-
yl)propionamide;

N-((4aS,6aR,6bS,8aR,12aS,14aR,14b5)-11-cyano-2,2,6a,
6b,9,9,12a-heptamethyl-10,14-dioxo-1,2,3,4,4a,5,6,6a,
6b,7,8,8a,9,10,12a,14,14a,14b-octadecahydropicen-4a-
yl)benzenesulfonamide;

(4aR,6aS,6bR,8aS,12aS,12bR,14bS)-8a-(dimethylamino)-
4,4,6a,6b,11,11,14b-heptamethyl-3,13-dioxo-3,4,4a,5,6,
6a,6b,7,8,8a,9,10,11,12,12a,12b,13,14b-octadecahydro-
picene-2-carbonitrile;

N-((4aS,6aR,6bS,8aR,12aS,14aR,14bS)-11-cyano-2,2,6a,
6b,9,9,12a-heptamethyl-10,14-dioxo-1,2,3,4,4a,5,6,6a,
6b,7,8,8a,9,10,12a,14,14a,14b-octadecahydropicen-4a-
yl)propiolamide;

N-((4aS,6aR,6bS,8aR,12aS,14aR,14b5)-11-cyano-2,2,6a,
6b,9,9,12a-heptamethyl-10,14-dioxo-1,2,3,4,4a,5,6,6a,
6b,7,8,8a,9,10,12a,14,14a,14b-octadecahydropicen-4a-
yl)-2,2,2-trifluoroethanesulfonamide;

1-((4aS,6aR,6bS,8aR,12aS,14aR,14bS)-11-cyano-2,2,6a,
6b,9,9,12a-heptamethyl-10,14-dioxo-1,2,3,4,4a,5,6,6a,
6b,7,8,8a,9,10,12a,14,14a,14b-octadecahydropicen-4a-
yl)-3-(4-hydroxyphenyl)urea;

1-((4aS,6aR,6bS,8aR,12aS,14aR,14bS)-11-cyano-2,2,6a,
6b,9,9,12a-heptamethyl-10,14-dioxo-1,2,3,4,4a,5,6,6a,
6b,7,8,8a,9,10,12a,14,14a,14b-octadecahydropicen-4a-
yl)-3-phenylurea;

(4aR,6aR,6bR,8aS,12aS,12bR,14bR)-8a-hydroxy-4,4,6a,
6b,11,11,14b-heptamethyl-3,13-dioxo-3,4,4a,5,6,6a,6b,7,
8,8a,9,10,11,12,12a,12b,13,14,14a,14b-icosahydro-
picene-2-carbonitrile;

(4aR,6aS,6bR,8aS,12aS,12bR,14bS)-8a-isocyanato-4,4,6a,
6b,11,11,14b-heptamethyl-3,13-dioxo-3,4,4a,5,6,6a,6b,7,
8,8a,9,10,11,12,12a,12b,13,14b-octadecahydropicene-2-
carbonitrile;

(4aS,6aR,6bR,8aR,13aR,13bR,15aR,15b5)-4a-hydroxy-2,2,
6a,6b,9,9,13a-heptamethyl-1,2,3,4,4a,5,6,6a,7,8,8a,9,13,
13a,13b,14,15a,15b-octadecahydropiceno[2,3-d]isox-
azol-15(6bH)-one;

(4aS,6aR,6bR,8aR,10S,12aR,12bR,14R,14aR,14bS)-10,14-
dihydroxy-2,2,6a,6b,9,9,12a-heptamethyldocosahydro-
picene-4a-carbaldehyde;

(4aS,6aR,6bR,8aR,10S,12aR,12bR,14R,14aR,14bS)-10,14-
dihydroxy-2,2,6a,6b,9,9,12a-heptamethyldocosahydropi-
cen-4a-yl formate;

(4aS,6aR,6bR,8aR,12aR,12bR,14aR,14bS)-2,2,6a,6b,9,9,
12a-heptamethyl-10,14-dioxodocosahydropicen-4a-yl
formate;

(4aR,6aR,6bR,8aS,12aS,12bR,14aR,14bR,E)-8a-hydroxy-
2-(hydroxymethylene)-4,4,6a,6b,11,11,14b-heptamethy-
loctadecahydropicene-3,13(4H,6bH)-dione;

N-((4aS,6aR,6bR,8aR,12aR,12bR,14aR,14bS)-11-cyano-2,
2,6a,6b,9,9,12a-heptamethyl-10,14-dioxo-1,2,3,4,4a,5,6,
6a,6b,7,8,8a,9,10,12a,12b,13,14,14a,14b-icosahydropi-
cen-4a-yl)-2,2,2-trifluoroethanesulfonamide;

(4aR,6aR,6bR,8aS,12aS,12bR,14aR,14bR)-8a-(cyanom-
ethylamino)-4,4,6a,6b,11,11,14b-heptamethyl-3,13-di-
oxo-3,4,4a,5,6,6a,6b,7,8,8a,9,10,11,12,12a,12b,13,14,
14a,14b-icosahydropicene-2-carbonitrile;

N-((4aS,6aR,6bR,8aR,12aR,12bR,14aR,14bS)-11-cyano-2,
2,6a,6b,9,9,12a-heptamethyl-10,14-dioxo-1,2,3,4,4a,5,6,
6a,6b,7,8,8a,9,10,12a,12b,13,14,14a,14b-icosahydropi-
cen-4a-yl)cyclopropanecarboxamide;

(4aR,6aR,6bR,8aS,12aS,12bR,14aR,14bR)-8a-(ethy-
lamino)-4,4,6a,6b,11,11,14b-heptamethyl-3,13-dioxo-3,
4,4a,5,6,6a,6b,7,8,8a,9,10,11,12,12a,12b,13,14,14a,14b-
icosahydropicene-2-carbonitrile;

tetrahydrofuran-3-yl (4aS,6aR,6bR,8aR,12aR,12bR,14aR,
14bS)-11-cyano-2,2,6a,6b,9,9,12a-heptamethyl-10,14-di-
oxo-1,2,3,4,4a,5,6,6a,6b,7,8,8a,9,10,12a,12b,13,14,14a,
14b-icosahydropicen-4a-ylcarbamate;

N-((4aS,6aR,6bR,8aR,12aR,12bR,14aR,14bS)-11-cyano-2,
2,6a,6b,9,9,12a-heptamethyl-10,14-dioxo-1,2,3,4,4a,5,6,
6a,6b,7,8,8a,9,10,12a,12b,13,14,14a,14b-icosahydropi-
cen-4a-yl)acetamide;

N-((4aS,6aR,6bR,8aR,12aR,12bR,14aR,14bS)-11-cyano-2,
2,6a,6b,9,9,12a-heptamethyl-10,14-dioxo-1,2,3,4,4a,5,6,
6a,6b,7,8,8a,9,10,12a,12b,13,14,14a,14b-icosahydropi-
cen-4a-yl)-2,2,2-trifluoroacetamide;

1-((4aS,6aR,6bR,8aR,12aR,12bR,14aR,14b5)-11-cyano-2,
2,6a,6b,9,9,12a-heptamethyl-10,14-dioxo-1,2,3,4,4a,5,6,
6a,6b,7,8,8a,9,10,12a,12b,13,14,14a,14b-icosahydropi-
cen-4a-yl)-3-methylurea; and methyl (4aS,6aR,6bR,8aR,12aR,12bR,14aR,14bS)-11-cy-
ano-2,2,6a,6b,9,9,12a-heptamethyl-10,14-dioxo-1,2,3,4,
4a,5,6,6a,6b,7,8,8a,9,10,12a,12b,13,14,14a,14b-icosahy-
dropicen-4a-ylcarbamate.

The present disclosure further provides compounds of the formula:

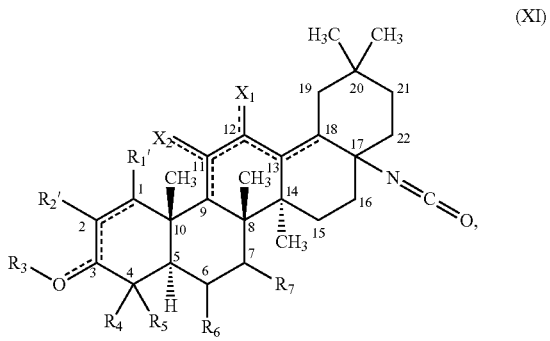

wherein: $X_1$ and $X_2$ are independently: hydrogen, $OR_b$, $NR_bR_c$, or $SR_b$, wherein $R_b$ and $R_c$ are each independently: hydrogen; alkyl$_{(C \leq 8)}$, aryl$_{(C \leq 8)}$, aralkyl$_{(C \leq 8)}$, acyl$_{(C \leq 8)}$, or a substituted version of any of these groups; or provided that $R_b$ is absent when the atom to which it is bound is part of a double bond, further provided that when $R_b$ is absent the atom to which it is bound is part of a double bond; $R_1'$ is: hydrogen, cyano, hydroxy, halo, or amino; or alkyl$_{(C \leq 8)}$, alkenyl$_{(C \leq 8)}$, alkynyl$_{(C \leq 8)}$, aryl$_{(C \leq 8)}$, aralkyl$_{(C \leq 8)}$, heteroaryl$_{(C \leq 8)}$, heteroaralkyl$_{(C \leq 8)}$, acyl$_{(C \leq 8)}$, alkoxy$_{(C \leq 8)}$, aryloxy$_{(C \leq 8)}$, acyloxy$_{(C \leq 8)}$, alkylamino$_{(C \leq 8)}$, arylamino$_{(C \leq 8)}$, amido$_{(C \leq 8)}$, or a substituted version of any of these groups; $R_2'$ is: cyano, hydroxy, halo or amino; or alkenyl$_{(C \leq 8)}$, alkynyl$_{(C \leq 8)}$, aryl$_{(C \leq 8)}$, heteroaryl$_{(C \leq 8)}$, acyl$_{(C \leq 8)}$, alkoxy$_{(C \leq 8)}$, aryloxy$_{(C \leq 8)}$, acyloxy$_{(C \leq 8)}$, alkylamino$_{(C \leq 8)}$, arylamino$_{(C \leq 8)}$, amido$_{(C \leq 8)}$, or a substituted version of any of these groups; $R_3$ is: absent or hydrogen; alkyl$_{(C \leq 8)}$, aryl$_{(C \leq 8)}$, aralkyl$_{(C \leq 8)}$, acyl$_{(C \leq 8)}$, or a substituted version of any of these groups; or provided that $R_3$ is absent when the oxygen atom to which it is bound is part of a double bond, further provided that when $R_3$ is absent the oxygen atom to which it is bound is part of a double bond; $R_4$ and $R_5$ are each independently alkyl$_{(C \leq 8)}$ or substituted alkyl$_{(C \leq 8)}$; and $R_6$ and $R_7$ are each independently hydrogen or hydroxy; or salts, esters, hydrates, solvates, tautomers, or optical isomers thereof.

In particular embodiments regarding a compound of formula (IX), $R_1'$ is hydrogen. In certain embodiments, $R_2'$ is cyano. In certain embodiments, wherein $R_3$ is absent. In certain embodiments, wherein $X_2$ is hydrogen. In certain embodiments, wherein the bond joining carbon 1 and carbon 2 is a double bond. In certain embodiments, wherein the bond joining carbon 9 and carbon 11 is a double bond.

In particular embodiments, the compound of formula (XI) is further defined as:

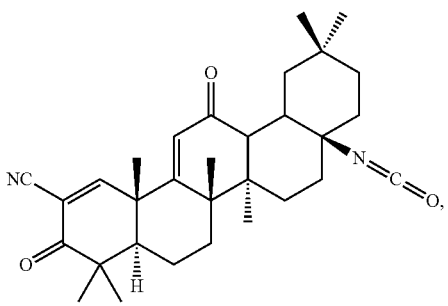

or salts, hydrates, solvates, tautomers, or optical isomers thereof. In certain embodiments, the following particular compound is contemplated:

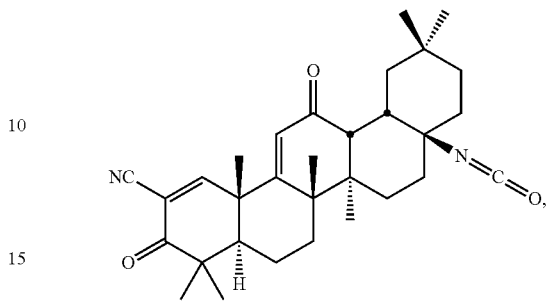

or salts thereof, and substantially free from other optical isomers thereof.

A further embodiment contemplated by the present disclosure is A compound of the formula:

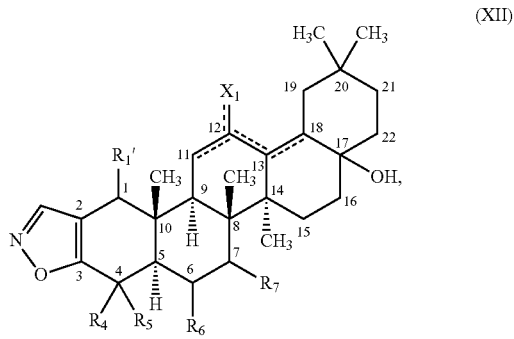

wherein: $X_1$ is hydrogen, $OR_b$, $NR_bR_c$, or $SR_b$, wherein $R_b$ and $R_c$ are each independently: hydrogen; alkyl$_{(C \leq 8)}$, aryl$_{(C \leq 8)}$, aralkyl$_{(C \leq 8)}$, acyl$_{(C \leq 8)}$, or a substituted version of any of these groups; or provided that $R_b$ is absent when the atom to which it is bound is part of a double bond, further provided that when $R_b$ is absent the atom to which it is bound is part of a double bond; $R_1'$ is: hydrogen, cyano, hydroxy, halo, or amino; or alkyl$_{(C \leq 8)}$, alkenyl$_{(C \leq 8)}$, alkynyl$_{(C \leq 8)}$, aryl$_{(C \leq 8)}$, aralkyl$_{(C \leq 8)}$, heteroaryl$_{(C \leq 8)}$, heteroaralkyl$_{(C \leq 8)}$, acyl$_{(C \leq 8)}$, alkoxy$_{(C \leq 8)}$, aryloxy$_{(C \leq 8)}$, acyloxy$_{(C \leq 8)}$, alkylamino$_{(C \leq 8)}$, arylamino$_{(C \leq 8)}$, amido$_{(C \leq 8)}$, or a substituted version of any of these groups; $R_4$ and $R_5$ are each independently alkyl$_{(C \leq 8)}$ or substituted alkyl$_{(C \leq 8)}$; and $R_6$ and $R_7$ are each independently hydrogen or hydroxy; or salts, esters, hydrates, solvates, tautomers, or optical isomers thereof.

In certain embodiments regarding compounds comprising $X_1$, $X_1$ is $OR_b$ and $R_b$ is absent. In certain embodiments regarding compounds comprising $R_4$ and $R_5$, $R_4$ and $R_5$ are each independently alkyl$_{(C \leq 4)}$. For example, $R_4$ and $R_5$ are each methyl in certain embodiments. In certain embodiments regarding compounds comprising $R_6$ and $R_7$, $R_6$ and $R_7$ are each hydrogen. In certain embodiments regarding compounds comprising a bond between carbons 13 and 18, the bond joining carbon 13 and carbon 18 is a single bond.

In particular embodiments, the compound of formula (XII) is further defined as:

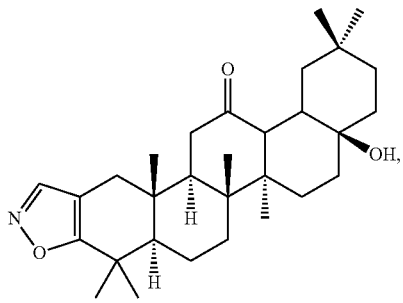

or salts, hydrates, solvates, tautomers, or optical isomers thereof. In certain embodiments, the following particular compound is contemplated:

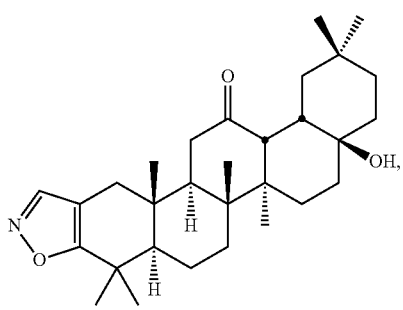

or salts thereof, and substantially free from other optical isomers thereof.

Another general aspect of the present disclosure contemplates a compound of the formula:

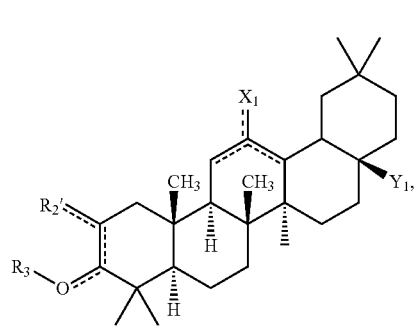

(XIII)

wherein: $X_1$ is —$OR_b$, wherein $R_b$ is hydrogen: provided that $R_b$ is absent when the oxygen atom to which it is bound is part of a double bond, further provided that when $R_b$ is absent the oxygen atom to which it is bound is part of a double bond; $Y_1$ is hydroxy, —CHO, or —OC(O)H: $R_2'$ is hydrogen or —C(H)(OH); $R_3$ is absent or hydrogen; provided that $R_3$ is absent when the oxygen atom to which it is bound is part of a double bond, further provided that when $R_3$ is absent the oxygen atom to which it is bound is part of a double bond; or salts, esters, hydrates, solvates, tautomers, or optical isomers thereof.

In particular embodiments, the compound of formula (XIII) is further defined as:

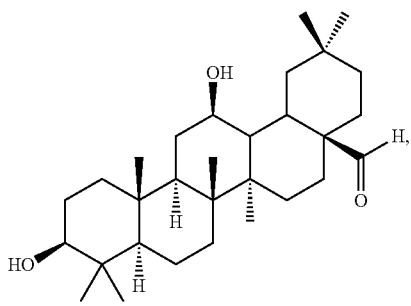

or salts, hydrates, solvates, tautomers, or optical isomers thereof. In certain embodiments, the following particular compound is contemplated:

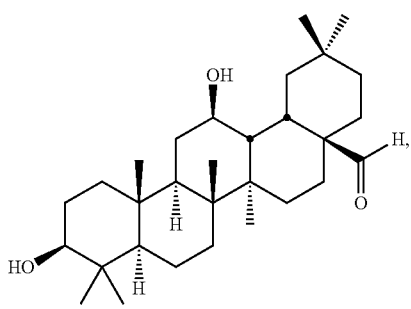

or salts thereof, and substantially free from other optical isomers thereof. In certain embodiments, the following compound is contemplated:

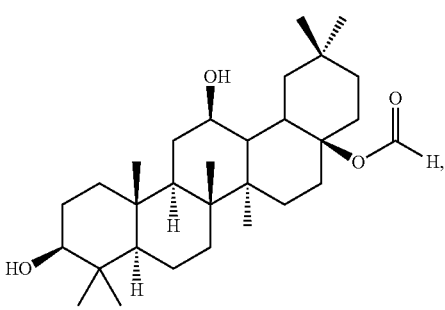

or salts, hydrates, solvates, tautomers, or optical isomers thereof. In certain embodiments, the following particular compound is contemplated:

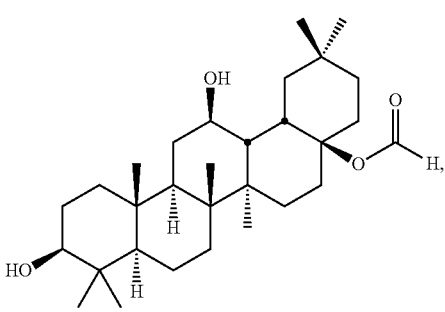

or salts thereof, and substantially free from other optical isomers thereof. In certain embodiments, the following compound is contemplated:

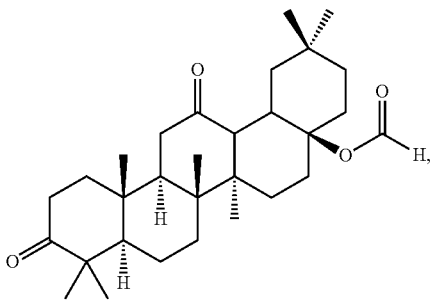

or salts, hydrates, solvates, tautomers, or optical isomers thereof. In certain embodiments, the following particular compound is contemplated:

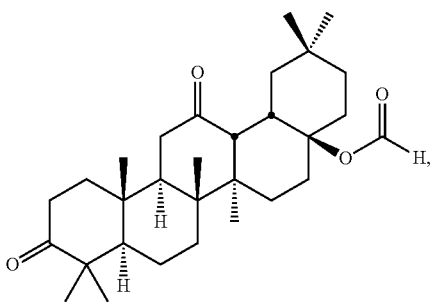

or salts thereof, and substantially free from other optical isomers thereof. In certain embodiments, the following compound is contemplated:

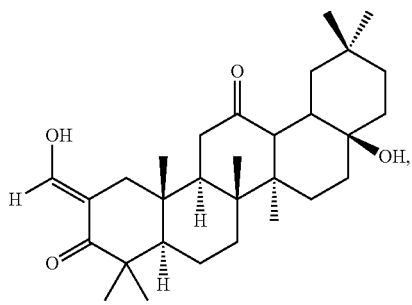

or salts, hydrates, solvates, tautomers, or optical isomers thereof. In certain embodiments, the following particular compound is contemplated:

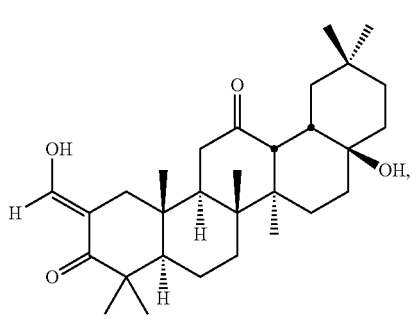

or salts thereof, and substantially free from other optical isomers thereof.

In some embodiments, compounds of the present disclosure are in the form of pharmaceutically acceptable salts. In other embodiments, compounds of the present disclosure are not be in the form of a salt. In certain embodiments, a compound of the present disclosure is a hydrate. In other embodiments, a compound of the present disclosure is not a hydrate. In certain embodiments, a compound of the present disclosure is a solvate. In other embodiments, a compound of the present disclosure is not a solvate.

In some embodiments, compounds of the present disclosure can be esters of the above formulas. The ester may, for example, result from a condensation reaction between a hydroxy group of the formula and the carboxylic acid group of biotin. In certain embodiments, a compound of the present disclosure is not an ester.

In some embodiments, the compounds of the present disclosure can be present as a mixture of stereoisomers. In certain embodiments, compounds of the present disclosure are present as predominantly one optical isomer. In other embodiments, the compounds of the present disclosure are present as single stereoisomers.

In some embodiments, compounds of the present disclosure may be inhibitors of IFN-γ-induced nitrous oxide (NO) production in macrophages, for example, having an $IC_{50}$ value of less than 0.2 μM.

Other general aspects of the present disclosure contemplate a pharmaceutical composition comprising as an active ingredient a compound of the present disclosure and a pharmaceutically acceptable carrier. The composition may, for example, be adapted for administration by a route selected from the group consisting of orally, intraadiposally, intraarterially, intraarticularly, intracranially, intradermally, intralesionally, intramuscularly, intranasally, intraocularally, intrapericardially, intraperitoneally, intrapleurally, intraprostaticaly, intrarectally, intrathecally, intratracheally, intratumorally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, via localized perfusion, bathing target cells directly, or any combination thereof. In particular embodiments, the composition may be formulated for oral delivery. In particular embodiments, the composition is formulated as a hard or soft capsule, a tablet, a syrup, a suspension, a wafer, or an elixir. In certain embodiments, the soft capsule is a gelatin capsule. Certain compositions may comprise a protective coating, such as those compositions formulated for oral delivery. Certain compositions further comprise an agent that delays absorption, such as those compositions formulated for oral delivery. Certain compositions may further comprise an agent that enhances solubility or dispersibility, such as those compositions formulated for oral delivery. Certain compositions may comprise a compound of the present disclosure, wherein the compound is dispersed in a liposome, an oil and water emulsion or a water and oil emulsion.

Yet another general aspect of the present disclosure contemplates a therapeutic method comprising administering a pharmaceutically effective amount of a compound of the present disclosure to a subject. The subject may, for example, be a human. These or any other methods of the present disclosure may further comprise identifying a subject in need of treatment.

Another method of the present disclosure contemplates a method of treating cancer in a subject, comprising administering to the subject a pharmaceutically effective amount of a compound of the present disclosure. The cancer may be any type of cancer, such as a carcinoma, sarcoma, lymphoma, leukemia, melanoma, mesothelioma, multiple myeloma, or seminoma. Other types of cancers include cancer of the bladder, blood, bone, brain, breast, central nervous system, colon, endometrium, esophagus, genitourinary tract, head, larynx, liver, lung, neck, ovary, pancreas, prostate, spleen, small intestine, large intestine, stomach, or testicle. In these or any other methods, the subject may be a primate. This or any other method may further comprise identifying a subject in need of treatment. The subject may have a family or patient history of cancer. In certain embodiments, the subject has symptoms of cancer. The compounds of the invention may be administered via any method described herein, such as locally. In certain embodiments, the compound is administered by direct intratumoral injection or by injection into tumor vasculature. In certain embodiments, the compounds may be administered systemically. The compounds may be administered intravenously, intra-arterially, intramuscularly, intraperitoneally, subcutaneously or orally, in certain embodiments.

In certain embodiments regarding methods of treating cancer in a subject, comprising administering to the subject a pharmaceutically effective amount of a compound of the present disclosure, the pharmaceutically effective amount is 0.1-1000 mg/kg. In certain embodiments, the pharmaceutically effective amount is administered in a single dose per day. In certain embodiments, the pharmaceutically effective amount is administered in two or more doses per day. The compound may be administered by contacting a tumor cell during ex vivo purging, for example. The method of treatment may comprise any one or more of the following: a) inducing cytotoxicity in a tumor cell; b) killing a tumor cell; c) inducing apoptosis in a tumor cell; d) inducing differentiation in a tumor cell; or e) inhibiting growth in a tumor cell. The tumor cell may be any type of tumor cell, such as a leukemia cell. Other types of cells include, for example, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

Combination treatment therapy is also contemplated by the present disclosure. For example, regarding methods of treating cancer in a subject, comprising administering to the subject a pharmaceutically effective amount of a compound of the present disclosure, the method may further comprise a treatment selected from the group consisting of administering a pharmaceutically effective amount of a second drug, radiotherapy, gene therapy, and surgery. Such methods may further comprise (1) contacting a tumor cell with the compound prior to contacting the tumor cell with the second drug, (2) contacting a tumor cell with the second drug prior to contacting the tumor cell with the compound, or (3) contacting a tumor cell with the compound and the second drug at the same time. The second drug may, in certain embodiments, be an antibiotic, anti-inflammatory, anti-neoplastic, anti-proliferative, anti-viral, immunomodulatory, or immunosuppressive. The second drug may be an alkylating agent, androgen receptor modulator, cytoskeletal disruptor, estrogen receptor modulator, histone-deacetylase inhibitor, HMG-CoA reductase inhibitor, prenyl-protein transferase inhibitor, retinoid receptor modulator, topoisomerase inhibitor, or tyrosine kinase inhibitor. In certain embodiments, the second drug is 5-azacitidine, 5-fluorouracil, 9-cis-retinoic acid, actinomycin D, alitretinoin, all-trans-retinoic acid, annamycin, axitinib, belinostat, bevacizumab, bexarotene, bosutinib, busulfan, capecitabine, carboplatin, carmustine, CD437, cediranib, cetuximab, chlorambucil, cisplatin, cyclophosphamide, cytarabine, dacarbazine, dasatinib, daunorubicin, decitabine, docetaxel, dolastatin-10, doxifluridine, doxorubicin, doxorubicin, epirubicin, erlotinib, etoposide, etoposide, gefitinib, gemcitabine, gemtuzumab ozogamicin, hexamethylmelamine, idarubicin, ifosfamide, imatinib, irinotecan, isotretinoin, ixabepilone, lapatinib, LBH589, lomustine, mechlorethamine, melphalan, mercaptopurine, methotrexate, mitomycin, mitoxantrone, MS-275, neratinib, nilotinib, nitrosourea, oxaliplatin, paclitaxel, plicamycin, procarbazine, semaxanib, semustine, sodium butyrate, sodium phenylacetate, streptozotocin, suberoylanilide hydroxamic acid, sunitinib, tamoxifen, teniposide, thiopeta, tioguanine, topotecan, TRAIL, trastuzumab, tretinoin, trichostatin A, valproic acid, valrubicin, vandetanib, vinblastine, vincristine, vindesine, or vinorelbine.

Methods of treating or preventing a disease with an inflammatory component in a subject, comprising administering to the subject a pharmaceutically effective amount of a compound of the present disclosure are also contemplated. The disease may be, for example, lupus or rheumatoid arthritis. The disease may be an inflammatory bowel disease, such as Crohn's disease or ulcerative colitis. The disease with an inflammatory component may be a cardiovascular disease. The disease with an inflammatory component may be diabetes, such as type 1 or type 2 diabetes. Compounds of the present disclosure may also be used to treat complications associated with diabetes. Such complications are well-known in the art and include, for example, obesity, hypertension, atherosclerosis, coronary heart disease, stroke, peripheral vascular disease, hypertension, nephropathy, neuropathy, myonecrosis, retinopathy and metabolic syndrome (syndrome X). The disease with an inflammatory component may be a skin disease, such as psoriasis, acne, or atopic dermatitis. Administration of a compound of the present disclosure in treatment methods of such skin diseases may be, for example, topical or oral.

The disease with an inflammatory component may be metabolic syndrome (syndrome X). A patient having this syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670, incorporated herein by reference. Patients with metabolic syndrome, whether or not they have or develop overt diabetes mellitus, have an increased risk of developing the macrovascular and microvascular complications that are listed above that occur with type 2 diabetes, such as atherosclerosis and coronary heart disease.

Another general method of the present disclosure entails a method of treating or preventing a cardiovascular disease in a subject, comprising administering to the subject a pharmaceutically effective amount of a compound of the present disclosure. The cardiovascular disease may be, for example, atherosclerosis, cardiomyopathy, congenital heart disease, congestive heart failure, myocarditis, rheumatic heart disease, valve disease, coronary artery disease, endocarditis, or myocardial infarction. Combination therapy is also contemplated for such methods. For example, such methods may further comprise administering a pharmaceutically effective amount of a second drug. The second drug may be, for example, a cholesterol lowering drug, an anti-hyperlipidemic, a calcium channel blocker, an anti-hypertensive, or an HMG-CoA reductase inhibitor. Non-limiting examples of second drugs include amlodipine, aspirin, ezetimibe, felodipine, lacidipine, lercanidipine, nicardipine, nifedipine, nimodipine, nisoldipine or nitrendipine. Other non-limiting examples of second drugs include atenolol, bucindolol, carvedilol, clonidine, doxazosin, indoramin, labetalol, methyldopa, metoprolol, nadolol, oxprenolol, phenoxybenzamine, phentolamine, pindolol, prazosin, propranolol, terazosin, timolol or tolazoline. The second drug may be, for example, a statin, such as atorvastatin, cerivastatin, fluvastatin, lovastatin, mevastatin, pitavastatin, pravastatin, rosuvastatin or simvastatin.

Methods of treating or preventing a neurodegenerative disease in a subject, comprising administering to the subject a pharmaceutically effective amount of a compound of the present disclosure are also contemplated. The neurodegenerative disease may, for example, be selected from the group consisting of Parkinson's disease, Alzheimer's disease, multiple sclerosis (MS), Huntington's disease and amyotrophic lateral sclerosis. In particular embodiments, the neurodegenerative disease is Alzheimer's disease. In particular embodiments, the neurodegenerative disease is MS, such as primary progressive, relapsing-remitting secondary progressive or progressive relapsing MS. The subject may be, for example, a primate. The subject may be a human.

In particular embodiments of methods of treating or preventing a neurodegenerative disease in a subject, comprising administering to the subject a pharmaceutically effective amount of a compound of the present disclosure, the treatment suppresses the demyelination of neurons in the subject's brain or spinal cord. In certain embodiments, the treatment suppresses inflammatory demyelination. In certain embodiments, the treatment suppresses the transection of neuron axons in the subject's brain or spinal cord. In certain embodiments, the treatment suppresses the transection of neurites in the subject's brain or spinal cord. In certain embodiments, the treatment suppresses neuronal apoptosis in the subject's brain or spinal cord. In certain embodiments, the treatment stimulates the remyelination of neuron axons in the subject's brain or spinal cord. In certain embodiments, the treatment restores lost function after an MS attack. In certain embodiments, the treatment prevents a new MS attack. In certain embodiments, the treatment prevents a disability resulting from an MS attack.

One general aspect of the present disclosure contemplates a method of treating or preventing a disorder characterized by overexpression of iNOS genes in a subject, comprising administering to the subject a pharmaceutically effective amount of a compound of the present disclosure.

Another general aspect of the present disclosure contemplates a method of inhibiting IFN-γ-induced nitric oxide production in cells of a subject, comprising administering to said subject a pharmaceutically effective amount of a compound of the present disclosure.

Yet another general method of the present disclosure contemplates a method of treating or preventing a disorder characterized by overexpression of COX-2 genes in a subject, comprising administering to the subject a pharmaceutically effective amount of compound of the present disclosure.

Methods of treating renal/kidney disease (RKD) in a subject, comprising administering to the subject a pharmaceutically effective amount of a compound of the present disclosure are also contemplated. See U.S. patent application Ser. No. 12/352,473, which is incorporated by reference herein in its entirety. The RKD may result from, for example, a toxic insult. The toxic insult may result from, for example, an imaging agent or a drug. The drug may be a chemotherapeutic, for example. The RKD may result from ischemia/reperfusion injury, in certain embodiments. In certain embodiments, the RKD results from diabetes or hypertension. The RKD may result from an autoimmune disease. The RKD may be further defined as chronic RKD, or acute RKD.

In certain methods of treating renal/kidney disease (RKD) in a subject, comprising administering to the subject a pharmaceutically effective amount of a compound of the present disclosure, the subject has undergone or is undergoing dialysis. In certain embodiments, the subject has undergone or is a candidate to undergo kidney transplant. The subject may be a primate. The primate may be a human. The subject in this or any other method may be, for example, a cow, horse, dog, cat, pig, mouse, rat or guinea pig.

Also contemplated by the present disclosure is a method for improving glomerular filtration rate or creatinine clearance in a subject, comprising administering to the subject a pharmaceutically effective amount of a compound of the present disclosure.

Methods of synthesizing compounds of the present disclosure are also contemplated. In particular embodiments, such methods comprise a method of making a first compound defined as:

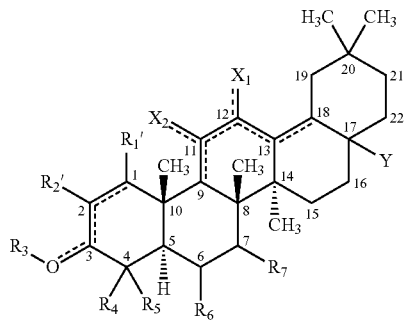

wherein: $X_1$ and $X_2$ are independently: hydrogen, $OR_b$, $NR_bR_c$, or $SR_b$, wherein $R_b$ and $R_c$ are each independently: hydrogen; alkyl$_{(C\leq8)}$, aryl$_{(C\leq8)}$, aralkyl$_{(C\leq8)}$, acyl$_{(C\leq8)}$, or a substituted version of any of these groups; or a substituent convertible in vivo to hydrogen; provided that $R_b$ is absent when the atom to which it is bound is part of a double bond, further provided that when $R_b$ is absent the atom to which it is bound is part of a double bond; Y is $NR_1R_2$, wherein: $R_1$ and $R_2$ are independently: hydrogen or hydroxy; or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkoxy$_{(C\leq12)}$, alkenyloxy$_{(C\leq12)}$, alkynyloxy$_{(C\leq12)}$, aryloxy$_{(C\leq12)}$, aralkoxy$_{(C\leq12)}$, heteroaryloxy$_{(C\leq12)}$, heteroaralkoxy$_{(C\leq12)}$, thioacyl$_{(C\leq12)}$, alkylsulfonyl$_{(C\leq12)}$, alkenylsulfonyl$_{(C\leq12)}$, alkynylsulfonyl$_{(C\leq12)}$, arylsulfonyl$_{(C\leq12)}$, aralkylsulfonyl$_{(C\leq12)}$, heteroarylsulfonyl$_{(C\leq12)}$, or heteroaralkylsulfonyl$_{(C\leq12)}$, or a substituted version of any of these groups; $R_1'$ is: hydrogen, cyano, hydroxy, halo, or amino; or alkyl$_{(C\leq8)}$, alkenyl$_{(C\leq8)}$, alkynyl$_{(C\leq8)}$, aryl$_{(C\leq8)}$, aralkyl$_{(C\leq8)}$, heteroaryl$_{(C\leq8)}$, heteroaralkyl$_{(C\leq8)}$, acyl$_{(C\leq8)}$, alkoxy$_{(C\leq8)}$, aryloxy$_{(C\leq8)}$, acyloxy$_{(C\leq8)}$, alkylamino$_{(C\leq8)}$, arylamino$_{(C\leq8)}$, amido$_{(C\leq8)}$, or a substituted version of any of these groups; $R_2'$ is: cyano, hydroxy, halo or amino; or alkenyl$_{(C\leq8)}$, alkynyl$_{(C\leq8)}$, aryl$_{(C\leq8)}$, heteroaryl$_{(C\leq8)}$, acyl$_{(C\leq8)}$, alkoxy$_{(C\leq8)}$, aryloxy$_{(C\leq8)}$, acyloxy$_{(C\leq8)}$, alkylamino$_{(C\leq8)}$, arylamino$_{(C\leq8)}$, amido$_{(C\leq8)}$, or a substituted version of any of these groups; $R_3$ is: absent or hydrogen; alkyl$_{(C\leq8)}$, aryl$_{(C\leq8)}$, aralkyl$_{(C\leq8)}$, acyl$_{(C\leq8)}$, or a substituted version of any of these groups; or a substituent convertible in vivo to hydrogen; provided that $R_3$ is absent when the oxygen atom to which it is bound is part of a double bond, further provided that when $R_3$ is absent the oxygen atom to which it is bound is part of a double bond; $R_4$ and $R_5$ are each independently alkyl$_{(C\leq8)}$ or substituted alkyl$_{(C\leq8)}$; and $R_6$ and $R_7$ are each independently hydrogen or hydroxy; wherein the first step of the synthesis comprises modification of the C-17 amino group of the following compound:

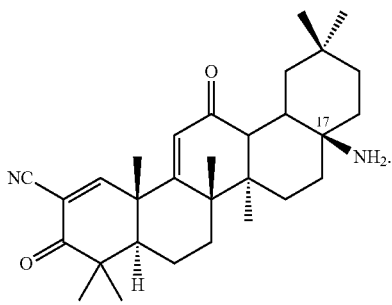

Kits are also contemplated by the present disclosure, such as a kit comprising: a compound of the present disclosure; and instructions which comprise one or more forms of information selected from the group consisting of indicating a disease state for which the compound is to be administered, storage information for the compound, dosing information and instructions regarding how to administer the compound. The kit may comprise a compound of the present disclosure in a multiple dose form.

Other general aspects of the present disclosure contemplate articles of manufacture. For example, an article of manufacture may comprise a compound of the present disclosure; and packaging materials. The packaging materials may comprise a container for housing the compound, in certain embodiments. The container may comprise, for example, a label indicating one or more members of the group consisting of a disease state for which the compound is to be administered, storage information, dosing information and/or instructions regarding how to administer the compound. In certain embodiments, the article of manufacture comprises the compound in a multiple dose form.

In some embodiments, the invention provides compounds that may prevent and/or treat diseases or disorders whose pathology involves oxidative stress, inflammation, and/or dysregulation of inflammatory signaling pathways. In some variations, the diseases or disorders can be characterized by overexpression of inducible nitric oxide synthase (iNOS) and/or inducible cyclooxygenase (COX-2) in affected tissues. In some variations, the diseases or disorders can be characterized by overproduction of reactive oxygen species (ROS) or reactive nitrogen species (RNS) such as superoxide, hydrogen peroxide, nitric oxide or peroxynitrite in affected tissues. In some variations, the disease or disorder is characterized by excessive production of inflammatory cytokines or other inflammation-related proteins such as TNFα, IL-6, IL-1, IL-8, ICAM-1, VCAM-1, and VEGF. Such diseases or disorders may, in some embodiments, involve undesirable proliferation of certain cells, as in the case of cancer (e.g., solid tumors, leukemias, myelomas, lymphomas, and other cancers), fibrosis associated with organ failure, or excessive scarring. Non limiting examples of the disease or disorder include: lupus, rheumatoid arthritis, juvenile-onset diabetes, multiple sclerosis, psoriasis, and Crohn's disease. Further non-limiting examples include cardiovascular diseases, such as atherosclerosis, heart failure, myocardial infarction, acute coronary syndrome, restenosis following vascular surgery, hypertension, and vasculitis; neurodegenerative or neuromuscular diseases such as Alzheimer's disease, Parkinson's disease, Huntington's disease, ALS, and muscular dystrophy; neurological disorders such as epilepsy and dystonia; neuropsychiatric conditions such as major depression, bipolar disorder, post-traumatic stress disorder, schizophrenia, anorexia nervosa, ADHD, and autism-spectrum disorders; retinal diseases such as macular degeneration, diabetic retinopathy, glaucoma, and retinitis; chronic and acute pain syndromes, including inflammatory and neuropathic pain; hearing loss and tinnitus; diabetes and complications of diabetes, including metabolic syndrome, diabetic nephropathy, diabetic neuropathy, and diabetic ulcers; respiratory diseases such as asthma, chronic obstructive pulmonary disease, acute respiratory distress syndrome, and cystic fibrosis; inflammatory bowel diseases; osteoporosis, osteoarthritis, and other degenerative conditions of bone and cartilage; acute or chronic organ failure, including renal failure, liver failure (including cirrhosis and hepatitis), and pancreatitis; ischemia-reperfusion injury associated with thrombotic or hemorrhagic stroke, subarachnoid hemorrhage, cerebral vasospasm, myocardial infarction, shock, or trauma; complications of organ or tissue transplantation including acute or chronic transplant failure or rejection and graft-versus-host disease; skin diseases including atopic dermatitis and acne; sepsis and septic shock; excessive inflammation associated with infection, including respiratory inflammation associated with influenza and upper respiratory infections; mucositis associated with cancer therapy, including radiation therapy or chemotherapy; and severe burns.

Non-limiting examples of compounds disclosed herein include:

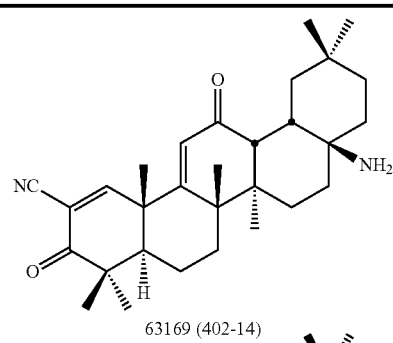

63169 (402-14)

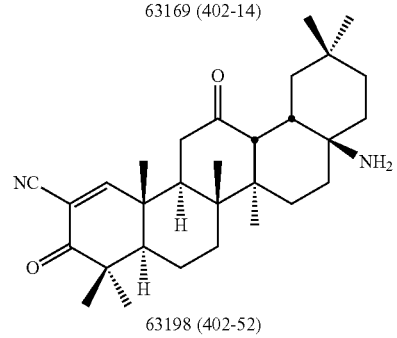

63198 (402-52)

-continued
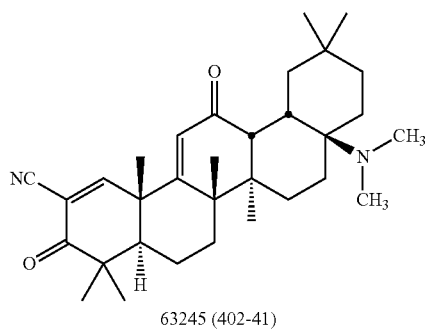
63245 (402-41)
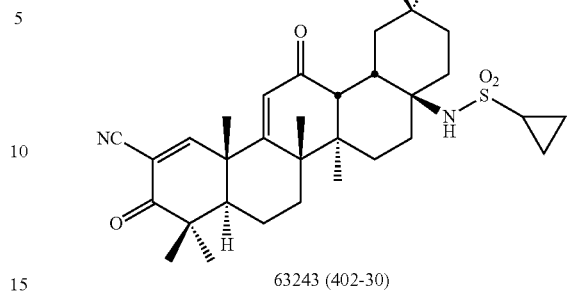
63243 (402-30)
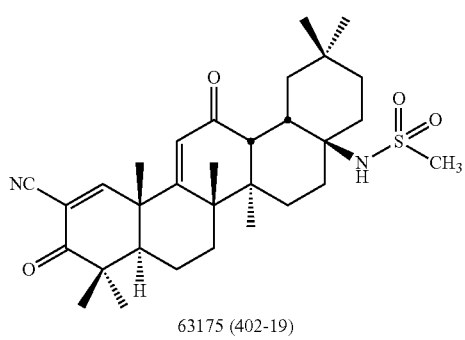
63175 (402-19)
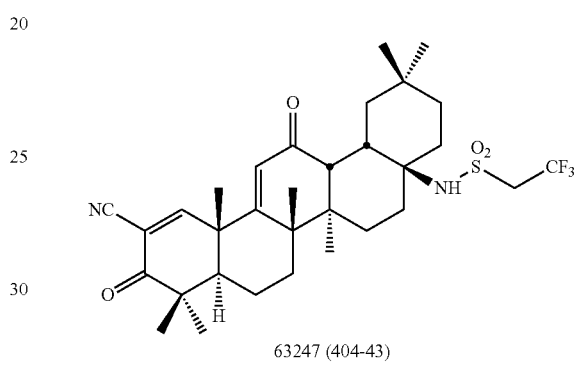
63247 (404-43)
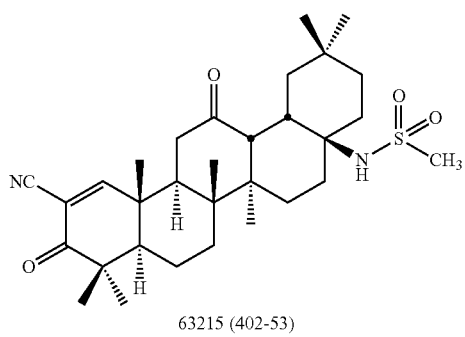
63215 (402-53)
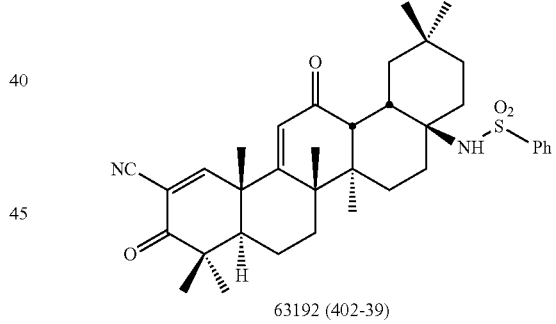
63192 (402-39)
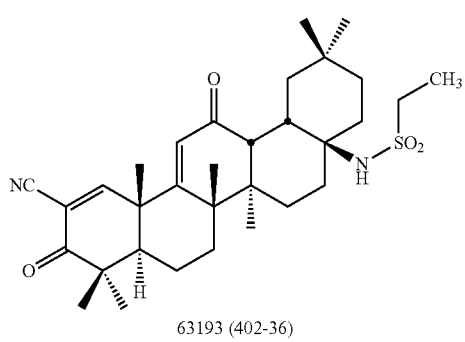
63193 (402-36)
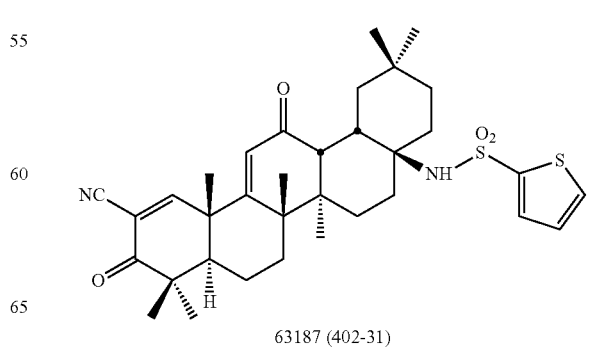
63187 (402-31)

-continued
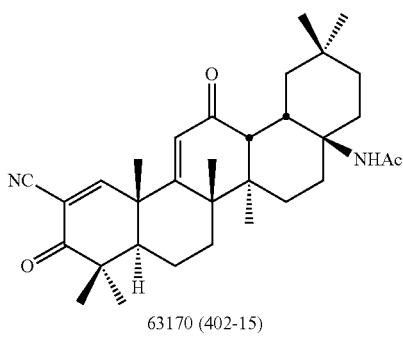
63170 (402-15)
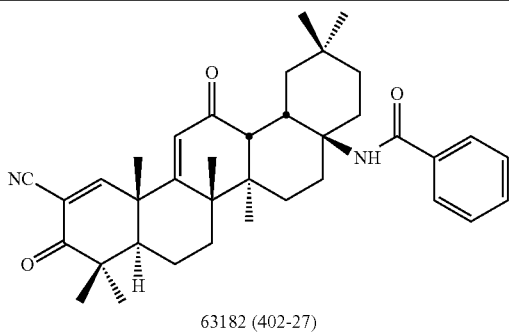
63182 (402-27)
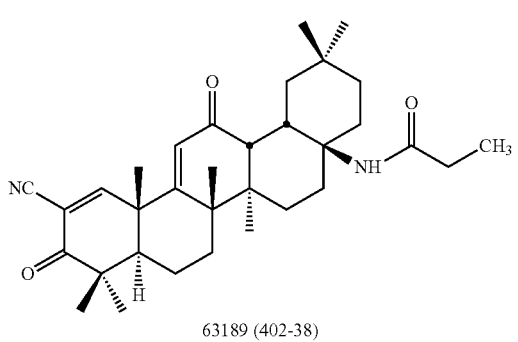
63189 (402-38)
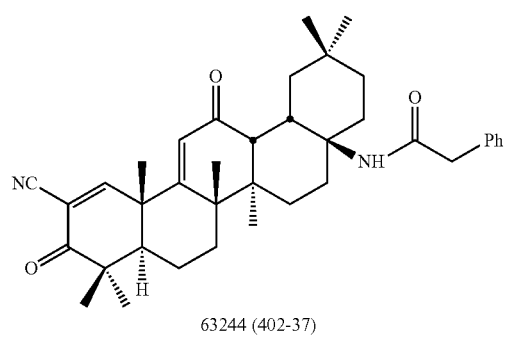
63244 (402-37)
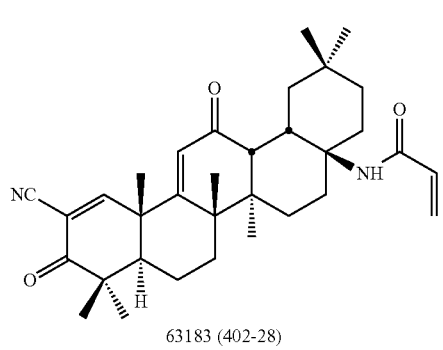
63183 (402-28)
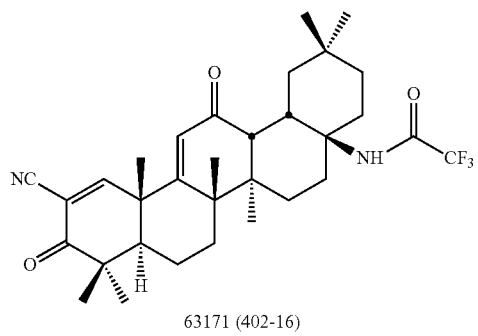
63171 (402-16)
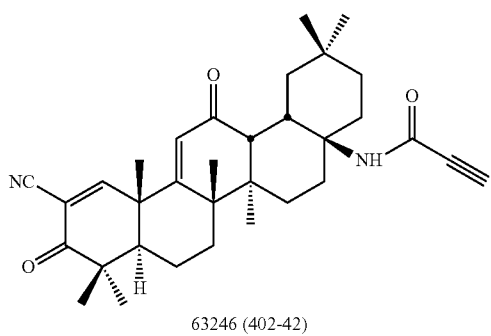
63246 (402-42)
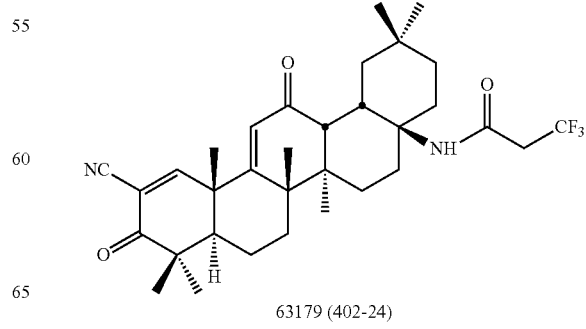
63179 (402-24)

TABLE 1-continued
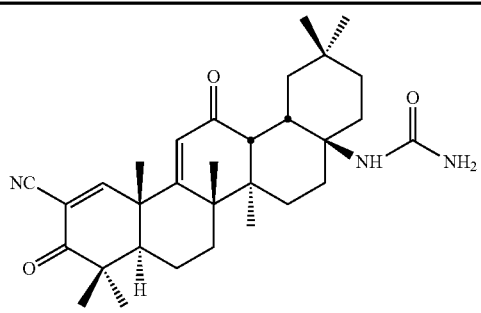
63176 (402-21)
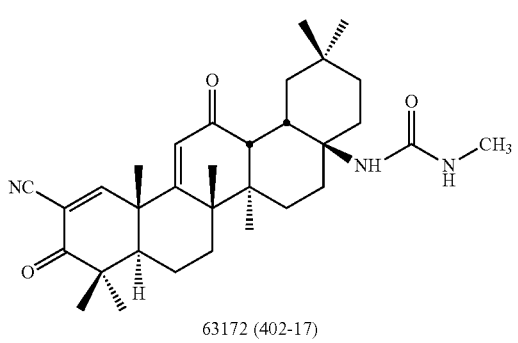
63172 (402-17)
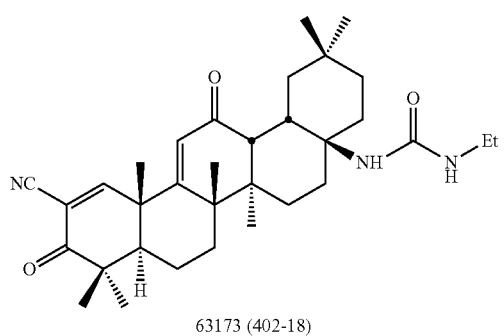
63173 (402-18)
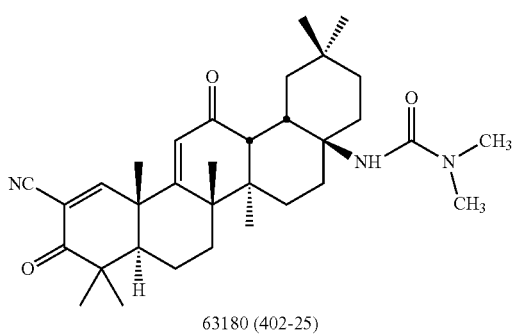
63180 (402-25)
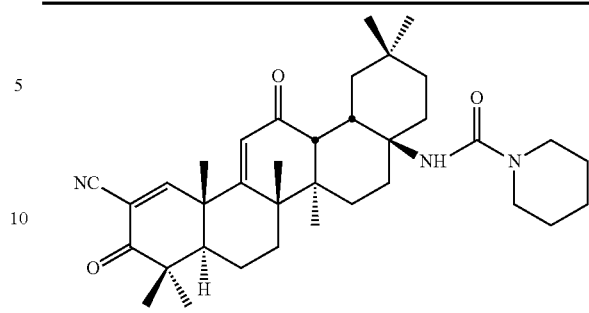
63181 (402-26)
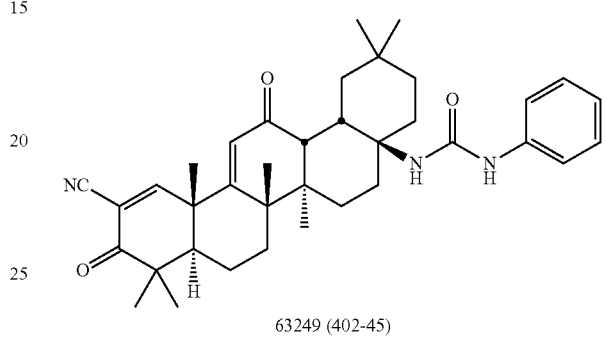
63249 (402-45)
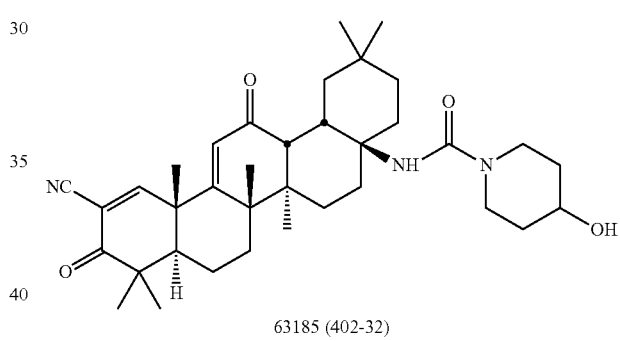
63185 (402-32)
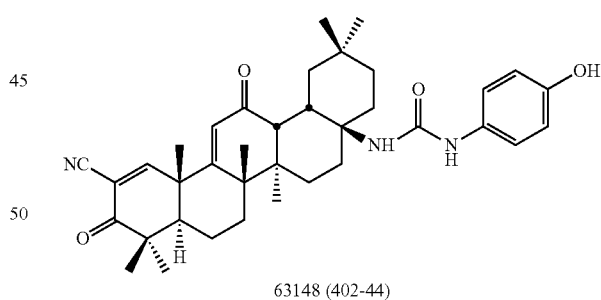
63148 (402-44)
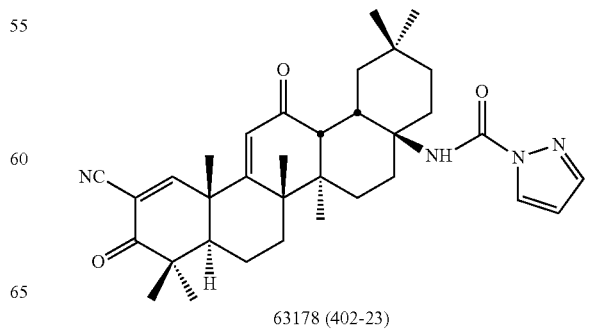
63178 (402-23)

-continued
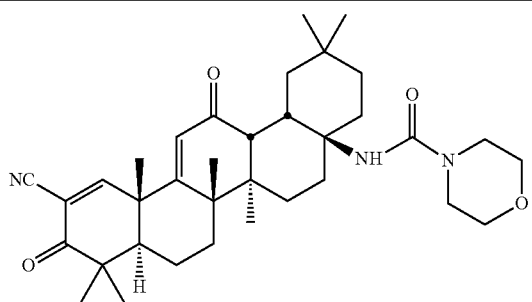
63188 (402-33)
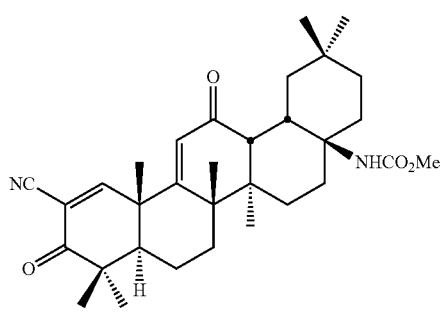
63167 (402-12)
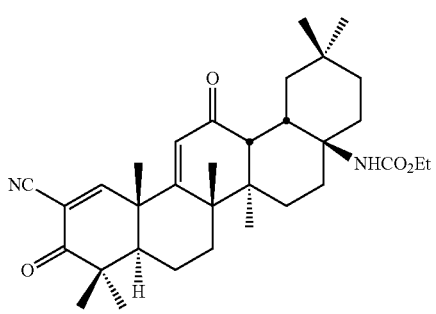
63168 (402-13)
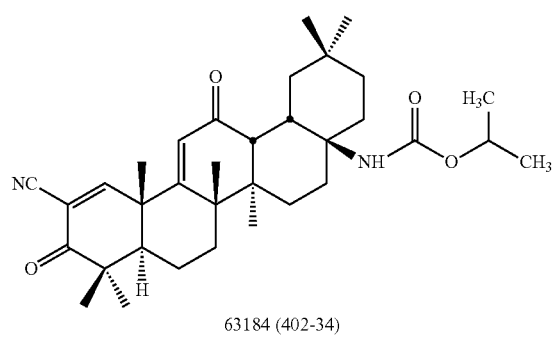
63184 (402-34)
-continued
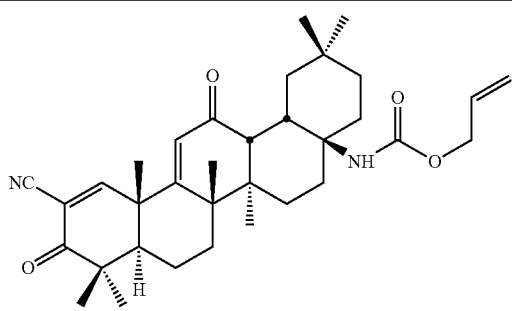
63129 (402-29)
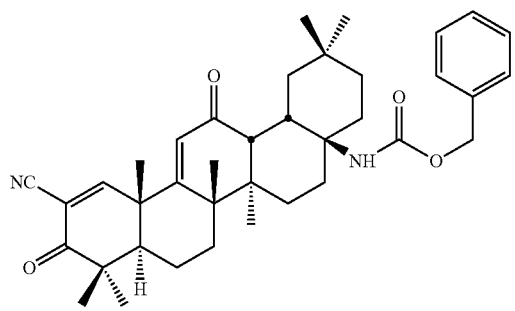
63174 (402-20)
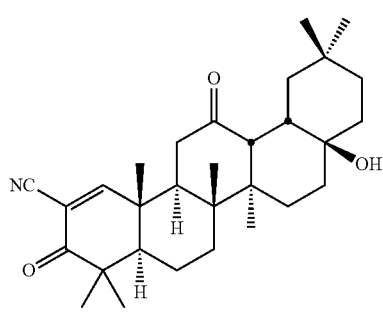
63208 (402-67)
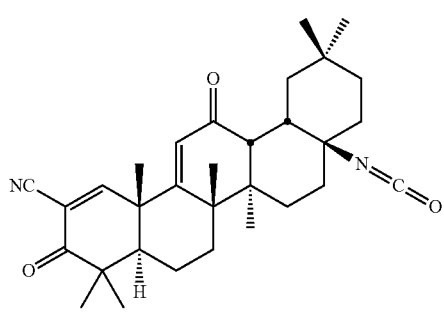
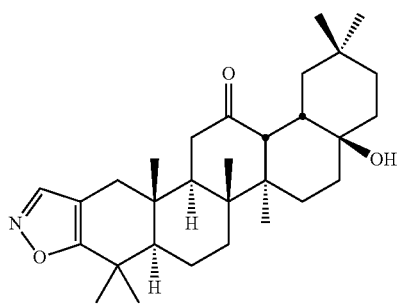

-continued
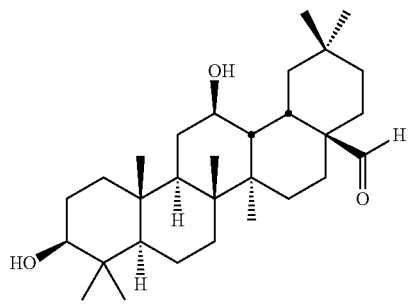
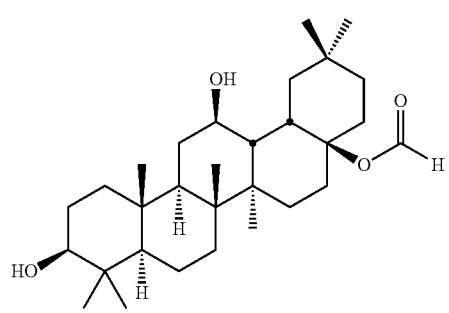
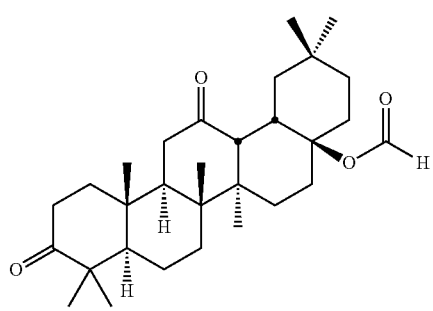
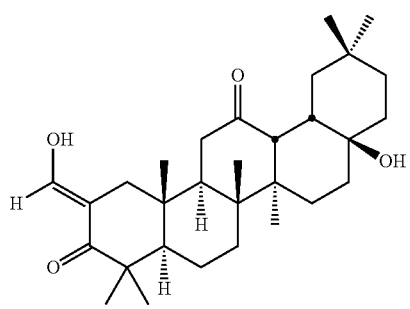
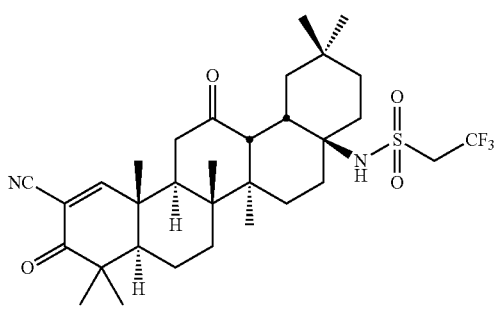
63254
-continued
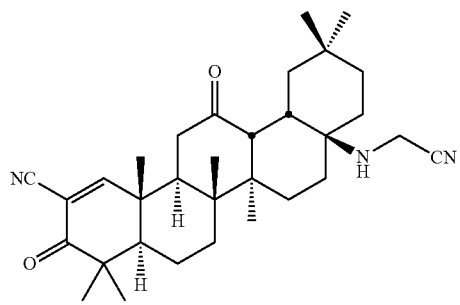
63222
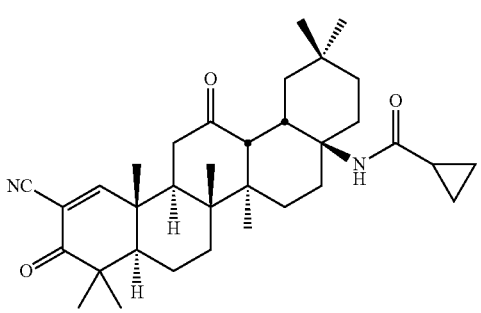
63236
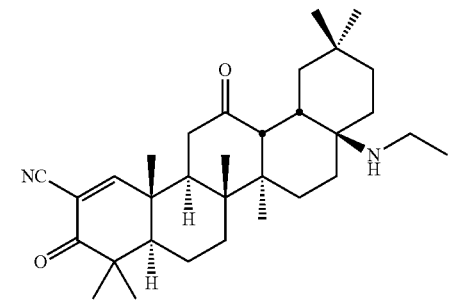
63238
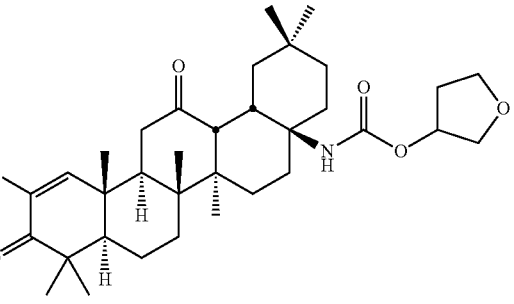
63265

-continued

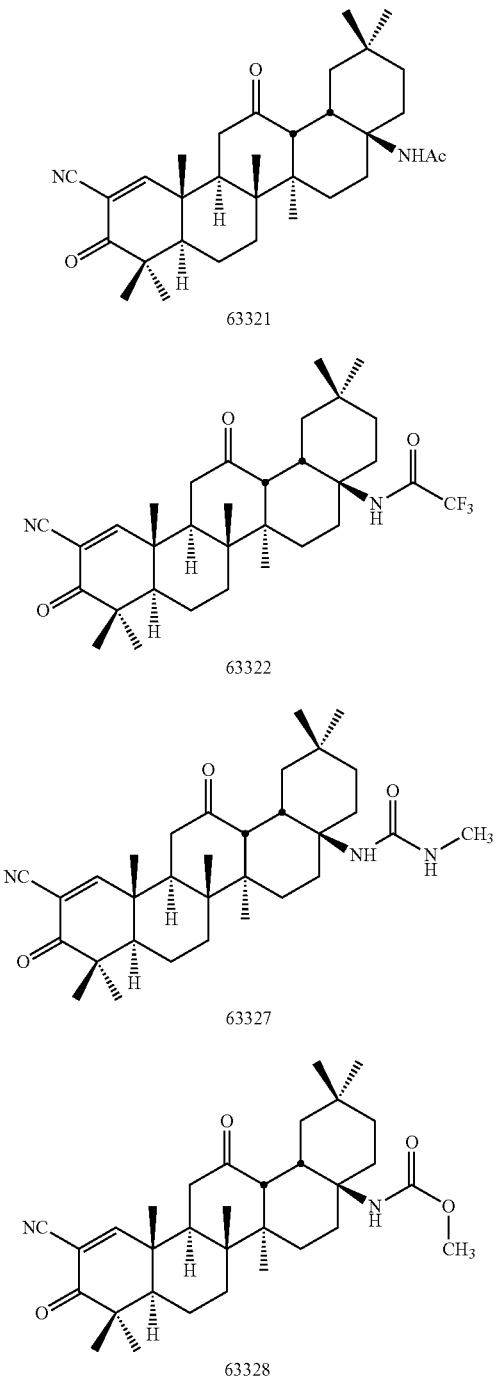

63321

63322

63327

63328

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

FIG. 43. Induction of HO-1. FIGS. 43A and 43B: MDA-MB-435 human melanoma cells were treated with vehicle (DMSO) or the indicated compounds and concentrations for 16 hours. HO-1 mRNA levels were quantified using qPCR and were normalized relative to a DMSO-treated sample run in parallel. Values are averages of duplicate wells. FIG. 43C: MDA-MB-435 cells were treated with vehicle (DMSO) or the indicated compounds at 400 nM for 16 hours. HO-1, TrxR1 and actin protein levels were assayed by immunoblotting. Actin served as a loading control.

FIGS. 44, 46 and 47—Induction of HO-1, TrxR1 and γ-GCS. FIGS. 44A-C, 45A-C, 46A-C, 47A-C: MDA-MB-435 human melanoma cells were treated with vehicle (DMSO) or the indicated compounds (400 nM) for 16 hours. HO-1, thioredoxin reductase-1 (TrxR1), and γ-glutamylcysteine synthetase (γ-GCS) mRNA levels were quantified using qPCR and were normalized relative to a DMSO-treated sample run in parallel. Values are averages of duplicate wells.

FIG. 45. Induction of HO-1, TrxR1 and γ-GCS. FIGS. 45 A-C: MDA-MB-435 cells were treated with vehicle (DMSO) or the indicated compounds at 160 nM for 16 hours. HO-1, TrxR1, and γ-GCS mRNA levels were quantified by qPCR and were normalized relative to a DMSO-treated sample run in parallel. Values are averages of duplicate wells. FIGS. 44D, 46D, 47D: MDA-MB-435 cells were treated with vehicle (DMSO) or the indicated compounds at 160 nM for 16 hours. HO-1, TrxR1 and actin protein levels were assayed by immunoblotting.

DESCRIPTION OF ILLUSTRATIVE EMBODIMENTS

Figure 1:
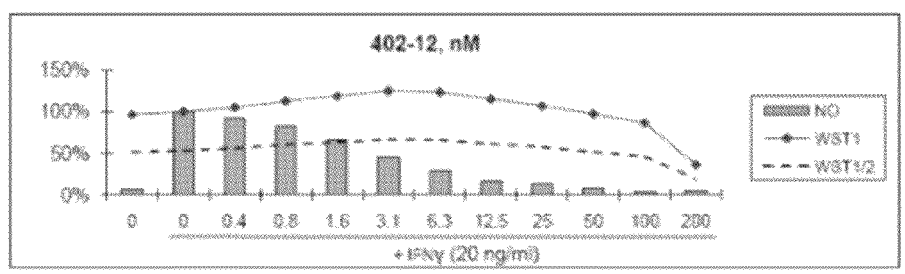
FIGS. 1-34 and 49-52. Inhibition of NO Production. RAW264.7 macrophages were pre-treated with DMSO or drugs at various concentrations (nM) for 2 hours, then treated with 20 ng/ml IFNγ for 24 hours. NO concentration in media was determined using the Griess reagent system; cell viability was determined using WST-1 reagent.
Figure 2:
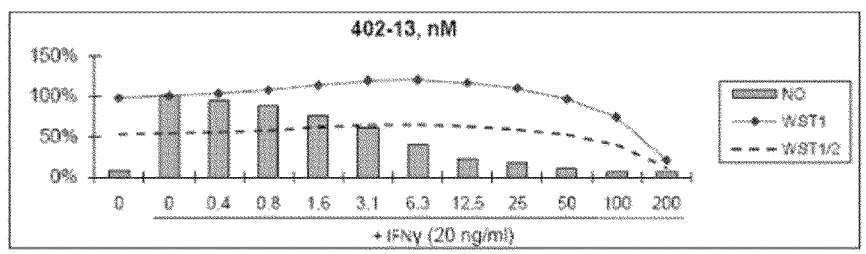
Figure 3:
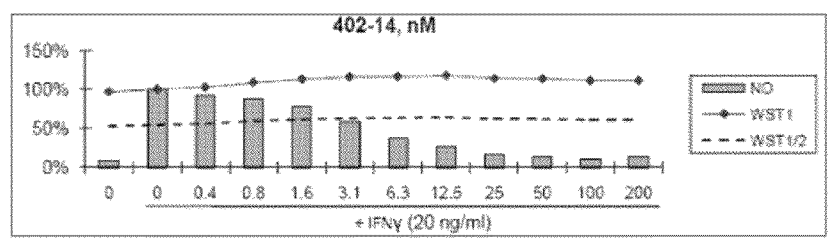
Figure 4:
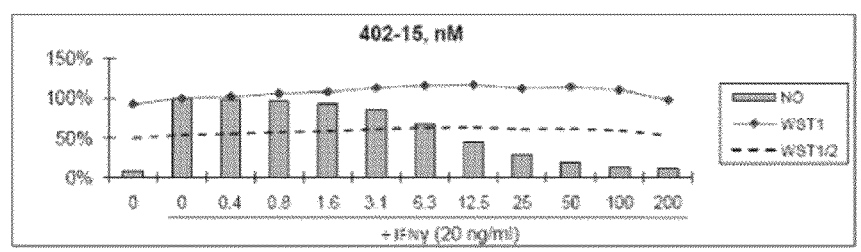
Figure 5:
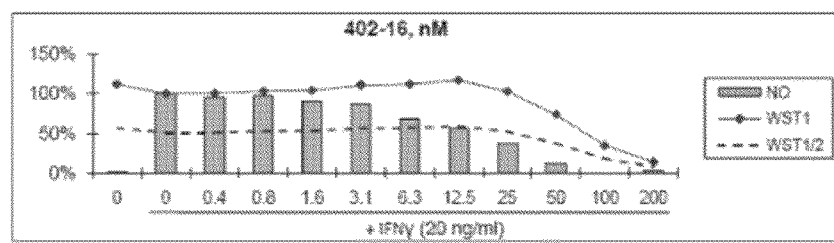
Figure 6:
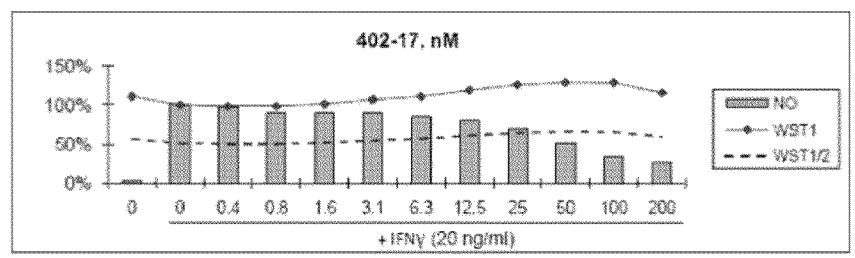
Figure 7:
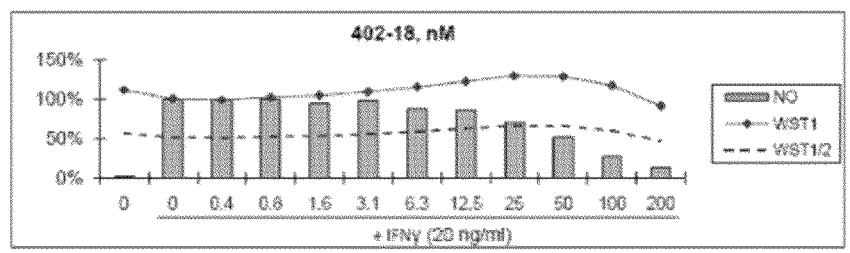
Figure 8:
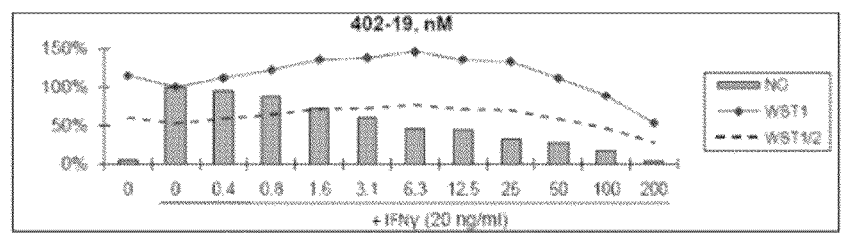
Figure 9:
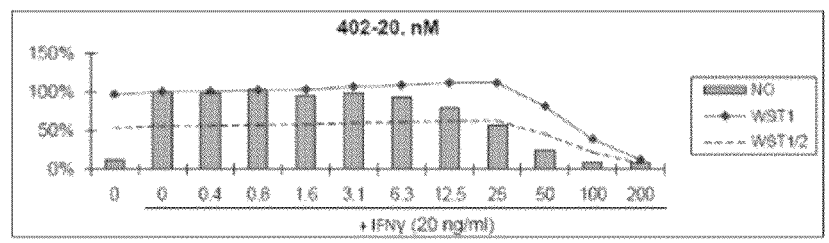
Figure 10:
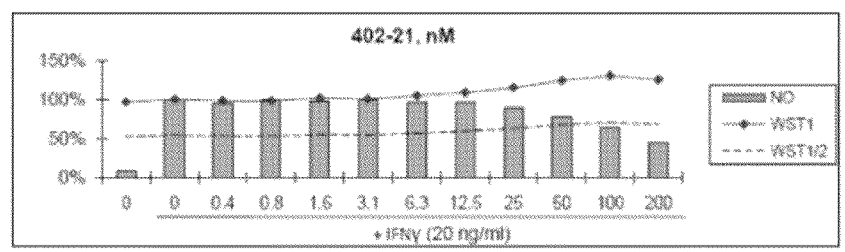
Figure 11:
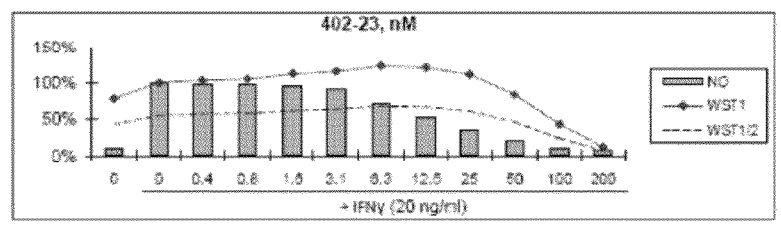
Figure 12:
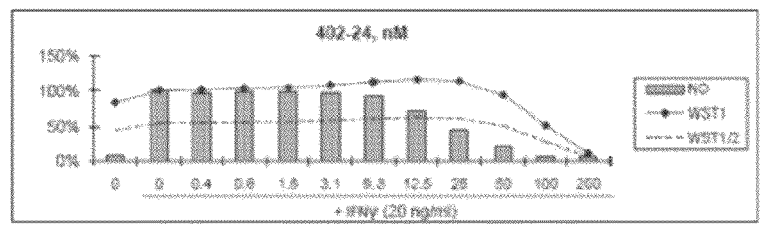
Figure 13:
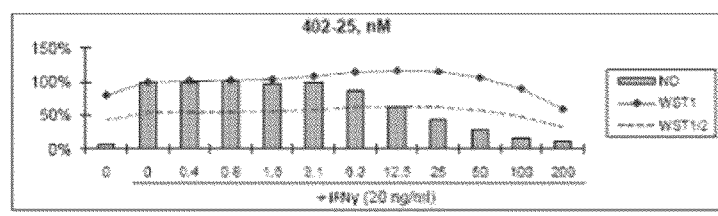
Figure 14:
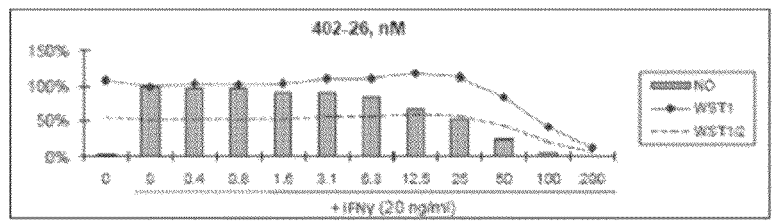
Figure 15:
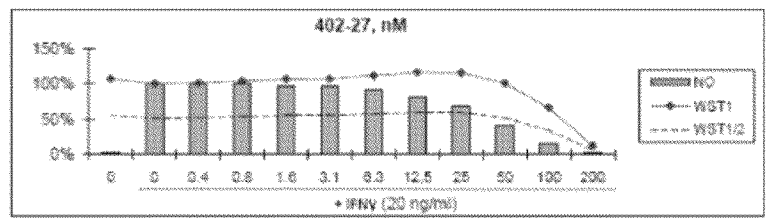
Figure 16:
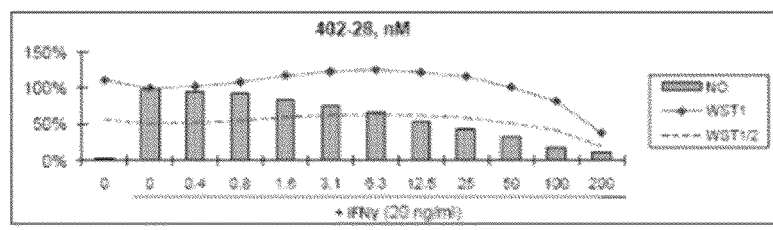
Figure 17:
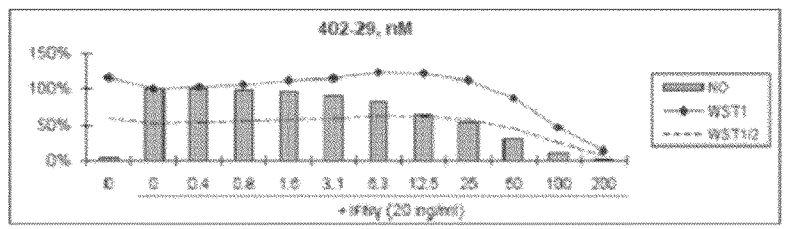
Figure 18:
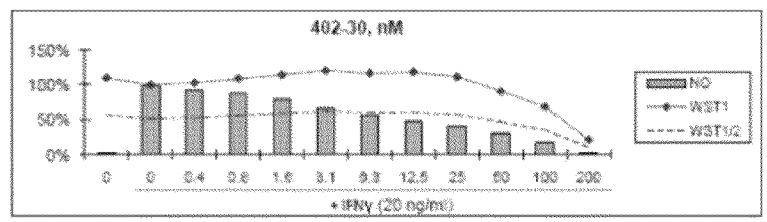
Figure 19:
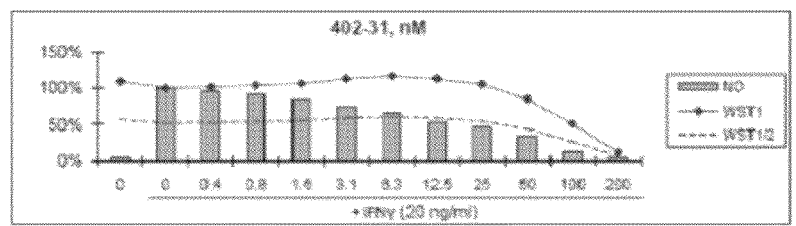
Figure 20:
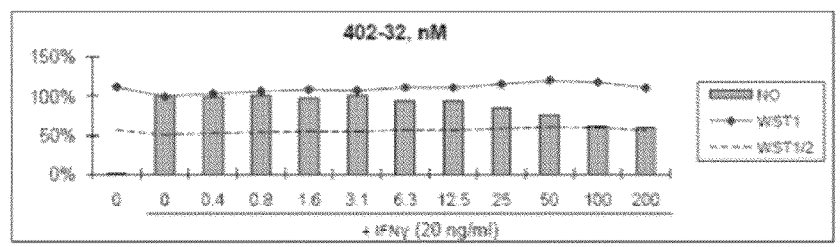
Figure 21:
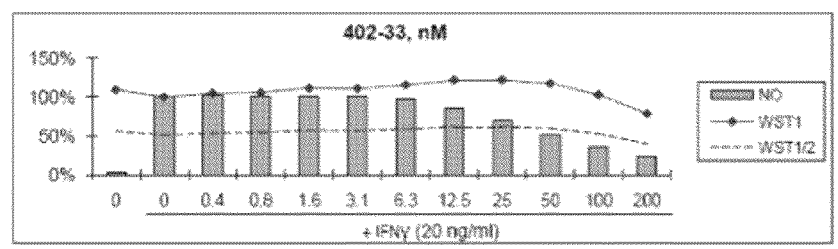
Figure 22:
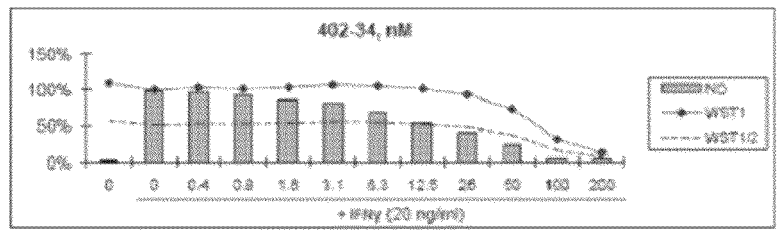
Figure 23:
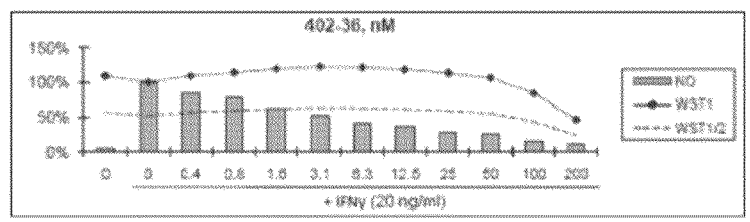
Figure 24:
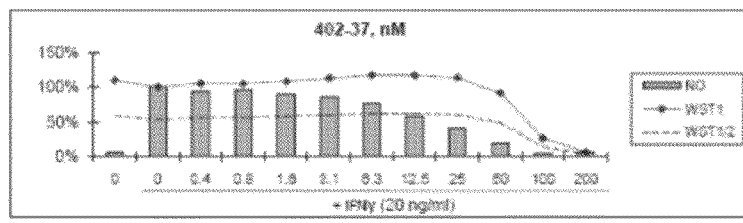
Figure 25:
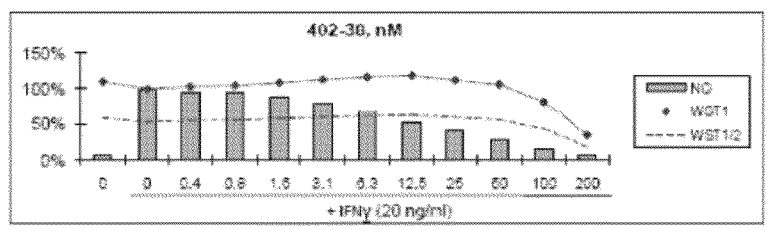
Figure 26:
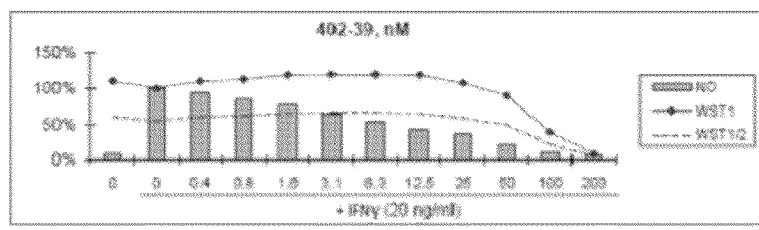
Figure 27:
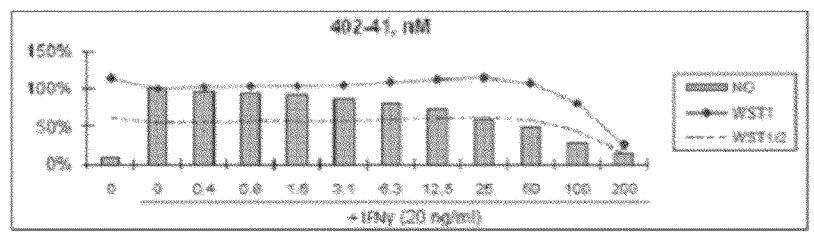
Figure 28:
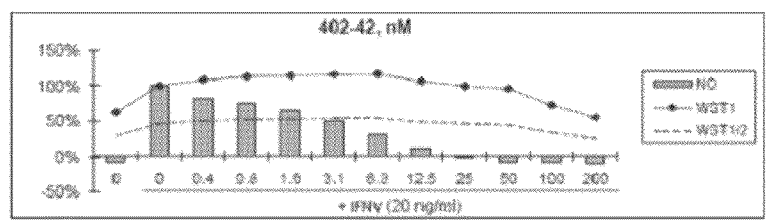
Figure 29:
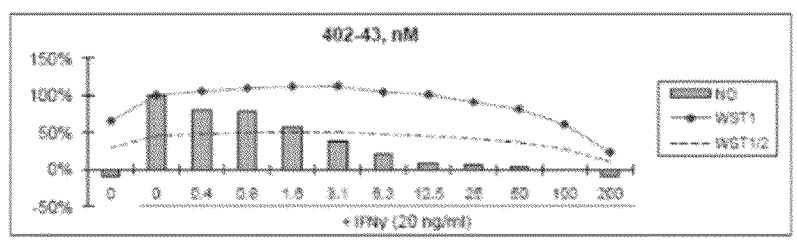
Figure 30:
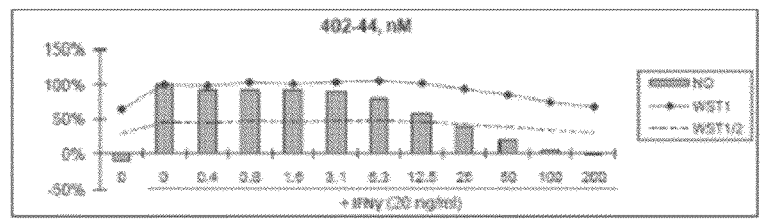
Figure 31:
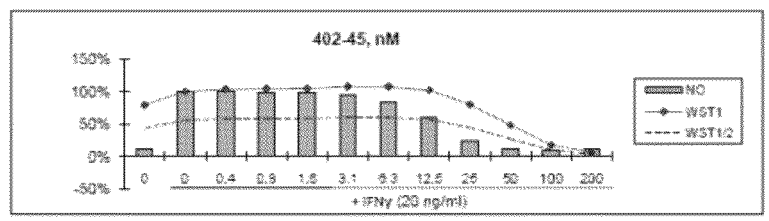
Figure 32:
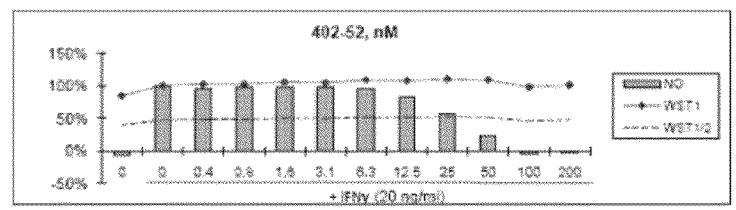
Figure 33:
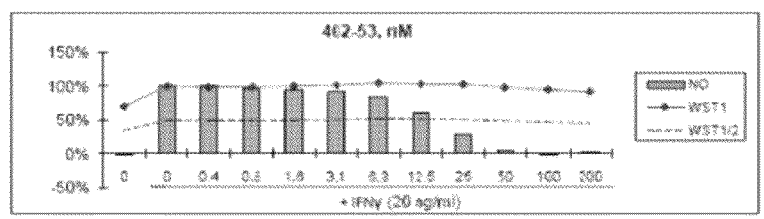
Figure 34:
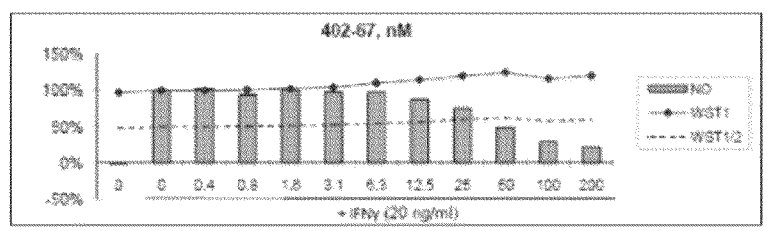

Disclosed herein are, for example, new compounds with antioxidant and anti-inflammatory properties, methods for their manufacture, and methods for their use, including for the treatment and/or prevention of disease.

I. Definitions

As used herein, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylamino); "cyano" means —CN; "azido" means —N$_3$; "mercapto" means —SH; "thio" means =S; "sulfonamido" means —NHS(O)$_2$— (see below for definitions of groups containing the term sulfonamido, e.g., alkylsulfonamido); "sulfonyl" means —S(O)$_2$— (see below for definitions of groups containing the term sulfonyl, e.g., alkylsulfonyl); and "silyl" means —SiH$_3$ (see below for definitions of group(s) containing the term silyl, e.g., alkylsilyl).

For the groups below, the following parenthetical subscripts further define the groups as follows: "(Cn)" defines the exact number (n) of carbon atoms in the group. "(C≤n)" defines the maximum number (n) of carbon atoms that can be in the group, with the minimum number of carbon atoms in such at least one, but otherwise as small as possible for the group in question. E.g., it is understood that the minimum number of carbon atoms in the group "alkenyl$_{(C≤8)}$" is 2. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3-10 carbon atoms)). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3-10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$.

The term "alkanediyl" when used without the "substituted" modifier refers to a non-aromatic divalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

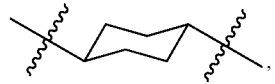 [SMILES: *C1CCC(*)CC1]

, are non-limiting examples of alkanediyl groups. The term "substituted alkanediyl" refers to a non-aromatic monovalent group, wherein the alkynediyl group is attached with two σ-bonds, with one or two saturated carbon atom(s) as the point(s) of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkanediyl groups: —CH(F)—, —CF$_2$—, —CH(Cl)—, —CH(OH)—, —CH(OCH$_3$)—, and —CH$_2$CH(Cl)—.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH=CHF, —CH=CHCl and —CH=CHBr, are non-limiting examples of substituted alkenyl groups.

The term "alkenediyl" when used without the "substituted" modifier refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

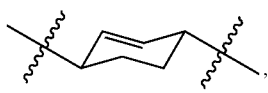 [SMILES: *C1C=CC(*)CC1]

are non-limiting examples of alkenediyl groups. The term "substituted alkenediyl" refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and at least one atom independently selected from the group consisting of N, O, F, Cl, Br, I, Si, P, and S. The following groups are non-limiting examples of substituted alkenediyl groups: —CF=CH—, —C(OH)=CH—, and —CH$_2$CH=C(Cl)—.

The term "alkynyl" when used without the "substituted" modifier refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and —CH$_2$C≡CCH$_3$, are non-limiting examples of alkynyl groups. The term "substituted alkynyl" refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH$_3$)$_3$, is a non-limiting example of a substituted alkynyl group.

The term "alkynediyl" when used without the "substituted" modifier refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and no atoms other than carbon and hydrogen. The groups, —C≡C—, —C≡CCH$_2$—, and —C≡CCH(CH$_3$)— are non-limiting examples of alkynediyl groups. The term "substituted alkynediyl" refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and at least one atom independently selected from the group consisting of N, O, F, Cl, Br, I, Si, P, and S. The groups —C≡CCFH— and —C≡CHCH(Cl)— are non-limiting examples of substituted alkynediyl groups.

The term "aryl" when used without the "substituted" modifier refers to a monovalent group with an aromatic carbon atom as the point of attachment, said carbon atom forming part of a six-membered aromatic ring structure wherein the ring atoms are all carbon, and wherein the monovalent group consists of no atoms other than carbon and hydrogen. Non-limiting examples of aryl groups include phenyl (Ph), methylphenyl, (dimethyl)phenyl, —C$_6$H$_4$CH$_2$CH$_3$ (ethylphenyl), —C$_6$H$_4$CH$_2$CH$_2$CH$_3$ (propylphenyl), —C$_6$H$_4$CH(CH$_3$)$_2$, —C$_6$H$_4$CH(CH$_2$)$_2$, —C$_6$H$_3$(CH$_3$)CH$_2$CH$_3$ (methylethylphenyl), —C$_6$H$_4$CH=CH$_2$ (vinylphenyl), —C$_6$H$_4$CH=CHCH$_3$, —C$_6$H$_4$C≡CH, —C$_6$H$_4$C≡CCH$_3$, naphthyl, and the monovalent group derived from biphenyl. The term "substituted aryl" refers to a monovalent group with an aromatic carbon atom as the point of attachment, said carbon atom forming part of a six-membered aromatic ring structure wherein the ring atoms are all carbon, and wherein the monovalent group further has at least one atom independently selected from the group consisting of N, O, F, Cl, Br, I, Si, P, and S. Non-limiting examples of substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OC(O)CH$_3$, —C$_6$H$_4$NH$_2$, C$_6$H$_4$NHCH$_3$, —C$_6$H$_4$N(CH$_3$)$_2$, —C$_6$H$_4$CH$_2$OH, —C$_6$H$_4$CH$_2$OC(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, and —C$_6$H$_4$CON(CH$_3$)$_2$.

The term "arenediyl" when used without the "substituted" modifier refers to a divalent group, wherein the arenediyl group is attached with two σ-bonds, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of arenediyl groups include:

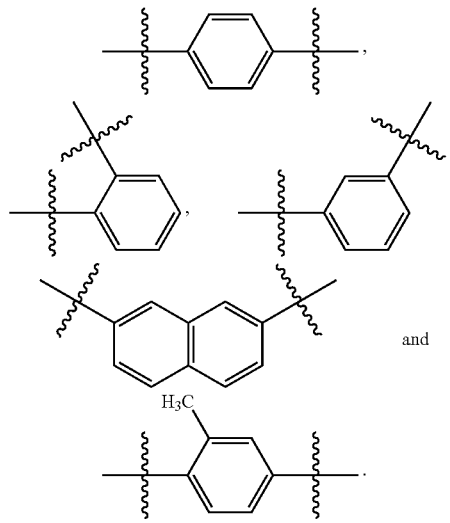

and

The term "substituted arenediyl" refers to a divalent group, wherein the arenediyl group is attached with two σ-bonds, with two aromatic carbon atoms as points of attachment, said carbon atoms forming part of one or more six-membered aromatic rings structure(s), wherein the ring atoms are all carbon, and wherein the divalent group further has at least one atom independently selected from the group consisting of N, O, F, Cl, Br, I, Si, P, and S.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl (phenylcarbonylmethyl), 2-chloro-2-phenyl-ethyl, chromanyl where the point of attachment is one of the saturated carbon atoms, and tetrahydroquinolinyl where the point of attachment is one of the saturated atoms.

The term "heteroaryl" when used without the "substituted" modifier refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

The term "heteroarenediyl" when used without the "substituted" modifier refers to a divalent group, wherein the heteroarenediyl group is attached with two σ-bonds, with an aromatic carbon atom or nitrogen atom as the point of attachment, said carbon atom or nitrogen atom two aromatic atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of heteroarenediyl groups include:

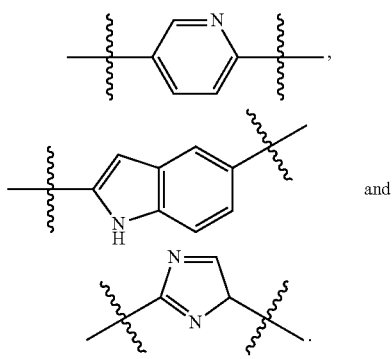

The term "substituted heteroarenediyl" refers to a divalent group, wherein the heteroarenediyl group is attached with two σ-bonds, with two aromatic carbon atoms as points of attachment, said carbon atoms forming part of one or more six-membered aromatic rings structure(s), wherein the ring atoms are all carbon, and wherein the divalent group further has at least one atom independently selected from the group consisting of N, O, F, Cl, Br, I, Si, P, and S.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of aralkyls are: pyridylmethyl, and thienylmethyl. When the term "heteroaralkyl" is used with the "substituted" modifier, either one or both the alkanediyl and the heteroaryl is substituted.

The term "acyl" when used without the "substituted" modifier refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, —COC$_6$H$_3$(CH$_3$)$_2$, and —C(O)CH$_2$C$_6$H$_5$, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group with a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH$_2$CF$_3$, —CO$_2$H (carboxyl), —CO$_2$CH$_3$ (methylcarboxyl), —CO$_2$CH$_2$CH$_3$, —CO$_2$CH$_2$CH$_2$CH$_3$, —CO$_2$C$_6$H$_5$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, —CONHCH$_2$CF$_3$, —CO-pyridyl, —CO-imidazoyl, and —C(O)N$_3$, are non-limiting examples of substituted acyl groups. The term "substituted acyl" encompasses, but is not limited to, "heteroaryl carbonyl" groups.

The term "alkylidene" when used without the "substituted" modifier refers to the divalent group =CRR', wherein the alkylidene group is attached with one σ-bond and one π-bond, in which R and R' are independently hydrogen, alkyl, or R and R' are taken together to represent alkanediyl. Non-limiting examples of alkylidene groups include: =CH$_2$, =CH(CH$_2$CH$_3$), and =C(CH$_3$)$_2$. The term "substituted alkylidene" refers to the group =CRR', wherein the alkylidene group is attached with one σ-bond and one π-bond, in which R and R' are independently hydrogen, alkyl, substituted alkyl, or R and R' are taken together to represent a substituted alkanediyl, provided that either one of R and R' is a substituted alkyl or R and R' are taken together to represent a substituted alkanediyl.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The term "substituted alkoxy" refers to the group —OR, in which R is a substituted alkyl, as that term is defined above. For example, —OCH$_2$CF$_3$ is a substituted alkoxy group.

Similarly, the terms "alkenyloxy", "alkynyloxy", "aryloxy", "aralkoxy", "heteroaryloxy", "heteroaralkoxy" and "acyloxy", when used without the "substituted" modifier, refers to groups, defined as —OR, in which R is alkenyl, alkynyl, aryl, aralkyl, heteroaryl, heteroaralkyl and acyl, respectively, as those terms are defined above. When any of the terms alkenyloxy, alkynyloxy, aryloxy, aralkyloxy and acyloxy is modified by "substituted," it refers to the group —OR, in which R is substituted alkenyl, alkynyl, aryl, aralkyl, heteroaryl, heteroaralkyl and acyl, respectively.

The term "alkylamino" when used without the "substituted" modifier refers to the group —NHR, in which R is an alkyl, as that term is defined above. Non-limiting examples of alkylamino groups include: —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH (CH$_3$)CH$_2$CH$_3$, —NHCH$_2$CH(CH$_3$)$_2$, —NHC(CH$_3$)$_3$, —NH-cyclopentyl, and —NH-cyclohexyl. The term "substituted alkylamino" refers to the group —NHR, in which R is a substituted alkyl, as that term is defined above. For example, —NHCH$_2$CF$_3$ is a substituted alkylamino group.

The term "dialkylamino" when used without the "substituted" modifier refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include: —NHC(CH$_3$)$_3$, —N(CH$_3$)CH$_2$CH$_3$, —N(CH$_2$CH$_3$)$_2$, N-pyrrolidinyl, and N-piperidinyl. The term "substituted dialkylamino" refers to the group —NRR', in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached to the nitrogen atom.

The terms "alkoxyamino", "alkenylamino", "alkynylamino", "arylamino", "aralkylamino", "heteroarylamino", "heteroaralkylamino", and "alkylsulfonylamino" when used without the "substituted" modifier, refers to groups, defined as —NHR, in which R is alkoxy, alkenyl, alkynyl, aryl, aralkyl, heteroaryl, heteroaralkyl and alkylsulfonyl, respectively, as those terms are defined above. A non-limiting example of an arylamino group is —NHC$_6$H$_5$. When any of the terms alkoxyamino, alkenylamino, alkynylamino, arylamino, aralkylamino, heteroarylamino, hetero aralkyl amino and alkylsulfonylamino is modified by "substituted," it refers to the group —NHR, in which R is substituted alkoxy, alkenyl, alkynyl, aryl, aralkyl, heteroaryl, heteroaralkyl and alkylsulfonyl, respectively.

The term "amido" (acylamino), when used without the "substituted" modifier, refers to the group —NHR, in which R is acyl, as that term is defined above. A non-limiting example of an acylamino group is —NHC(O)CH$_3$. When the term amido is used with the "substituted" modifier, it refers to groups, defined as —NHR, in which R is substituted acyl, as that term is defined above. The groups —NHC(O)OCH$_3$ and —NHC(O)NHCH$_3$ are non-limiting examples of substituted amido groups.

The term "alkylimino" when used without the "substituted" modifier refers to the group =NR, wherein the alkylimino group is attached with one σ-bond and one π-bond, in which R is an alkyl, as that term is defined above. Non-limiting examples of alkylimino groups include: =NCH$_3$, =NCH$_2$CH$_3$ and =N-cyclohexyl. The term "substituted alkylimino" refers to the group =NR, wherein the alkylimino group is attached with one σ-bond and one π-bond, in which R is a substituted alkyl, as that term is defined above. For example, =NCH$_2$CF$_3$ is a substituted alkylimino group.

Similarly, the terms "alkenylimino", "alkynylimino", "arylimino", "aralkylimino", "heteroarylimino", "heteroaralkylimino" and "acylimino", when used without the "substituted" modifier, refers to groups, defined as =NR, wherein the alkylimino group is attached with one σ-bond and one π-bond, in which R is alkenyl, alkynyl, aryl, aralkyl, heteroaryl, heteroaralkyl and acyl, respectively, as those terms are defined above. When any of the terms alkenylimino, alkynylimino, arylimino, aralkylimino and acylimino is modified by "substituted," it refers to the group =NR, wherein the alkylimino group is attached with one σ-bond and one π-bond, in which R is substituted alkenyl, alkynyl, aryl, aralkyl, heteroaryl, heteroaralkyl and acyl, respectively.

The term "fluoroalkyl" when used without the "substituted" modifier refers to an alkyl, as that term is defined above, in which one or more fluorines have been substituted for hydrogens. The groups, —CH$_2$F, —CF$_3$, and —CH$_2$CF$_3$ are non-limiting examples of fluoroalkyl groups. The term "substituted fluoroalkyl" refers to a non-aromatic monovalent group with a saturated carbon atom as the point of attachment, a linear or branched, cyclo, cyclic or acyclic structure, at least one fluorine atom, no carbon-carbon double or triple bonds, and at least one atom independently selected from the group consisting of N, O, Cl, Br, I, Si, P, and S. The following group is a non-limiting example of a substituted fluoroalkyl: —CFHOH.

The term "alkylthio" when used without the "substituted" modifier refers to the group —SR, in which R is an alkyl, as that term is defined above. Non-limiting examples of alkylthio groups include: —SCH$_3$, —SCH$_2$CH$_3$, —SCH$_2$CH$_2$CH$_3$, —SCH(CH$_3$)$_2$, —SCH(CH$_2$)$_2$, —S-cyclopentyl, and —S-cyclohexyl. The term "substituted alkylthio" refers to the group —SR, in which R is a substituted alkyl, as that term is defined above. For example, —SCH$_2$CF$_3$ is a substituted alkylthio group.

Similarly, the terms "alkenylthio", "alkynylthio", "arylthio", "aralkylthio", "heteroarylthio", "heteroaralkylthio", and "acylthio", when used without the "substituted" modifier, refers to groups, defined as —SR, in which R is alkenyl, alkynyl, aryl, aralkyl, heteroaryl, heteroaralkyl and acyl, respectively, as those terms are defined above. When any of the terms alkenylthio, alkynylthio, arylthio, aralkylthio, heteroarylthio, heteroaralkylthio, and acylthio is modified by "substituted," it refers to the group —SR, in which R is substituted alkenyl, alkynyl, aryl, aralkyl, heteroaryl, heteroaralkyl and acyl, respectively.

The term "thioacyl" when used without the "substituted" modifier refers to a monovalent group with a carbon atom of a thiocarbonyl group as the point of attachment, further having a linear or branched, cyclo, cyclic or acyclic structure, further having no additional atoms that are not carbon or hydrogen, beyond the sulfur atom of the carbonyl group. The groups, —CHS, —C(S)CH$_3$, —C(S)CH$_2$CH$_3$, —C(S)CH$_2$CH$_2$CH$_3$, —C(S)CH(CH$_3$)$_2$, —C(S)CH(CH$_2$)$_2$, —C(S)C$_6$H$_5$, —C(S)C$_6$H$_4$CH$_3$, —C(S)C$_6$H$_4$CH$_2$CH$_3$, —C(S)C$_6$H$_3$(CH$_3$)$_2$, and —C(S)CH$_2$C$_6$H$_5$, are non-limiting examples of thioacyl groups. The term "thioacyl" therefore encompasses, but is not limited to, groups sometimes referred to as "alkyl thiocarbonyl" and "aryl thiocarbonyl" groups. The term "substituted thioacyl" refers to a radical with a carbon atom as the point of attachment, the carbon atom being part of a thiocarbonyl group, further having a linear or branched, cyclo, cyclic or acyclic structure, further having at least one atom, in addition to the sulfur atom of the carbonyl group, independently selected from the group consisting of N, O, F, Cl, Br, I, Si, P, and S. The groups, —C(S)CH$_2$CF$_3$, —C(S)O$_2$H, —C(S)OCH$_3$, —C(S)OCH$_2$CH$_3$, —C(S)OCH$_2$CH$_2$CH$_3$, —C(S)OC$_6$H$_5$, —C(S)OCH(CH$_3$)$_2$, —C(S)OCH(CH$_2$)$_2$, —C(S)NH$_2$, and —C(S)NHCH$_3$, are non-limiting examples of substituted thioacyl groups. The term "substituted thioacyl" encompasses, but is not limited to, "heteroaryl thiocarbonyl" groups.

The term "alkylsulfonyl" when used without the "substituted" modifier refers to the group —S(O)₂R, in which R is an alkyl, as that term is defined above. Non-limiting examples of alkylsulfonyl groups include: —S(O)₂CH₃, —S(O)₂CH₂CH₃, —S(O)₂CH₂CH₂CH₃, —S(O)₂CH(CH₃)₂, —S(O)₂CH(CH₂)₂, —S(O)₂-cyclopentyl, and —S(O)₂-cyclohexyl. The term "substituted alkylsulfonyl" refers to the group —S(O)₂R, in which R is a substituted alkyl, as that term is defined above. For example, —S(O)₂CH₂CF₃ is a substituted alkylsulfonyl group.

Similarly, the terms "alkenylsulfonyl", "alkynylsulfonyl", "arylsulfonyl", "aralkylsulfonyl", "heteroarylsulfonyl", and "heteroaralkylsulfonyl" when used without the "substituted" modifier, refers to groups, defined as —S(O)₂R, in which R is alkenyl, alkynyl, aryl, aralkyl, heteroaryl, and heteroaralkyl, respectively, as those terms are defined above. When any of the terms alkenylsulfonyl, alkynylsulfonyl, arylsulfonyl, aralkylsulfonyl, heteroarylsulfonyl, and heteroaralkylsulfonyl is modified by "substituted," it refers to the group —S(O)₂R, in which R is substituted alkenyl, alkynyl, aryl, aralkyl, heteroaryl and heteroaralkyl, respectively.

The term "alkylammonium" when used without the "substituted" modifier refers to a group, defined as —NH₂R⁺, —NHRR'⁺, or —NRR'R"⁺, in which R, R' and R" are the same or different alkyl groups, or any combination of two of R, R' and R" can be taken together to represent an alkanediyl. Non-limiting examples of alkylammonium cation groups include: —NH₂(CH₃)⁺, —NH₂(CH₂CH₃)+, —NH₂(CH₂CH₂CH₃)+, —NH(CH₃)₂⁺, —NH(CH₂CH₃)₂⁺, —NH(CH₂CH₂CH₃)₂⁺, —N(CH₃)₃⁺, —N(CH₃)(CH₂CH₃)₂⁺, —N(CH₃)₂(CH₂CH₃)⁺, —NH₂C(CH₃)₃⁺, —NH(cyclopentyl)₂⁺, and —NH₂(cyclohexyl)⁺. The term "substituted alkylammonium" refers —NH₂R⁺, —NHRR'⁺, or —NRR'R"⁺, in which at least one of R, R' and R" is a substituted alkyl or two of R, R' and R" can be taken together to represent a substituted alkanediyl. When more than one of R, R' and R" is a substituted alkyl, they can be the same of different. Any of R, R' and R" that are not either substituted alkyl or substituted alkanediyl, can be either alkyl, either the same or different, or can be taken together to represent a alkanediyl with two or more carbon atoms, at least two of which are attached to the nitrogen atom shown in the formula.

The term "alkylsulfonium" when used without the "substituted" modifier refers to the group —SRR'⁺, in which R and R' can be the same or different alkyl groups, or R and R' can be taken together to represent an alkanediyl. Non-limiting examples of alkylsulfonium groups include: —SH(CH₃)⁺, —SH(CH₂CH₃)⁺, —SH(CH₂CH₂CH₃)⁺, —S(CH₃)₂⁺, —S(CH₂CH₃)₂⁺, —S(CH₂CH₂CH₃)₂⁺, SH(cyclopentyl)⁺, and —SH(cyclohexyl)⁺. The term "substituted alkylsulfonium" refers to the group —SRR'⁺, in which R and R' can be the same or different substituted alkyl groups, one of R or R' is an alkyl and the other is a substituted alkyl, or R and R' can be taken together to represent a substituted alkanediyl. For example, —SH(CH₂CF₃)⁺ is a substituted alkylsulfonium group.

The term "alkylsilyl" when used without the "substituted" modifier refers to a monovalent group, defined as —SiH₂R, —SiHRR', or —SiRR'R", in which R, R' and R" can be the same or different alkyl groups, or any combination of two of R, R' and R" can be taken together to represent an alkanediyl. The groups, —SiH₂CH₃, —SiH(CH₃)₂, —Si(CH₃)₃ and —Si(CH₃)₂C(CH₃)₃, are non-limiting examples of unsubstituted alkylsilyl groups. The term "substituted alkylsilyl" refers —SiH₂R, —SiHRR', or —SiRR'R", in which at least one of R, R' and R" is a substituted alkyl or two of R, R' and R" can be taken together to represent a substituted alkanediyl. When more than one of R, R' and R" is a substituted alkyl, they can be the same of different. Any of R, R' and R" that are not either substituted alkyl or substituted alkanediyl, can be either alkyl, either the same or different, or can be taken together to represent a alkanediyl with two or more saturated carbon atoms, at least two of which are attached to the silicon atom.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include ¹³C and ¹⁴C. Similarly, it is contemplated that one or more carbon atom(s) of a compound of the present disclosure may be replaced by a silicon atom(s). Furthermore, it is contemplated that one or more oxygen atom(s) of a compound of the present disclosure may be replaced by a sulfur or selenium atom(s).

A compound having a formula that is represented with a dashed bond is intended to include the formulae optionally having zero, one or more double bonds. Thus, for example, the structure

includes the structures

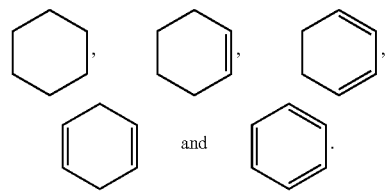

As will be understood by a person of skill in the art, no one such ring atom forms part of more than one double bond.

Any undefined valency on an atom of a structure shown in this application implicitly represents a hydrogen atom bonded to the atom.

A ring structure shown with an unconnected "R" group, indicates that any implicit hydrogen atom on that ring can be replaced with that R group. In the case of a divalent R group (e.g., oxo, imino, thio, alkylidene, etc.), any pair of implicit hydrogen atoms attached to one atom of that ring can be replaced by that R group. This concept is as exemplified below:

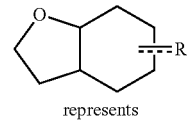

represents

-continued

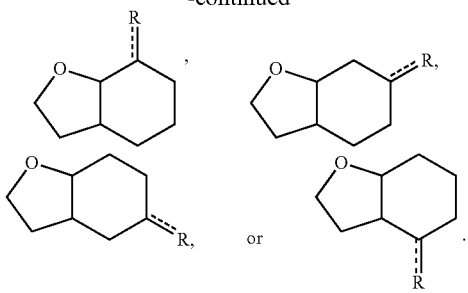

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalene-sulfonic acid, 3-phenylpropionic acid, 4,4'-methylenebis(3-hydroxy-2-ene-1-carboxylic acid), 4-methylbicyclo[2.2.2] oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002), As used herein, "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present disclosure. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methane-sulfonates, ethanesulfonates, benzenesulfonates, p-toluenesulfonates, cyclohexyl-sulfamates, quinates, esters of amino acids, and the like. Similarly, a compound comprising an amine group may be administered as an amide that is converted by hydrolysis in vivo to the amine compound.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

The invention contemplates that for any stereocenter or axis of chirality for which stereochemistry has not been defined, that stereocenter or axis of chirality can be present in its R form, S form, or as a mixture of the R and S forms, including racemic and non-racemic mixtures.

"Substituent convertible to hydrogen in vivo" means any group that is convertible to a hydrogen atom by enzymological or chemical means including, but not limited to, hydrolysis and hydrogenolysis. Examples include acyl groups, groups having an oxycarbonyl group, amino acid residues, peptide residues, o-nitrophenylsulfenyl, trimethylsilyl, tetrahydro-pyranyl, diphenylphosphinyl, hydroxy or alkoxy substituents on imino groups, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$), benzyloxycarbonyl, p-methoxy-benzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), tert-butoxycarbonyl groups (—C(O)OC(CH$_3$)$_3$), and the like. Suitable peptide residues include peptide residues comprising two to five, and optionally amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

"Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

As used herein, the term "water soluble" means that the compound dissolves in water at least to the extent of 0.010 mole/liter or is classified as soluble according to literature precedence.

Other abbreviations used herein are as follows: DMSO, dimethyl sulfoxide; NO, nitric oxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFNγ or IFN-γ, interferon-γ; LPS, bacterial endotoxic lipopolysaccharide; TNFα or TNF-α, tumor necrosis factor-α; IL-1β, interleukin-1β; GAPDH, glyceraldehyde-3-phosphate dehydrogenase; MTT, 3-[4,5-dimethylthiazol-2-yl]-2, 5-diphenyltetrazolium bromide; TCA, trichloroacetic acid; HO-1, inducible heme oxygenase.

The above definitions supersede any conflicting definition in any of the reference that is incorporated by reference herein. The fact that certain terms are defined, however, should not be considered as indicative that any term that is undefined is indefinite.

Rather, all terms used are believed to describe the invention in terms such that one of ordinary skill can appreciate the scope and practice the present disclosure.

II. Synthetic Methods

Compounds of the present disclosure may be made using the methods outlined in the Examples section (Example 2 and 3). These methods can be further modified and optimized using the principles and techniques of organic chemistry as applied by a person skilled in the art. Such principles and techniques are taught, for example, in March's Advanced Organic Chemistry: Reactions, Mechanisms, and Structure (2007), which is incorporated by reference herein.

III. Biological Activity of Oleanolic Acid Derivatives

Biological activity results are provided throughout the present disclosure. These include: inhibition of inhibition of NO production, iNOS induction, Nrf2 target gene induction, inhibition of COX-2 induction, inhibition of STAT3 phosphorylation, suppression of IL-6 induced phosphorylation, inhibition of TNFα-induced IκBα degradation, inhibition of NF-κB activation, induction of HO-1, induction of TrxR1, induction of γ-GCS, and/or induction of ferritin heavy chain.

See figures and figure descriptions. Suppression of NO production and induction of Nrf2 induction results can be respectively summarized as shown Tables 1a and 1b, below. Further results, including toxicity studies, are provided in the Examples section.

TABLE 1a

Suppression of IFNγ-Induced NO Production.

| | | RAW264.7 | | | |
|---|---|---|---|---|---|
| Compound ID(s) | MW | NO IC$_{50}$ (nM) | WST-1 IC$_{50}$ (nM) | iNOS suppr. qPCR | iNOS suppr. WB |
| 63167 (402-12) | 520.70 | 2 | 180 | ~50% | ~90% |
| 63168 402-13 | 534.70 | 3.2 | 150 | | |
| 63169 402-14 | 462.70 | 3.6 | >200 | ~50% | ~90% |
| 63170 402-15 | 504.70 | 10.8 | >200 | | |
| 63171 402-16 | 558.70 | 12 | 90 | | |
| 63172 402-17 | 519.70 | 30 | >200 | | |
| 63173 402-18 | 533.70 | 31 | >200 | | |
| 63175 402-19 | 540.80 | 2 | 200 | ~65% | ~90% |
| 63174 402-20 | 596.80 | 26 | 80 | | |
| 63176 402-21 | 505.70 | 100 | >200 | | |
| 63178 402-23 | 556.70 | 6.8 | 80 | | |
| 63179 402-24 | 527.20 | 16 | 100 | | |
| 63180 402-25 | 533.74 | 13.5 | 200 | | |
| 63181 402-26 | 573.80 | est. 4-8 | 75 | | |
| 63182 402-27 | 566.80 | est. 7-13 | 125 | | |
| 63183 402-28 | 516.70 | 4 | 150 | 50% | ~90% |
| 63186 402-29 | 546.70 | est. 3-6 | 100 | | |
| 63243 402-30 | 566.80 | 2.9 | 150 | 50% | ~90% |

TABLE 1a-continued

Suppression of IFNγ-Induced NO Production.

| | | RAW264.7 | | | |
|---|---|---|---|---|---|
| Compound ID(s) | MW | NO IC$_{50}$ (nM) | WST-1 IC$_{50}$ (nM) | iNOS suppr. qPCR | iNOS suppr. WB |
| 63187 402-31 | 608.90 | est. 2-5 | 100 | | >90% |
| 63185 402-32 | 589.81 | 91 | >200 | 0% | 0% |
| 63188 402-33 | 575.78 | 27 | >200 | | |
| 63184 402-34 | 548.80 | 14.5 | 75 | | |
| 63193 402-36 | 554.80 | 1.5 | >200 | ~65% | >90% |
| 63244 402-37 | 580.80 | 10 | 200 | | |
| 63189 402-38 | 518.70 | 7.5 | 75 | | |
| 63192 402-39 | 502.80 | 2.8 | 150 | ~60% | >90% |
| 63245 402-41 | 490.72 | 33 | >200 | | |
| 63246 402-42 | 514.70 | ~3 | >200 | | >90% |
| 63247 402-43 | 608.80 | ~2 | 150 | | >90% |
| 63148 402-44 | 597.80 | ~25 | >200 | | |
| 63249 402-45 | 581.79 | | 50 | | |
| 63198 402-52 | 464.68 | ~30 | >200 | | |
| 63215 402-53 | 542.77 | ~15 | >200 | | |
| 63208 402-67 | 465.67 | ~40 | >200 | | |
| 63222 | 503.72 | ~45 | >200 | | |
| 63236 | 532.80 | ~120 | >200 | | |
| 63238 | 492.74 | ~120 | >200 | | |
| 63254 | 492.74 | ~25 | >200 | | |
| 63265 | 578.80 | ~100 | >200 | | |
| 63321 | 506.70 | ~70 | See FIG. | | |
| 63322 | 560.70 | ~50 | See FIG. | | |
| 63327 | 521.70 | ~100 | See FIG. | | |
| 63328 | 522.70 | ~25 | See FIG. | | |

Blank entry: Not determined.

TABLE 1b

Induction of HO-1, TrxR1 and γ-GCS in Human Melanoma Cells.

Nrf2 target gene induction in MDA-MB-435 cells

| Compound ID(s) | 160 nM* | | | 400 nM* | | | 250 nM** | | |
|---|---|---|---|---|---|---|---|---|---|
| | HO-1 | TrxR1 | γ-GCS | HO-1 | TrxR1 | γ-GCS | HO-1 | NQO1 | γ-GCS |
| 402-12 | | | | 61 | 62 | | | | |
| 402-14 | 2 | 129 | 73 | | | | | | |
| 402-17 | 4 | 43 | 27 | | | | | | |
| 402-19 | 15 | 86 | 64 | 10 | 48 | | | | |
| 402-28 | 28 | 71 | 55 | | | | | | |
| 402-30 | 25 | 57 | 36 | | | | | | |
| 402-31 | | | | 32 | 90 | 90 | | | |
| 402-32 | 1 | 71 | 27 | | | | | | |
| 402-36 | 6 | 86 | 55 | | | | | | |
| 402-39 | 1 | 14 | 9 | | | | | | |
| 402-42 | | | | 25 | 66 | 77 | | | |
| 402-43 | | | | 19 | 76 | 75 | | | |
| 402-52 | | | | 2 | 71 | | 1.4 | 1.8 | 2.8 |
| 402-53 | | | | 1 | 36 | 21 | 1.7 | 1.7 | 3.8 |

TABLE 1b-continued

Induction of HO-1, TrxR1 and γ-GCS in Human Melanoma Cells.

Nrf2 target gene induction in MDA-MB-435 cells

| Compound ID(s) | 160 nM* | | | 400 nM* | | | 250 nM** | | |
|---|---|---|---|---|---|---|---|---|---|
| | HO-1 | TrxR1 | γ-GCS | HO-1 | TrxR1 | γ-GCS | HO-1 | NQO1 | γ-GCS |
| 402-67 | | | | | | | 1.1 | 1.7 | 3.2 |
| 63254 | | | | | | | 2 | 1.7 | 3 |

Blank entry: Not determined.
*Data expressed as a percent of induction observed for RTA 402.
**Data expressed as fold induction above DMSO control.

IV. Diseases Associated with Inflammation and/or Oxidative Stress

Inflammation is a biological process that provides resistance to infectious or parasitic organisms and the repair of damaged tissue. Inflammation is commonly characterized by localized vasodilation, redness, swelling, and pain, the recruitment of leukocytes to the site of infection or injury, production of inflammatory cytokines such as TNF-α and IL-1, and production of reactive oxygen or nitrogen species such as hydrogen peroxide, superoxide and peroxynitrite. In later stages of inflammation, tissue remodeling, angiogenesis, and scar formation (fibrosis) may occur as part of the wound healing process. Under normal circumstances, the inflammatory response is regulated and temporary and is resolved in an orchestrated fashion once the infection or injury has been dealt with adequately. However, acute inflammation can become excessive and life-threatening if regulatory mechanisms fail. Alternatively, inflammation can become chronic and cause cumulative tissue damage or systemic complications.

Many serious and intractable human diseases involve dysregulation of inflammatory processes, including diseases such as cancer, atherosclerosis, and diabetes, which were not traditionally viewed as inflammatory conditions. In the case of cancer, the inflammatory processes are associated with tumor formation, progression, metastasis, and resistance to therapy. Atherosclerosis, long viewed as a disorder of lipid metabolism, is now understood to be primarily an inflammatory condition, with activated macrophages playing an important role in the formation and eventual rupture of atherosclerotic plaques. Activation of inflammatory signaling pathways has also been shown to play a role in the development of insulin resistance, as well as in the peripheral tissue damage associated with diabetic hyperglycemia. Excessive production of reactive oxygen species and reactive nitrogen species such as superoxide, hydrogen peroxide, nitric oxide, and peroxynitrite is a hallmark of inflammatory conditions. Evidence of dysregulated peroxynitrite production has been reported in a wide variety of diseases (Szabo et al., 2007; Schulz et al., 2008; Forstermann, 2006; Pall, 2007).

Autoimmune diseases such as rheumatoid arthritis, lupus, psoriasis, and multiple sclerosis involve inappropriate and chronic activation of inflammatory processes in affected tissues, arising from dysfunction of self vs. non-self recognition and response mechanisms in the immune system. In neurodegenerative diseases such as Alzheimer's and Parkinson's diseases, neural damage is correlated with activation of microglia and elevated levels of pro-inflammatory proteins such as inducible nitric oxide synthase (iNOS). Chronic organ failure such as renal failure, heart failure, and chronic obstructive pulmonary disease is closely associated with the presence of chronic oxidative stress and inflammation, leading to the development of fibrosis and eventual loss of organ function.

Many other disorders involve oxidative stress and inflammation in affected tissues, including inflammatory bowel disease; inflammatory skin diseases; mucositis related to radiation therapy and chemotherapy; eye diseases such as uveitis, glaucoma, macular degeneration, and various forms of retinopathy; transplant failure and rejection; ischemia-reperfusion injury; chronic pain; degenerative conditions of the bones and joints including osteoarthritis and osteoporosis; asthma and cystic fibrosis; seizure disorders; and neuropsychiatric conditions including schizophrenia, depression, bipolar disorder, post-traumatic stress disorder, attention deficit disorders, autism-spectrum disorders, and eating disorders such as anorexia nervosa. Dysregulation of inflammatory signaling pathways is believed to be a major factor in the pathology of muscle wasting diseases including muscular dystrophy and various forms of cachexia.

A variety of life-threatening acute disorders also involve dysregulated inflammatory signaling, including acute organ failure involving the pancreas, kidneys, liver, or lungs, myocardial infarction or acute coronary syndrome, stroke, septic shock, trauma, severe burns, and anaphylaxis.

Many complications of infectious diseases also involve dysregulation of inflammatory responses. Although an inflammatory response can kill invading pathogens, an excessive inflammatory response can also be quite destructive and in some cases can be a primary source of damage in infected tissues. Furthermore, an excessive inflammatory response can also lead to systemic complications due to overproduction of inflammatory cytokines such as TNF-α and IL-1. This is believed to be a factor in mortality arising from severe influenza, severe acute respiratory syndrome, and sepsis.

The aberrant or excessive expression of either iNOS or cyclooxygenase-2 (COX-2) has been implicated in the pathogenesis of many disease processes. For example, it is clear that NO is a potent mutagen (Tamir and Tannebaum, 1996), and that nitric oxide can also activate COX-2 (Salvemini et al., 1994). Furthermore, there is a marked increase in iNOS in rat colon tumors induced by the carcinogen, azoxymethane (Takahashi et al., 1997). A series of synthetic triterpenoid analogs of oleanolic acid have been shown to be powerful inhibitors of cellular inflammatory processes, such as the induction by IFN-γ of inducible nitric oxide synthase (iNOS) and of COX-2 in mouse macrophages. See Honda et al. (2000a); Honda et al. (2000b), and Honda et al. (2002), which are all incorporated herein by reference.

In one aspect, compounds of the invention are characterized by their ability to inhibit the production of nitric oxide in macrophage-derived RAW 264.7 cells induced by exposure to γ-interferon. They are further characterized by their ability to induce the expression of antioxidant proteins such as NQO1 and reduce the expression of pro-inflammatory proteins such as COX-2 and inducible nitric oxide synthase (iNOS). These properties are relevant to the treatment of a wide array of diseases involving oxidative stress and dysregulation of inflammatory processes including cancer, mucositis resulting from radiation therapy or chemotherapy, autoimmune diseases, cardiovascular diseases including atherosclerosis, ischemia-reperfusion injury, acute and chronic organ failure including renal failure and heart failure, respiratory diseases, diabetes and complications of diabetes, severe allergies, transplant rejection, graft-versus-host disease, neurodegenerative diseases, diseases of the eye and retina, acute and chronic pain, degenerative bone diseases including osteoarthritis and osteoporosis, inflammatory bowel diseases, dermatitis and other skin diseases, sepsis, burns, seizure disorders, and neuropsychiatric disorders.

Without being bound by theory, the activation of the antioxidant/anti-inflammatory Keap1/Nrf2/ARE pathway is believed to be implicated in both the anti-inflammatory and anti-carcinogenic properties of the present oleanolic acid derivatives.

In another aspect, compounds of the invention may be used for treating a subject having a condition caused by elevated levels of oxidative stress in one or more tissues. Oxidative stress results from abnormally high or prolonged levels of reactive oxygen species such as superoxide, hydrogen peroxide, nitric oxide, and peroxynitrite (formed by the reaction of nitric oxide and superoxide). The oxidative stress may be accompanied by either acute or chronic inflammation. The oxidative stress may be caused by mitochondrial dysfunction, by activation of immune cells such as macrophages and neutrophils, by acute exposure to an external agent such as ionizing radiation or a cytotoxic chemotherapy agent (e.g., doxorubicin), by trauma or other acute tissue injury, by ischemia/reperfusion, by poor circulation or anemia, by localized or systemic hypoxia or hyperoxia, by elevated levels of inflammatory cytokines and other inflammation-related proteins, and/or by other abnormal physiological states such as hyperglycemia or hypoglycemia.

In animal models of many such conditions, stimulating expression of inducible heme oxygenase (HO-1), a target gene of the Nrf2 pathway, has been shown to have a significant therapeutic effect including models of myocardial infarction, renal failure, transplant failure and rejection, stroke, cardiovascular disease, and autoimmune disease (e.g., Sacerdoti et al., 2005; Abraham & Kappas, 2005; Bach, 2006; Araujo et al., 2003; Liu et al., 2006; Ishikawa et al., 2001; Kruger et al., 2006; Satoh et al., 2006; Zhou et al., 2005; Morse and Choi, 2005; Morse and Choi, 2002). This enzyme breaks free heme down into iron, carbon monoxide (CO), and biliverdin (which is subsequently converted to the potent antioxidant molecule, bilirubin).

In another aspect, compounds of this invention may be used in preventing or treating tissue damage or organ failure, acute and chronic, resulting from oxidative stress exacerbated by inflammation. Examples of diseases that fall in this category include: heart failure, liver failure, transplant failure and rejection, renal failure, pancreatitis, fibrotic lung diseases (cystic fibrosis and COPD, among others), diabetes (including complications), atherosclerosis, ischemia-reperfusion injury, glaucoma, stroke, autoimmune disease, autism, macular degeneration, and muscular dystrophy. For example, in the case of autism, studies suggest that increased oxidative stress in the central nervous system may contribute to the development of the disease (Chauhan and Chauhan, 2006).

Evidence also links oxidative stress and inflammation to the development and pathology of many other disorders of the central nervous system, including psychiatric disorders such as psychosis, major depression, and bipolar disorder; seizure disorders such as epilepsy; pain and sensory syndromes such as migraine, neuropathic pain or tinnitus; and behavioral syndromes such as the attention deficit disorders. See, e.g., Dickerson et al., 2007; Hanson et al., 2005; Kendall-Tackett, 2007; Lencz et al., 2007; Dudhgaonkar et al., 2006; Lee et al., 2007; Morris et al., 2002; Ruster et al., 2005; McIver et al., 2005; Sarchielli et al., 2006; Kawakami et al., 2006; Ross et al., 2003, which are all incorporated by reference herein. For example, elevated levels of inflammatory cytokines, including TNF, interferon-γ, and IL-6, are associated with major mental illness (Dickerson et al., 2007). Microglial activation has also been linked to major mental illness. Therefore, downregulating inflammatory cytokines and inhibiting excessive activation of microglia could be beneficial in patients with schizophrenia, major depression, bipolar disorder, autism-spectrum disorders, and other neuropsychiatric disorders.

Accordingly, in pathologies involving oxidative stress alone or oxidative stress exacerbated by inflammation, treatment may comprise administering to a subject a therapeutically effective amount of a compound of this invention, such as those described above or throughout this specification. Treatment may be administered preventively, in advance of a predictable state of oxidative stress (e.g., organ transplantation or the administration of radiation therapy to a cancer patient), or it may be administered therapeutically in settings involving established oxidative stress and inflammation.

The compounds of the invention may be generally applied to the treatment of inflammatory conditions, such as sepsis, dermatitis, autoimmune disease and osteoarthritis. In one aspect, the compounds of this invention may be used to treat inflammatory pain and/or neuropathic pain, for example, by inducing Nrf2 and/or inhibiting NF-κB.

In one aspect, the compounds of the invention may be used to function as antioxidant inflammation modulators (AIMs) having potent anti-inflammatory properties that mimic the biological activity of cyclopentenone prostaglandins (cyPGs). In one embodiment, the compounds of the invention may be used to control the production of pro-inflammatory cytokines by selectively targeting regulatory cysteine residues (RCRs) on proteins that regulate the transcriptional activity of redox-sensitive transcription factors. Activation of RCRs by cyPGs or AIMs has been shown to initiate a pro-resolution program in which the activity of the antioxidant and cytoprotective transcription factor Nrf2 is potently induced, and the activities of the pro-oxidant and pro-inflammatory transcription factors NF-κB and the STATs are suppressed. This increases the production of antioxidant and reductive molecules (e.g., NQO1, HO-1, SOD1, and/or γ-GCS) and/or decreases oxidative stress and the production of pro-oxidant and pro-inflammatory molecules (e.g., iNOS, COX-2, and/or TNF-α).

In some embodiments, the compounds of the invention may be used in the treatment and prevention of diseases such as cancer, inflammation, Alzheimer's disease, Parkinson's disease, multiple sclerosis, autism, amyotrophic lateral sclerosis, autoimmune diseases such as rheumatoid arthritis, lupus, and MS, inflammatory bowel disease, all other diseases whose pathogenesis is believed to involve excessive production of either nitric oxide or prostaglandins, and pathologies involving oxidative stress alone or oxidative stress exacerbated by inflammation.

Another aspect of inflammation is the production of inflammatory prostaglandins such as prostaglandin E. These molecules promote vasodilation, plasma extravasation, localized pain, elevated temperature, and other symptoms of inflammation. The inducible form of the enzyme COX-2 is associated with their production, and high levels of COX-2 are found in inflamed tissues. Consequently, inhibition of COX-2 may relieve many symptoms of inflammation and a number of important anti-inflammatory drugs (e.g., ibuprofen and celecoxib) act by inhibiting COX-2 activity. Recent research, however, has demonstrated that a class of cyclopentenone prostaglandins (cyPGs) (e.g., 15-deoxy prostaglandin J2, a.k.a. PGJ2) plays a role in stimulating the orchestrated resolution of inflammation (e.g., Rajakariar et al., 2007). COX-2 is also associated with the production of cyclopentenone prostaglandins. Consequently, inhibition of COX-2 may interfere with the full resolution of inflammation, potentially promoting the persistence of activated immune cells in tissues and leading to chronic, "smoldering" inflammation. This effect may be responsible for the increased incidence of cardiovascular disease in patients using selective COX-2 inhibitors for long periods of time.

In one aspect, the compounds of the invention may be used to control the production of pro-inflammatory cytokines within the cell by selectively activating regulatory cysteine residues (RCRs) on proteins that regulate the activity of redox-sensitive transcription factors. Activation of RCRs by cyPGs has been shown to initiate a pro-resolution program in which the activity of the antioxidant and cytoprotective transcription factor Nrf2 is potently induced and the activities of the pro-oxidant and pro-inflammatory transcription factors NF-κB and the STATs are suppressed. In some embodiments, this increases the production of antioxidant and reductive molecules (NQO1, HO-1, SOD1, γ-GCS) and decreases oxidative stress and the production of pro-oxidant and pro-inflammatory molecules (iNOS, COX-2, TNF-α). In some embodiments, the compounds of this invention may cause the cells that host the inflammatory event to revert to a non-inflammatory state by promoting the resolution of inflammation and limiting excessive tissue damage to the host.

A. Cancer

Further, the compounds of the present disclosure may be used to induce apoptosis in tumor cells, to induce cell differentiation, to inhibit cancer cell proliferation, to inhibit an inflammatory response, and/or to function in a chemopreventative capacity. For example, the invention provides new compounds that have one or more of the following properties: (1) an ability to induce apoptosis and differentiate both malignant and non-malignant cells, (2) an activity at sub-micromolar or nanomolar levels as an inhibitor of proliferation of many malignant or premalignant cells, (3) an ability to suppress the de novo synthesis of the inflammatory enzyme inducible nitric oxide synthase (iNOS), (4) an ability to inhibit NF-κB activation, and (5) an ability to induce the expression of heme oxygenase-1 (HO-1).

The levels of iNOS and COX-2 are elevated in certain cancers and have been implicated in carcinogenesis and COX-2 inhibitors have been shown to reduce the incidence of primary colonic adenomas in humans (Rostom et al., 2007; Brown and DuBois, 2005; Crowel et al., 2003). iNOS is expressed in myeloid-derived suppressor cells (MDSCs) (Angulo et al., 2000) and COX-2 activity in cancer cells has been shown to result in the production of prostaglandin $E_2$ ($PGE_2$), which has been shown to induce the expression of arginase in MDSCs (Sinha et al., 2007). Arginase and iNOS are enzymes that utilize L-arginine as a substrate and produce L-ornithine and urea, and L-citrulline and NO, respectively. The depletion of arginine from the tumor microenvironment by MDSCs, combined with the production of NO and peroxynitrite has been shown to inhibit proliferation and induce apoptosis of T cells (Bronte et al., 2003) Inhibition of COX-2 and iNOS has been shown to reduce the accumulation of MDSCs, restore cytotoxic activity of tumor-associated T cells, and delay tumor growth (Sinha et al., 2007; Mazzoni et al., 2002; Zhou et al., 2007).

Inhibition of the NF-κB and JAK/STAT signaling pathways has been implicated as a strategy to inhibit proliferation of cancer epithelial cells and induce their apoptosis. Activation of STAT3 and NF-κB has been shown to result in suppression of apoptosis in cancer cells, and promotion of proliferation, invasion, and metastasis. Many of the target genes involved in these processes have been shown to be transcriptionally regulated by both NF-κB and STAT3 (Yu et al., 2007).

In addition to their direct roles in cancer epithelial cells, NF-κB and STAT3 also have important roles in other cells found within the tumor microenvironment. Experiments in animal models have demonstrated that NF-κB is required in both cancer cells and hematopoeitic cells to propagate the effects of inflammation on cancer initiation and progression (Greten et al., 2004). NF-κB inhibition in cancer and myeloid cells reduces the number and size, respectively, of the resultant tumors. Activation of STAT3 in cancer cells results in the production of several cytokines (IL-6, IL-10) which suppress the maturation of tumor-associated dendritic cells (DC). Furthermore, STAT3 is activated by these cytokines in the dendritic cells themselves Inhibition of STAT3 in mouse models of cancer restores DC maturation, promotes antitumor immunity, and inhibits tumor growth (Kortylewski et al., 2005).

B. Treatment of Multiple Sclerosis and Other Neurodegenerative Conditions

The compounds and methods of this invention may be used for treating patients for multiple sclerosis (MS). MS is known to be an inflammatory condition of the central nervous system (Williams et al., 1994; Merrill and Benvenist, 1996; Genain and Nauser, 1997). Based on several investigations, there is evidence suggesting that inflammatory, oxidative, and/or immune mechanisms are involved in the pathogenesis of Alzheimer's disease (AD), Parkinson's disease (PD), amyotrophic lateral sclerosis (ALS), and MS (Bagasra et al., 1995; McGeer and McGeer, 1995; Simonian and Coyle, 1996; Kaltschmidt et al., 1997). Both reactive astrocytes and activated microglia have been implicated in causation of neurodegenerative disease (NDD) and neuroinflammatory disease (NID); there has been a particular emphasis on microglia as cells that synthesize both NO and prostaglandins as products of the respective enzymes, iNOS and COX-2. De novo formation of these enzymes may be driven by inflammatory cytokines such as interferon-γ or interleukin-1. In turn, excessive production of NO may lead to inflammatory cascades and/or oxidative damage in cells and tissues of many organs, including neurons and oligodendrocytes of the nervous system, with consequent manifestations in AD and MS, and possible PD and ALS (Coyle and Puttfarcken, 1993; Beal, 1996; Merrill and Benvenist, 1996; Simonian and Coyle, 1996; Vodovotz et al., 1996). Epidemiologic data indicate that chronic use of NSAID's which block synthesis of prostaglandins from arachidonate, markedly lower the risk for development of AD (McGeer et al., 1996; Stewart et al., 1997). Thus, agents that block formation of NO and prostaglandins, may be used in approaches to prevention and treatment of NDD. Successful therapeutic candidates for treating such a disease typically require an ability to penetrate the blood-brain barrier. See, for example, U.S. Patent Publication 2009/0060873, which is incorporated by reference herein in its entirety.

C. Neuroinflammation

The compounds and methods of this invention may be used for treating patients with neuroinflammation. Neuroinflammation encapsulates the idea that microglial and astrocytic responses and actions in the central nervous system have a fundamentally inflammation-like character, and that these responses are central to the pathogenesis and progression of a wide variety of neurological disorders. This idea originated in the field of Alzheimer's disease (Griffin et al., 1989; Rogers et al., 1988), where it has revolutionized our understanding of this disease (Akiyama et al., 2000). These ideas have been extended to other neurodegenerative diseases (Eikelenboom et al., 2002; Ishizawa and Dickson, 2001), to ischemic/toxic diseases (Gehrmann et al., 1995; Touzani et al., 1999), to tumor biology (Graeber et al., 2002) and even to normal brain development.

Neuroinflammation incorporates a wide spectrum of complex cellular responses that include activation of microglia and astrocytes and induction of cytokines, chemokines, complement proteins, acute phase proteins, oxidative injury, and related molecular processes. These events may have detrimental effects on neuronal function, leading to neuronal injury, further glial activation, and ultimately neurodegeneration.

D. Treatment of Renal Failure

The compounds and methods of this invention may be used for treating patients with renal failure. See U.S. patent application Ser. No. 12/352,473, which is incorporated by reference herein in its entirety. Another aspect of the present disclosure concerns new methods and compounds for the treatment and prevention of renal disease. Renal failure, resulting in inadequate clearance of metabolic waste products from the blood and abnormal concentrations of electrolytes in the blood, is a significant medical problem throughout the world, especially in developed countries. Diabetes and hypertension are among the most important causes of chronic renal failure, also known as chronic kidney disease (CKD), but it is also associated with other conditions such as lupus. Acute renal failure may arise from exposure to certain drugs (e.g., acetaminophen) or toxic chemicals, or from ischemia-reperfusion injury associated with shock or surgical procedures such as transplantation, and may result in chronic renal failure. In many patients, renal failure advances to a stage in which the patient requires regular dialysis or kidney transplantation to continue living. Both of these procedures are highly invasive and associated with significant side effects and quality of life issues. Although there are effective treatments for some complications of renal failure, such as hyperparathyroidism and hyperphosphatemia, no available treatment has been shown to halt or reverse the underlying progression of renal failure. Thus, agents that can improve compromised renal function would represent a significant advance in the treatment of renal failure.

Inflammation contributes significantly to the pathology of CKD. There is also a strong mechanistic link between oxidative stress and renal dysfunction. The NF-κB signaling pathway plays an important role in the progression of CKD as NF-κB regulates the transcription of MCP-1, a chemokine that is responsible for the recruitment of monocytes/macrophages resulting in an inflammatory response that ultimately injures the kidney (Wardle, 2001). The Keap1/Nrf2/ARE pathway controls the transcription of several genes encoding antioxidant enzymes, including heme oxygenase-1 (HO-1). Ablation of the Nrf2 gene in female mice results in the development of lupus-like glomerular nephritis (Yoh et al., 2001). Furthermore, several studies have demonstrated that HO-1 expression is induced in response to renal damage and inflammation and that this enzyme and its products—bilirubin and carbon monoxide—play a protective role in the kidney (Nath et al., 2006).

The glomerulus and the surrounding Bowman's capsule constitute the basic functional unit of the kidney. Glomerular filtration rate (GFR) is the standard measure of renal function. Creatinine clearance is commonly used to measure GFR. However, the level of serum creatinine is commonly used as a surrogate measure of creatinine clearance. For instance, excessive levels of serum creatinine are generally accepted to indicate inadequate renal function and reductions in serum creatinine over time are accepted as an indication of improved renal function. Normal levels of creatinine in the blood are approximately 0.6 to 1.2 milligrams (mg) per deciliter (dl) in adult males and 0.5 to 1.1 milligrams per deciliter in adult females.

Acute kidney injury (AKI) can occur following ischemia-reperfusion, treatment with certain pharmacological agents such as cisplatin and rapamycin, and intravenous injection of radiocontrast media used in medical imaging. As in CKD, inflammation and oxidative stress contribute to the pathology of AKI. The molecular mechanisms underlying radiocontrast-induced nephropathy (RCN) are not well understood; however, it is likely that a combination of events including prolonged vasoconstriction, impaired kidney autoregulation, and direct toxicity of the contrast media all contribute to renal failure (Tumlin et al., 2006). Vasoconstriction results in decreased renal blood flow and causes ischemia-reperfusion and the production of reactive oxygen species. HO-1 is strongly induced under these conditions and has been demonstrated to prevent ischemia-reperfusion injury in several different organs, including the kidney (Nath et al., 2006). Specifically, induction of HO-1 has been shown to be protective in a rat model of RCN (Goodman et al., 2007). Reperfusion also induces an inflammatory response, in part though activation of NF-κB signaling (Nichols, 2004). Targeting NF-κB has been proposed as a therapeutic strategy to prevent organ damage (Zingarelli et al., 2003).

E. Cardiovascular Disease

The compounds and methods of this invention may be used for treating patients with cardiovascular disease. See U.S. patent application Ser. No. 12/352,473, which is incorporated by reference herein in its entirety. Cardiovascular (CV) disease is among the most important causes of mortality worldwide, and is the leading cause of death in many developed nations. The etiology of CV disease is complex, but the majority of causes are related to inadequate or completely disrupted supply of blood to a critical organ or tissue. Frequently such a condition arises from the rupture of one or more atherosclerotic plaques, which leads to the formation of a thrombus that blocks blood flow in a critical vessel. Such thrombosis is the principal cause of heart attacks, in which one or more of the coronary arteries is blocked and blood flow to the heart itself is disrupted. The resulting ischemia is highly damaging to cardiac tissue, both from lack of oxygen during the ischemic event and from excessive formation of free radicals after blood flow is restored (a phenomenon known as ischemia-reperfusion injury). Similar damage occurs in the brain during a thrombotic stroke, when a cerebral artery or other major vessel is blocked by thrombosis. Hemorrhagic strokes, in contrast, involve rupture of a blood vessel and bleeding into the surrounding brain tissue. This creates oxidative stress in the immediate area of the hemorrhage, due to the presence of large amounts of free heme and other reactive species, and ischemia in other parts of the brain due to compromised blood flow. Subarachnoid hemorrhage, which is frequently accompanied by cerebral vasospasm, also causes ischemia/reperfusion injury in the brain.

Alternatively, atherosclerosis may be so extensive in critical blood vessels that stenosis (narrowing of the arteries) develops and blood flow to critical organs (including the heart) is chronically insufficient. Such chronic ischemia can lead to end-organ damage of many kinds, including the cardiac hypertrophy associated with congestive heart failure.

Atherosclerosis, the underlying defect leading to many forms of cardiovascular disease, occurs when a physical defect or injury to the lining (endothelium) of an artery triggers an inflammatory response involving the proliferation of vascular smooth muscle cells and the infiltration of leukocytes into the affected area. Ultimately, a complicated lesion known as an atherosclerotic plaque may form, composed of the above-mentioned cells combined with deposits of cholesterol-bearing lipoproteins and other materials (e.g., Hansson et al., 2006).

Pharmaceutical treatments for cardiovascular disease include preventive treatments, such as the use of drugs intended to lower blood pressure or circulating levels of cholesterol and lipoproteins, as well as treatments designed to reduce the adherent tendencies of platelets and other blood cells (thereby reducing the rate of plaque progression and the risk of thrombus formation). More recently, drugs such as streptokinase and tissue plasminogen activator have been introduced and are used to dissolve the thrombus and restore blood flow. Surgical treatments include coronary artery bypass grafting to create an alternative blood supply, balloon angioplasty to compress plaque tissue and increase the diameter of the arterial lumen, and carotid endarterectomy to remove plaque tissue in the carotid artery. Such treatments, especially balloon angioplasty, may be accompanied by the use of stents, expandable mesh tubes designed to support the artery walls in the affected area and keep the vessel open. Recently, the use of drug-eluting stents has become common in order to prevent post-surgical restenosis (renarrowing of the artery) in the affected area. These devices are wire stents coated with a biocompatible polymer matrix containing a drug that inhibits cell proliferation (e.g., paclitaxel or rapamycin). The polymer allows a slow, localized release of the drug in the affected area with minimal exposure of non-target tissues. Despite the significant benefits offered by such treatments, mortality from cardiovascular disease remains high and significant unmet needs in the treatment of cardiovascular disease remain.

As noted above, induction of HO-1 has been shown to be beneficial in a variety of models of cardiovascular disease, and low levels of HO-1 expression have been clinically correlated with elevated risk of CV disease. Compounds of the invention, therefore, may be used in treating or preventing a variety of cardiovascular disorders including but not limited to atherosclerosis, hypertension, myocardial infarction, chronic heart failure, stroke, subarachnoid hemorrhage, and restenosis.

F. Diabetes

The compounds and methods of this invention may be used for treating patients with diabetes. See U.S. patent application Ser. No. 12/352,473, which is incorporated by reference herein in its entirety. Diabetes is a complex disease characterized by the body's failure to regulate circulating levels of glucose. This failure may result from a lack of insulin, a peptide hormone that regulates both the production and absorption of glucose in various tissues. Deficient insulin compromises the ability of muscle, fat, and other tissues to absorb glucose properly, leading to hyperglycemia (abnormally high levels of glucose in the blood). Most commonly, such insulin deficiency results from inadequate production in the islet cells of the pancreas. In the majority of cases this arises from autoimmune destruction of these cells, a condition known as type 1 or juvenile-onset diabetes, but may also be due to physical trauma or some other cause.

Diabetes may also arise when muscle and fat cells become less responsive to insulin and do not absorb glucose properly, resulting in hyperglycemia. This phenomenon is known as insulin resistance, and the resulting condition is known as Type 2 diabetes. Type 2 diabetes, the most common type, is highly associated with obesity and hypertension. Obesity is associated with an inflammatory state of adipose tissue that is thought to play a major role in the development of insulin resistance (e.g., Hotamisligil, 2006; Guilherme et al., 2008).

Diabetes is associated with damage to many tissues, largely because hyperglycemia (and hypoglycemia, which can result from excessive or poorly timed doses of insulin) is a significant source of oxidative stress. Chronic kidney failure, retinopathy, peripheral neuropathy, peripheral vasculitis, and the development of dermal ulcers that heal slowly or not at all are among the common complications of diabetes. Because of their ability to protect against oxidative stress, particularly by the induction of HO-1 expression, compounds of the invention may be used in treatments for many complications of diabetes. As noted above (Cai et al., 2005), chronic inflammation and oxidative stress in the liver are suspected to be primary contributing factors in the development of Type 2 diabetes. Furthermore, PPARγ agonists such as thiazolidinediones are capable of reducing insulin resistance and are known to be effective treatments for Type 2 diabetes.

The effect of treatment of diabetes may be evaluated as follows. Both the biological efficacy of the treatment modality as well as the clinical efficacy are evaluated, if possible. For example, because the disease manifests itself by increased blood sugar, the biological efficacy of the treatment therefore can be evaluated, for example, by observation of return of the evaluated blood glucose towards normal. Measurement of glycosylated hemoglobin, also called A1c or HbA1c, is another commonly used parameter of blood glucose control. Measuring a clinical endpoint which can give an indication of b-cell regeneration after, for example, a six-month period of time, can give an indication of the clinical efficacy of the treatment regimen.

G. Rheumatoid Arthritis

The compounds and methods of this invention may be used for treating patients with RA. Typically the first signs of rheumatoid arthritis (RA) appear in the synovial lining layer, with proliferation of synovial fibroblasts and their attachment to the articular surface at the joint margin (Lipsky, 1998). Subsequently, macrophages, T cells and other inflammatory cells are recruited into the joint, where they produce a number of mediators, including the cytokines interleukin-1 (IL-1), which contributes to the chronic sequelae leading to bone and cartilage destruction, and tumour necrosis factor (TNF-α), which plays a role in inflammation (Dinarello, 1998; Arend and Dayer, 1995; van den Berg, 2001). The concentration of IL-1 in plasma is significantly higher in patients with RA than in healthy individuals and, notably, plasma IL-1 levels correlate with RA disease activity (Eastgate et al., 1988). Moreover, synovial fluid levels of IL-1 are correlated with various radiographic and histologic features of RA (Kahle et al., 1992; Rooney et al., 1990).

In normal joints, the effects of these and other proinflammatory cytokines are balanced by a variety of anti-inflammatory cytokines and regulatory factors (Burger and Dayer, 1995). The significance of this cytokine balance is illustrated in juvenile RA patients, who have cyclical increases in fever throughout the day (Prieur et al., 1987). After each peak in fever, a factor that blocks the effects of IL-1 is found in serum and urine. This factor has been isolated, cloned and identified as IL-1 receptor antagonist (IL-1ra), a member of the IL-1 gene family (Hannum et al., 1990). IL-1ra, as its name indicates, is a natural receptor antagonist that competes with IL-1 for binding to type I IL-1 receptors and, as a result, blocks the effects of IL-1 (Arend et al., 1998). A 10- to 100-fold excess of IL-1ra may be needed to block IL-1 effectively; however, synovial cells isolated from patients with RA do not appear to produce enough IL-1ra to counteract the effects of IL-1 (Firestein et al., 1994; Fujikawa et al., 1995).

H. Psoriatic Arthritis

The compounds and methods of this invention may be used for treating patients with psoriatic arthritis. Psoriasis is an inflammatory and proliferative skin disorder with a prevalence of 1.5-3%. Approximately 20% of patients with psoriasis develop a characteristic form of arthritis that has several patterns (Gladman, 1992; Jones et al., 1994; Gladman et al., 1995). Some individuals present with joint symptoms first but in the majority, skin psoriasis presents first. About one-third of patients have simultaneous exacerbations of their skin and joint disease (Gladman et al., 1987) and there is a topographic relationship between nail and distal interphalangeal joint disease (Jones et al., 1994; Wright, 1956). Although the inflammatory processes which link skin, nail and joint disease remain elusive, an immune-mediated pathology is implicated.

Psoriatic arthritis (PsA) is a chronic inflammatory arthropathy characterized by the association of arthritis and psoriasis and was recognized as a clinical entity distinct from rheumatoid arthritis (RA) in 1964 (Blumberg et al., 1964). Subsequent studies have revealed that PsA shares a number of genetic, pathogenic and clinical features with other spondyloarthropathies (SpAs), a group of diseases that comprise ankylosing spondylitis, reactive arthritis and enteropathic arthritis (Wright, 1979). The notion that PsA belongs to the SpA group has recently gained further support from imaging studies demonstrating widespread enthesitis in the, including PsA but not RA (McGonagle et al., 1999; McGonagle et al., 1998). More specifically, enthesitis has been postulated to be one of the earliest events occurring in the SpAs, leading to bone remodeling and ankylosis in the spine, as well as to articular synovitis when the inflamed entheses are close to peripheral joints. However, the link between enthesitis and the clinical manifestations in PsA remains largely unclear, as PsA can present with fairly heterogeneous patterns of joint involvement with variable degrees of severity (Marsal et al., 1999; Salvarani et al., 1998). Thus, other factors must be posited to account for the multifarious features of PsA, only a few of which (such as the expression of the HLA-B27 molecule, which is strongly associated with axial disease) have been identified. As a consequence, it remains difficult to map the disease manifestations to specific pathogenic mechanisms, which means that the treatment of this condition remains largely empirical.

Family studies have suggested a genetic contribution to the development of PsA (Moll and Wright, 1973). Other chronic inflammatory forms of arthritis, such as ankylosing spondylitis and rheumatoid arthritis, are thought to have a complex genetic basis. However, the genetic component of PsA has been difficult to assess for several reasons. There is strong evidence for a genetic predisposition to psoriasis alone that may mask the genetic factors that are important for the development of PsA. Although most would accept PsA as a distinct disease entity, at times there is a phenotypic overlap with rheumatoid arthritis and ankylosing spondylitis. Also, PsA itself is not a homogeneous condition and various subgroups have been proposed.

Increased amounts of TNF-α have been reported in both psoriatic skin (Ettehadi et al., 1994) and synovial fluid (Partsch et al., 1997). Recent trials have shown a positive benefit of anti-TNF treatment in both PsA (Mease et al., 2000) and ankylosing spondylitis (Brandt et al., 2000).

I. Reactive Arthritis

The compounds and methods of this invention may be used for treating patients with reactive arthritis. In reactive arthritis (ReA) the mechanism of joint damage is unclear, but it is likely that cytokines play critical roles. A more prevalent Th1 profile high levels of interferon gamma (IFN-γ) and low levels of interleukin 4 (IL-4) has been reported (Lahesmaa et al., 1992; Schlaak et al., 1992; Simon et al., 1993; Schlaak et al., 1996; Kotake et al., 1999; Ribbens et al., 2000), but several studies have shown relative predominance of IL-4 and IL-10 and relative lack of IFN-γ and tumour necrosis factor alpha (TNF-α) in the synovial membrane (Simon et al., 1994; Yin et al., 1999) and fluid (SF) (Yin et al., 1999; Yin et al., 1997) of reactive arthritis patients compared with rheumatoid arthritis (RA) patients. A lower level of TNF-α secretion in reactive arthritis than in RA patients has also been reported after ex vivo stimulation of peripheral blood mononuclear cells (PBMC) (Braun et al., 1999).

It has been argued that clearance of reactive arthritis-associated bacteria requires the production of appropriate levels of IFN-γ and TNF-α, while IL-10 acts by suppressing these responses (Autenrieth et al., 1994; Sieper and Braun, 1995). IL-10 is a regulatory cytokine that inhibits the synthesis of IL-12 and TNF-γ by activated macrophages (de Waal et al., 1991; Hart et al., 1995; Chomarat et al., 1995) and of IFN-γ by T cells (Macatonia et al., 1993).

J. Enteropathic Arthritis

The compounds and methods of this invention may be used for treating patients with enteropathic arthritis. Typically enteropathic arthritis (EA) occurs in combination with inflammatory bowel diseases (IBD) such as Crohn's disease or ulcerative colitis. It also can affect the spine and sacroiliac joints. Enteropathic arthritis involves the peripheral joints, usually in the lower extremities such as the knees or ankles It commonly involves only a few or a limited number of joints and may closely follow the bowel condition. This occurs in approximately 11% of patients with ulcerative colitis and 21% of those with Crohn's disease. The synovitis is generally self-limited and non-deforming.

Enteropathic arthropathies comprise a collection of rheumatologic conditions that share a link to GI pathology. These conditions include reactive (i.e., infection-related) arthritis due to bacteria (e.g., *Shigella, Salmonella, Campylobacter, Yersinia* species, *Clostridium difficile*), parasites (e.g., *Strongyloides stercoralis, Taenia saginata, Giardia lamblia, Ascaris lumbricoides, Cryptosporidium* species), and spondyloarthropathies associated with inflammatory bowel disease (IBD). Other conditions and disorders include intestinal bypass (jejunoileal), arthritis, celiac disease, Whipple disease, and collagenous colitis.

K. Juvenile Rheumatoid Arthritis

The compounds and methods of this invention may be used for treating patients with JRA. Juvenile rheumatoid arthritis (JRA), a term for the most prevalent form of arthritis in children, is applied to a family of illnesses characterized by chronic inflammation and hypertrophy of the synovial membranes. The term overlaps, but is not completely synonymous, with the family of illnesses referred to as juvenile chronic arthritis and/or juvenile idiopathic arthritis in Europe.

Both innate and adaptive immune systems use multiple cell types, a vast array of cell surface and secreted proteins, and interconnected networks of positive and negative feedback (Lo et al., 1999). Furthermore, while separable in thought, the innate and adaptive wings of the immune system are functionally intersected (Fearon and Locksley, 1996), and pathologic events occurring at these intersecting points are likely to be highly relevant to our understanding of pathogenesis of adult and childhood forms of chronic arthritis (Warrington, et al., 2001).

Polyarticular JRA is a distinct clinical subtype characterized by inflammation and synovial proliferation in multiple joints (four or more), including the small joints of the hands (Jarvis, 2002). This subtype of JRA may be severe, because of both its multiple joint involvement and its capacity to progress rapidly over time. Although clinically distinct, polyarticular JRA is not homogeneous, and patients vary in disease manifestations, age of onset, prognosis, and therapeutic response. These differences very likely reflect a spectrum of variation in the nature of the immune and inflammatory attack that can occur in this disease (Jarvis, 1998).

L. Early Inflammatory Arthritis

The compounds and methods of this invention may be used for treating patients with early inflammatory arthritis. The clinical presentation of different inflammatory arthropathies is similar early in the course of disease. As a result, it is often difficult to distinguish patients who are at risk of developing the severe and persistent synovitis that leads to erosive joint damage from those whose arthritis is more self-limited. Such distinction is critical in order to target therapy appropriately, treating aggressively those with erosive disease and avoiding unnecessary toxicity in patients with more self-limited disease. Current clinical criteria for diagnosing erosive arthropathies such as rheumatoid arthritis (RA) are less effective in early disease and traditional markers of disease activity such as joint counts and acute phase response do not adequately identify patients likely to have poor outcomes (Harrison et al., 1998). Parameters reflective of the pathologic events occurring in the synovium are most likely to be of significant prognostic value.

Recent efforts to identify predictors of poor outcome in early inflammatory arthritis have identified the presence of RA specific autoantibodies, in particular antibodies towards citrullinated peptides, to be associated with erosive and persistent disease in early inflammatory arthritis cohorts. On the basis of this, a cyclical citrullinated peptide (CCP) has been developed to assist in the identification of anti-CCP antibodies in patient sera. Using this approach, the presence of anti-CCP antibodies has been shown to be specific and sensitive for RA, can distinguish RA from other arthropathies, and can potentially predict persistent, erosive synovitis before these outcomes become clinically manifest. Importantly, anti-CCP antibodies are often detectable in sera many years prior to clinical symptoms suggesting that they may be reflective of subclinical immune events (Nielen et al., 2004; Rantapaa-Dahlqvist et al., 2003).

M. Ankylosing Spondylitis

The compounds and methods of this invention may be used for treating patients with ankylosing spondylitis. AS is a disease subset within a broader disease classification of spondyloarthropathy. Patients affected with the various subsets of spondyloarthropathy have disease etiologies that are often very different, ranging from bacterial infections to inheritance. Yet, in all subgroups, the end result of the disease process is axial arthritis. Despite the early clinically differences seen in the various patient populations, many of them end up nearly identical after a disease course of ten-to-twenty years. Recent studies suggest the mean time to clinical diagnosis of ankylosing spondylitis from disease onset of disease is 7.5 years (Khan, 1998). These same studies suggest that the spondyloarthropathies may have prevalence close to that of rheumatoid arthritis (Feldtkeller et al., 2003; Doran et al., 2003).

AS is a chronic systemic inflammatory rheumatic disorder of the axial skeleton with or without extraskeletal manifestations. Sacroiliac joints and the spine are primarily affected, but hip and shoulder joints, and less commonly peripheral joints or certain extra-articular structures such as the eye, vasculature, nervous system, and gastrointestinal system may also be involved. Its etiology is not yet fully understood (Wordsworth, 1995; Calin and Taurog, 1998). It is strongly associated with the major histocompatibility class I (MHC I) HLA-B27 allele (Cahn and Taurog, 1998). AS affects individuals in the prime of their life and is feared because of its potential to cause chronic pain and irreversible damage of tendons, ligaments, joints, and bones (Brewerton et al., 1973a; Brewerton et al., 1973b; Schlosstein et al., 1973). AS may occur alone or in association with another form of spondyloarthropathy such as reactive arthritis, psoriasis, psoriatic arthritis, enthesitis, ulcerative colitis, irritable bowel disease, or Crohn's disease, in which case it is classified as secondary AS.

Typically, the affected sites include the discovertebral, apophyseal, costovertebral, and costotransverse joints of the spine, and the paravertebral ligamentous structures. Inflammation of the entheses, which are sites of musculotendinous and ligamentous attachment to bones, is also prominent in this disease (Calin and Taurog, 1998). The site of enthesitis is known to be infiltrated by plasma cells, lymphocytes, and polymorphonuclear cells. The inflammatory process frequently results in gradual fibrous and bony ankylosis, (Ball, 1971; Khan, 1990).

Delayed diagnosis is common because symptoms are often attributed to more common back problems. A dramatic loss of flexibility in the lumbar spine is an early sign of AS. Other common symptoms include chronic pain and stiffness in the lower back which usually starts where the lower spine is joined to the pelvis, or hip. Although most symptoms begin in the lumbar and sacroiliac areas, they may involve the neck and upper back as well. Arthritis may also occur in the shoulder, hips and feet. Some patients have eye inflammation, and more severe cases must be observed for heart valve involvement.

The most frequent presentation is back pain, but disease can begin atypically in peripheral joints, especially in children and women, and rarely with acute iritis (anterior uveitis). Additional early symptoms and signs are diminished chest expansion from diffuse costovertebral involvement, low-grade fever, fatigue, anorexia, weight loss, and anemia. Recurrent back pain—often nocturnal and of varying intensity—is an eventual complaint, as is morning stiffness typically relieved by activity. A flexed or bent-over posture eases back pain and paraspinal muscle spasm; thus, some degree of kyphosis is common in untreated patients.

Systemic manifestations occur in ⅓ of patients. Recurrent, usually self-limited, acute iritis (anterior uveitis) rarely is protracted and severe enough to impair vision. Neurologic signs can occasionally result from compression radiculitis or sciatica, vertebral fracture or subluxation, and cauda equina syndrome (which consists of impotence, nocturnal urinary incontinence, diminished bladder and rectal sensation, and absence of ankle jerks). Cardiovascular manifestations can include aortic insufficiency, angina, pericarditis, and ECG conduction abnormalities. A rare pulmonary finding is upper lobe fibrosis, occasionally with cavitation that may be mistaken for TB and can be complicated by infection with *Aspergillus*.

AS is characterized by mild or moderate flares of active spondylitis alternating with periods of almost or totally inactive inflammation. Proper treatment in most patients results in minimal or no disability and in full, productive lives despite back stiffness. Occasionally, the course is severe and progressive, resulting in pronounced incapacitating deformities. The prognosis is bleak for patients with refractory iritis and for the rare patient with secondary amyloidosis.

N. Ulcerative Colitis

The compounds and methods of this invention may be used for treating patients with ulcerative colitis. Ulcerative colitis is a disease that causes inflammation and sores, called ulcers, in the lining of the large intestine. The inflammation usually occurs in the rectum and lower part of the colon, but it may affect the entire colon. Ulcerative colitis rarely affects the small intestine except for the end section, called the terminal ileum. Ulcerative colitis may also be called colitis or proctitis. The inflammation makes the colon empty frequently, causing diarrhea. Ulcers form in places where the inflammation has killed the cells lining the colon; the ulcers bleed and produce pus.

Ulcerative colitis is an inflammatory bowel disease (IBD), the general name for diseases that cause inflammation in the small intestine and colon. Ulcerative colitis can be difficult to diagnose because its symptoms are similar to other intestinal disorders and to another type of IBD, Crohn's disease. Crohn's disease differs from ulcerative colitis because it causes inflammation deeper within the intestinal wall. Also, Crohn's disease usually occurs in the small intestine, although it can also occur in the mouth, esophagus, stomach, duodenum, large intestine, appendix, and anus.

Ulcerative colitis may occur in people of any age, but most often it starts between ages 15 and 30, or less frequently between ages 50 and 70. Children and adolescents sometimes develop the disease. Ulcerative colitis affects men and women equally and appears to run in some families. Theories about what causes ulcerative colitis abound, but none have been proven. The most popular theory is that the body's immune system reacts to a virus or a bacterium by causing ongoing inflammation in the intestinal wall. People with ulcerative colitis have abnormalities of the immune system, but doctors do not know whether these abnormalities are a cause or a result of the disease. Ulcerative colitis is not caused by emotional distress or sensitivity to certain foods or food products, but these factors may trigger symptoms in some people.

The most common symptoms of ulcerative colitis are abdominal pain and bloody diarrhea. Patients also may experience fatigue, weight loss, loss of appetite, rectal bleeding, and loss of body fluids and nutrients. About half of patients have mild symptoms. Others suffer frequent fever, bloody diarrhea, nausea, and severe abdominal cramps. Ulcerative colitis may also cause problems such as arthritis, inflammation of the eye, liver disease (hepatitis, cirrhosis, and primary sclerosing cholangitis), osteoporosis, skin rashes, and anemia. No one knows for sure why problems occur outside the colon. Scientists think these complications may occur when the immune system triggers inflammation in other parts of the body. Some of these problems go away when the colitis is treated.

A thorough physical exam and a series of tests may be required to diagnose ulcerative colitis. Blood tests may be done to check for anemia, which could indicate bleeding in the colon or rectum. Blood tests may also uncover a high white blood cell count, which is a sign of inflammation somewhere in the body. By testing a stool sample, the doctor can detect bleeding or infection in the colon or rectum. The doctor may do a colonoscopy or sigmoidoscopy. For either test, the doctor inserts an endoscope—a long, flexible, lighted tube connected to a computer and TV monitor—into the anus to see the inside of the colon and rectum. The doctor will be able to see any inflammation, bleeding, or ulcers on the colon wall. During the exam, the doctor may do a biopsy, which involves taking a sample of tissue from the lining of the colon to view with a microscope. A barium enema x ray of the colon may also be required. This procedure involves filling the colon with barium, a chalky white solution. The barium shows up white on x-ray film, allowing the doctor a clear view of the colon, including any ulcers or other abnormalities that might be there.

Treatment for ulcerative colitis depends on the seriousness of the disease. Most people are treated with medication. In severe cases, a patient may need surgery to remove the diseased colon. Surgery is the only cure for ulcerative colitis. Some people whose symptoms are triggered by certain foods are able to control the symptoms by avoiding foods that upset their intestines, like highly seasoned foods, raw fruits and vegetables, or milk sugar (lactose). Each person may experience ulcerative colitis differently, so treatment is adjusted for each individual. Emotional and psychological support is important. Some people have remissions—periods when the symptoms go away—that last for months or even years. However, most patients' symptoms eventually return. This changing pattern of the disease means one cannot always tell when a treatment has helped. Some people with ulcerative colitis may need medical care for some time, with regular doctor visits to monitor the condition.

O. Crohn's Disease

The compounds and methods of this invention may be used for treating patients with Crohn's disease. Another disorder for which immunosuppression has been tried is Crohn's disease. Crohn's disease symptoms include intestinal inflammation and the development of intestinal stenosis and fistulas; neuropathy often accompanies these symptoms. Anti-inflammatory drugs, such as 5-aminosalicylates (e.g., mesalamine) or corticosteroids, are typically prescribed, but are not always effective (reviewed in Botoman et al., 1998). Immunosuppression with cyclosporine is sometimes beneficial for patients resistant to or intolerant of corticosteroids (Brynskov et al., 1989).

Efforts to develop diagnostic and treatment tools against Crohn's disease have focused on the central role of cytokines (Schreiber, 1998; van Hogezand and Verspaget, 1998). Cytokines are small secreted proteins or factors (5 to 20 kD) that have specific effects on cell-to-cell interactions, intercellular communication, or the behavior of other cells. Cytokines are produced by lymphocytes, especially $T_H1$ and $T_H2$ lymphocytes, monocytes, intestinal macrophages, granulocytes, epithelial cells, and fibroblasts (reviewed in Rogler and. Andus, 1998; Galley and Webster, 1996). Some cytokines are pro-inflammatory (e.g., TNF-α, IL-1(α and β), IL-6, IL-8, IL-12, or leukemia inhibitory factor [LIF]); others are anti-inflammatory (e.g., IL-1 receptor antagonist, IL-4, IL-10, IL-11, and TGF-β). However, there may be overlap and functional redundancy in their effects under certain inflammatory conditions.

In active cases of Crohn's disease, elevated concentrations of TNF-α and IL-6 are secreted into the blood circulation, and TNF-α, IL-1, IL-6, and IL-8 are produced in excess locally by mucosal cells (id.; Funakoshi et al., 1998). These cytokines can have far-ranging effects on physiological systems including bone development, hematopoiesis, and liver, thyroid, and neuropsychiatric function. Also, an imbalance of the IL-1β/IL-1ra ratio, in favor of pro-inflammatory IL-1β, has been observed in patients with Crohn's disease (Rogler and Andus, 1998; Saiki et al., 1998; Dionne et al., 1998; but see Kuboyama, 1998). One study suggested that cytokine profiles in stool samples could be a useful diagnostic tool for Crohn's disease (Saiki et al., 1998).

Treatments that have been proposed for Crohn's disease include the use of various cytokine antagonists (e.g., IL-1ra), inhibitors (e.g., of IL-1β converting enzyme and antioxidants) and anti-cytokine antibodies (Rogler and Andus, 1998; van Hogezand and Verspaget, 1998; Reimund et al., 1998; Lugering et al., 1998; McAlindon et al., 1998). In particular, monoclonal antibodies against TNF-α have been tried with some success in the treatment of Crohn's disease (Targan et al., 1997; Stack et al., 1997; van Dullemen et al., 1995). These compounds may be used in combination therapy with compounds of the present disclosure.

Another approach to the treatment of Crohn's disease has focused on at least partially eradicating the bacterial community that may be triggering the inflammatory response and replacing it with a non-pathogenic community. For example, U.S. Pat. No. 5,599,795 discloses a method for the prevention and treatment of Crohn's disease in human patients. Their method was directed to sterilizing the intestinal tract with at least one antibiotic and at least one anti-fungal agent to kill off the existing flora and replacing them with different, select, well-characterized bacteria taken from normal humans. Borody taught a method of treating Crohn's disease by at least partial removal of the existing intestinal microflora by lavage and replacement with a new bacterial community introduced by fecal inoculum from a disease-screened human donor or by a composition comprising *Bacteroides* and *Escherichia coli* species. (U.S. Pat. No. 5,443,826).

P. Systemic Lupus Erythematosus

The compounds and methods of this invention may be used for treating patients with SLE. There has also been no known cause for autoimmune diseases such as systemic lupus erythematosus. Systemic lupus erythematosus (SLE) is an autoimmune rheumatic disease characterized by deposition in tissues of autoantibodies and immune complexes leading to tissue injury (Kotzin, 1996). In contrast to autoimmune diseases such as MS and type 1 diabetes mellitus, SLE potentially involves multiple organ systems directly, and its clinical manifestations are diverse and variable (reviewed by Kotzin and O'Dell, 1995). For example, some patients may demonstrate primarily skin rash and joint pain, show spontaneous remissions, and require little medication. At the other end of the spectrum are patients who demonstrate severe and progressive kidney involvement that requires therapy with high doses of steroids and cytotoxic drugs such as cyclophosphamide (Kotzin, 1996).

The serological hallmark of SLE, and the primary diagnostic test available, is elevated serum levels of IgG antibodies to constituents of the cell nucleus, such as double-stranded DNA (dsDNA), single-stranded DNA (ss-DNA), and chromatin. Among these autoantibodies, IgG anti-dsDNA antibodies play a major role in the development of lupus glomerulonephritis (G N) (Hahn and Tsao, 1993; Ohnishi et al., 1994). Glomerulonephritis is a serious condition in which the capillary walls of the kidney's blood purifying glomeruli become thickened by accretions on the epithelial side of glomerular basement membranes. The disease is often chronic and progressive and may lead to eventual renal failure.

Q. Irritable Bowel Syndrome

The compounds and methods of this invention may be used for treating patients with Irritable bowel syndrome (IBS). IBS is a functional disorder characterized by abdominal pain and altered bowel habits. This syndrome may begin in young adulthood and can be associated with significant disability. This syndrome is not a homogeneous disorder. Rather, subtypes of IBS have been described on the basis of the predominant symptom—diarrhea, constipation, or pain. In the absence of "alarm" symptoms, such as fever, weight loss, and gastrointestinal bleeding, a limited workup is needed. Once a diagnosis of IBS is made, an integrated treatment approach can effectively reduce the severity of symptoms. IBS is a common disorder, although its prevalence rates have varied. In general, IBS affects about 15% of US adults and occurs about three times more often in women than in men (Jailwala et al., 2000).

IBS accounts for between 2.4 million and 3.5 million visits to physicians each year. It not only is the most common condition seen by gastroenterologists but also is one of the most common gastrointestinal conditions seen by primary care physicians (Everhart et al., 1991; Sandler, 1990).

IBS is also a costly disorder. Compared with persons who do not have bowel symptoms, persons with IBS miss three times as many workdays and are more likely to report being too sick to work (Drossman et al., 1993; Drossman et al., 1997). Moreover, those with IBS incur hundreds of dollars more in medical charges than persons without bowel disorders (Talley et al., 1995).

No specific abnormality accounts for the exacerbations and remissions of abdominal pain and altered bowel habits experienced by patients with IBS. The evolving theory of IBS suggests dysregulation at multiple levels of the brain-gut axis. Dysmotility, visceral hypersensitivity, abnormal modulation of the central nervous system (CNS), and infection have all been implicated. In addition, psychosocial factors play an important modifying role. Abnormal intestinal motility has long been considered a factor in the pathogenesis of IBS. Transit time through the small intestine after a meal has been shown to be shorter in patients with diarrhea-predominant IBS than in patients who have the constipation-predominant or pain-predominant subtype (Cann et al., 1983).

In studies of the small intestine during fasting, the presence of both discrete, clustered contractions and prolonged, propagated contractions has been reported in patients with IBS (Kellow and Phillips, 1987). They also experience pain with irregular contractions more often than healthy persons (Kellow and Phillips, 1987; Horwitz and Fisher, 2001)

These motility findings do not account for the entire symptom complex in patients with IBS; in fact, most of these patients do not have demonstrable abnormalities (Rothstein, 2000). Patients with IBS have increased sensitivity to visceral pain. Studies involving balloon distention of the rectosigmoid colon have shown that patients with IBS experience pain and bloating at pressures and volumes much lower than control subjects (Whitehead et al., 1990). These patients maintain normal perception of somatic stimuli.

Multiple theories have been proposed to explain this phenomenon. For example, receptors in the viscera may have increased sensitivity in response to distention or intraluminal contents. Neurons in the dorsal horn of the spinal cord may have increased excitability. In addition, alteration in CNS processing of sensations may be involved (Drossman et al., 1997). Functional magnetic resonance imaging studies have recently shown that compared with control subjects, patients with IBS have increased activation of the anterior cingulate cortex, an important pain center, in response to a painful rectal stimulus (Mertz et al., 2000).

Increasingly, evidence suggests a relationship between infectious enteritis and subsequent development of IBS. Inflammatory cytokines may play a role. In a survey of patients with a history of confirmed bacterial gastroenteritis (Neal et al., 1997), 25% reported persistent alteration of bowel habits. Persistence of symptoms may be due to psychological stress at the time of acute infection (Gwee et al., 1999).

Recent data suggest that bacterial overgrowth in the small intestine may have a role in IBS symptoms. In one study (Pimentel et al., 2000), 157 (78%) of 202 IBS patients referred for hydrogen breath testing had test findings that were positive for bacterial overgrowth. Of the 47 subjects who had follow-up testing, 25 (53%) reported improvement in symptoms (i.e., abdominal pain and diarrhea) with antibiotic treatment.

IBS may present with a range of symptoms. However, abdominal pain and altered bowel habits remain the primary features. Abdominal discomfort is often described as crampy in nature and located in the left lower quadrant, although the severity and location can differ greatly. Patients may report diarrhea, constipation, or alternating episodes of diarrhea and constipation. Diarrheal symptoms are typically described as small-volume, loose stools, and stool is sometimes accompanied by mucus discharge. Patients also may report bloating, fecal urgency, incomplete evacuation, and abdominal distention. Upper gastrointestinal symptoms, such as gastroesophageal reflux, dyspepsia, or nausea, may also be present (Lynn and Friedman, 1993).

Persistence of symptoms is not an indication for further testing; it is a characteristic of IBS and is itself an expected symptom of the syndrome. More extensive diagnostic evaluation is indicated in patients whose symptoms are worsening or changing. Indications for further testing also include presence of alarm symptoms, onset of symptoms after age 50, and a family history of colon cancer. Tests may include colonoscopy, computed tomography of the abdomen and pelvis, and barium studies of the small or large intestine.

R. Sjögren's Syndrome

The compounds and methods of this invention may be used for treating patients with SS. Primary Sjögren's syndrome (SS) is a chronic, slowly progressive, systemic autoimmune disease, which affects predominantly middle-aged women (female-to-male ratio 9:1), although it can be seen in all ages including childhood (Jonsson et al., 2002). It is characterized by lymphocytic infiltration and destruction of the exocrine glands, which are infiltrated by mononuclear cells including CD4+, CD8+ lymphocytes and B-cells (Jonsson et al., 2002). In addition, extraglandular (systemic) manifestations are seen in one-third of patients (Jonsson et al., 2001).

The glandular lymphocytic infiltration is a progressive feature (Jonsson et al., 1993), which, when extensive, may replace large portions of the organs. Interestingly, the glandular infiltrates in some patients closely resemble ectopic lymphoid microstructures in the salivary glands (denoted as ectopic germinal centers) (Salomonsson et al., 2002; Xanthou et al., 2001). In SS, ectopic GCs are defined as T and B cell aggregates of proliferating cells with a network of follicular dendritic cells and activated endothelial cells. These GC-like structures formed within the target tissue also portray functional properties with production of autoantibodies (anti-Ro/SSA and anti-La/SSB) (Salomonsson and Jonsson, 2003).

In other systemic autoimmune diseases, such as RA, factors critical for ectopic GCs have been identified. Rheumatoid synovial tissues with GCs were shown to produce chemokines CXCL13, CCL21 and lymphotoxin (LT)-β (detected on follicular center and mantle zone B cells). Multivariate regression analysis of these analytes identified CXCL13 and LT-β as the solitary cytokines predicting GCs in rheumatoid synovitis (Weyand and Goronzy, 2003). Recently CXCL13 and CXCR5 in salivary glands has been shown to play an essential role in the inflammatory process by recruiting B and T cells, therefore contributing to lymphoid neogenesis and ectopic GC formation in SS (Salomonsson et al., 2002).

S. Psoriasis

The compounds and methods of this invention may be used for treating patients with psoriasis. Psoriasis is a chronic skin disease of scaling and inflammation that affects 2 to 2.6 percent of the United States population, or between 5.8 and 7.5 million people. Although the disease occurs in all age groups, it primarily affects adults. It appears about equally in males and females. Psoriasis occurs when skin cells quickly rise from their origin below the surface of the skin and pile up on the surface before they have a chance to mature. Usually this movement (also called turnover) takes about a month, but in psoriasis it may occur in only a few days. In its typical form, psoriasis results in patches of thick, red (inflamed) skin covered with silvery scales. These patches, which are sometimes referred to as plaques, usually itch or feel sore. They most often occur on the elbows, knees, other parts of the legs, scalp, lower back, face, palms, and soles of the feet, but they can occur on skin anywhere on the body. The disease may also affect the fingernails, the toenails, and the soft tissues of the genitals and inside the mouth. While it is not unusual for the skin around affected joints to crack, approximately 1 million people with psoriasis experience joint inflammation that produces symptoms of arthritis. This condition is called psoriatic arthritis.

Psoriasis is a skin disorder driven by the immune system, especially involving a type of white blood cell called a T cell. Normally, T cells help protect the body against infection and disease. In the case of psoriasis, T cells are put into action by mistake and become so active that they trigger other immune responses, which lead to inflammation and to rapid turnover of skin cells. In about one-third of the cases, there is a family history of psoriasis. Researchers have studied a large number of families affected by psoriasis and identified genes linked to the disease. People with psoriasis may notice that there are times when their skin worsens, then improves. Conditions that may cause flareups include infections, stress, and changes in climate that dry the skin. Also, certain medicines, including lithium and beta blockers, which are prescribed for high blood pressure, may trigger an outbreak or worsen the disease.

T. Infectious diseases

Compounds of the present disclosure may be useful in the treatment of infectious diseases, including viral and bacterial infections. As noted above, such infections may be associated with severe localized or systemic inflammatory responses. For example, influenza may cause severe inflammation of the lung and bacterial infection can cause the systemic hyperinflammatory response, including the excessive production of multiple inflammatory cytokines, that is the hallmark of sepsis. In addition, compounds of the invention may be useful in directly inhibiting the replication of viral pathogens. Previous studies have demonstrated that related compounds such as CDDO can inhibit the replication of HIV in macrophages (Vazquez et al., 2005). Other studies have indicated that inhibition of NF-kappa B signaling may inhibit influenza virus replication, and that cyclopentenone prostaglandins may inhibit viral replication (e.g., Mazur et al., 2007; Pica et al., 2000).

V. Pharmaceutical Formulations and Routes of Administration

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. A "therapeutically effective amount" preferably reduces the amount of symptoms of the condition in the infected patient by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1,000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending, of course, of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some particular embodiments, the amount is less than 10,000 mg per day with a range, for example, of 750 mg to 9,000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 microgram/kg/body weight, about 5 microgram/kg/body weight, about 10 micro-gram/kg/body weight, about 50 microgram/kg/body weight, about 100 micro-gram/kg/body weight, about 200 microgram/kg/body weight, about 350 micro-gram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milli-gram/kg/body weight, about 350 milligram/kg/body weight, about 500 milligram/kg/body weight, to about 1,000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

VI. Combination Therapy

In addition to being used as a monotherapy, the compounds of the present disclosure may also find use in combination therapies. Effective combination therapy may be achieved with a single composition or pharmacological formulation that includes both agents, or with two distinct compositions or formulations, at the same time, wherein one composition includes the oleanolic acid derivative according to the methods of this invention, and the other includes the second agent(s). Alternatively, the therapy may precede or follow the other agent treatment by intervals ranging from minutes to months.

Various combinations may be employed, such as when a compound of the present disclosure is "A" and "B" represents a secondary agent, non-limiting examples of which are described below:

| | | | |
|---|---|---|---|
| A/B/A | B/A/B | B/B/A | A/A/B |
| A/B/B | B/A/A | A/B/B/B | B/A/B/B |
| B/B/B/A | B/B/A/B | A/A/B/B | A/B/A/B |
| A/B/B/A | B/B/A/A | B/A/B/A | B/A/A/B |
| A/A/A/B | B/A/A/A | A/B/A/A | A/A/B/A |

Administration of the compounds of the present disclosure to a patient will follow general protocols for the administration of pharmaceuticals, taking into account the toxicity, if any, of the drug. It is expected that the treatment cycles would be repeated as necessary.

Beta interferons may be suitable secondary agents. These are medications derived from human cytokines which help regulate the immune system. They include interferon β-1b and interferon β-1a. Betaseron has been approved by the FDA for relapsing forms of secondary progressive MS. Furthermore, the FDA has approved the use of several β-interferons as treatments for people who have experienced a single attack that suggests multiple sclerosis, and who may be at risk of future attacks and developing definite MS. For example, risk of MS may be suggested when an MRI scan of the brain shows lesions that predict a high risk of conversion to definite MS.

Glatiramer acetate is a further example of a secondary agent that may be used in a combination treatment. Glatiramer is presently used to treat relapsing remitting MS. It is made of four amino acids that are found in myelin. This drug is reported to stimulate T cells in the body's immune system to change from harmful, pro-inflammatory agents to beneficial, anti-inflammatory agents that work to reduce inflammation at lesion sites.

Another potential secondary agent is mitoxantrone, a chemotherapy drug used for many cancers. This drug is also FDA-approved for treatment of aggressive forms of relapsing remitting MS, as well as certain forms of progressive MS. It is given intravenously, typically every three months. This medication is effective, but is limited by cardiac toxicity. Novantrone has been approved by the FDA for secondary progressive, progressive-relapsing, and worsening relapsing-remitting MS.

Another potential secondary agent is natalizumab. In general, natalizumab works by blocking the attachment of immune cells to brain blood vessels, which is a necessary step for immune cells to cross into the brain, thus reducing the immune cells' inflammatory action on brain neurons. Natalizumab has been shown to significantly reduce the frequency of attacks in people with relapsing MS.

In the case of relapsing remitting MS, patients may be given intravenous corticosteroids, such as methylprednisolone, as a secondary agent, to end the attack sooner and leave fewer lasting deficits.

Other common drugs for MS that may be used in combination with the oleanolic acid derivatives include immunosuppressive drugs such as azathioprine, cladribine and cyclophosphamide.

It is contemplated that other anti-inflammatory agents may be used in conjunction with the treatments of the current invention. Other COX inhibitors may be used, including arylcarboxylic acids (salicylic acid, acetylsalicylic acid, diflunisal, choline magnesium trisalicylate, salicylate, benorylate, flufenamic acid, mefenamic acid, meclofenamic acid and triflumic acid), arylalkanoic acids (diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin and sulindac) and enolic acids (phenylbutazone, oxyphenbutazone, azapropazone, feprazone, piroxicam, and isoxicam. See also U.S. Pat. No. 6,025,395, which is incorporated herein by reference.

Histamine H2 receptor blocking agents may also be used in conjunction with the compounds of the current invention, including cimetidine, ranitidine, famotidine and nizatidine.

Treatment with acetylcholinesterase inhibitors such as tacrine, donepizil, metrifonate and rivastigmine for the treatment of Alzheimer's and other disease in conjunction with the compounds of the present disclosure is contemplated. Other acetylcholinesterase inhibitors may be developed which may be used once approved include rivastigmine and metrifonate. Acetylcholinesterase inhibitors increase the amount of neurotransmitter acetylcholine at the nerve terminal by decreasing its breakdown by the enzyme cholinesterase.

MAO-B inhibitors such as selegilene may be used in conjunction with the compounds of the current invention. Selegilene is used for Parkinson's disease and irreversibly inhibits monoamine oxidase type B (MAO-B). Monoamine oxidase is an enzyme that inactivates the monoamine neurotransmitters norepinephrine, serotonin and dopamine.

Dietary and nutritional supplements with reported benefits for treatment or prevention of Parkinson's, Alzheimer's, multiple sclerosis, amyotrophic lateral sclerosis, rheumatoid arthritis, inflammatory bowel disease, and all other diseases whose pathogenesis is believed to involve excessive production of either nitric oxide (NO) or prostaglandins, such as acetyl-L-carnitine, octacosanol, evening primrose oil, vitamin B6, tyrosine, phenylalanine, vitamin C, L-dopa, or a combination of several antioxidants may be used in conjunction with the compounds of the current invention. For the treatment or prevention of cancer, compounds of the invention may be combined with one or more of the following: radiation, chemotherapy agents (e.g., cytotoxic agents such as anthracyclines, vincristine, vinblastin, microtubule-targeting agents such as paclitaxel and docetaxel, 5-FU and related agents, cisplatin and other platinum-containing compounds, irinotecan and topotecan, gemcitabine, temozolomide, etc.), targeted therapies (e.g., imatinib, bortezomib, bevacizumab, rituximab), or vaccine therapies designed to promote an enhanced immune response targeting cancer cells.

For the treatment or prevention of autoimmune disease, compounds of the invention may be combined with one or more of the following: corticosteroids, methotrexate, anti-TNF antibodies, other TNF-targeting protein therapies, and NSAIDs. For the treatment of prevention of cardiovascular diseases, compounds of the invention may be combined with antithrombotic therapies, anticholesterol therapies such as statins (e.g., atorvastatin), and surgical interventions such as stenting or coronary artery bypass grafting. For the treatment of osteoporosis, compounds of the invention may be combined with antiresorptive agents such as bisphosphonates or anabolic therapies such as teriparatide or parathyroid hormone. For the treatment of neuropsychiatric conditions, compounds of the invention may be combined with antidepressants (e.g., imipramine or SSRIs such as fluoxetine), antipsychotic agents (e.g., olanzapine, sertindole, risperidone), mood stabilizers (e.g., lithium, valproate semisodium), or other standard agents such as anxiolytic agents. For the treatment of neurological disorders, compounds of the invention may be combined with anticonvulsant agents (e.g., valproate semisodium, gabapentin, phenyloin, carbamazepine, and topiramate), antithrombotic agents (e.g., tissue plasminogen activator), or analgesics (e.g., opioids, sodium channel blockers, and other antinociceptive agents).

For the treatment of disorders involving oxidative stress, compounds of the present disclosure may be combined with tetrahydrobiopterin (BH4) or related compounds. BH4 is a cofactor for constitutive forms of nitric oxide synthase, and may be depleted by reactions with peroxynitrite. Peroxynitrite is formed by the reaction of nitric oxide and superoxide. Thus, under conditions of oxidative stress excessive levels of superoxide can deplete normal, beneficial levels of nitric oxide by converting NO to peroxynitrite. The resulting depletion of BH4 by reaction with peroxynitrite results in the "uncoupling" of nitric oxide synthases so that they form superoxide rather than NO. This adds to the oversupply of superoxide and prolongs the depletion of NO. Addition of exogenous BH4 can reverse this uncoupling phenomenon, restoring the production of NO and reducing the level of oxidative stress in tissues. This mechanism is expected to complement the actions of compounds of the invention, which reduce oxidative stress by other means, as discussed above and throughout this invention.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods and Materials

Nitric Oxide production and cell viability. RAW264.7 macrophages were pre-treated with DMSO or drugs for 2 hours, then treated with recombinant mouse IFNγ (Sigma) for 24 hours. NO concentration in media was determined using the Griess reagent system (Promega). Cell viability was determined using WST-1 reagent (Roche).

STAT3 phosphorylation. HeLa cells were treated with the indicated compounds and concentrations for 6 hours and subsequently stimulated with 20 ng/ml recombinant human IL-6 (R&D Systems) for 15 minutes. Lysates were immunoblotted with antibodies against phosphorylated or total STAT3 (Cell Signaling).

iNOS induction qPCR. RAW264.7 mouse macrophage cells were pre-treated for 2 hours with compounds at the indicated concentrations and subsequently stimulated with 10 ng/ml IFNγ for an additional 2 hours. mRNA levels of iNOS were quantified by qPCR and are shown relative to the vehicle-treated IFNγ-stimulated sample which was normalized to a value of 1. Values are averages of duplicate PCR reactions, each with triplicate wells.

iNOS and COX-2 induction Western blot. RAW264.7 cells were pre-treated for 2 hours with indicated compounds and subsequently stimulated with 10 ng/ml IFNγ for an additional 24 hours. iNOS and COX-2 protein levels were assayed by immunoblotting. Actin was used as a loading control.

Nrf2 target gene induction. MDA-MB-435 human melanoma cells were treated with vehicle (DMSO) or the indicated compounds and concentrations for 16 hours. HO-1, thioredoxin reductase-1 (TrxR1), γ-glutamylcysteine synthetase (γ-GCS), and ferritin heavy chain mRNA levels were quantified using qPCR and were normalized relative to a DMSO-treated sample run in parallel. Values are averages of duplicate wells. Primer sequences are as follows.

```
HO-1 FW:                  (SEQ ID NO: 1)
TCCGATGGGTCCTTACACTC,

HO-1 REV:                 (SEQ ID NO: 2)
TAGGCTCCTTCCTCCTTTCC,

TrxR1 FW:                 (SEQ ID NO: 3)
GCAGCACTGAGTGGTCAAAA,

TrxR1 REV:                (SEQ ID NO: 4)
GGTCAACTGCCTCAATTGCT,

γ-GCS FW:                 (SEQ ID NO: 5)
GCTGTGGCTACTGCGGTATT,

γ-GCS REV                 (SEQ ID NO: 6)
ATCTGCCTCAATGACACCAT,

Ferritin HC FW:           (SEQ ID NO: 7)
ATGAGCAGGTGAAAGCCATC,

Ferritin HC REV:          (SEQ ID NO: 8)
TAAAGGAAACCCCAACATGC,

S9 FW:                    (SEQ ID NO: 9)
GATTACATCCTGGGCCTGAA,

S9 REV:                   (SEQ ID NO: 10)
GAGCGCAGAGAGAAGTCGAT.
```

Figure 35:
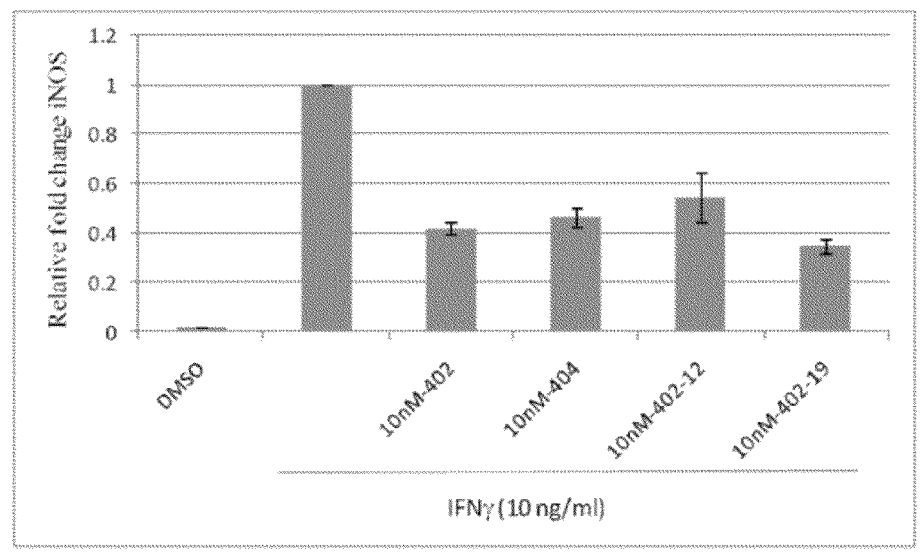
FIG. 35. Suppression of iNOS mRNA induction. RAW264.7 mouse macrophages were pre-treated for 2 hours with compounds at the indicated concentrations and subsequently stimulated with 10 ng/ml IFNγ for an additional 2 hours. mRNA levels of iNOS were quantified by qPCR and are shown relative to the vehicle-treated IFNγ-stimulated sample which was normalized to a value of 1. Values are averages of duplicate PCR reactions, each with triplicate wells.
Figure 36:
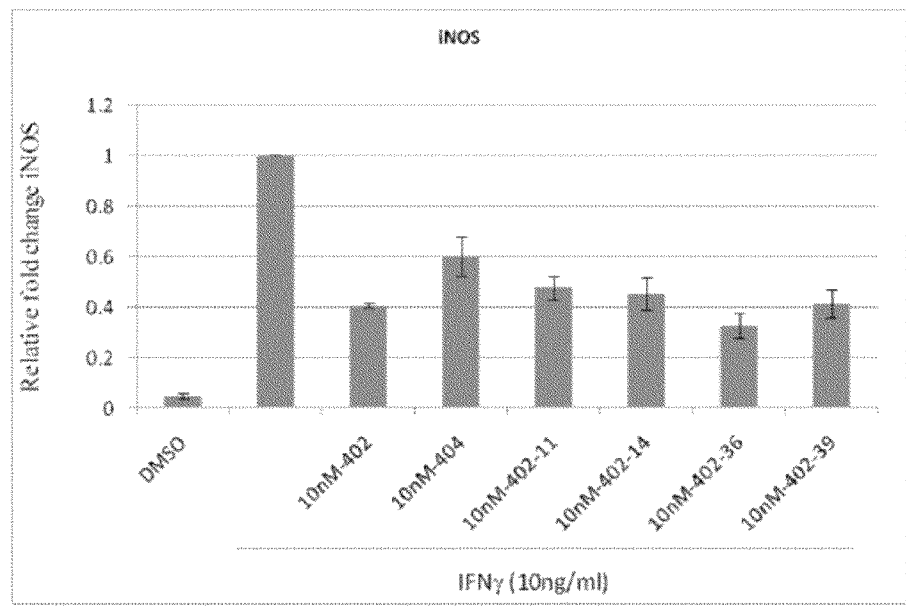
FIG. 36. Suppression of iNOS mRNA induction. RAW264.7 mouse macrophages were pre-treated for 2 hours with compounds at the indicated concentrations and subsequently stimulated with 10 ng/ml IFNγ for an additional 2 hours. mRNA levels of iNOS were quantified by qPCR and are shown relative to the vehicle-treated IFNγ-stimulated sample which was normalized to a value of 1. Values are averages of duplicate PCR reactions, each with triplicate wells.
Figure 37:
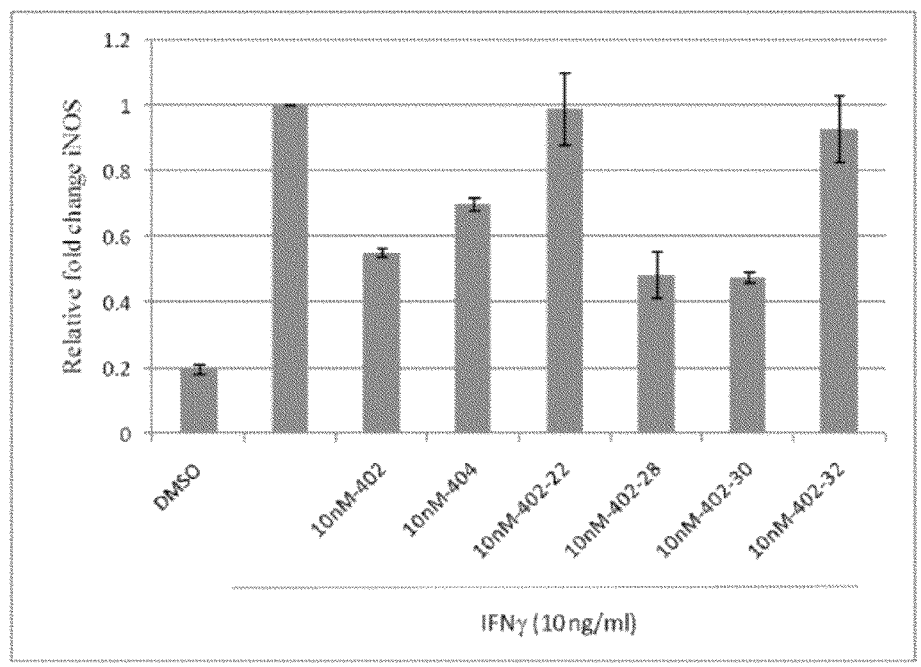
FIG. 37. Suppression of iNOS mRNA induction. RAW264.7 mouse macrophages were pre-treated for 2 hours with compounds at the indicated concentrations and subsequently stimulated with 10 ng/ml IFNγ for an additional 2 hours. mRNA levels of iNOS were quantified by qPCR and are shown relative to the vehicle-treated IFNγ-stimulated sample which was normalized to a value of 1. Values are averages of duplicate PCR reactions, each with triplicate wells.
Figure 38:
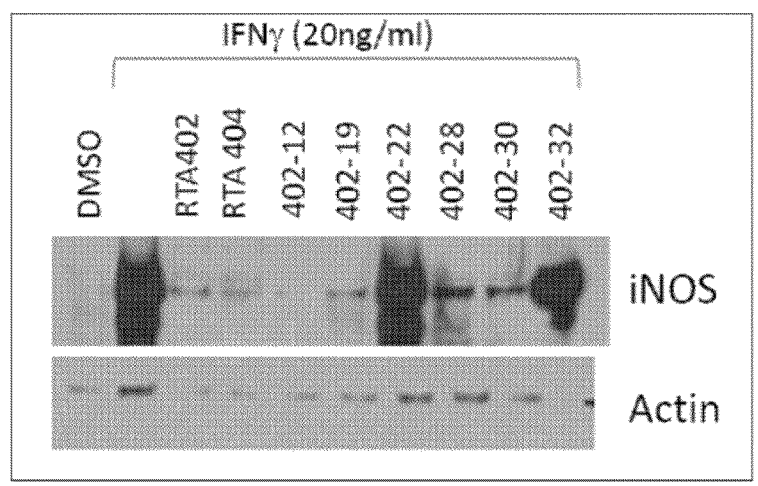
FIGS. 38-40. iNOS Western Blot in RAW264.7 mouse macrophages. Cells were pretreated by compounds at 300 nM for 2 hours, followed by 24 hour induction by IFNγ (20 ng/ml).
Figure 39:
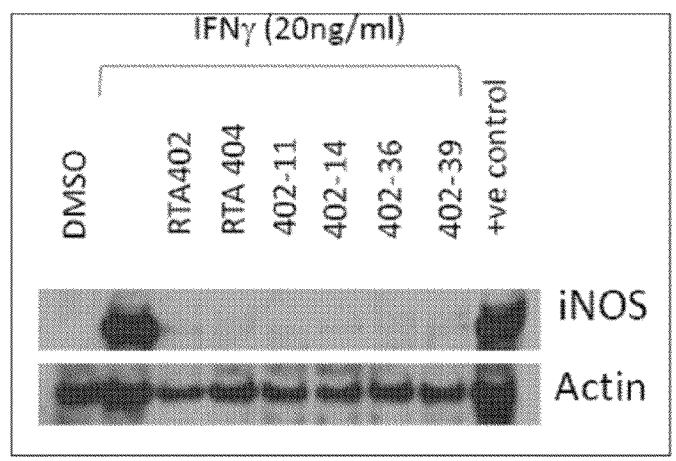
Figure 40:
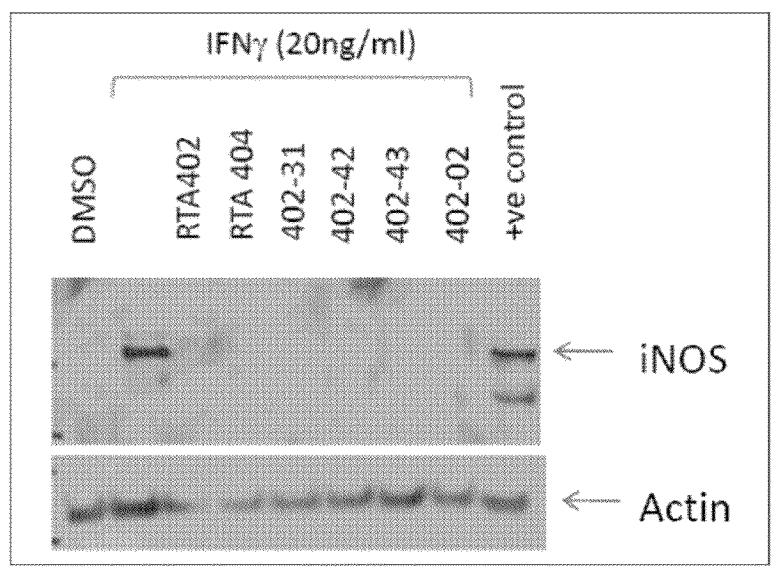
Figure 41:
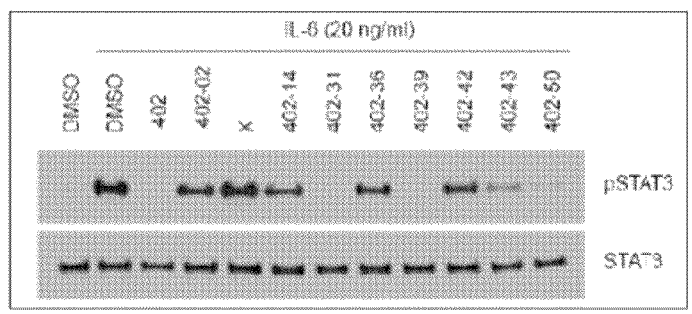
FIGS. 41-42. Suppression of IL-6 Induced STAT3 Phosphorylation. HeLa cells were treated with DMSO or the indicated compounds at 2 μM for 6 hours and subsequently stimulated with 20 ng/ml IL-6 for 15 minutes. Phosphorylated STAT3 and total STAT3 levels were assayed by immunoblotting.
Figure 42:
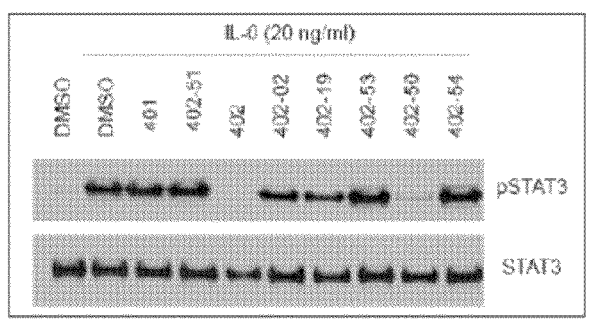
Figure 44D:
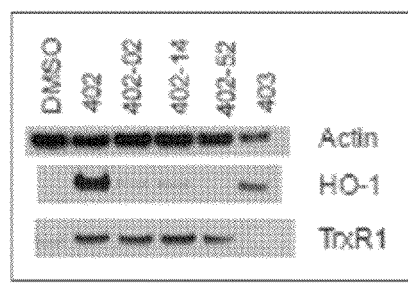
FIGS. 44D, 46D, 47D: MDA-MB-435 cells were treated with vehicle (DMSO) or the indicated compounds at 400 nM for 16 hours. HO-1, TrxR1 and actin protein levels were assayed by immunoblotting.
Figure 46D:
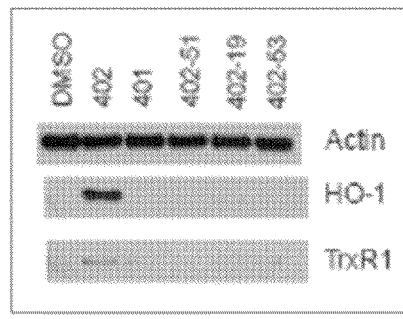
Figure 47D:
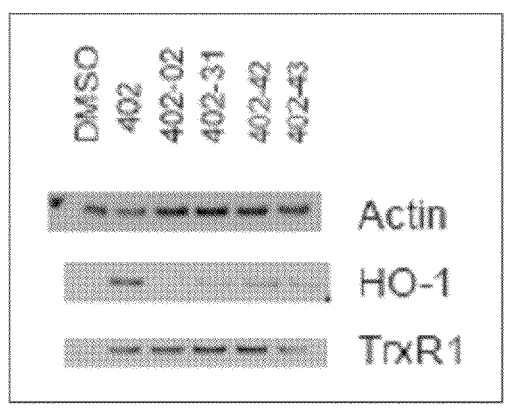
Figure 48:
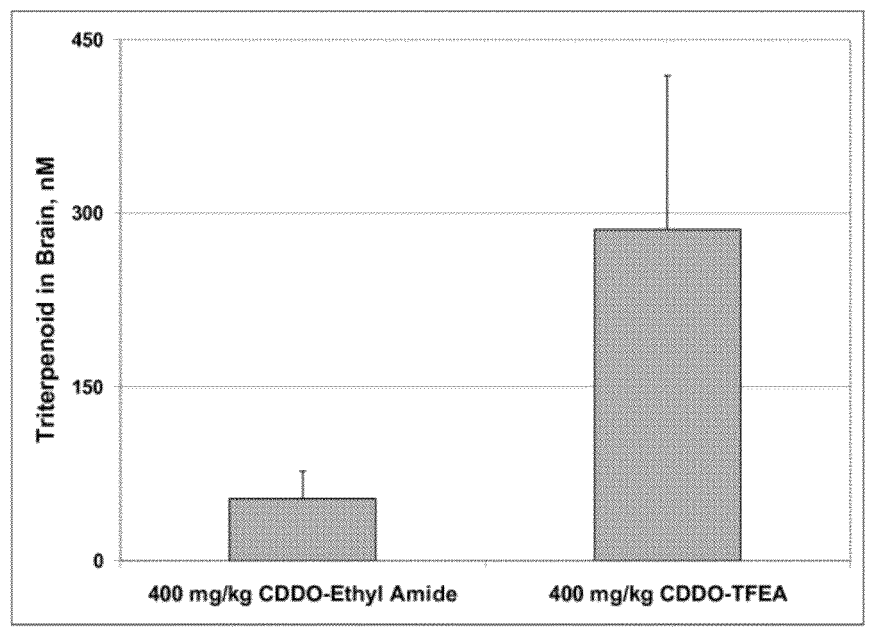
FIG. 48. CDDO-TFEA (TP-500) Is Detected at Higher Levels in Mouse Brain than CDDO-EA (TP-319). CD-1 mice were fed either 200 or 400 mg/kg diet of either TP-319 or TP-500 for 3.5 days, and TP levels in the brains of the mice were analyzed by LC/MS. The structures of TP-319 and TP-500 are shown herein.
Figure 49:
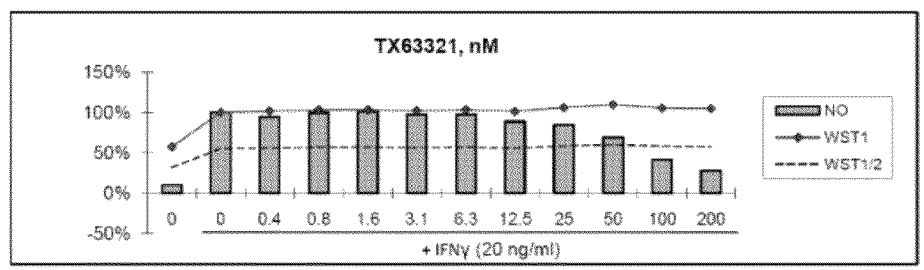
Figure 50:
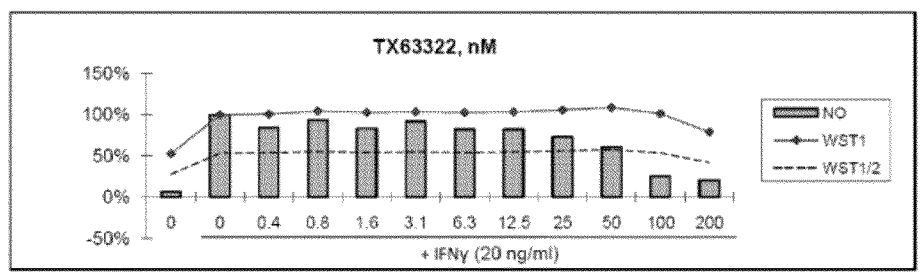
Figure 51:
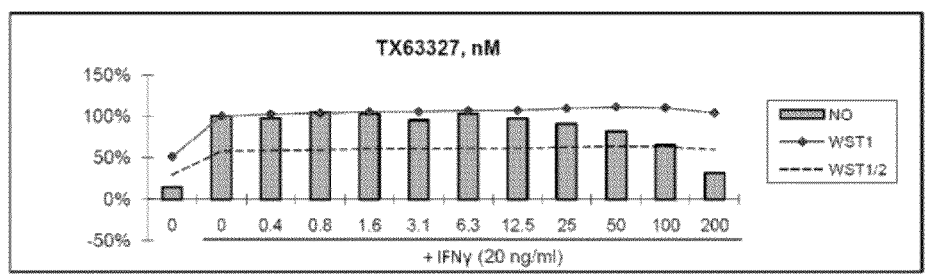
Figure 52:
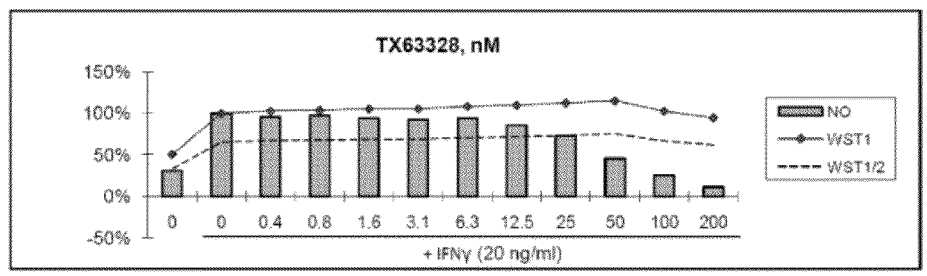

Comparison Compounds. In some of the experiments (e.g., FIGS. 35-47), certain compounds of this invention were compared with other compounds, such as 402, 403, 404, 402-11 and others. A list of comparison compounds is shown here:

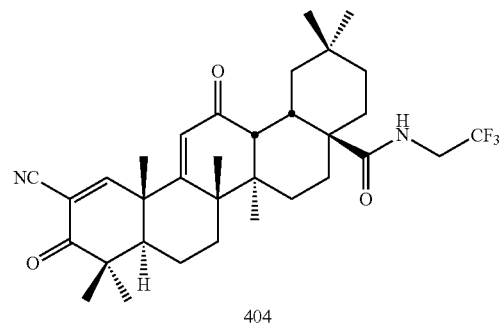

404

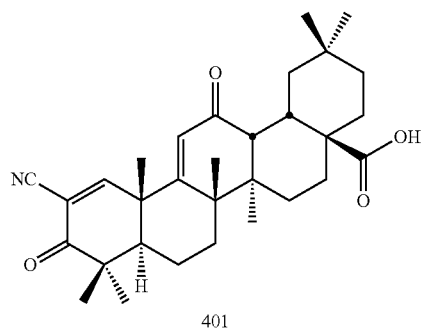

401

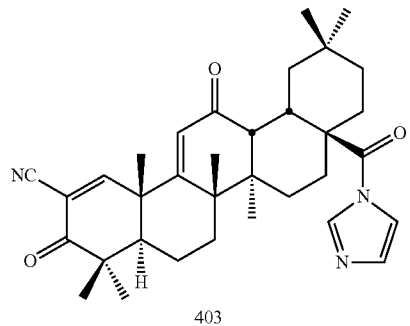

403

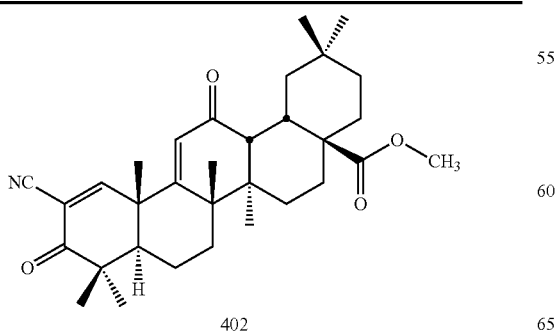

402

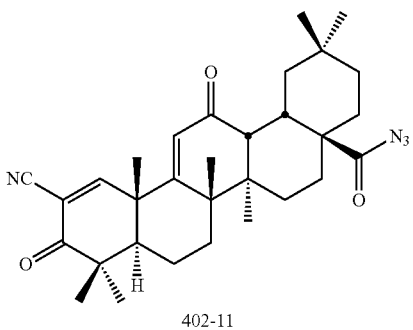

402-11

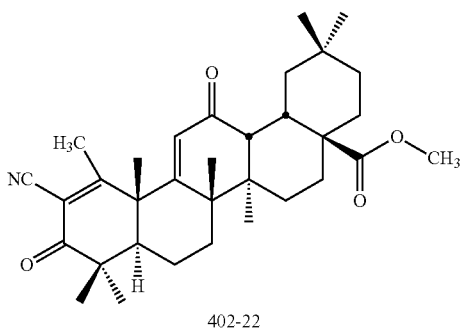

402-22

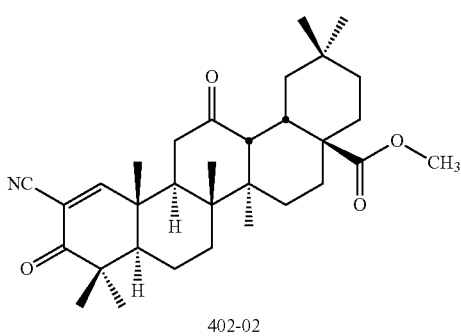

402-02

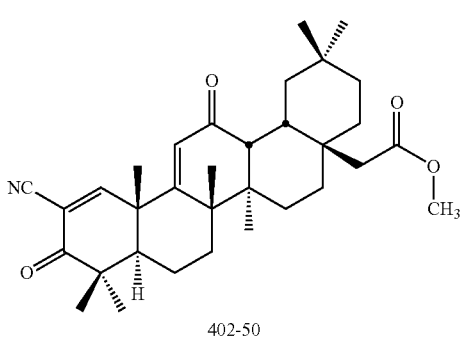

402-50

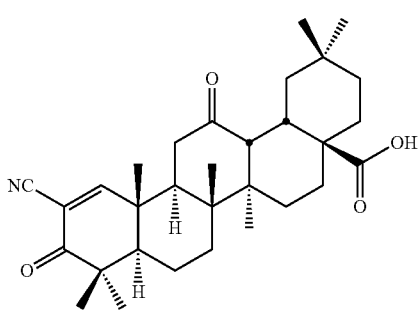

402-51

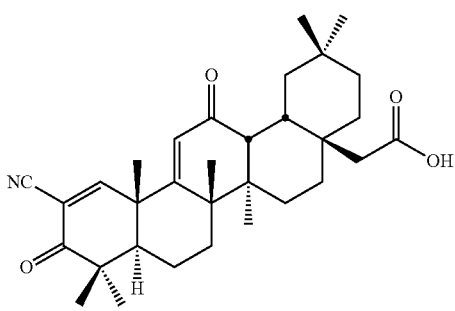

63199

Compounds 401, 402, 402-02, 403, and 404 can be prepared according to the methods taught by U.S. Pat. No. 6,326,507, Honda et al. (1998), Honda et al. (2000b), Honda et al. (2002) and Yates et al. (2007), which are all incorporated herein by reference. The synthesis of the other compounds are disclosed in the following applications, each of which is incorporated herein by reference: U.S. Application Nos. 61/046,332, 61/046,352, 61/046,366, 61/111,333, and 61/111,294. The synthesis of the other compounds are also disclosed in the following separate applications filed concurrently herewith, each of which is incorporated herein by reference in their entireties: U.S. patent application Ser. No. 12/426,737 by Eric Anderson, Xin Jiang, Xiaofeng Liu; Melean Visnick, entitled "Antioxidant Inflammation Modulators: Oleanolic Acid Derivatives With Saturation in the C-Ring," filed Apr. 17, 2009; U.S. patent application Ser. No. 12/426,791 by Xin Jiang, Jack Greiner, Lester L. Maravetz, Stephen S. Szucs, Melean Visnick, entitled "Antioxidant Inflammation Modulators: Novel Derivatives of Oleanolic Acid," filed Apr. 20, 2009; U.S. patent application Ser. No. 12/426,832 by Xin Jiang, Xioafeng Liu, Jack Greiner, Stephen S. Szucs, Melean Visnick entitled, "Antioxidant Inflammation Modulators: C-17 Homologated Oleanolic Acid Derivatives," filed Apr. 20, 2009.

Aqueous Solubility Determination. The following procedure was used to obtain the aqueous solubility results summarized in Example 4. Step 1. Determination of optimal UV/vis wavelengths and generation of standard curves for a compound of interest:

(1) For eight standard calibration curves (one plate), prepare 34 mL of 50:50 (v:v) universal buffer:acetonitrile in a 50 mL tube.

(2) Using a multichannel pipet, dispense (in μL) the buffer: acetonitrile in a deep well plate as follows:

|   | 1 | 2 | 3 | 4 | 5 | 6 | 7 | 8 | 9 | 10 | 11 | 12 |
|---|---|---|---|---|---|---|---|---|---|----|----|----|
| A | 285 | 285 | 380 | 380 | 285 | 285 | 285 | 285 | 285 | 285 | 285 | 285 |
| B |   |   |   |   |   |   |   |   |   |    |    |    |
| C |   |   |   |   |   |   |   |   |   |    |    |    |
| D |   |   |   |   |   |   |   |   |   |    |    |    |
| E |   |   |   |   |   |   |   |   |   |    |    |    |
| F |   |   |   |   |   |   |   |   |   |    |    |    |
| G |   |   |   |   |   |   |   |   |   |    |    |    |
| H |   |   |   |   |   |   |   |   |   |    |    |    |

(3) Using a multichannel pipet, dispense DMSO into the same plate as follows:

|   | 1 | 2 | 3 | 4 | 5 | 6 | 7 | 8 | 9 | 10 | 11 | 12 |
|---|---|---|---|---|---|---|---|---|---|----|----|----|
| A |   |   | 12 µL | 12 µL | 15 µL | 15 µL | 15 µL | 15 µL | 15 µL | 15 µL | 15 µL | 15 µL |
| B |   |   | µL | µL | µL | µL | µL | µL | µL | µL | µL | µL |
| C |   |   |   |   |   |   |   |   |   |   |   |   |
| D |   |   |   |   |   |   |   |   |   |   |   |   |
| E |   |   |   |   |   |   |   |   |   |   |   |   |
| G |   |   |   |   |   |   |   |   |   |   |   |   |
| H |   |   |   |   |   |   |   |   |   |   |   |   |

(4) Add 10 mM compound in DMSO into the plates as follows:

|   | 1 | 2 | 3 | 4 | 5 6 7 8 9 | 10 | 11 | 12 |
|---|---|---|---|---|---|---|---|---|
| A | 15 µL cmpd1 | 15 µL cmpd1 | 8 µL cmpd1 | 8 µL cmpd1 | | | | |
| B | 15 µL cmpd2 | 15 µL cmpd2 | 8 µL cmpd2 | 8 µL cmpd2 | | | | |
| C | 15 µL cmpd3 | 15 µL cmpd3 | 8 µL cmpd3 | 8 µL cmpd3 | | | | |
| D | 15 µL cmpd4 | 15 µL cmpd4 | 8 µL cmpd4 | 8 µL cmpd4 | | | | |
| E | 15 µL cmpd5 | 15 µL cmpd5 | 8 µL cmpd5 | 8 µL cmpd5 | | | | |
| F | 15 µL cmpd6 | 15 µL cmpd6 | 8 µL cmpd6 | 8 µL cmpd6 | | | | |
| G | 15 µL cmpd7 | 15 µL cmpd7 | 8 µL cmpd7 | 8 µL cmpd7 | | | | |
| H | 15 µL cmpd8 | 15 µL cmpd8 | 8 µL cmpd8 | 8 µL cmpd8 | | | | |

(5) Mix columns 1 and 2 by pipetting each up and down 10 times. Mix columns 3 and 4 by pipetting up and down 10 times. Serially dilute as follows (pipet up and down 10 times after each transfer):

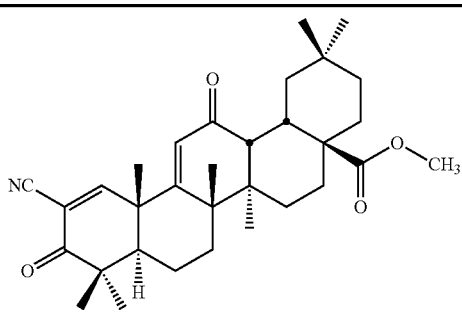

402

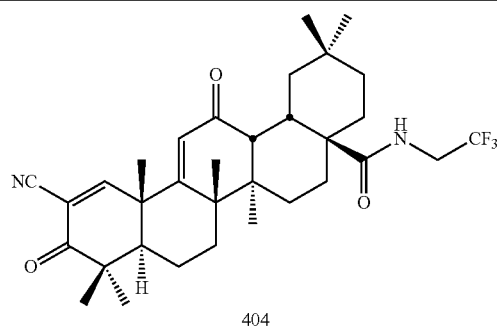

404

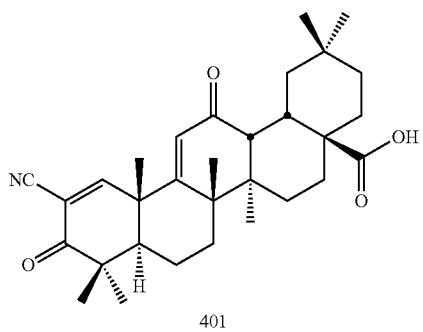

401

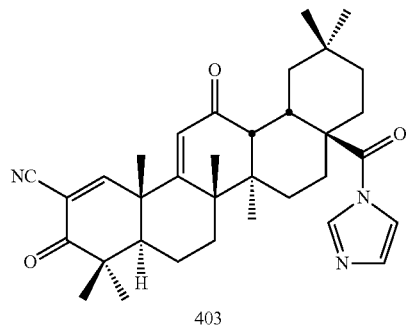

403

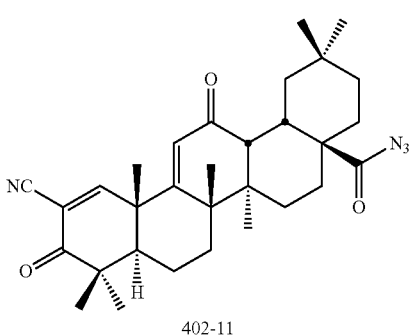

402-11

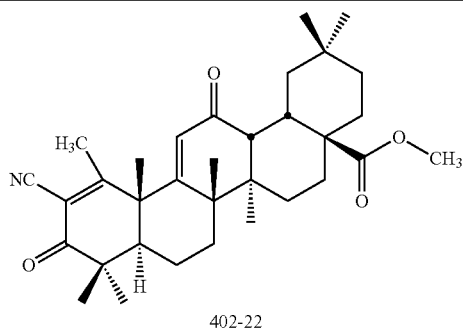

402-22

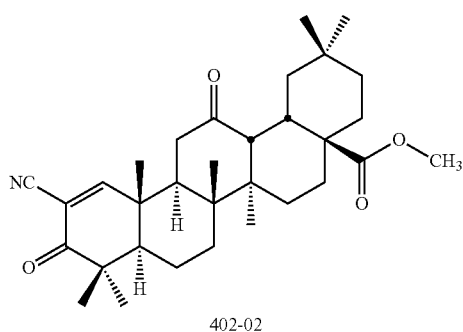

402-02

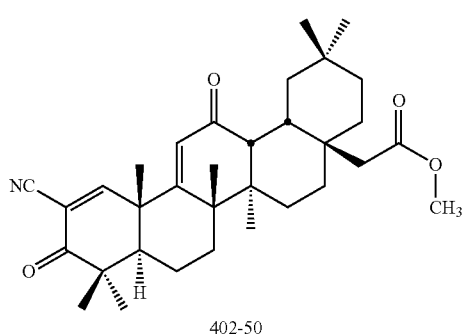

402-50

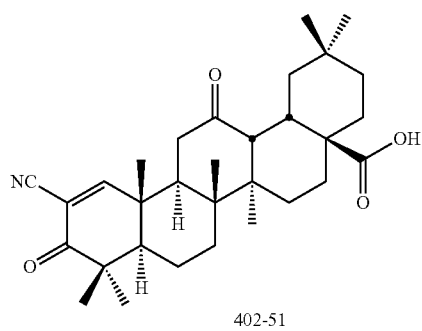

402-51

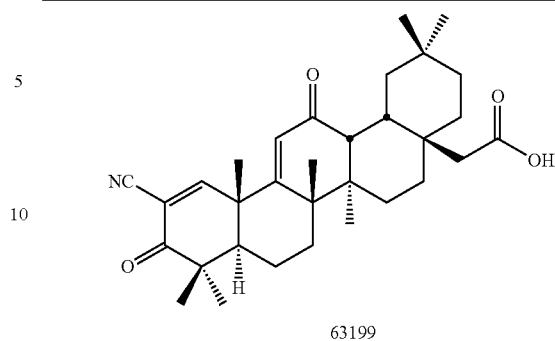

63199

Note columns 11 and 12 contain DMSO only and so compound should not be transferred to these wells.

(6) Cover plate with lid and shake (200-300 rpm) at room temperature for 20 minutes.
(7) Mix all wells by pipetting up and down 10 times.
(8) Transfer 120 µL from each well to a UV transparent plate. Cover and shake for 3-5 minutes. Remove any bubbles in the wells using a pipet.
(9) Read from 220 nm to 500 nm at 10 nm increments on a spectrophotometer (e.g., SpectraMax®).

Step 2. Compound Solubility Testing Procedures using the Millipore™ Multiscreen® Solubility Filter Plate.

Consumables: Millipore™ Multiscreen® Solubility Filter Plate #MSSLBPC10 Greiner® 96 well disposable UV-Star analysis plate, VWR#655801 Greiner® 96 well polypropylene V-bottom collection plate, VWR#651201

Universal Aqueous Buffer:
(a) To prepare 500 mL of universal buffer, add the following: 250 mL Nanopure water; 1.36 mL (45 mM) ethanolamine; 3.08 g (45 mM) potassium dihydrogen phosphate; 2.21 g (45 mM) potassium acetate; thoroughly mix.
(b) Adjust pH to 7.4 with HCl and q.s. to 500 mL with 0.15 M KCl.
(c) Filter to remove particulates and reduce bacterial growth.
(d) Store at 4° C. in the dark.

Solubility Protocol:
(a) Add 285 µL of Universal Aqueous Buffer to desired wells of the Millipore™ Multiscreen® Solubility filter plate.
(b) Add 15 µL of 10 mM compound in DMSO to the appropriate wells. Add 15 µL of 100% DMSO only to 6 wells of the filter plate for blanks
(c) Using a multichannel pipet, mix wells by pipetting up and down 10 times. Be careful not to touch the filters in the plate with the tips.
(d) Cover and gently shake (200-300 rpm) filter plate for 90 minutes at room temperature.
(e) Vacuum filter the aqueous solution from the Multiscreen® solubility filter plate into a polypropylene V-bottom plate.
(f) Transfer 60 µL of filtrate to a UV transparent plate (Greiner® UV-Star Analysis Plate).
(g) Add 60 µL of acetonitrile to each well and mix by pipetting up and down 10 times.
(h) Cover and gently shake for 3-5 minutes. Remove any bubbles with a pipet.
(i) Measure the absorbance of each well in the plate on the spectrophotometer (UV/vis) at the desired wavelength.

For compounds in a plate with different absorbance peaks, set the spectrophotometer to read a spectrum (e.g., from 220 nm to 460 nm).

(j) Identify concentration using measured absorbance for each compound and the predetermined standard curve (see Step 1).

Example 2

Synthesis of Oleanolic Acid Derivatives

Scheme 1:

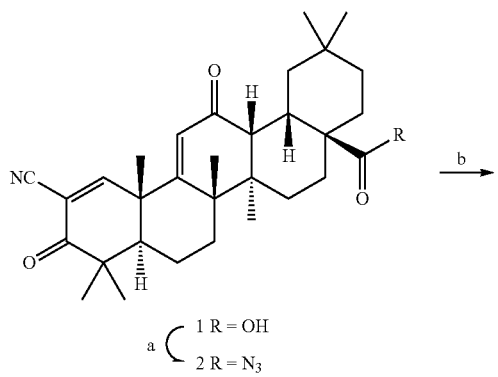

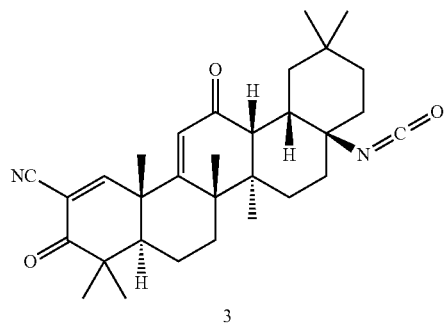

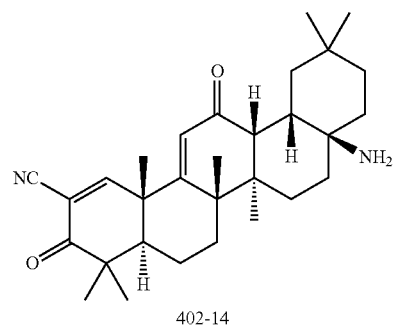

402-14

Reagents and conditions pertaining to Scheme 1: (a) DPPA, Et$_3$N, 0° C. to rt, 6 h, 90%; (b) 80° C., 2 h; (c) 12 N HCl (aq), 99%.

Amine 402-14 was synthesized from acid 1 (Honda et al., 2000b) in 3 steps (Scheme 1). Acid 1 (Honda et al., 2000b) was treated with DPPA/Et$_3$N to give the corresponding azide 402-11 in 90% yield. The Curtius rearrangement of compound 2 gave isocyanate 3, which was treated with concentrated HCl to give amine 402-14 in quantitative yield.

Scheme 2:

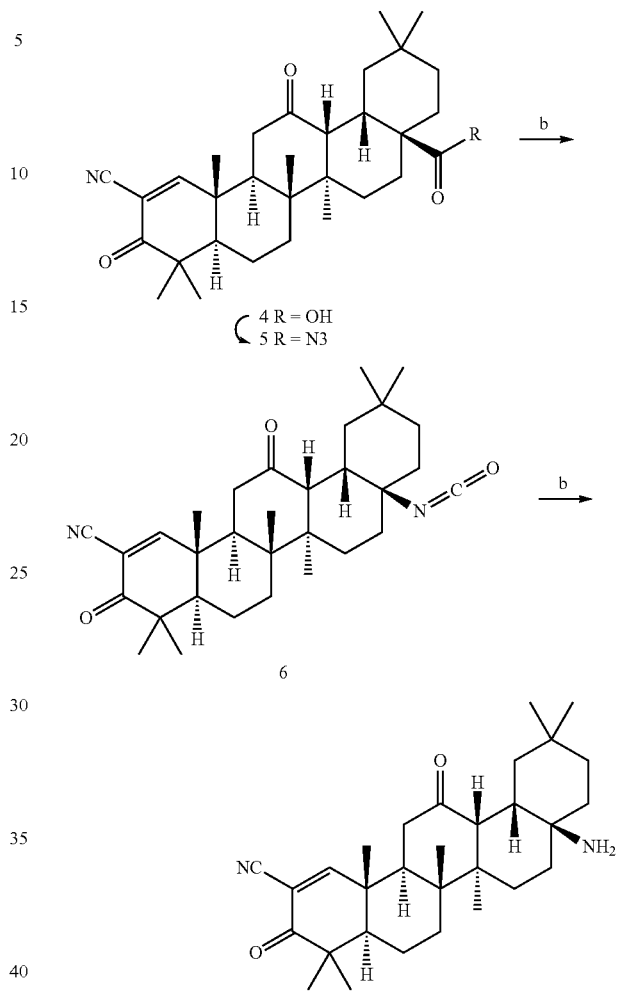

Reagents and conditions pertaining to Scheme 2: (a) DPPA, Et$_3$N, 0° C. to rt, 6 h, 99%; (b) 80° C., 2 h; (c) 12 N HCl (aq), 81%.

Using the same protocol as shown for 402-14, acid 4 was transformed to amine 402-52 in 80% overall yield (Scheme 2).

Scheme 3:

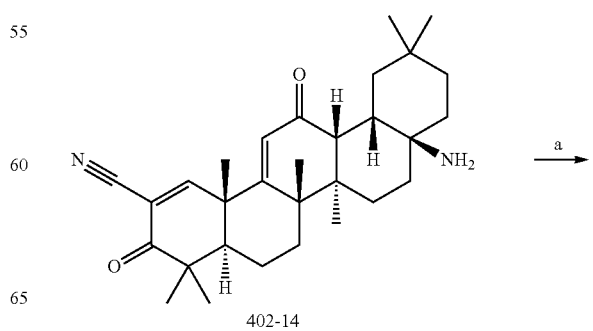

402-14

-continued

Scheme 5:

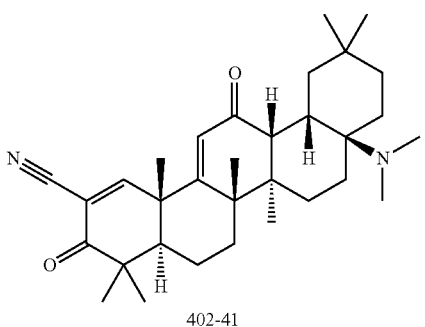
402-41

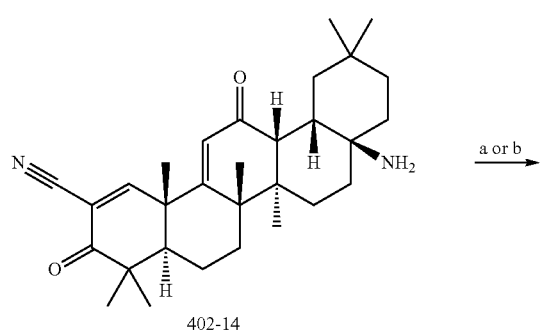
402-52

Reagents and conditions pertaining to Scheme 3: (a) MeI, K₂CO₃, DMF, 14%.

Amine 402-14 was transformed into dimethylamine 402-41 in 14% yield by treatment with iodomethane and K₂CO₃ (Scheme 3).

Scheme 4:

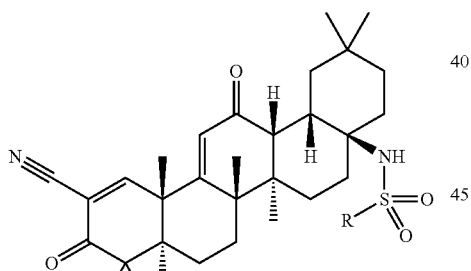
402-14

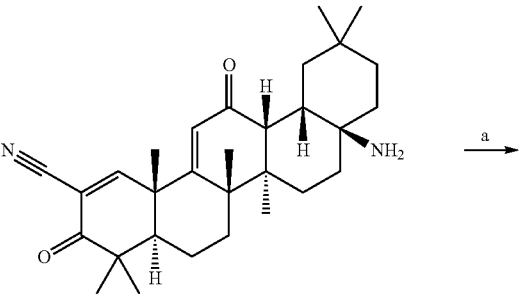
402-53

Reagents and conditions pertaining to Scheme 5: (a) Et₃N, MeSO₂Cl, 0° C., 1.5 h, 78%.

Compound 402-53 was prepared from amine 402-52 using general method A (Scheme 5).

Scheme 6:

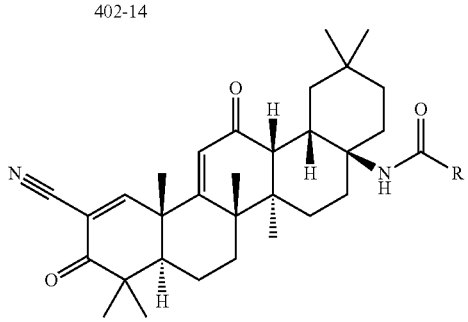
402-14

Reagents and conditions pertaining to Scheme 4: (a) Et₃N, RSO₂Cl, 0° C.; (b) RSO₂Cl, 120° C.

Amine 402-14 was transformed to the corresponding sulfonamide derivatives using general methods A or B (Scheme 4). See Table 2 for the details of reaction conditions.

TABLE 2

| Compound Name | R | Method | Rxn. Time | Yield |
|---|---|---|---|---|
| 402-19 | Me | A | 1.5 h | 68% |
| 402-36 | Et | A | 2 h | 9.4% |
| 402-30 | cyclopropyl | B | 4 h | 59% |
| 402-43 | CH₂CF₃ | A | 0.5 h | 77% |
| 402-39 | Ph | B | 1 h | 77% |
| 402-31 | 2-thiophenyl | B | 2 h | 76% |

Reagents and conditions pertaining to Scheme 6: (a) Et₃N, acylation agent, 0° C. to rt.

Amine 402-14 was transformed to the corresponding amide derivatives using general method C (Scheme 6). See Table 3 for the details of reaction conditions.

TABLE 3

| Compound Name | R | Acylation agent | Solvent | Rxn. Time | Yield (%) |
|---|---|---|---|---|---|
| 402-15 | Me | MeCOCl (2 eq) | benzene | 10 min | 67 |
| 402-38 | Et | EtCOCl (1.5 eq) | $CH_2Cl_2$ | 30 min | 76 |
| 402-28 | vinyl | $CH_2$=CHCOCl (1.5 eq) | $CH_2Cl_2$ | 1 h | 60 |
| 402-42 | acetylenyl | CHCCOCl* (1.5 eq) | $CH_2Cl_2$ | 20 min | 9 |
| 402-27 | Ph | PhCOCl (1.5 eq) | $CH_2Cl_2$ | 1 h | 70 |
| 402-37 | $PhCH_2$ | $PhCH_2COCl$ (4.5 eq) | $CH_2Cl_2$ | 2 h | 72 |
| 402-16 | $CF_3$ | $(CF_3CO)_2O$ (2 eq) | benzene | 5 min | 56 |
| 402-24 | $CF_3CH_2$ | $CF_3CH_2COCl$** (3 eq) | $CH_2Cl_2$ | 1.5 h | 48 |

*2-Propynoyl chloride was prepared the reaction of 2-propynoic acid with oxalyl chloride (1 eq.) in the presence of catalytic amount of DMF. After stirring at 0° C. for 2 h, the reaction mixture was used to react with amine 402-14 directly.

**3,3,3-Trifluoropropionyl chloride was prepared by the reaction of 3,3,3-trifluoropropionic acid with oxalyl chloride (1 eq.) in the presence of catalytic amount of DMF. After stirring at room temperature for 1.5 h, the reaction mixture was used to react with amine 402-14 directly.

*2-Propynoyl chloride was prepared by the reaction of 2-propynoic acid with oxalyl chloride (1 eq.) in the presence of catalytic amount of DMF. After stirring at 0° C. for 2 h, the reaction mixture was used to react with amine 402-14 directly.

**3,3,3-Trifluoropropionyl chloride was prepared by the reaction of 3,3,3-trifluoropropionic acid with oxalyl chloride (1 eq.) in the presence of catalytic amount of DMF. After stirring at room temperature for 1.5 h, the reaction mixture was used to react with amine 402-14 directly.

Scheme 7:

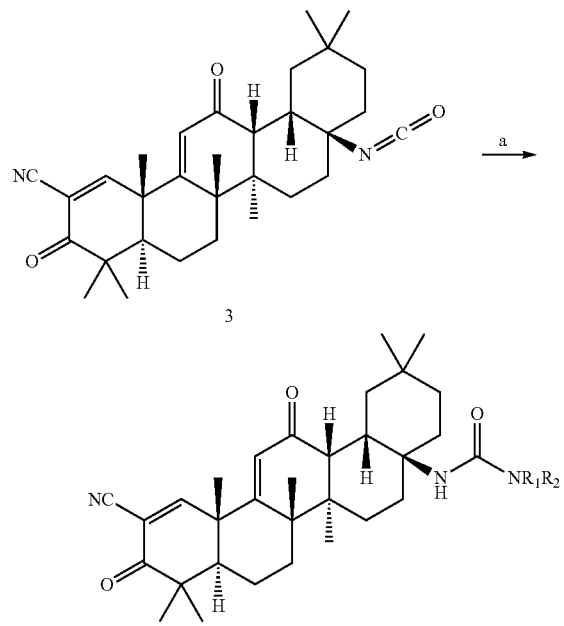

Reagents and conditions pertaining to Scheme 7: (a) $NHR_1R_2$, rt.

Compound 3 was transformed to the corresponding urea derivatives using general method D (Scheme 7). See Table 4 for the details of reaction conditions.

TABLE 4

| Compound Name | $NHR_1R_2$ | Solvent | Rxn. Time | Yield (%) |
|---|---|---|---|---|
| 402-21 | $NH_3$ (2 M in MeOH) (10 eq) | $CH_2Cl_2$ | 4 h | 91 |
| 402-17 | $NH_2Me$ (2 M in THF) (1.2 eq) | THF | 10 min | 86 |
| 402-18 | $NH_2Et$ (2 M in THF) (1.2 eq) | THF | 10 min | 85 |
| 402-26 | Piperidine (1.5 eq) | THF | 1 h | 75 |
| 402-23 | Pyrazole (5 eq) | THF | 20 h | 79 |
| 402-25 | $NHMe_2$ | THF | 118 h | 59 |
| 402-32 | 4-piperidinol | THF | 6 h | 41 |
| 402-45 | $PhNH_2$* | THF | 49 h | 29 |
| 402-44 | 4-aminophenol | THF | 48 h | 74 |
| 402-33 | morpholine | THF | 118 h | 55 |

*$Et_3N$ used as base.

Scheme 8:

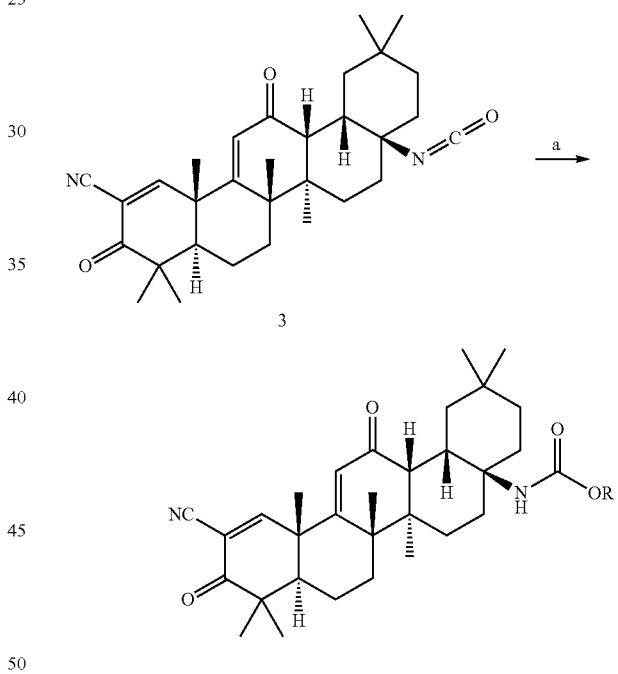

Reagents and conditions pertaining to Scheme 8: (a) ROH, 100° C.

Compound 3 was transformed to the corresponding carbamate derivatives using general method E (Scheme 8). See Table 5 for the details of reaction conditions.

TABLE 5

| Compound Name | ROH | Rxn. Time | Yield (%) |
|---|---|---|---|
| 402-12 | MeOH | 20 h | 80 |
| 402-13 | EtOH | 16 h | 61 |
| 402-34 | $Me_2CHOH$ | 20 h | 45 |
| 402-29 | $CH_2$=$CHCH_2OH$ | 16 h | 48 |
| 402-20 | $PhCH_2OH$ | 16 h | 26 |

Scheme 9:

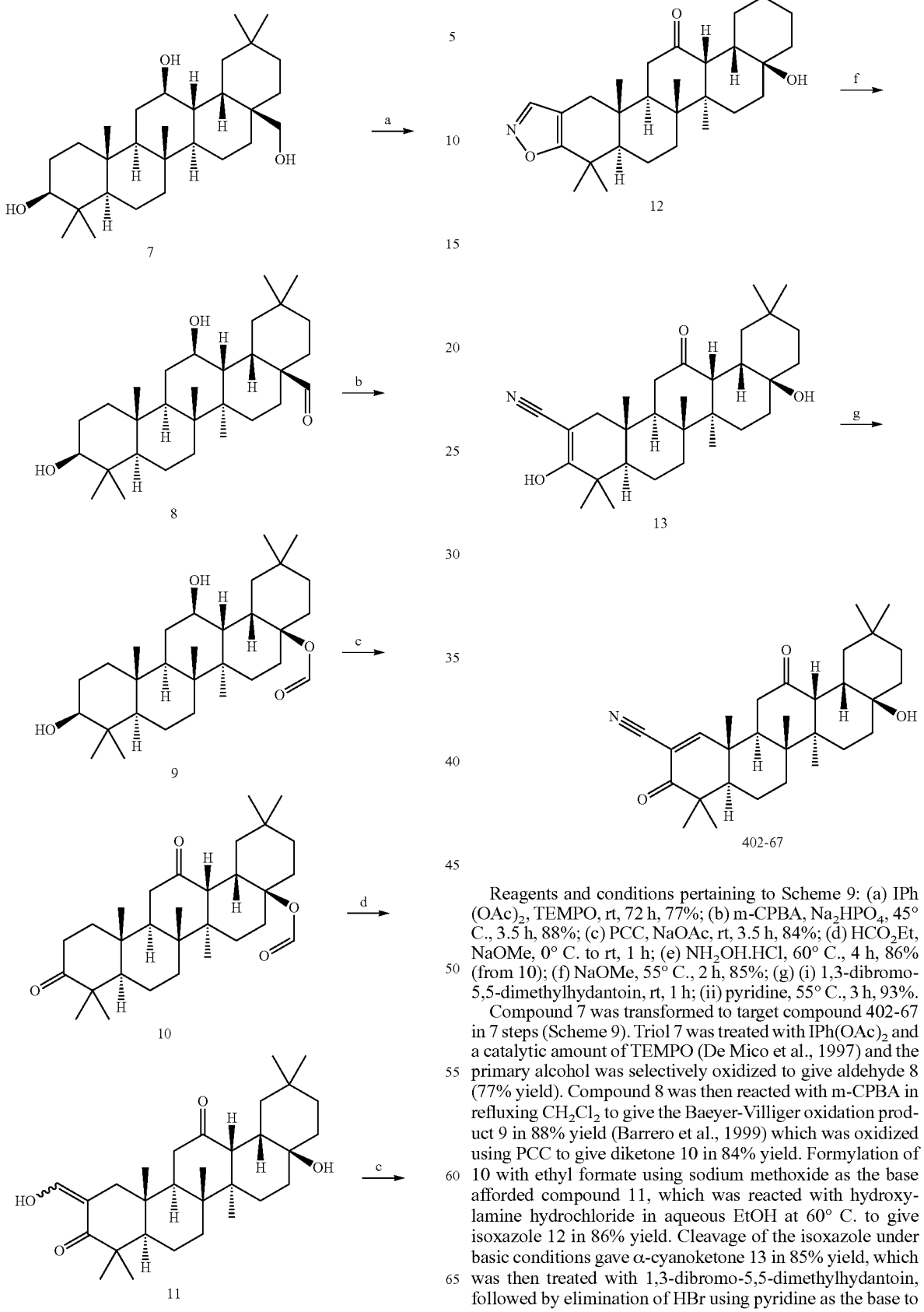

Reagents and conditions pertaining to Scheme 9: (a) IPh(OAc)$_2$, TEMPO, rt, 72 h, 77%; (b) m-CPBA, Na$_2$HPO$_4$, 45° C., 3.5 h, 88%; (c) PCC, NaOAc, rt, 3.5 h, 84%; (d) HCO$_2$Et, NaOMe, 0° C. to rt, 1 h; (e) NH$_2$OH.HCl, 60° C., 4 h, 86% (from 10); (f) NaOMe, 55° C., 2 h, 85%; (g) (i) 1,3-dibromo-5,5-dimethylhydantoin, rt, 1 h; (ii) pyridine, 55° C., 3 h, 93%.

Compound 7 was transformed to target compound 402-67 in 7 steps (Scheme 9). Triol 7 was treated with IPh(OAc)$_2$ and a catalytic amount of TEMPO (De Mico et al., 1997) and the primary alcohol was selectively oxidized to give aldehyde 8 (77% yield). Compound 8 was then reacted with m-CPBA in refluxing CH$_2$Cl$_2$ to give the Baeyer-Villiger oxidation product 9 in 88% yield (Barrero et al., 1999) which was oxidized using PCC to give diketone 10 in 84% yield. Formylation of 10 with ethyl formate using sodium methoxide as the base afforded compound 11, which was reacted with hydroxylamine hydrochloride in aqueous EtOH at 60° C. to give isoxazole 12 in 86% yield. Cleavage of the isoxazole under basic conditions gave α-cyanoketone 13 in 85% yield, which was then treated with 1,3-dibromo-5,5-dimethylhydantoin, followed by elimination of HBr using pyridine as the base to give compound 402-67 in 93% yield.

Scheme 10:

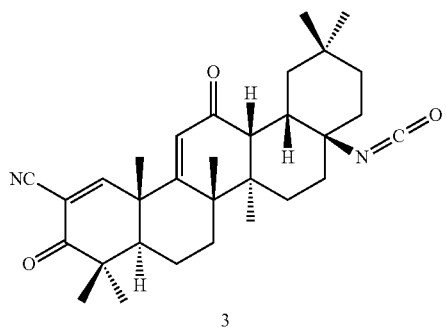

3

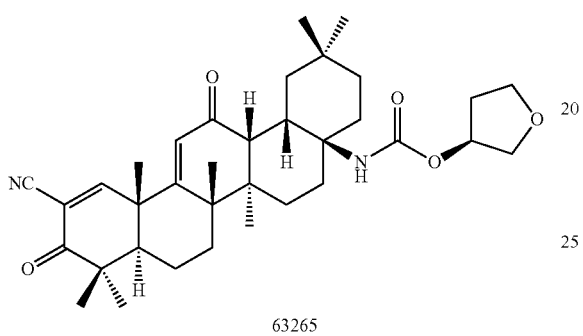

63265

Reagents and conditions pertaining to Scheme 10: (a) 3-(S)-Hydroxyfuran, NaH, THF, r.t., 10 min, 73%.

Compound 6 was treated with 3-(S)-hydroxyfuran and sodium hydride in THF to yield 63265 in 73% yield.

Scheme 11:

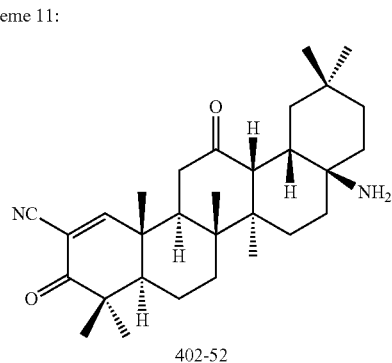

402-52

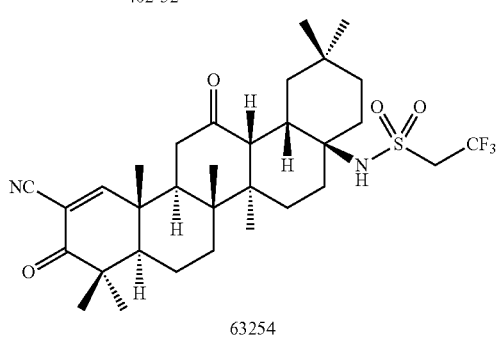

63254

Reagents and conditions pertaining to Scheme 11: (a) Et₃N, CF₃CH₂SO₂Cl, CH₂Cl₂, 0° C., 1.5 h, 91%.

Compound 63254 was prepared from amine 402-52 using general method A (Scheme 5).

Scheme 12:

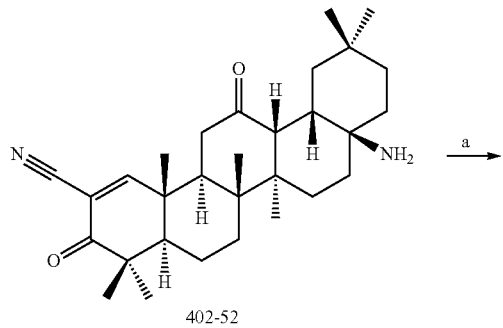

402-52

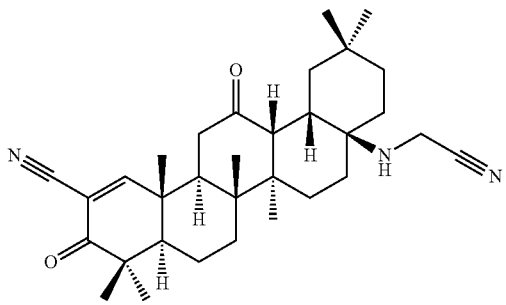

63222

Reagents and conditions pertaining to Scheme 12: (a) BrCH₂CN, i-Pr₂NEt, NaI, THF, 50° C., 14 h, 6%.

Treatment of amine 402-52 with i-Pr₂Net, bromoacetonitrile, and NaI at 50° C. gave compound 63222 in 6% yield (Scheme 12).

Scheme 13:

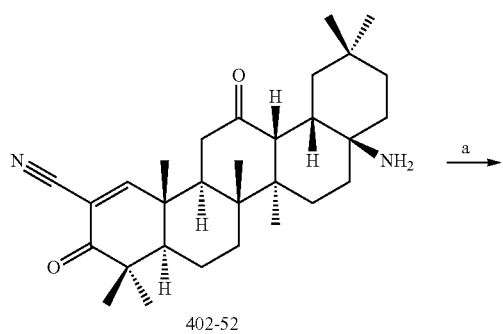

402-52

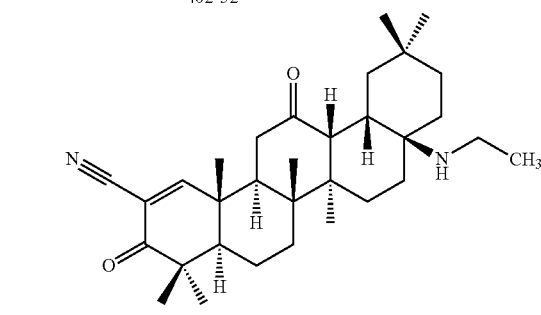

63238

Reagents and conditions pertaining to Scheme 13: (a) EtI, K₂CO₃, DMF, r.t., 20 h, 41%.

Treatment of amine 402-52 with ethyl iodide and potassium carbonate in DMF gave compound 63238 in 41% yield (Scheme 13).

Scheme 14:

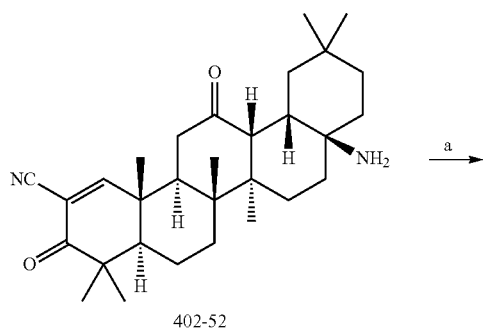

402-52

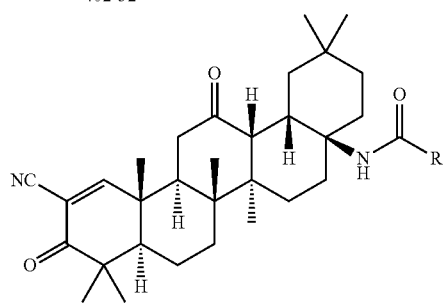

Reagents and conditions applicable to Scheme 14: (a) Et₃N, acylation agent, 0° C. to rt.

Amine 402-52 was transformed to the corresponding amide derivatives using general method C (Scheme 14). See Table 6 for the details of reaction conditions.

TABLE 6

| Compound Name | R | Acylation agent | Solvent | Rxn. Time | Yield (%) |
|---|---|---|---|---|---|
| 63236 | cyclopropyl | C₃H₅COCl* (3.3 eq) | CH₂Cl₂ | 30 min | 48 |
| 63321 | Me | MeCOCl (2 eq) | benzene | 20 min | 83 |
| 63322 | CF₃ | (CF₃CO)₂O (2 eq) | benzene | 10 min | 90 |

* Cyclopropanecarbonyl chloride was prepared by the reaction of cyclopropanecarboxylic acid with oxalyl chloride (1 eq.) in the presence of catalytic amount of DMF. After stirring at 0° C. for 2 h, the reaction mixture was used to react with amine 402-52 directly.

Scheme 15:

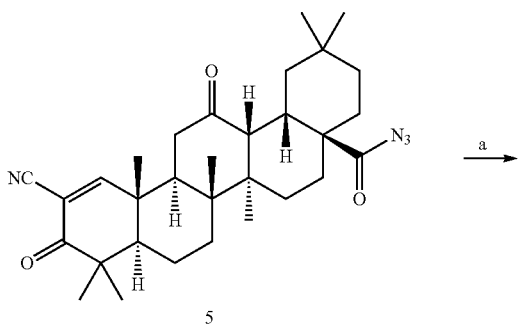

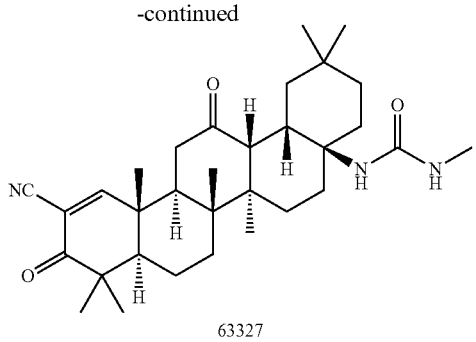

63327

Reagents and conditions applicable to Scheme 15: (a) (i) benzene, reflux; (ii) MeNH₂, THF, 0° C.

Scheme 16:

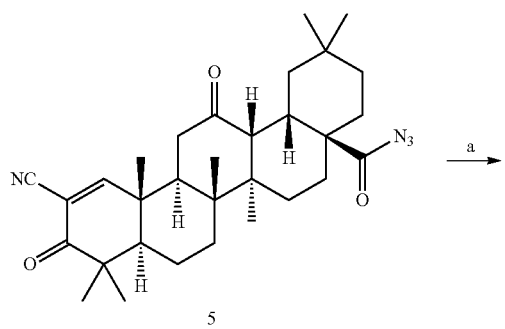

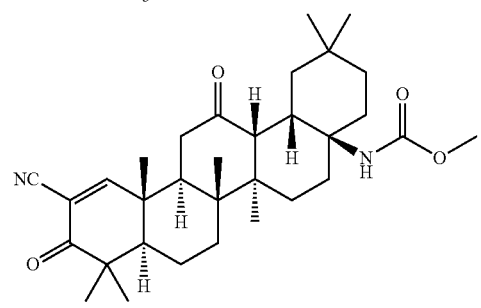

63328

Reagents and conditions applicable to Scheme 16: (a) (i) benzene, reflux; (ii) MeOH, benzene, reflux.

Example 3

Synthesis and Characterization of Oleanolic Acid Derivatives

Compound 2: Et₃N (8.44 mL, 60.7 mmol) and DPPA (2.50 g, 9.08 mmol) were added successively to a solution of compound 1 (1.49 g, 3.03 mmol) in toluene (30 mL) at 0° C. After stirring at room temperature for 6 h, the solvent was removed by evaporation to give an oil which was purified by column chromatography (silica gel, 0 to 10% EtOAc in CH₂Cl₂) to give azide 2 (1.41 g, 90%) as a white foam solid: ¹H NMR (400 MHz, CDCl₃) δ 8.03 (s, 1H), 5.98 (s, 1H), 2.98 (m, 1H), 2.93 (d, 1H, J=4.8 Hz), 1.66-1.96 (m, 8H), 1.49 (s, 3H), 1.46-1.62 (m, 3H), 1.36 (s, 3H), 1.26 (s, 3H), 1.18-1.34 (m, 4H), 1.18 (s, 3H), 1.01 (s, 3H), 1.00 (s, 3H), 0.91 (s, 3H); m/z 517.3 (M+1), 489.3 (M−N₂+1).

Compound 3: Azide 2 (1.41 g, 2.73 mmol) was dissolved in benzene (100 mL) and the mixture was refluxed for 2 h. After removing benzene by evaporation, compound 3 (1.33 g, 100%) was obtained as a white foam solid and was used in the next step without further purification: $^1$H NMR (400 MHz, CDCl$_3$) δ 8.03 (s, 1H), 5.98 (s, 1H), 3.26 (d, 1H, J=4.8 Hz), 2.52 (m, 1H), 1.96-2.12 (m, 3H), 1.52-1.86 (m, 7H), 1.51 (s, 6H), 1.26 (s, 3H), 1.18 (s, 3H), 1.13-1.37 (m, 5H), 1.02 (s, 3H), 0.98 (s, 3H), 0.90 (s, 3H); m/z 489.3 (M+1).

Compound 402-14: 12 N HCl (aq) (3.0 mL, 36.0 mmol) was added dropwise to compound 3 (300 mg, 0.61 mmol) in MeCN (3.0 mL) at room temperature. After stirring for 20 min, EtOAc was added, and the reaction mixture was cooled to 0° C. 10% NaOH (aq) solution (14.4 mL, 36.0 mmol) and saturated NaHCO$_3$ (aq) solution (10 mL) were added successively. After stirring for 5 min, the organic phase was separated, washed with brine, and then dried with MgSO$_4$ and concentrated. The residue obtained was purified by column (silica gel, 0 to 15% MeOH in CH$_2$Cl$_2$) to give compound 402-14 (280 mg, 99%) as a light yellow foam solid: $^1$H NMR (400 MHz, CDCl$_3$) δ 8.06 (s, 1H), 5.98 (s, 1H), 3.62 (d, 1H, J=4.4 Hz), 2.22 (m, 1H), 2.10 (m, 1H), 1.98 (m, 1H), 1.51 (s, 6H), 1.42-1.86 (m, 13H), 1.27 (s, 3H), 1.31 (m, 1H), 1.19 (s, 3H), 1.04 (m, 1H), 0.99 (s, 6H), 0.90 (s, 3H); m/z 463.3 (M+1).

Compound 5: Et$_3$N (16.93 mL, 122 mmol) and DPPA (5.26 mL, 24.3 mmol) were added successively to compound 4 (6.00 g, 12.2 mmol) in toluene (75 mL) at 0° C. After stirring at room temperature for 6 h, the solvent was removed by evaporation to give an oil which was purified by column chromatography (silica gel, 0 to 40% EtOAc in Hexanes) to produce azide 5 (6.25 g, 99%) as a white foam solid: $^1$H NMR (400 MHz, CDCl$_3$) δ 7.65 (s, 1H), 2.76 (m, 1H), 2.68 (d, 1H, J=4.0 Hz), 2.46 (dd, 1H, J=4.8, 16.0 Hz), 2.37 (dd, 1H, J=13.2, 16.0 Hz), 1.62-2.02 (m, 9H), 1.42-1.54 (m, 3H), 1.32 (m, 1H), 1.23 (s, 3H), 1.17 (s, 3H), 1.16 (s, 3H), 1.12-1.30 (m, 3H), 1.11 (s, 3H), 0.98 (s, 3H), 0.97 (s, 3H), 0.93 (s, 3H); m/z 491.2 (M−N$_2$+1).

Compound 402-52: Azide 5 (6.25 g, 12.0 mmol) was dissolved in benzene (300 mL) and the mixture was refluxed for 2 h. The solvent was removed by evaporation to give compound 6 (5.95 g) as a white foam solid, which was used in the next step without further purification.

12 N HCl (aq) (30 mL, 360 mmol) was added dropwise to compound 6 (5.95 g, 12.1 mmol) in MeCN (60 mL) at room temperature. After stirring for 25 min, EtOAc was added, and the reaction mixture was cooled to 0° C. 10% NaOH (aq) solution (144 mL, 360 mmol) and saturated NaHCO$_3$ (aq) solution (100 mL) were added successively. After stirring for 5 min, the organic phase was separated, washed with brine, and then dried with MgSO$_4$. After concentration, a white solid was obtained, which was mixed with ether (60 mL) and refluxed for 10 min. After cooling to room temperature, the white precipitate was collected by filtration to give compound 402-52 (4.54 g, 81%) as a white solid: $^1$H NMR (400 MHz, CDCl$_3$) δ 7.66 (s, 1H), 3.42 (d, 1H, J=4.4 Hz), 2.45 (dd, 1H, J=5.6, 16.0 Hz), 2.37 (dd, 1H, J=12.8, 16.0 Hz), 1.94-2.08 (m, 4H), 1.84 (m, 1H), 1.51-1.72 (m, 6H), 1.42 (m, 1H), 1.31 (m, 1H), 1.28 (s, 3H), 1.23 (s, 3H), 1.19 (s, 3H), 1.16 (s, 3H), 1.15-1.30 (m, 2H), 0.99 (m, 1H), 0.97 (s, 3H), 0.95 (m, 1H), 0.94 (s, 3H), 0.91 (s, 3H); m/z 465.3 (M+1).

Compound 402-41: To a solution of 402-14 (40 mg, 0.086 mmol) in DMF (0.86 mL) were added K$_2$CO$_3$ (23 mg, 0.166 mmol) and Iodomethane (0.01 mL, 0.160 mmol). The reaction was stirred at room temperature for 24 h, after which it was extracted with EtOAc (2 mL×2). The EtOAc extracts were washed with water (2 mL×2) and brine (2 mL), then dried over MgSO$_4$, filtered, and evaporated. The crude residue was purified by column chromatography (silica gel, 4% to 32% EtOAc in hexanes) to give 402-41 (17 mg) as a colorless film. This product was purified further by preparative TLC (silica gel, 33% EtOAc in hexanes) to give 402-41 (5 mg, 14% yield) as a colorless film: $^1$H NMR (400 MHz, CDCl$_3$) δ 8.04 (s, 1H), 5.93 (s, 1H), 3.38 (d, 1H, J=4 Hz), 2.67 (br d, 1H, J=13 Hz), 2.19 (s, 6H), 1.82-2.02 (m, 3H), 1.64-1.82 (m, 6H), 1.44 (s, 3H), 1.12-1.34 (m, 6H), 1.25 (s, 3H), 1.24 (s, 3H), 1.17 (s, 3H), 0.98 (s, 3H), 0.95 (s, 3H), 0.87 (s, 3H); m/z 491.3 (M+1).

General method A: RSO$_2$Cl (0.13 mmol) was added to a solution of compound 402-14 (0.10 mmol) and Et$_3$N (0.15 mmol) in CH$_2$Cl$_2$ (2 mL) at 0° C. After stirring at 0° C. for the reaction time as shown in Table 2, NaHCO$_3$ (aq) solution was added. After stirring at room temperature for 10 min, the mixture was extracted with CH$_2$Cl$_2$. The combined extracts were dried with MgSO$_4$ and concentrated. The residue obtained was purified by column chromatography to give the corresponding sulfonamide.

General method B: A mixture of compound 402-14 (46 mg, 0.10 mmol) and RSO$_2$Cl (0.12 mmol) was heated at 120° C. for the reaction time as shown in Table 2, and then cooled to room temperature. EtOAc was added and the mixture was washed with NaHCO$_3$ (aq) solution, then dried with MgSO$_4$ and concentrated. The residue obtained was purified by column chromatography to give the corresponding sulfonamide derivatives.

Compound 402-19: White foam solid; $^1$H NMR (400 MHz, CDCl$_3$) δ 8.08 (s, 1H), 6.12 (s, 1H), 4.41 (bs, 1H), 3.16 (d, 1H, J=4.8 Hz), 3.11 (s, 3H), 2.54 (m, 1H), 1.68-2.20 (m, 8H), 1.58 (m, 1H), 1.49 (s, 6H), 1.28-1.36 (m, 3H), 1.26 (s, 3H), 1.17 (s, 3H), 1.13 (m, 3H), 1.05 (s, 3H), 1.01 (s, 3H), 0.92 (s, 3H); m/z 541.3 (M+1).

Compound 402-30: White foam solid; $^1$H NMR (400 MHz, CDCl$_3$) δ 8.09 (s, 1H), 6.10 (s, 1H), 4.36 (bs, 1H), 3.23 (d, 1H, J=3.6 Hz), 2.55 (m, 1H), 2.49 (m, 1H), 2.17-2.24 (m, 2H), 2.02 (m, 1H), 1.96 (m, 1H), 1.70-1.86 (m, 5H), 1.52-1.62 (m, 2H), 1.48 (s, 6H), 1.28-1.36 (m, 4H), 1.26 (s, 3H), 1.19 (m, 1H), 1.16 (s, 3H), 1.10 (m, 1H), 1.05 (s, 3H), 1.03 (m, 2H), 1.01 (s, 3H), 0.91 (s, 3H); m/z 446.3 (M-C$_3$H$_5$SO$_2$NH).

Compound 402-31: White foam solid; $^1$H NMR (400 MHz, CDCl$_3$) δ 8.03 (s, 1H), 7.62 (d, 1H, J=3.6 Hz), 7.55 (d, 1H, J=4.4 Hz), 7.05 (dd, 1H, J=3.6, 4.4 Hz), 5.99 (s, 1H), 4.30 (s, 1H), 3.17 (d, 1H, J=5.2 Hz), 2.61 (m, 1H), 1.90-2.11 (m, 3H), 1.60-1.82 (m, 6H), 1.53 (m, 1H), 1.49 (s, 3H), 1.36 (s, 3H), 1.28 (m, 2H), 1.26 (s, 3H), 1.20 (m, 2H), 1.18 (s, 3H), 1.10 (m, 1H), 1.00 (s, 3H), 0.97 (s, 3H), 0.87 (s, 3H); m/z 446.3 (M-C$_4$H$_3$S—SO$_2$NH).

Compound 402-36: White foam solid; $^1$H NMR (400 MHz, CDCl$_3$) δ 8.09 (s, 1H), 6.10 (s, 1H), 4.30 (s, 1H), 3.17 (m, 3H), 2.55 (m, 1H), 1.52-2.20 (m, 11H), 1.49 (s, 6H), 1.44 (t, 3H, J=7.2 Hz), 1.28-1.36 (m, 3H), 1.26 (s, 3H), 1.17 (s, 3H), 1.13 (m, 1H), 1.04 (s, 3H), 1.02 (s, 3H), 0.91 (s, 3H); m/z 555.3 (M+1), 446.3 (M-C$_2$H$_5$SO$_2$NH).

Compound 402-39: White foam solid; $^1$H NMR (400 MHz, CDCl$_3$) δ 8.02 (s, 1H), 7.89 (m, 2H), 7.52 (m, 3H), 5.98 (s, 1H), 4.23 (s, 1H), 3.09 (d, 1H, J=4.8 Hz), 2.60 (m, 1H), 1.46-1.98 (m, 12H), 1.46 (s, 3H), 1.25 (s, 3H), 1.23 (s, 3H), 1.17 (s, 3H), 1.16 (m, 2H), 1.06 (m, 1H), 0.97 (s, 3H), 0.96 (s, 3H), 0.85 (s, 3H); m/z 446.3 (M-C$_6$H$_5$SO$_2$NH).

Compound 402-43: White foam solid; $^1$H NMR (400 MHz, CDCl$_3$) δ 8.04 (s, 1H), 6.09 (s, 1H), 4.80 (s, 1H), 3.90 (m, 2H), 3.08 (d, 1H, J=4.8 Hz), 2.61 (m, 1H), 1.68-1.96 (m, 9H), 1.54-1.63 (m, 2H), 1.48 (s, 3H), 1.47 (s, 3H), 1.28-1.36 (m, 3H), 1.25 (s, 3H), 1.16 (m, 1H), 1.16 (s, 3H), 1.03 (s, 3H), 1.01 (s, 3H), 0.91 (s, 3H); m/z 609.3 (M+1), 446.3 (M-CF$_3$CH$_2$SO$_2$NH).

Compound 402-53: White foam solid; $^1$H NMR (400 MHz, CDCl$_3$) δ 7.62 (s, 1H), 3.80 (bs, 1H), 3.12 (d, 1H, J=4.4 Hz), 3.06 (s, 3H), 2.34-2.50 (m, 3H), 1.92-2.16 (m, 4H), 1.86 (m, 1H), 1.61-1.73 (m, 4H), 1.52 (m, 2H), 1.29 (s, 3H), 1.27-1.34 (m, 3H), 1.22 (s, 3H), 1.17 (s, 3H), 1.15 (s, 3H), 1.09 (m, 1H), 1.01 (s, 3H), 0.97 (s, 3H), 0.92 (s, 3H); m/z 448.3 (M-MeSO$_2$NH).

General method C: The acylation agent was added dropwise to a mixture of 402-14 (30 mg, 65 μmol) and Et$_3$N (2 eq of the acylation agent) in solvent (1 mL, benzene or CH$_2$Cl$_2$, see Table 3 for details) at 0° C. After stirring at ambient temperature for the reaction time as shown in Table 3, NaHCO$_3$ (aq) solution was added and the mixture was stirred for 5 min at room temperature. The mixture was extracted with EtOAc and the combined extracts were washed with water, then dried with MgSO$_4$ and concentrated. The residue obtained was purified by column chromatography to give the corresponding amide derivatives.

Compound 402-15: White foam solid; $^1$H NMR (400 MHz, CDCl$_3$) δ 8.03 (s, 1H), 6.00 (s, 1H), 4.98 (bs, 1H), 3.07 (d, 1H, J=4.4 Hz), 2.58 (m, 1H), 2.28 (m, 1H), 2.08 (m, 1H), 1.97 (s, 3H), 1.70-1.84 (m, 7H), 1.52-1.62 (m, 2H), 1.50 (s, 3H), 1.44 (s, 3H), 1.27 (s, 3H), 1.24-1.36 (m, 3H), 1.18 (s, 3H), 1.14 (m, 1H), 1.03 (s, 6H), 0.90 (s, 3H); m/z 505.3 (M+1).

Compound 402-16: White foam solid; $^1$H NMR (400 MHz, CDCl$_3$) δ 8.03 (s, 1H), 6.01 (s, 1H), 5.78 (bs, 1H), 2.97 (d, 1H, J=4.8 Hz), 2.72 (m, 1H), 2.19 (m, 1H), 1.93-2.07 (m, 3H), 1.56-1.84 (m, 7H), 1.50 (s, 3H), 1.41 (s, 3H), 1.27 (s, 3H), 1.19-1.37 (m, 4H), 1.18 (s, 3H), 1.05 (s, 3H), 1.05 (s, 3H), 0.92 (s, 3H); m/z 559.3 (M+1).

Compound 402-24: White foam solid; $^1$H NMR (400 MHz, CDCl$_3$) δ 8.03 (s, 1H), 6.00 (s, 1H), 5.38 (bs, 1H), 3.05 (q, 2H, J=10.8 Hz), 3.00 (d, 1H, J=5.6 Hz), 2.65 (m, 1H), 2.25 (m, 1H), 2.09 (m, 1H), 1.88-1.96 (m, 2H), 1.73-1.82 (m, 5H), 1.50-1.60 (m, 2H), 1.50 (s, 3H), 1.41 (s, 3H), 1.27-1.35 (m, 3H), 1.27 (s, 3H), 1.18 (s, 3H), 1.17 (m, 1H), 1.04 (s, 6H), 0.90 (s, 3H); m/z 573.3 (M+1).

Compound 402-27: White foam solid; $^1$H NMR (400 MHz, CDCl$_3$) δ 8.04 (s, 1H), 7.71 (m, 1H), 7.50 (m, 1H), 7.43 (m, 2H), 6.01 (s, 1H), 5.66 (bs, 1H), 3.21 (d, 1H, J=4.4 Hz), 2.76 (m, 1H), 2.44 (m, 1H), 2.20 (m, 1H), 2.02 (m, 2H), 1.72-1.93 (m, 5H), 1.59 (m, 1H), 1.48 (s, 3H), 1.43 (s, 3H), 1.26 (s, 3H), 1.17 (s, 3H), 1.07 (s, 6H), 1.05-1.38 (m, 6H), 0.93 (s, 3H); m/z 567.3 (M+1).

Compound 402-28: White foam solid; $^1$H NMR (400 MHz, CDCl$_3$) δ 8.03 (s, 1H), 6.25 (dd, 1H, J=1.2, 16.8 Hz), 6.05 (dd, 1H, J=10.4, 16.8 Hz), 6.00 (s, 1H), 5.61 (dd, 1H, J=1.2, 10.4 Hz), 5.11 (bs, 1H), 3.08 (d, 1H, J=4.4 Hz), 2.67 (m, 1H), 2.34 (m, 1H), 2.10 (m, 1H), 1.90-1.99 (m, 2H), 1.69-1.82 (m, 5H), 1.53-1.59 (m, 2H), 1.49 (s, 3H), 1.40 (s, 3H), 1.28-1.37 (m, 3H), 1.26 (s, 3H), 1.18 (s, 3H), 1.17 (m, 1H), 1.05 (s, 3H), 1.04 (s, 3H), 0.91 (s, 3H); m/z 517.3 (M+1).

Compound 402-37: White foam solid; $^1$H NMR (400 MHz, CDCl$_3$) δ 8.00 (s, 1H), 7.23-7.35 (m, 5H), 5.93 (s, 1H), 4.97 (bs, 1H), 3.51 (m, 2H), 2.72 (d, 1H, J=4.8 Hz), 2.58 (m, 1H), 2.07 (m, 1H), 1.94-2.00 (m, 2H), 1.86 (m, 1H), 1.62-1.80 (m, 4H), 1.47 (s, 3H), 1.42-1.54 (m, 3H), 1.26 (m, 3H), 1.25 (s, 3H), 1.17 (s, 3H), 1.09 (s, 3H), 1.04 (m, 1H), 1.02 (s, 3H), 0.96 (s, 3H), 0.87 (s, 3H); m/z 581.3 (M+1).

Compound 402-38: White foam solid; $^1$H NMR (400 MHz, CDCl$_3$) δ 8.03 (s, 1H), 6.00 (s, 1H), 4.94 (bs, 1H), 3.06 (d, 1H, J=4.8 Hz), 2.61 (m, 1H), 2.27 (m, 1H), 2.17 (q, 2H, J=7.6 Hz), 2.05 (m, 1H), 1.74-1.94 (m, 7H), 1.51-1.60 (m, 2H), 1.50 (s, 3H), 1.43 (s, 3H), 1.27 (s, 3H), 1.24-1.35 (m, 3H), 1.18 (s, 3H), 1.14 (t, 3H, J=7.6 Hz), 1.14 (m, 1H), 1.04 (m, 1H), 1.03 (s, 3H), 0.90 (s, 3H); m/z 519.3 (M+1).

Compound 402-42: White foam solid; $^1$H NMR (400 MHz, CDCl$_3$) δ 8.03 (s, 1H), 6.00 (s, 1H), 5.43 (bs, 1H), 3.06 (d, 1H, J=4.4 Hz), 2.71 (s, 1H), 2.62 (m, 1H), 2.22 (m, 1H), 2.06 (m, 1H), 1.88-1.99 (m, 2H), 1.70-1.84 (m, 5H), 1.54-1.62 (m, 2H), 1.50 (s, 3H), 1.48 (s, 3H), 1.27 (s, 3H), 1.26-1.34 (m, 3H), 1.19 (s, 3H), 1.18 (m, 1H), 1.03 (s, 6H), 0.91 (s, 3H); m/z 515.3 (M+1).

General method D: NHR$_1$R$_2$ (See Table 4 for the amount) was added to compound 3 (30 mg, 61 μmol) in the solvent (0.5 mL, CH$_2$Cl$_2$ or THF, see Table 4). After stirring at room temperature for the reaction time as shown in Table 3, EtOAc was added and the mixture was washed with 1 N HCl (aq), water, and then dried with MgSO$_4$ and concentrated. The residue obtained was purified by column chromatography to give the corresponding urea derivatives.

Compound 402-17: White foam solid; $^1$H NMR (400 MHz, CDCl$_3$) δ 8.03 (s, 1H), 5.97 (s, 1H), 4.31 (q, 1H, J=4.8 Hz), 3.98 (s, 1H), 3.14 (d, 1H, J=4.8 Hz), 2.76 (d, 3H, J=4.4 Hz), 2.47 (m, 1H), 2.28 (m, 1H), 2.12 (m, 1H), 1.70-1.84 (m, 7H), 1.59 (m, 1H), 1.50 (m, 1H), 1.48 (s, 3H), 1.42 (s, 3H), 1.26 (s, 3H), 1.24-1.37 (m, 3H), 1.18 (s, 3H), 1.12 (m, 1H), 1.03 (s, 3H), 1.02 (s, 3H), 0.90 (s, 3H); m/z 520.3 (M+1).

Compound 402-18: White foam solid; $^1$H NMR (400 MHz, CDCl$_3$) δ 8.02 (s, 1H), 5.96 (s, 1H), 4.34 (t, 1H, J=5.2 Hz), 4.00 (s, 1H), 3.19 (m, 2H), 3.14 (d, 1H, J=4.8 Hz), 2.44 (m, 1H), 2.30 (m, 1H), 2.14 (m, 1H), 1.72-1.90 (m, 7H), 1.58 (m, 1H), 1.49 (m, 1H), 1.47 (s, 3H), 1.42 (s, 3H), 1.26 (s, 3H), 1.24-1.37 (m, 3H), 1.18 (s, 3H), 1.13 (t, 3H, J=7.2 Hz), 1.12 (m, 1H), 1.03 (s, 3H), 1.02 (s, 3H), 0.90 (s, 3H); m/z 534.3 (M+1).

Compound 402-21: White foam solid; $^1$H NMR (400 MHz, CDCl$_3$) δ 8.02 (s, 1H), 5.96 (s, 1H), 4.99 (s, 1H), 4.59 (s, 2H), 3.07 (d, 1H, J=4.4 Hz), 2.34-2.42 (m, 2H), 2.24 (m, 1H), 1.72-1.84 (m, 7H), 1.60 (m, 1H), 1.44 (s, 3H), 1.39 (s, 3H), 1.27 (s, 3H), 1.26-1.41 (m, 4H), 1.18 (s, 3H), 1.12 (m, 1H), 1.04 (s, 3H), 1.01 (s, 3H), 0.90 (s, 3H); m/z 506.3 (M+1).

Compound 402-23: White foam solid; $^1$H NMR (400 MHz, CDCl$_3$) δ 8.19 (d, 1H, J=2.4 Hz), 8.03 (s, 1H), 7.55 (d, 1H, J=0.8 Hz), 7.12 (s, 1H), 6.38 (dd, 1H, J=1.6, 2.4 Hz), 5.99 (s, 1H), 3.16 (d, 1H, J=4.8 Hz), 2.97 (m, 1H), 2.26 (m, 1H), 1.52-2.16 (m, 11H), 1.46 (s, 3H), 1.37 (s, 3H), 1.31-1.40 (m, 3H), 1.26 (s, 3H), 1.19-1.28 (m, 2H), 1.16 (s, 3H), 1.10 (s, 3H), 1.06 (s, 3H), 0.93 (s, 3H); m/z 557.3 (M+1), 489.2 (M-C$_3$H$_3$N$_2$).

Compound 402-25: White solid; $^1$H NMR (400 MHz, CDCl$_3$) δ 8.04 (s, 1H), 5.99 (s, 1H), 3.83 (br s, 1H), 3.21 (br d, 1H, J=4.4 Hz), 2.89 (s, 6H), 2.55 (br dt, 1H), 2.28 (m, 1H), 2.13 (br dt, 1H), 1.72-1.92 (m, 6H), 1.49 (s, 3H), 1.45 (s, 3H), 1.27 (s, 3H), 1.18 (s, 3H), 1.08-1.60 (m, 7H), 1.04 (s, 3H), 1.03 (s, 3H), 0.90 (s, 3H); m/z 534.3 (M+1).

Compound 402-26: White foam solid; $^1$H NMR (400 MHz, CDCl$_3$) δ 8.04 (s, 1H), 5.99 (s, 1H), 3.87 (s, 1H), 3.29 (m, 4H), 3.20 (d, 1H, J=4.8 Hz), 2.52 (m, 1H), 2.30 (m, 1H), 2.14 (m, 1H), 1.70-1.92 (m, 7H), 1.50-1.59 (m, 8H), 1.49 (s, 3H), 1.44 (s, 3H), 1.26 (s, 3H), 1.24-1.38 (m, 3H), 1.18 (s, 3H), 1.12 (m, 1H), 1.04 (s, 3H), 1.03 (s, 3H), 0.90 (s, 3H); m/z 574.4 (M+1).

Compound 402-32: White solid; $^1$H NMR (400 MHz, d$_6$-DMSO) δ 8.63 (s, 1H), 6.18 (s, 1H), 5.55 (t, 1H, J=4 Hz), 4.58 (d, 1H, J=4 Hz), 3.68 (m, 2H), 3.54 (m, 1H), 3.13 (br d, 1H, J=2.4 Hz), 2.92 (br m, 1H), 2.80 (m, 2H), 2.02 (m, 1H), 1.77-1.88 (m, 5H), 1.59-1.74 (m, 6H), 1.43 (s, 3H), 1.38 (s, 3H), 1.17 (s, 3H), 1.12-1.34 (m, 6H), 1.05 (s, 3H), 0.97 (s, 3H), 0.92 (s, 3H), 0.83 (s, 3H); m/z 590.4 (M+1).

Compound 402-33: White solid: $^1$H NMR (400 MHz, CDCl$_3$) δ 8.04 (s, 1H), 6.00 (s, 1H), 3.90 (br s, 1H), 3.67 (m, 4H), 3.31 (m, 4H), 3.14 (br d, 1H, J=4.8 Hz), 2.57 (br dt, 1H), 2.25 (br d, 1H), 2.11 (br dt, 1H), 1.72-1.96 (m, 6H), 1.50 (s, 3H), 1.43 (s, 3H), 1.27 (s, 3H), 1.18 (s, 3H), 1.10-1.60 (m, 7H), 1.04 (br s, 6H), 0.91 (s, 3H); m/z 576.4 (M+1).

Compound 402-44: White foam solid; $^1$H NMR (400 MHz, CDCl$_3$-CD$_3$OD) δ 8.12 (s, 1H), 7.10 (m, 2H), 6.76 (m, 2H), 6.00 (s, 1H), 5.03 (bs, 1H), 3.14 (d, 1H, J=4.4 Hz), 2.57 (m, 1H), 2.12 (m, 1H), 1.68-2.02 (m, 7H), 1.51 (s, 3H), 1.44 (s, 3H), 1.27 (s, 3H), 1.24-1.61 (m, 6H), 1.19 (s, 3H), 1.12 (m, 1H), 1.03 (s, 6H), 0.90 (s, 3H); m/z 598.3 (M+1).

Compound 402-45: White solid; $^1$H NMR (400 MHz, CDCl$_3$) δ 7.99 (s, 1H), 7.32 (d, 4H, J=4.4 Hz), 7.08 (q, 1H, J=4.2 Hz), 6.71 (br s, 1H), 5.97 (s, 1H), 4.65 (br s, 1H), 3.04 (br d, 1H, J=4 Hz), 2.47 (br m, 1H), 2.36 (br m, 1H), 2.25 (br m, 1H), 1.70-1.95 (m, 8H), 1.45 (s, 3H), 1.36 (s, 3H), 1.27 (s, 3H), 1.18 (s, 3H), 1.10-1.50 (m, 5H) 1.04 (s, 6H), 0.89 (s, 3H); m/z 582.3 (M+1).

General method E: Compound 3 (30 mg, 61 µmol) was dissolved in ROH (1-2 mL, see Table 5) and the mixture was heated in a 100° C. oil bath for the reaction time as shown in Table 5. After removal of ROH by evaporation, the residue obtained was purified by column chromatography to give the corresponding carbamate derivatives.

Compound 402-12: White foam solid; $^1$H NMR (400 MHz, CDCl$_3$) δ 8.03 (s, 1H), 5.98 (s, 1H), 4.37 (s, 1H), 3.63 (s, 3H), 3.11 (d, 1H, J=4.8 Hz), 2.69 (m, 1H), 1.68-2.04 (m, 9H), 1.53-1.59 (m, 2H), 1.50 (s, 3H), 1.45 (s, 3H), 1.26-1.33 (m, 3H), 1.26 (s, 3H), 1.18 (s, 3H), 1.14 (m, 1H), 1.04 (s, 3H), 1.02 (s, 3H), 0.90 (s, 3H); m/z 521.3 (M+1); 446.2 (M-NHCO$_2$CH$_3$).

Compound 402-13: White foam solid; $^1$H NMR (400 MHz, CDCl$_3$) δ 8.04 (s, 1H), 5.98 (s, 1H), 4.34 (s, 1H), 4.07 (m, 2H), 3.12 (d, 1H, J=4.8 Hz), 2.70 (m, 1H), 1.69-2.05 (m, 9H), 1.53-1.60 (m, 2H), 1.50 (s, 3H), 1.46 (s, 3H), 1.26-1.33 (m, 3H), 1.26 (s, 3H), 1.22 (t, 3H, J=7.2 Hz), 1.18 (s, 3H), 1.14 (m, 1H), 1.04 (s, 3H), 1.02 (s, 3H), 0.90 (s, 3H); m/z 535.3 (M+1); 446.2 (M-NHCO$_2$C$_2$H$_5$).

Compound 402-20: White foam solid; $^1$H NMR (400 MHz, CDCl$_3$) δ 8.03 (s, 1H), 7.29-7.37 (m, 5H), 5.98 (s, 1H), 5.07 (s, 2H), 4.49 (s, 1H), 3.09 (d, 1H, J=4.4 Hz), 2.70 (m, 1H), 1.68-2.06 (m, 9H), 1.54-1.57 (m, 2H), 1.49 (s, 3H), 1.39 (s, 3H), 1.26-1.33 (m, 2H), 1.26 (s, 6H), 1.18 (s, 3H), 1.12 (m, 1H), 1.03 (m, 1H), 1.02 (s, 3H), 0.90 (s, 3H); m/z 597.3 (M+1); 446.3 (M-NHCO$_2$CH$_3$).

Compound 402-29: White foam solid; $^1$H NMR (400 MHz, CDCl$_3$) δ 8.03 (s, 1H), 5.98 (s, 1H), 5.90 (m, 1H), 5.23 (m, 2H), 4.53 (m, 2H), 4.43 (s, 1H), 3.11 (d, 1H, J=4.8 Hz), 2.68 (m, 1H), 1.68-2.04 (m, 9H), 1.53-1.61 (m, 2H), 1.50 (s, 3H), 1.45 (s, 3H), 1.26-1.34 (m, 3H), 1.26 (s, 3H), 1.18 (s, 3H), 1.14 (m, 1H), 1.04 (s, 3H), 1.02 (s, 3H), 0.90 (s, 3H); m/z 446.3 (M-NHCO$_2$C$_3$H$_5$).

Compound 401-34: White foam solid; $^1$H NMR (400 MHz, CDCl$_3$) δ 8.03 (s, 1H), 5.98 (s, 1H), 4.88 (m, 1H), 4.29 (s, 1H), 3.12 (d, 1H, J=4.8 Hz), 2.69 (m, 1H), 1.68-2.04 (m, 9H), 1.54-1.59 (m, 2H), 1.50 (s, 3H), 1.45 (s, 3H), 1.26-1.33 (m, 3H), 1.26 (s, 3H), 1.21 (d, 6H, J=6.4 Hz), 1.18 (s, 3H), 1.13 (m, 1H), 1.04 (s, 3H), 1.02 (s, 3H), 0.90 (s, 3H); m/z 446.2 (M-NHCO$_2$C$_3$H$_7$).

Compound 8: TEMPO (27 mg×4, 0.17 mmol×4) and IPh(OAc)$_2$ (563 mg×4, 1.74 mmol×4) was added to a mixture of compound 7 (725 mg, 1.59 mmol) in CH$_2$Cl$_2$ (200 mL) and water (0.1 mL) at 0 h, 2 h, 24 h and 48 h. After stirring at room temperature for 72 h, the reaction mixture was concentrated and the residue obtained was purified by column chromatography (silica gel, 0 to 75% EtOAc in hexanes) to give compound 8 (560 mg, 77%) as a white solid: $^1$H NMR (400 MHz, CDCl$_3$) δ 9.37 (d, 1H, J=1.2 Hz), 3.77 (m, 1H), 3.18 (dd, 1H, J=4.8, 11.2 Hz), 2.51 (m, 1H), 0.98-1.87 (m, 23H), 0.97 (s, 3H), 0.96 (s, 3H), 0.94 (s, 3H), 0.92 (m, 1H), 0.90 (s, 3H), 0.86 (s, 3H), 0.82 (s, 3H), 0.75 (s, 3H), 0.65 (m, 1H); m/z 441.3 (M–H$_2$O+1), 423.3 (M–2×H$_2$O+1).

Compound 9: A mixture of compound 8 (480 mg, 1.05 mmol), m-CPBA (586 mg, 2.60 mmol) and Na$_2$HPO$_4$ (409 mg, 2.88 mmol) in CH$_2$Cl$_2$ (30 mL) was refluxed for 3.5 h. After cooled to room temperature, Na$_2$S$_2$O$_3$ (aq) solution was added and stirred for 5 min. The organic phase was separated, washed with NaHCO$_3$ (aq) solution and then dried with MgSO$_4$. After concentration, the residue obtained was purified by column chromatography (silica gel, 0 to 70% EtOAc in hexanes) to give compound 9 (435 mg, 88%) as a white foam solid: $^1$H NMR (400 MHz, CDCl$_3$) δ 8.10 (s, 1H), 3.71 (m, 1H), 3.19 (dd, 1H, J=4.8, 11.2 Hz), 2.45 (m, 1H), 2.25 (m, 1H), 1.86-2.12 (m, 5H), 1.52-1.74 (m, 5H), 1.24-1.48 (m, 10H), 0.99 (s, 3H), 0.97 (s, 6H), 0.96 (s, 3H), 0.92 (s, 3H), 0.88-1.02 (m, 4H), 0.84 (s, 3H), 0.76 (s, 3H), 0.66 (m, 1H); m/z 411.3 (M–H$_2$O—HCO$_2$H+1), 393.3 (M–2×H$_2$O—HCO$_2$H+1).

Compound 10: NaOAc (294 mg, 3.59 mmol) and PCC (579 mg, 2.68 mmol) were added to compound 9 (425 mg, 0.89 mmol) in CH$_2$Cl$_2$ (18 mL) at room temperature. After stirring for 3.5 h, a mixture of hexanes/EtOAc (1:1, 50 mL) was added and stirred for 5 min. The brown slurry was filtered through a pad of silica gel, and the filtrate was concentrated. The residue obtained was purified by column chromatography (silica gel, 20% EtOAc in hexanes) to give compound 10 (355 mg, 84%) as a white solid: $^1$H NMR (400 MHz, CDCl$_3$) δ 8.09 (s, 1H), 3.03 (d, 1H, J=4.8 Hz), 2.49-2.57 (m, 2H), 2.38 (m, 1H), 2.22-2.32 (m, 3H), 2.16 (m, 1H), 1.91-2.05 (m, 3H), 1.71-1.84 (m, 3H), 1.57-1.63 (m, 2H), 1.19-1.50 (m, 7H), 1.15 (s, 3H), 1.10 (m, 1H), 1.09 (s, 3H), 1.05 (s, 3H), 1.02 (s, 3H), 1.00 (s, 3H), 0.96 (s, 3H), 0.90 (s, 3H); m/z 425.3 (M+1).

Compound 11: NaOMe solution (25% w/w in MeOH, 0.29 mL, 1.27 mmol) was added dropwise to a mixture of compound 10 (40 mg, 0.085 mmol) and HCO$_2$Et (0.20 mL, 0.025 mmol) at 0° C. under N$_2$. After stirring at room temperature for 1 h, t-BuOMe (5 mL) was added. The mixture was cooled to 0° C., and 12 N HCl (aq) (0.11 mL, 1.32 mmol) was added dropwise. The mixture was extracted with EtOAc, and the combined extracts were washed with water, and dried with MgSO$_4$. After concentration, crude compound 11 (41 mg) was obtained as a white foam solid and used in the next step without further purification: m/z 471.3 (M+1), 453.3 (M–H$_2$O+1).

Compound 12: Compound 11 (41 mg, 0.082 mmol), NH$_2$OH—HCl (9.1 mg, 0.13 mmol), EtOH (2 mL), and water (0.2 mL) were mixed together and heated at 60° C. for 4 h. EtOH was removed by evaporation, and the white slurry obtained was extracted with EtOAc. The combined extracts were washed with water, dried with MgSO$_4$, and concentrated. The residue obtained was purified by column chromatography (silica gel, 0% to 50% EtOAc in hexanes) to give compound 12 (34 mg, 86% from 10) as a white solid: $^1$H NMR (400 MHz, CDCl$_3$) δ 7.98 (s, 1H), 3.23 (d, 1H, J=4.4 Hz), 2.36 (d, 1H, J=14.4 Hz), 2.29 (d, 1H, J=8.8 Hz), 2.16 (m, 1H), 1.94-2.06 (m, 3H), 1.84 (dd, 1H, J=9.2, 9.2 Hz), 1.50-1.74 (m, 8H), 1.32 (s, 3H), 1.26-1.37 (m, 3H), 1.23 (s, 3H), 1.20 (s, 3H), 1.12-1.20 (m, 2H), 1.00 (s, 3H), 0.98-1.08 (m, 2H), 0.95 (s, 3H), 0.90 (s, 3H), 0.86 (s, 3H); m/z 468.3 (M+1).

Compound 13: NaOMe solution (25% w/w in MeOH, 19 µL, 0.083 mmol) was added to a suspension of isoxazole 12 (32.5 mg, 0.070 mmol) in MeOH (0.3 mL). The mixture was stirred at 55° C. for 2 h and cooled to 0° C. t-BuOMe (5 mL) and 1 N HCl (aq) (1 mL) were added successively. The mixture was extracted with EtOAc, and the combined extracts were washed with water, dried with MgSO$_4$, and concentrated. The residue obtained was purified by column chromatography (silica gel, 0% to 60% EtOAc in hexanes) to give compound 13 (27 mg, 85%) as a white solid: m/z 450.2 (M–H$_2$O+1).

Compound 402-67: 1,3-Dibromo-5,5-dimethylhydantoin (9.9 mg, 0.035 mmol) was added to a solution of compound 13 (27 mg, 0.058 mmol) in DMF (0.3 mL) at room temperature. After stirring for 1 h, pyridine (14 µL, 0.17 mmol) was added and the reaction mixture was heated to 55° C. for 3 h. After cooling to room temperature, EtOAc (30 mL) was added, and the mixture was washed with 1 N HCl (aq), water, then dried with MgSO$_4$ and concentrated. The residue obtained was purified by column chromatography (silica gel, 0% to 60% EtOAc in hexanes) to give compound 402-67 (25 mg, 93%) as a white solid: $^1$H NMR (400 MHz, CDCl$_3$) δ 7.64 (s, 1H), 3.24 (d, 1H, J=4.4 Hz), 2.44 (dd, 1H, J=5.2, 16.4 Hz), 2.37 (dd, 1H, J=12.8, 16.4 Hz), 2.16 (m, 1H), 1.91-2.08 (m, 4H), 1.61-1.73 (m, 5H), 1.50-1.56 (m, 3H), 1.27-1.31 (m, 2H), 1.25 (s, 3H), 1.22 (s, 3H), 1.18 (s, 3H), 1.15 (s, 3H), 1.13-1.20 (m, 2H), 1.03 (m, 1H), 1.00 (s, 3H), 0.94 (s, 3H), 0.91 (s, 3H); m/z 448.2 (M–H$_2$O+1).

Compound 63265: To a suspension of NaH (33 mg, 0.825 mmol) in THF (2.0 mL) was added 3-(S)-hydroxyfuran (75 µL). The mixture was stirred at room temperature for 10 min, after which a solution of 3 (100 mg, 0.205 mmol) in 3-(S)-hydroxyfuran (500 µL). The addition syringe was washed with THF (0.25 mL×2). After stirring for 10 min, the reaction was diluted with t-BuOMe and cooled to 0° C. The reaction mixture was quenched by addition of 1 N HCl (aq) (5 mL) and was stirred 2 min. EtOAc (30 mL) was then added, and the mixture was washed with water 4×, then dried with MgSO$_4$ and concentrated. The residue obtained was purified by column chromatography (silica gel, 0% to 60% EtOAc in hexanes) to give desired product, which was then purified again by column chromatography (silica gel, 0% to 30% EtOAc in hexanes) to give compound 63265 (89 mg, 73%) as a white solid: $^1$H NMR (400 MHz, CDCl$_3$) δ 7.66 (s, 1H), 5.24 (m, 1H), 4.36 (m, 1H), 3.84 (m, 4H), 2.90 (br d, 1H), 2.65 (br d, 1H), 2.42 (m, 2H), 2.16 (m, 1H), 1.93-2.08 (m, 5H), 1.64-1.78 (m, 5H), 1.61 (s, 3H), 1.53 (br dt, 2H), 1.25-1.31 (m, 3H), 1.24 (s, 3H), 1.22 (s, 3H), 1.19 (s, 3H), 1.17 (s, 3H), 1.05 (s, 3H), 0.99 (s, 3H), 0.93 (s, 3H); m/z 579.4 (M+H), 448.3 (M-NH-COOR, 100%).

Compound 63254: To a solution of 402-52 (252 mg, 0.542 mmol) in CH$_2$Cl$_2$ (5.4 mL) at 0° C. were added Et$_3$N (0.11 mL, 0.789 mmol) and 2,2,2-trifluoroethylsulfonyl chloride (0.08 mL, 0.724 mmol). The reaction was stirred at 0° C. 1.5 hrs, after which saturated NaHCO$_3$(aq) (5 mL) was added. After stirring 1 min, the reaction mixture was extracted with EtOAc (50 mL) and was washed with sat. NaHCO$_3$(aq) (30 mL) and water (30 mL). The EtOAc extracts were dried over Na$_2$SO$_4$, filtered, and concentrated. The residue obtained was purified by column chromatography (silica gel, 5% to 50% EtOAc in hexanes) to give compound 63254 (302 mg, 91%) as a white solid: $^1$H NMR (400 MHz, CDCl$_3$) δ 7.63 (s, 1H), 4.19 (s, 1H), 3.87 (q, J=8.8 Hz, 2H), 3.03 (br d, J=4.0 Hz), 2.37-2.51 (m, 3H), 1.90-2.19 (m 5H), 1.80 (m, 1H), 1.61-1.75 (m, 4H), 1.55 (s, 3H), 1.50-1.58 (m, 2H), 1.34 (m, 2H), 1.29 (s, 3H), 1.22 (s, 3H), 1.18 (s, 3H), 1.15 (s, 3H), 1.01 (s, 3H), 0.98 (s, 3H), 0.92 (s, 3H); m/z 448.2 (M-NHSO$_2$CH$_2$CF$_3$).

Compound 63222: To a solution of 402-52 (76 mg, 0.164 mmol) in THF (1.6 mL) was added i-Pr$_2$NEt (0.04 mL, 0.230 mmol). A solution of bromoacetonitrile (0.012 mL, 0.180 mmol) in THF (0.1 mL) was added to the reaction, and the reaction was stirred at room temperature 5 hrs with no product formed by TLC. Sodium iodide (95 mg, 0.634 mmol) was added, and the reaction was stirred at 4 hrs. Reaction TLC again indicated no product. The reaction was heated at 50° C. for 14 hrs—TLC showed ~50% conversion to product. After cooling, the reaction mixture was extracted with EtOAc (30 mL) and was washed with 5% Na$_2$S$_2$O$_3$(aq) (20 mL), then Brine (20 mL). The EtOAc extracts were dried over Na$_2$SO$_4$, filtered, and concentrated. The residue obtained was purified by column chromatography (silica gel, 5% to 40% EtOAc in hexanes) to give compound 63222 (4.7 mg, 6%) as a colorless oil: $^1$H NMR (400 MHz, CDCl$_3$) δ 7.64 (s, 1H), 3.68 (m, 1H), 3.51 (s, 2H), 3.39 (br d, J=4.4 Hz, 1H), 2.33-2.48 (m, 3H), 1.88-2.02 (m, 5H), 1.49-1.70 (m, 12H), 1.24-1.30 (m, 2H), 1.26 (s, 3H), 1.22 (s, 3H), 1.18 (s, 3H), 1.16 (s, 3H), 0.96 (s, 3H), 0.95 (s, 3H), 0.91 (s, 3H); m/z 448.2 (M-NHCH$_2$CN).

Compound 63238: To a solution of 402-52 (122 mg, 0.263 mmol) in DMF (1.7 mL) was added K$_2$CO$_3$ (72 mg, 0.521 mmol). A solution of EtI (0.024 mL, 0.298 mmol) in DMF (0.1 mL) was then added, and the reaction was stirred at room temperature for 20 hrs. The reaction mixture was extracted with EtOAc (25 mL) and was washed with water (10 mL×3). The EtOAc extracts were dried over Na$_2$SO$_4$, filtered, and concentrated. The residue obtained was purified by column chromatography (silica gel, 0% to 15% MeOH in CH$_2$Cl$_2$) to give compound 63238 (53 mg, 41%) as a white solid: $^1$H NMR (400 MHz, CDCl$_3$) δ 7.66 (s, 1H), 3.52 (br d, 1H), 2.55 (m, 1H), 2.32-2.48 (m, 3H), 1.81-2.04 (m, 5H), 1.48-1.70 (m, 12H), 1.25 (m, 8H), 1.22 (s, 3H), 1.17 (s, 3H), 1.16 (s, 3H), 1.04 (br t, J=7.2 Hz, 3H), 0.95 (s, 3H), 0.93 (s, 3H), 0.90 (s, 3H); m/z 493.3 (M+H).

Compound 63236: Cyclopropyl acid chloride was prepared according to the following procedure: to a solution of cyclopropylcarboxylic acid (258 mg, 3.00 mmol) and DMF (1 drop, cat.) in CH$_2$Cl$_2$ (3 mL) at 0° C. was added oxalyl chloride (0.254 mL 3.0 mmol). The mixture was stirred at 0° C. 2 hrs to give a solution of cyclopropyl acid chloride. To a solution of 402-52 (70 mg, 0.15 mmol) in CH$_2$Cl$_2$ (2 mL) at 0° C. was added Et$_3$N (0.125 mL, 0.45 mmol), followed by the cyclopropyl acid chloride solution (1 M solution, 0.5 mL, 0.5 mmol). The reaction was stirred at 0° C. 0.5 hrs, after which the reaction mixture was extracted with EtOAc and was washed with NaHCO$_3$(aq), water, and brine. The EtOAc extracts were dried over Na$_2$SO$_4$, filtered, and concentrated. The residue obtained was purified by column chromatography (silica gel, 0% to 50% EtOAc in hexanes) to give compound 63236 (39 mg, 48%) as a white solid: $^1$H NMR (400 MHz, CDCl$_3$) δ 7.66 (s, 1H), 5.12 (s, 1H), 2.92 (d, J=4.4 Hz, 1H), 2.67 (dt, J=13.2, 3.6 Hz, 1H), 2.48 (dd, J=16.4, 4.8 Hz, 1H), 2.37 (dd, J=16.0, 13.2 Hz, 1H), 1.87-2.09 (m, 5H), 1.60-1.86 (m, 5H), 1.47-1.56 (m, 2H), 1.20-1.43 (m, 7H), 1.23 (s, 3H), 1.18 (s, 3H), 1.16 (s, 3H), 1.09 (dt, J=13.6, 2.8 Hz, 1H), 1.03 (s, 3H), 0.98 (s, 3H), 0.86-0.94 (m, 2H), 0.91 (s, 3H), 0.64-0.70 (m, 2H); m/z 533.3 (M+H).

Compound 63321: Using General Method C, 402-52 (70 mg 0.151 mmol) was converted to product 63321 (64.0 mg, 83.6%) as a white solid: $^1$H NMR (400 MHz, CDCl$_3$) δ 7.65 (s, 1H), 4.90 (s, 1H), 2.86 (d, 1H, J=4.4 Hz), 2.65 (dt, 1H, J=13.2, 3.6 Hz), 2.48 (dd, 1H, J=16.4, 3.6 Hz), 2.36 (dd, 1H, J=16.4, 13.2 Hz), 1.46-2.06 (m, 13H), 1.05-1.35 (m, 3H), 1.96 (s, 3H), 1.23 (s, 3H), 1.21 (s, 3H), 1.18 (s, 3H), 1.16 (s, 3H), 1.03 (s, 3H), 0.98 (s, 3H), 0.91 (s, 3H); m/z 507.4 (M+1).

Compound 63322: Using General Method C, 402-52 (111 mg, 0.239 mmol) was converted to product 63322 (121.5 mg, 90.7%) as a white solid: $^1$H NMR (400 MHz, CDCl$_3$) δ 7.64 (s, 1H), 5.71 (s, 1H), 2.66-2.78 (m, 2H), 2.50 (dd, 1H, J=16.4, 4.4 Hz), 2.39 (dd, 1H, J=16.4, 13.2 Hz), 1.82-2.14 (m, 6H), 1.46-1.76 (m, 7H), 1.21-1.35 (m, 3H), 1.23 (s, 3H), 1.183 (s, 3H), 1.178 (s, 3H), 1.16 (s, 3H), 1.05 (s, 3H), 1.00 (s, 3H), 0.94 (s, 3H); m/z 561.4 (M+1).

Compound 63327: Using the procedure described for the synthesis of compound 6 from compound 5 and then using General Method D, compound 5 (53 mg, 0.102 mmol) was converted to product 63327 (47.6 mg, 89.5%) as a white solid: ¹H NMR (400 MHz, CDCl₃) δ 7.72 (s, 1H), 4.49 (q, 1H, J=4.4 Hz), 4.14 (s, br, 1H), 3.02 (d, 1H, J=4.0 Hz), 2.73 (d, 1H, J=4.8 Hz), 2.42-2.60 (m, 2H), 2.36 (dd, 1H, J=16.4, 13.2 Hz), 1.80-2.06 (m, 7H), 1.44-1.78 (m, 7H), 1.12-1.40 (m, 3H), 0.88-1.10 (m, 1H), 1.23 (s, 3H), 1.22 (s, 3H), 1.18 (s, 3H), 1.16 (s, 3H), 1.01 (s, 3H), 0.97 (s, 3H), 0.91 (s, 3H); m/z 522.3 (M+1).

Compound 63328: Using the procedure described for the synthesis of compound 6 from compound 5 and then using General Method E, compound 6 (66 mg, 0.127 mmol) was converted to product 63328 (49.1 mg, 74%) as a white solid: ¹H NMR (400 MHz, CDCl₃) δ 7.65 (s, 1H), 4.32 (s, br, 1H), 3.62 (s, 3H), 2.90 (d, 1H, J=4.4 Hz), 2.66 (dt, 1H, J=13.2, 3.6 Hz), 2.47 (dd, 1H, J=16.4, 4.8 Hz), 2.37 (dd, 1H, J=16.4, 13.2 Hz), 1.85-2.16 (m, 5H), 1.44-1.84 (m, 8H), 1.00-1.40 (m, 3H), 1.23 (s, 3H), 1.22 (s, 3H), 1.18 (s, 3H), 1.16 (s, 3H), 1.04 (s, 3H), 0.98 (s, 3H), 0.91 (s, 3H); m/z 448.3 (M+1).

Example 4

Aqueous Solubility of Oleanolic Acid Derivatives

The aqueous solubility of the compounds shown here was determined using the procedures outlined in Example 1.

| Compound ID(s) | Structure | Aqueous Solubility (μM) |
|---|---|---|
| 63097 (402) | | 1.46 |
| 63102 (dh404) | | 0.06 |
| 63198 | 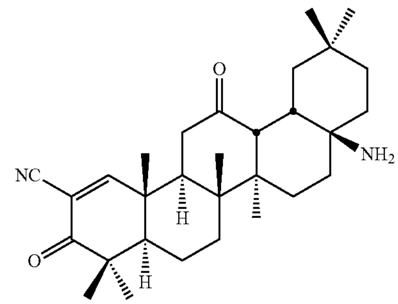 | 163.6 |
| 63202 | 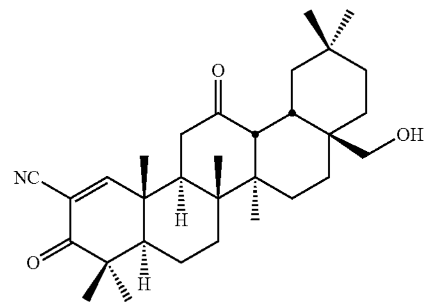 | 1.89 |
| 63208 | 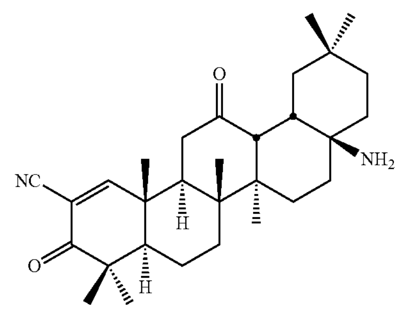 | 9.49 |
| 63214 | 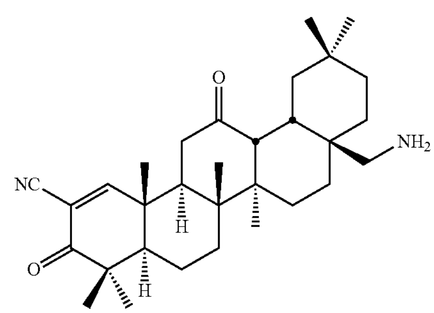 | 112.2 |
| 63219 | 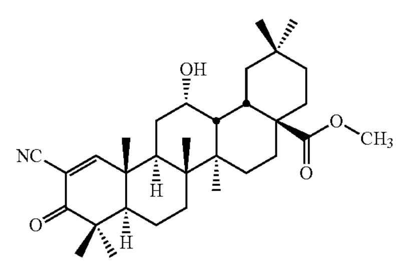 | 13.58 |

-continued

| Compound ID(s) | Structure | Aqueous Solubility (μM) |
|---|---|---|
| 63221 | 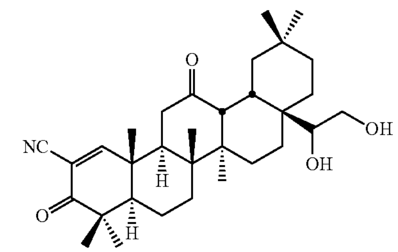 | 8.78 |
| 63226 | 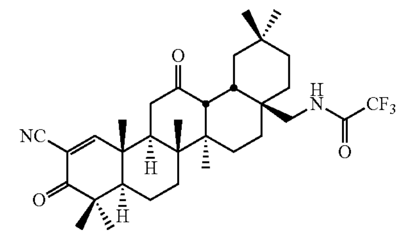 | 0.71 |
| 63231 | 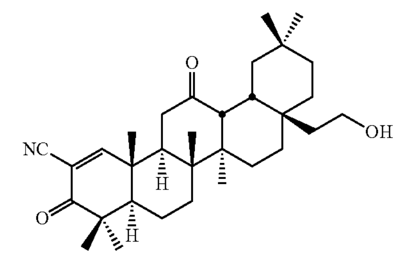 | 1.23 |
| 63232 | 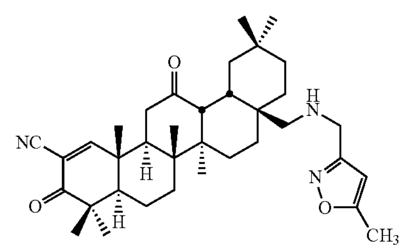 | 0.75 |
| 63237 | 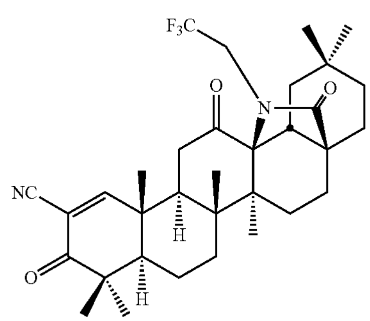 | 5.16 |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,443,826
U.S. Pat. No. 5,599,795
U.S. Pat. No. 6,025,395
U.S. Pat. No. 6,974,801
U.S. Provisional Application No. 61/046,332
U.S. Provisional Application No. 61/046,352
U.S. Provisional Application No. 61/046,363
U.S. Provisional Application No. 61/046,366
U.S. Provisional Application No. 61/111,333
U.S. Provisional Application No. 61/111,294
U.S. Ser. No. 12/151,425
U.S. Ser. No. 12/352,473
U.S. Patent Publication 2009/0060873
U.S. patent application Ser. No. 12/426,889 by Eric Anderson, Gary L. Bolton, Deborah Ferguson, Xin Jiang, Robert M. Kral, Jr., Patrick M. O'Brian and Melean Visnick, entitled "Natural Products Including an Anti-Inflammatory Pharmacore and Methods of Use," filed Apr. 20, 2009.
U.S. patent application Ser. No. 12/426,737 by Eric Anderson, Xin Jiang, Xiaofeng Liu; Melean Visnick, entitled "Antioxidant Inflammation Modulators: Oleanolic Acid Derivatives With Saturation in the C-Ring," filed Apr. 20, 2009.
U.S. patent application Ser. No. 12/426,791 by Xin Jiang, Jack Greiner, Lester L. Maravetz, Stephen S. Szucs, Melean Visnick, entitled "Antioxidant Inflammation Modulators: Novel Derivatives of Oleanolic Acid," filed Apr. 20, 2009.
U.S. patent application Ser. No. 12/426,832 by Xin Jiang, Xioafeng Liu, Jack Greiner, Stephen S. Szucs, Melean Visnick entitled, "Antioxidant Inflammation Modulators: C-17 Homologated Oleanolic Acid Derivatives," filed Apr. 20, 2009.
Abraham and Kappas, *Free Radic. Biol. Med.,* 39(1):1-25, 2005.
Ahmad et al., *Cancer Res.,* 68(8):2920-2926, 2008.
Ahmad et al., *J Biol. Chem.,* 281(47):35764-35769, 2006.
Akiyama et al., *Alzheimer Dis. Assoc. Disord.,* 14(1):547-53, 2000.
Angulo et al., *Eur. J. Immunol.,* 30:1263-1271, 2000.
Araujo et al., *J. Immunol.,* 171(3):1572-1580, 2003.
Arend and Dayer, *Arthritis Rheum.,* 38:151-160, 1995.
Arend et al., *Annu. Rev. Immunol.,* 16:27-55, 1998.
Autenrieth et al., *Infect. Immun.,* 62:2590-2599, 1994.
Bach, *Hum. Immunol.,* 67(6):430-432, 2006.
Bagasra et al., *Proc. Natl. Acad. Sci. USA,* 92:12041-12045, 1995.
Ball, *Ann. Rheum. Dis.,* 30:213-223, 1971.
Barrero et al., *Synlett,* 713, 1999.
Beal, *Curr. Opin. Neurobiol.,* 6:661-666, 1996.
Bendzen et al., *Scand. J. Rheumatol.,* 28:599-606, 1988.
Blumberg et al., *Arthritis Rheum.,* 7:93-97, 1964.
Botoman et al., *Am. Fam. Physician,* 57(1):57-68, 1998.

Brandt et al., *Arthritis Rheum.*, 43:1346-1352, 2000.
Braun et al., *Arthritis Rheum.*, 42:2039-2044, 1999.
Brewerton et al., *Lancet.*, 1:904-907, 1973a.
Brewerton et al., *Lancet.*, 1:956-957, 1973b.
Bronte et al., *Trends Immunol.*, 24:302-306, 2003.
Brown and DuBois, *J. Clin. Oncol.*, 23:2840-2855, 2005.
Brynskov et al., *N. Engl. J. Med.*, 321(13):845-850, 1989.
Burger and Dayer, *Neurology*, 45(65-6):539-43, 1995.
Cai et al., *Nat. Med.*, 11(2):183-190, 2005.
Calin and Taurog, In: *The Spondylarthritides*, Calin et al. (Eds.), Oxford, UK. Oxford University Press, 179, 1998.
Cann et al., *Gut.*, 24(12):1135-1140, 1983.
Chauhan and Chauhan, *Pathophysiology*, 13(3):171-181 2006.
Chomarat et al., *Arthritis Rheum.*, 38:1046-1054, 1995.
Coyle and Puttfarcken, *Science*, 262:689-695, 1993.
Crowell et al., *Mol. Cancer Ther.*, 2:815-823, 2003.
Culver et al., *Science*, 256:1550-1552, 1992.
De Mico et al., *J. Org. Chem.*, 62:6974, 1997.
de Waal et al., *J. Exp. Med.*, 174:1209-1220, 1991.
Dickerson et al., *Prog Neuropsychopharmacol Biol. Psychiatry*, Mar. 6, 2007.
Dinarello, *Int. Rev. Immunol.*, 16:457-499, 1998.
Dinkova-Kostova et al., *Proc Natl Acad Sci USA*, 102(12):4584-4589, 2005.
Dionne et al., *Clin. Exp. Immunol.*, 112(3):435-442, 1998.
Doran et al., *J. Rheumatol.*, 30(2):316-320, 2003.
Drossman et al., *Dig. Dis. Sci.*, 38(9):1569-1580, 1993.
Drossman et al., *Gastroenterol.*, 112(6):2120-2137, 1997.
Dudhgaonkar et al., *Eur. J. Pain*, 10(7):573-9, 2006.
Eikelenboom et al., *Glia*, 40(2):232-239, 2002.
Ettehadi et al., *Clin. Exp. Immunol.*, 96(1):146-151, 1994.
Everhart et al., *Gastroenterol.*, 100(4):998-1005, 1991.
Fearon and Locksley, *Science*, 272(5258):50-53, 1996.
Feldtkeller et al., *Rheumatol. Int.*, 23(2):61-66, 2003.
Firestein et al., *Arthritis Rheum.*, 37:644-652, 1994.
Forstermann, *Biol. Chem.*, 387:1521, 2006.
Fujikawa et al., *Ann. Rheum. Dis.*, 54:318-320, 1995.
Funakoshi et al., *Digestion*, 59(1):73-78, 1998.
Galley and Webster, *Br. J. Anaesth.*, 77:11-16, 1996.
Gehrmann et al., *Glia*, 15(2):141-151, 1995.
Genain and Nauser, *J. Mol. Med.*, 75:187-197, 1997.
Gladman et al., *Br. J. Rheumatol.*, 22:675-679, 1995.
Gladman et al., *J. Med.*, 62:127-141, 1987.
Gladman, *Rheum. Dis. Clin. North Am.*, 18:247-256, 1992.
Goodman et al., *Kidney Int.*, 72(8):945-953, 2007.
Graeber et al., *Glia*, 40(2):252-259, 2002.
Greten et al., *Cell*, 118:285-296, 2004.
Griffin et al., *Proc. Natl. Acad. Sci. USA*, 86(19):7611-7615, 1989.
Guilherme et al., *Nat. Rev. Mol. Cell. Biol.*, 9(5):367-77, 2008.
Gwee et al., *Gut.*, 44(3):400-406., 1999.
Hahn and Tsao, In: *Dubois' Lupus Erythematosus*, 4th Ed, Wallace and Hahn (Eds.), Lea and Febiger, Philadelphia, 195-201, 1993.
*Handbook of Pharmaceutical Salts: Properties, Selection and Use* (Stahl & Wermuth, Eds.), Verlag Helvetica Chimica Acta, 2002.
Hannum et al., *Nature*, 343:336-340, 1990.
Hanson et al., *BMC Medical Genetics*, 6(7), 2005.
Hansson et al., *Annu. Rev. Pathol. Mech. Dis.*, 1:297-329, 2006.
Harrison and Symmons et al., *Ann. Rheum. Dis.*, 57(6):375-377, 1998.
Harrison et al., *J. Rheumatol.*, 25(12):2324-2330, 1998.
Hart et al., *Immunology*, 84:536-542, 1995.
Hohler et al., *Arthritis Rheum.*, 41:1489-1492, 1998.
Hohler et al., *J. Invest. Dermatol.*, 109:562-565, 1997.
Honda et al., *Bioorg. Med. Chem. Lett.*, 12:1027-1030, 2002.
Honda et al., *Bioorg. Med. Chem. Lett.*, 19:2711-2714, 1998.
Honda et al., *Bioorg. Med. Chem. Lett.*, 9:3429-3434, 1999.
Honda et al., *J. Med. Chem.*, 43:1866-1877, 2000a.
Honda et al., *J. Med. Chem.*, 43:4233-4246, 2000b.
Horwitz and Fisher, *N. Engl. J. Med.*, 344(24):1846-1850, 2001.
Hotamisligil, *Nature*, 444(7121):860-7, 2006.
Ishikawa et al., *Circulation*, 104(15):1831-1836, 2001.
Ishizawa and Dickson, *J. Neuropathol. Exp. Neurol.*, 60(6):647-657, 2001.
Jacob et al., *Proc. Natl. Acad. Sci. USA*, 87:1233-1237, 1990.
Jailwala et al., *Ann. Intern. Med.*, 133(2):136-147, 2000.
Jarvis, *Curr. Opin. Rheumatol.*, 10(5):459-467, 1998.
Jarvis, *Pediatr. Ann.*, 31(7):437-446, 2002.
Jones et al., *Br. J. Rheumatol.*, 33(9):834-839, 1994.
Jonsson et al., *Br. J. Rheumatol.*, 32(7):578-581 1993.
Jonsson et al., *Oral Dis.*, 8(3):130-140, 2002.
Jonsson et al., *Trends Immunol.*, 22(12):653-654, 2001.
Kahle et al., *Ann. Rheum. Dis.*, 51:731-734, 1992.
Kaltschmidt et al., *Proc. Natl. Acad. Sci. USA*, 94:2642-2647, 1997.
Kawakami et al., *Brain Dev.*, 28(4):243-246, 2006.
Kellow and Phillips, *Gastroenterol.*, 92(6):1885-1893, 1987.
Kendall-Tackett, *Trauma Violence Abuse*, 8(2):117-126, 2007.
Khan et al., *J. Neurochem.*, 71:78-87, 1998.
Khan et al., *Toxicol. Applied Pharmacol.*, 103:482-490, 1990.
Kortylewski et al., *Nat. Med.*, 11:1314-1321, 2005.
Kotake et al., *Infect. Immun.*, 67:2682-2686, 1999.
Kotzin and O'Dell, In: *Samler's Immunologic Diseases*, 5th Ed., Frank et al. (Eds.), Little Brown & Co., Boston, 667-697, 1995.
Kotzin, *Cell*, 85:303-306, 1996.
Kruger et al., *J. Pharmacol. Exp. Ther.*, 319(3):1144-1152, 2006.
Kuboyama, *Kurume Med. J.*, 45(1):33-37, 1998.
Lahesmaa et al., *J. Immunol.*, 148:3079-3085, 1992.
Lee et al., *Glia.*, 55(7):712-22, 2007.
Lencz et al., *Mol. Psychiatry*, 12(6):572-80, 2007.
Liby et al., *Nat. Rev. Cancer*, 7(5):357-369, 2007.
Lipsky, In: *Harrison's principles of internal medicine*, Fauci et al., (Eds.), 14th Ed., NY, McGraw-Hill, 1880-1888, 1998.
Liu et al., *FASEB J.*, 20(2):207-216, 2006.
Lo et al., *Curr. Dir. Autoimmun.*, 1:226-246, 1999.
Lugering et al., *Ital. J. Gastroenterol. Hepatol.*, 30(3):338-344, 1998.
Lynn and Friedman, *N. Engl. J. Med.*, 329(26):1940-1945, 1993.
Macatonia et al., *J. Immunol.*, 150:3755-3765, 1993.
March's Advanced Organic Chemistry: Reactions, Mechanisms, and Structure (March's Advanced Organic Chemistry), Smith and March (Eds.), 2007.
Marsal et al., *Rheumatology*, 38:332-337, 1999.
Mazur et al., *Cell Microbiol.*, 9(7):1683-94, 2007.
Mazzoni et al., *J. Immunol.*, 168:689-695, 2002.
McAlindon et al., *Gut*, 42(2):214-219, 1998.
McGeer and McGeer, *Brain Res. Brain Res. Rev.*, 21:195-218, 1995.
McGeer et al., *Neurology*, 19:331-338, 1996.
McGonagle et al., *Arthritis Rheum.*, 41:694-700, 1998.
McGonagle et al., *Curr. Opin. Rheumatol.*, 11:244-250, 1999.
McIver et al., *Pain*, 120(1-2):161-9, 2005.
Mease et al., *Lancet*, 356:385-390, 2000.

Merrill and Benvenist, *Trends Neurosci.*, 19:331-338, 1996.
Mertz et al., *Gastroenterol.*, 118(5):842-848, 2000.
Moll and Wright, *Ann. Rheum. Dis.*, 32:181-201, 1973.
Moll and Wright, *Semin. Arthritis Rheum.*, 3:55-78, 1973.
Morris et al., *J. Mol. Med.*, 80(2):96-104, 2002.
Morse and Choi, *Am. J. Respir. Crit. Care Med.*, 172(6):660-670, 2005.
Morse and Choi, *Am. J. Respir. Crit. Care Med.*, 27(1):8-16, 2002.
Nath et al., *Neurology*, 66(1):149-150, 2006.
Neal et al., *BMJ.*, 314(7083):779-782, 1997.
Nichols, *Drug News Perspect.*, 17(2):99-104, 2004.
Nielen et al., *Arthritis Rheum.*, 50(2):380-386, 2004.
Ohnishi et al., *Int. Immunol.*, 6:817-830, 1994.
Pall, *Med. Hypoth.*, 69:821-825, 2007.
Partsch et al., *Br. J. Rheumatol.*, 24:518-523, 1997.
Pica et al., *Antimicrob Agents Chemother.*, 44(1):200-4, 2000.
Pimentel et al., *Am. J. Gastroenterol.*, 95(12):3503-3506, 2000.
Pociot et al., *Scand. J. Immunol.*, 42(4):501-504, 1995.
Prieur et al., *Lancet.*, 2:1240-1242, 1987.
Rajakariar et al., *Proc. Natl. Acad. Sci. USA*, 104(52):20979-84, 2007.
Rantapaa-Dahlqvist et al., *Arthritis Rheum.*, 48(10):2741-2749, 2003.
Reimund et al., *Eur. J. Clin. Invest.*, 28(2):145-150, 1998.
Ribbens et al., *Eur. Cytokine Netw.*, 11:669-676, 2000.
Rogers et al., *Neurobiol Aging*, 9(4):339-349, 1988.
Rogler and Andus, *World J. Surg.*, 22(4):382-389, 1998.
Rooney et al., *Rheumatol. Int.*, 10:217-219, 1990.
Ross et al., *Nutr. Neurosci.*, 6(5):277-81, 2003.
Rostom et al., *Ann. Intern. Med.*, 146, 376-389, 2007.
Rothstein, *Med. Clin. North Am.*, 84(5):1247-1257, 2000.
Ruster et al., *Scand. J. Rheumatol.*, 34(6):460-3, 2005.
Sacerdoti et al., *Curr Neurovasc Res.* 2(2):103-111, 2005.
Saiki et al., *Scand. J. Gastroenterol.*, 33(6):616-622, 1998.
Salomonsson and Jonsson, *Arthritis Rheum.*, 48(11):3187-3201, 2003.
Salomonsson et al., *Scand. J. Immunol.*, 55(4):336-342, 2002.
Salvarani et al., *Curr. Opin. Rheumatol.* 1998; 10:299-305, 1998.
Salvemini et al., *J. Clin. Invest.*, 93:1940-1947, 1994.
Sandler, *Gastroenterol.*, 99(2):409-415, 1990.
Sarchielli et al., *Cephalalgia*, 26(9):1071-1079, 2006.
Satoh et al., *Proc. Natl. Acad. Sci. USA*, 103(3):768-773, 2006.
Schellekens et al., *Arthritis Rheum.*, 43(1):155-163, 2000.
Schlaak et al., *Clin. Exp. Rheumatol.*, 14:155-162, 1996.
Schlaak et al., *Eur. J. Immunol.*, 22:2771-2776, 1992.
Schlosstein et al., *NE J. Medicine*, 288:704-706, 1973.
Schreiber, *Neth. J. Med.*, 53(6):524-31, 1998.
Schulz et al., *Antioxid. Redox. Sig.*, 10:115, 2008.
Sieper and Braun, *Arthritis Rheum.*, 38:1547-1554, 1995.
Simon et al., *Clin. Exp. Immunol.*, 94:122-126, 1993.
Simon et al., *Proc. Natl. Acad. Sci. USA*, 91:8562-85666, 1994.
Simonian and Coyle, *Annu. Rev. Pharmacol. Toxicol.*, 36:83-106, 1996.
Sinha et al., *Cancer Res.*, 67:4507-4513, 2007.
Stack et al., *Lancet*, 349(9051):521-524, 1997.
Stewart et al., *Neurology*, 48:626-632, 1997.
Strejan et al., *J. Neuroimmunol.*, 7:27, 1984.
Szabo et al., *Nature Rev. Drug Disc.*, 6:662-680, 2007.
Takahashi et al., *Cancer Res.*, 57:1233-1237, 1997.
Talley et al., *Gastroenterol.*, 109(6):1736-1741, 1995.
Tamir and Tannenbaum, *Biochim. Biophys. Acta.*, 1288:F31-F36, 1996.
Targan et al., *N. Engl. J. Med.*, 337(15):1029-1035, 1997.
Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670.
Touzani et al., *J. Neuroimmunol.*, 100(1-2):203-215, 1999.
Tumlin et al., *Am. J. Cardiol.*, 98(6A):14K-20K, 2006.
van den Berg, *Semin. Arthritis Rheum.*, 30(55-2):7-16, 2001.
van Dullemen et al., *Gastroenterol.*, 109(1):129-135, 1995.
van Hogezand and Verspaget, *Drugs*, 56(3):299-305, 1998.
Vazquez et al., *J. Virol.*, 79(7):4479-91, 2005.
Vodovotz et al., In; *Handbook of Experimental Immunology*, Volumes I-IV, 1996.
Wardle, *Nephrol. Dial. Transplant.*, 16(9):1764-8, 2001.
Warrington et al., *Arthritis and Rheumatism*, 44:13-20, 2001.
Weyand and Goronzy, *Ann. NY Acad. Sci.*, 987:140-149, 2003.
Whitehead et al., *Gastroenterol.*, 98(5 Pt 1):1187-1192, 1990.
Williams et al., *Clin. Neurosci.*, 2(3-4):229-245, 1994.
Wordsworth, In: *Genes and Arthritis*, Brit. Medical Bulletin, 51:249-266, 1995.
Wright, *Ann. Rheum. Dis.*, 15:348-356, 1956.
Wright, *Clin. Orthop. Related Res.*, 143:8-14, 1979.
Xanthou et al., *Arthritis Rheum.*, 44(2):408-418, 2001.
Yates et al., *Cancer Res.*, 66(4): 2488-2494, 2006.
Yin et al., *Arthritis Rheum.*, 40:1788-1797, 1997.
Yin et al., Rheumatology, 38:1058-1067, 1999.
Yoh et al., *Kidney Int.*, 60(4):1343-1353, 2001.
Yu et al., *Nat. Rev. Immunol.*, 7:41-51, 2007.
Zhou et al., Am. J. Pathol., 166(1):27-37, 2005.
Zhou et al., *Cancer Sci.*, 98:882-889, 2007.
Zingarelli et al., *J. Immunol.*, 171(12):6827-6837, 2003.

What is claimed is:

1. A pharmaceutical composition comprising a compound of the formula:

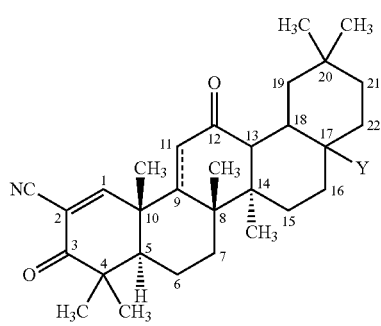

wherein:
  Y is hydroxy or $NR_1R_2$, wherein:
    $R_1$ and $R_2$ are independently:
      hydrogen or hydroxy; or
      $alkyl_{(C \leq 12)}$, $alkenyl_{(C \leq 12)}$, $alkynyl_{(C \leq 12)}$, $aryl_{(C \leq 12)}$, $aralkyl_{(C \leq 12)}$, $heteroaryl_{(C \leq 12)}$, $heteroaralkyl_{(C \leq 12)}$, $acyl_{(C \leq 12)}$, $alkoxy_{(C \leq 12)}$, $alkenyloxy_{(C \leq 12)}$, $alkynyl\text{-}oxy_{(C \leq 12)}$, $aryloxy_{(C \leq 12)}$, $aralkoxy_{(C \leq 12)}$, $heteroaryl\text{-}oxy_{(C \leq 12)}$, $heteroaralkoxy_{(C \leq 12)}$, $thioacyl_{(C \leq 12)}$, $alkylsulfonyl_{(C \leq 12)}$, $alkenylsulfonyl_{(C \leq 12)}$, $alkynyl\text{-}sulfonyl_{(C \leq 12)}$, $arylsulfonyl_{(C \leq 12)}$, $aralkyl\text{-}sulfonyl_{(C \leq 12)}$, $heteroarylsulfonyl_{(C \leq 12)}$, or $hetero\text{-}aralkylsulfonyl_{(C \leq 12)}$, or a substituted version of any of these groups;
  or a pharmaceutically acceptable salt, tautomer, or optical isomer thereof; and
a pharmaceutically acceptable carrier.

2. The pharmaceutical composition of claim 1, wherein the compound is further defined as:

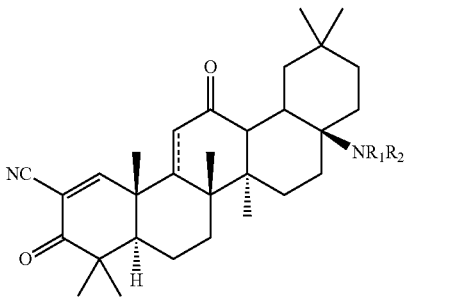

wherein:
  $R_1$ and $R_2$ are independently:
    hydrogen; or
    $alkyl_{(C \leq 12)}$, $alkenyl_{(C \leq 12)}$, $alkynyl_{(C \leq 12)}$, $aryl_{(C \leq 12)}$, $aralkyl_{(C \leq 12)}$, $heteroaryl_{(C \leq 12)}$, $heteroaralkyl_{(C \leq 12)}$, $acyl_{(C \leq 12)}$, alkylsulphonyl, $alkenylsulphonyl_{(C \leq 12)}$, $alkynylsulphonyl_{(C \leq 12)}$, $arylsulphonyl_{(C \leq 12)}$, $aralkylsulphonyl_{(C \leq 12)}$, $heteroarylsulphonyl_{(C \leq 12)}$, $heteroaralkyl\text{-}sulphonyl_{(C \leq 12)}$, or a substituted version of any of these groups;

or pharmaceutically acceptable salts, tautomers, or optical isomers thereof.

3. The pharmaceutical composition of claim 2, wherein the bond joining carbon 9 and carbon 11 of the compound is a double bond.

4. The pharmaceutical composition of claim 2, wherein the bond joining carbon 9 and carbon 11 of the compound is a single bond.

5. The pharmaceutical composition of claim 2, wherein the compound is further defined as:
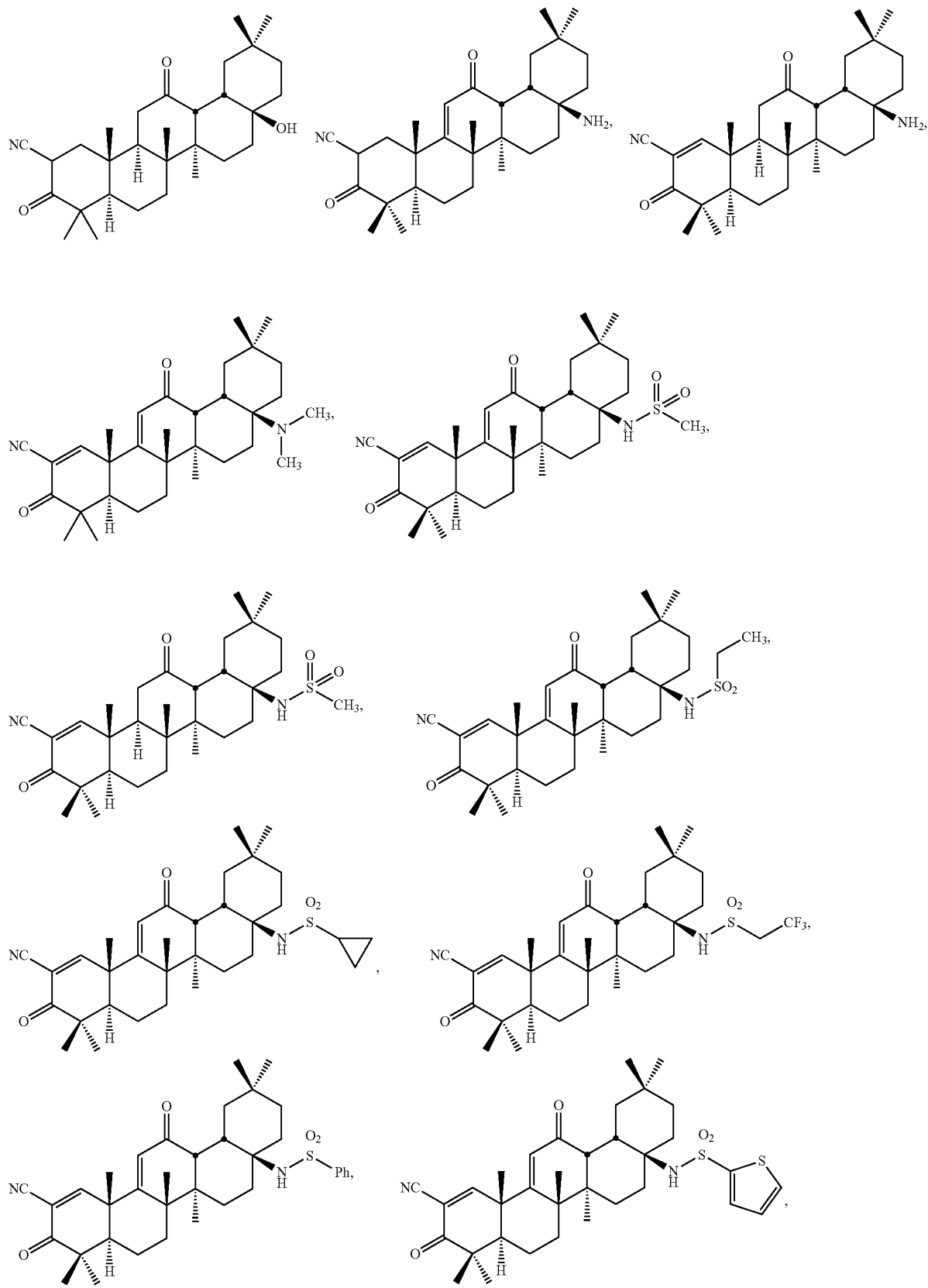

123
124
-continued
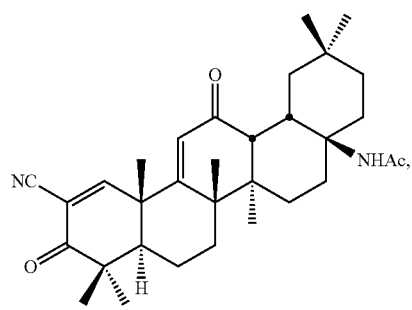
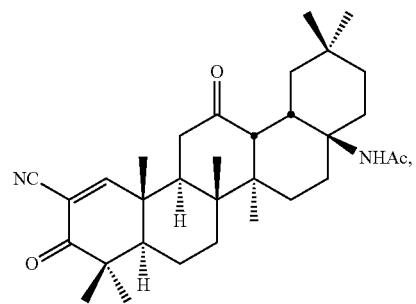
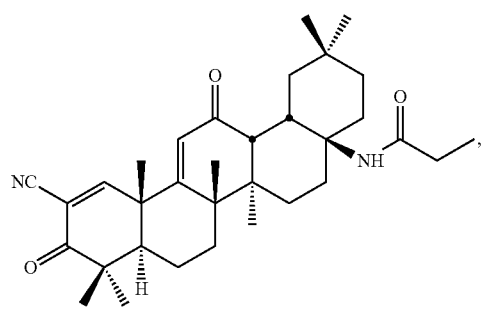
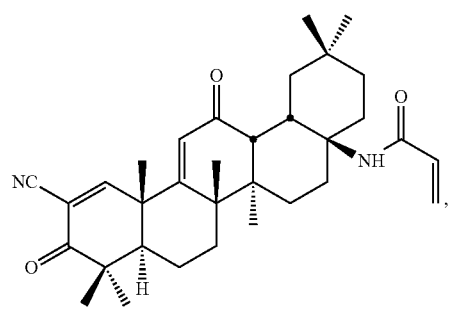
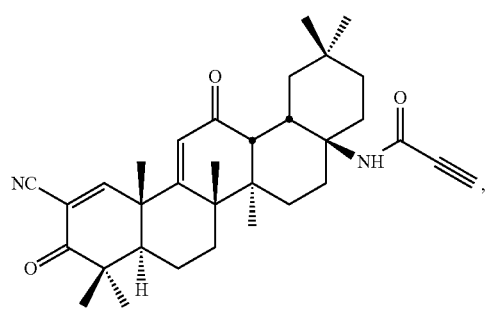
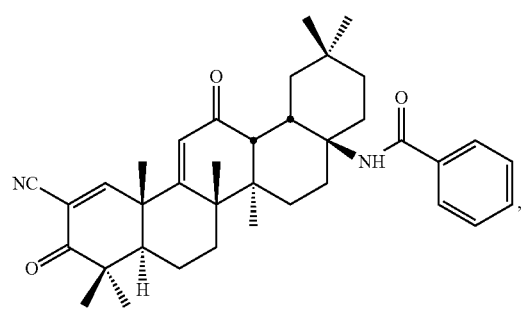
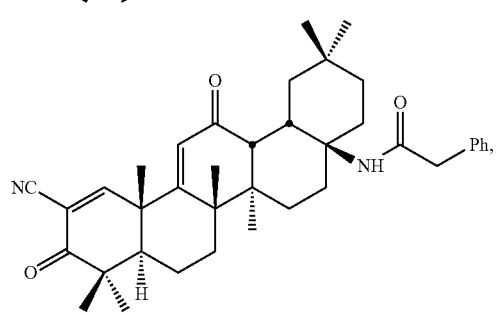
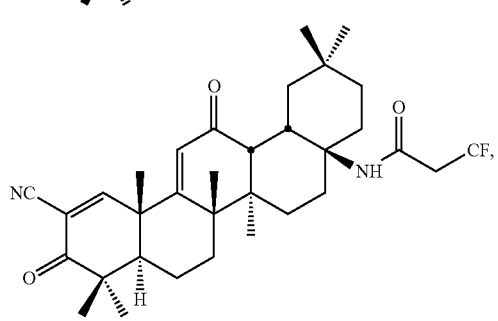
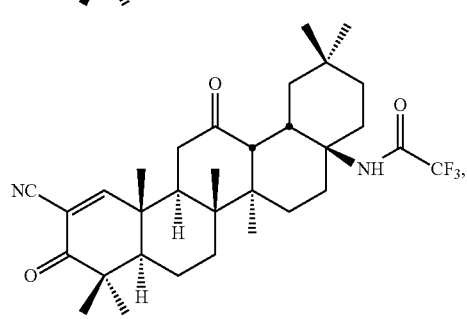
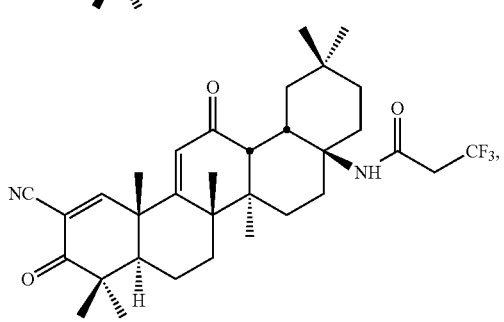

125
126
-continued
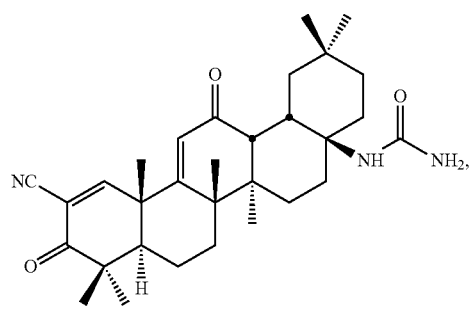
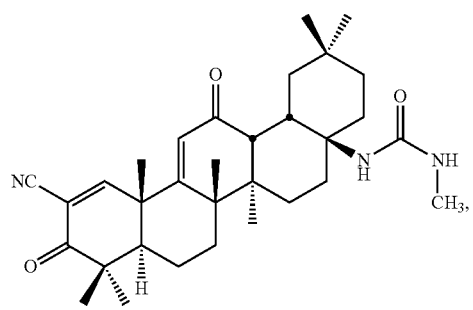
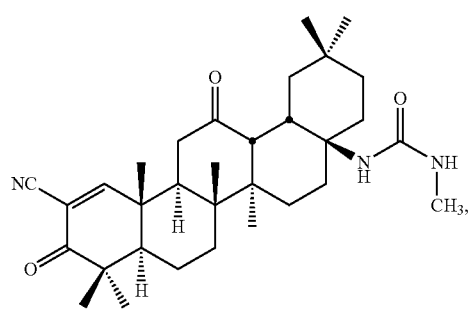
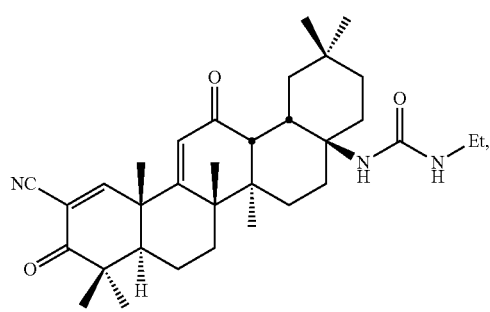
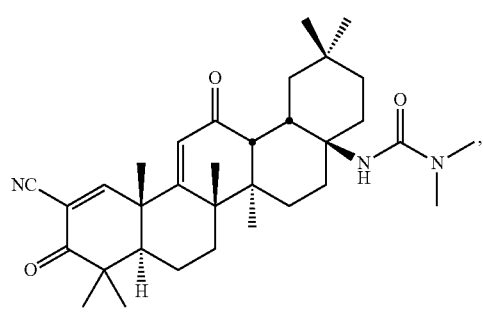
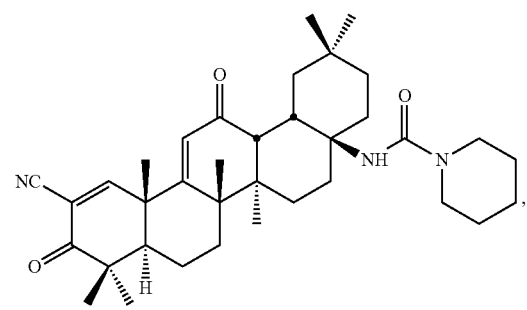
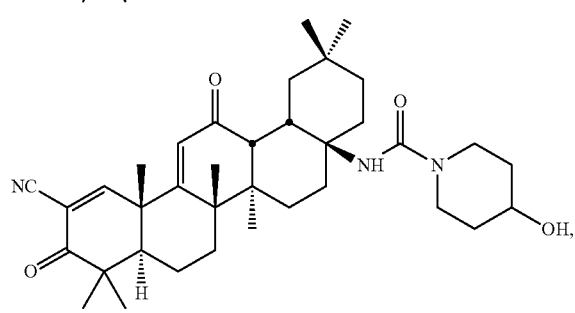
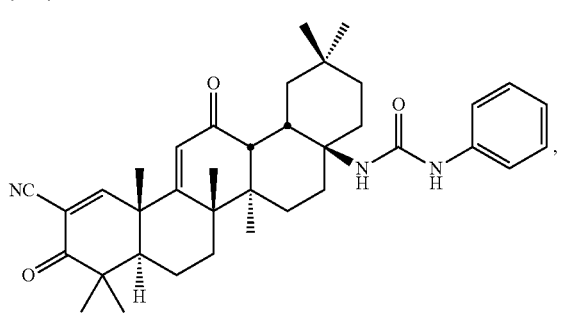
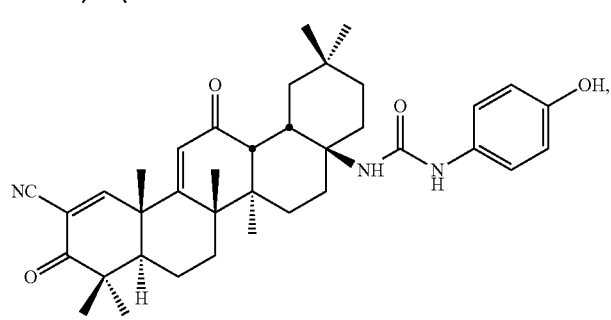
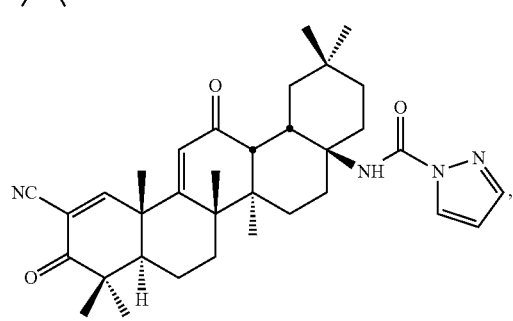

127
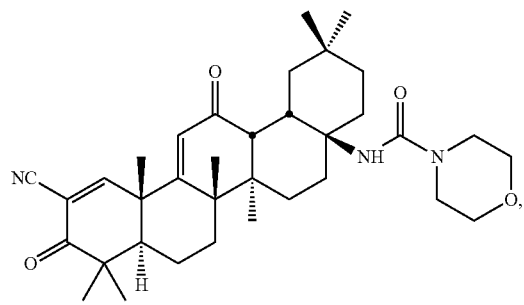
128
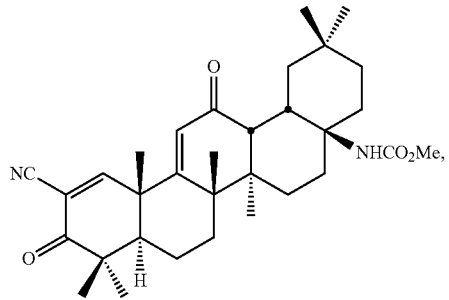
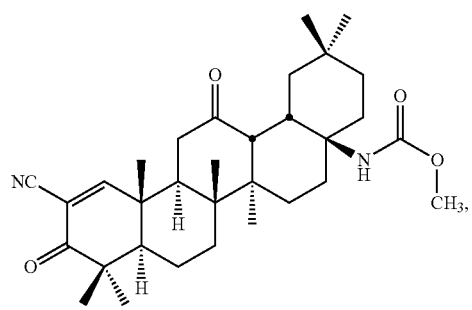
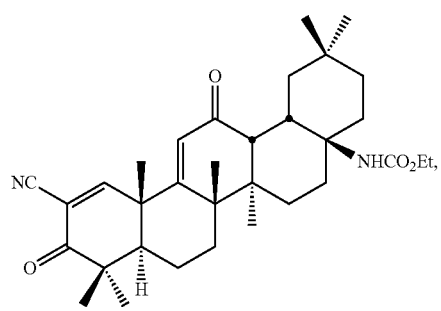
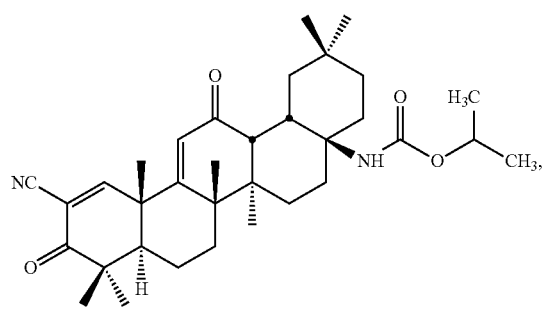
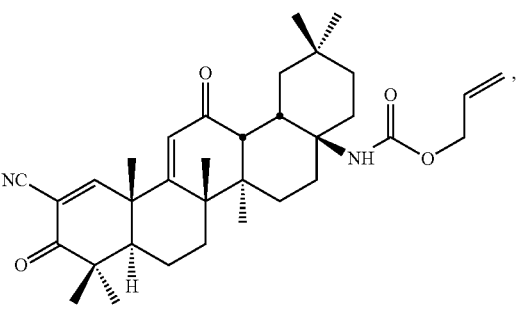
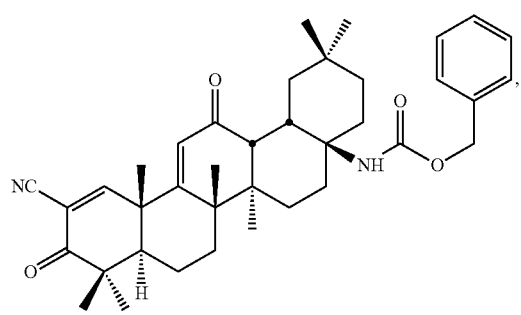
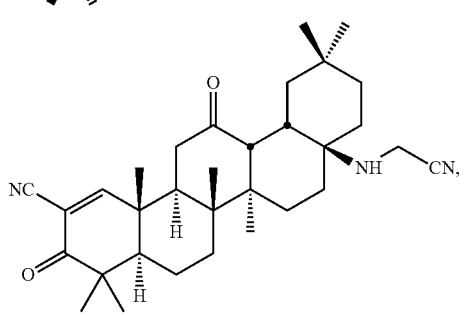
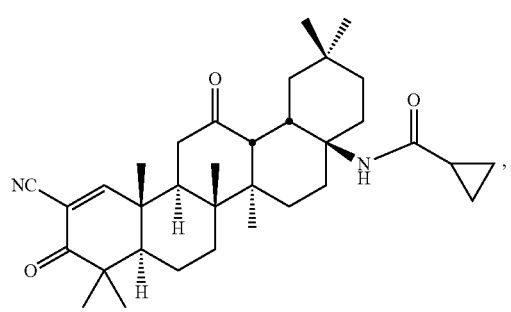
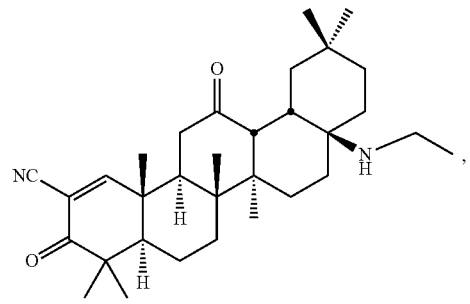

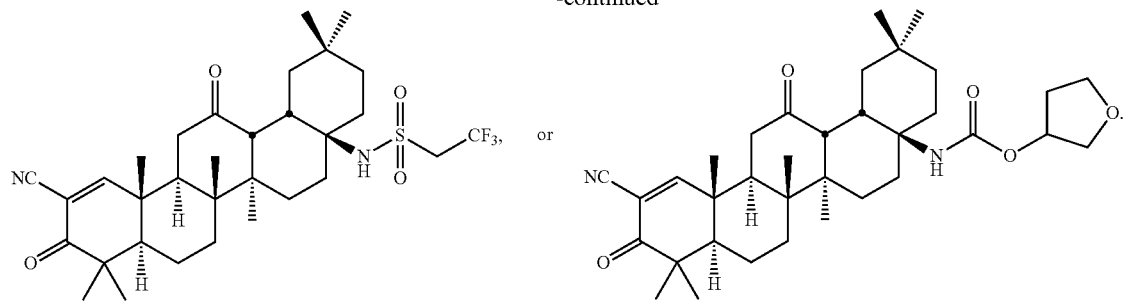
6. The pharmaceutical composition of claim 1, wherein the composition is formulated for oral delivery.
7. A pharmaceutical composition comprising a compound of the formula:
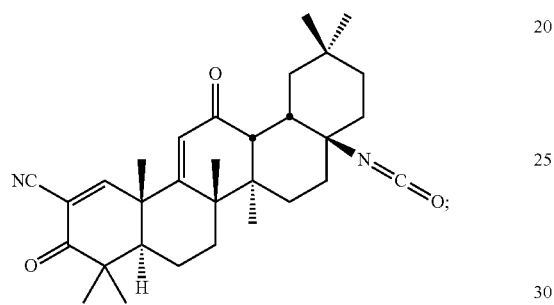
and
a pharmaceutically acceptable carrier.
* * * * *

UNITED STATES PATENT AND TRADEMARK OFFICE
CERTIFICATE OF CORRECTION

PATENT NO.            : 8,440,854 B2
APPLICATION NO.       : 13/356455
DATED                 : May 14, 2013
INVENTOR(S)           : Eric Anderson et al.

It is certified that error appears in the above-identified patent and that said Letters Patent is hereby corrected as shown below:

On the Title Page, Item 54 and in the Specification, column 1, lines 1-4, Title, please delete "Antioxidant Inflammation Modulators: Oleanolic Acid Derivatives with Amino Acid and Other Modifications at C-17" and replace with --Antioxidant Inflammation Modulators: Oleanolic Acid Derivatives with Amino and Other Modifications at C-17-- therefor.

In the Claims

In claim 2, column 120, lines 50-57, please delete "alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkylsulphonyl, alkenylsulphonyl$_{(C \leq 12)}$, alkynylsulphonyl$_{(C \leq 12)}$, arylsulphonyl$_{(C \leq 12)}$, aralkylsulphonyl$_{(C \leq 12)}$, heteroarylsulphonyl$_{(C \leq 12)}$, heteroaralkyl-sulphonyl$_{(C \leq 12)}$, or a substituted version of any of these groups;" and replace with --alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkylsulfonyl$_{(C \leq 12)}$, alkenylsulfonyl$_{(C \leq 12)}$, alkynylsulfonyl$_{(C \leq 12)}$, arylsulfonyl$_{(C \leq 12)}$, aralkylsulfonyl$_{(C \leq 12)}$, heteroarylsulfonyl$_{(C \leq 12)}$, heteroaralkylsulfonyl$_{(C \leq 12)}$, or a substituted version of any of these groups;-- therefor.

In claim 5, column 121, line 1, please delete "5. The pharmaceutical composition of claim 2, wherein the" and replace with --5. The pharmaceutical composition of claim 1, wherein the-- therefor.

Signed and Sealed this
Twelfth Day of August, 2014

Michelle K. Lee
*Deputy Director of the United States Patent and Trademark Office*

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial
<220> FEATURE:
<223> OTHER INFORMATION: Synthetic primer

<400> SEQUENCE: 1
tccgatgggt ccttacactc                                              20
```

```
<210> SEQ ID NO 2
<211> LENGTH: 20
<212> TYPE: DNA
<213> ORGANISM: Artificial
<220> FEATURE:
<223> OTHER INFORMATION: Synthetic primer

<400> SEQUENCE: 2
taggctcctt cctcctttcc                                               20

<210> SEQ ID NO 3
<211> LENGTH: 20
<212> TYPE: DNA
<213> ORGANISM: Artificial
<220> FEATURE:
<223> OTHER INFORMATION: Synthetic primer

<400> SEQUENCE: 3
gcagcactga gtggtcaaaa                                               20

<210> SEQ ID NO 4
<211> LENGTH: 20
<212> TYPE: DNA
<213> ORGANISM: Artificial
<220> FEATURE:
<223> OTHER INFORMATION: Synthetic primer

<400> SEQUENCE: 4
ggtcaactgc ctcaattgct                                               20

<210> SEQ ID NO 5
<211> LENGTH: 20
<212> TYPE: DNA
<213> ORGANISM: Artificial
<220> FEATURE:
<223> OTHER INFORMATION: Synthetic primer

<400> SEQUENCE: 5
gctgtggcta ctgcggtatt                                               20

<210> SEQ ID NO 6
<211> LENGTH: 20
<212> TYPE: DNA
<213> ORGANISM: Artificial
<220> FEATURE:
<223> OTHER INFORMATION: Synthetic primer

<400> SEQUENCE: 6
atctgcctca atgacaccat                                               20

<210> SEQ ID NO 7
<211> LENGTH: 20
<212> TYPE: DNA
<213> ORGANISM: Artificial
<220> FEATURE:
<223> OTHER INFORMATION: Synthetic primer

<400> SEQUENCE: 7
atgagcaggt gaaagccatc                                               20

<210> SEQ ID NO 8
<211> LENGTH: 20
<212> TYPE: DNA
<213> ORGANISM: Artificial
<220> FEATURE:
<223> OTHER INFORMATION: Synthetic primer
```

```
<400> SEQUENCE: 8
taaaggaaac cccaacatgc                                              20

<210> SEQ ID NO 9
<211> LENGTH: 20
<212> TYPE: DNA
<213> ORGANISM: Artificial
<220> FEATURE:
<223> OTHER INFORMATION: Synthetic primer

<400> SEQUENCE: 9
gattacatcc tgggcctgaa                                              20

<210> SEQ ID NO 10
<211> LENGTH: 20
<212> TYPE: DNA
<213> ORGANISM: Artificial
<220> FEATURE:
<223> OTHER INFORMATION: Synthetic primer

<400> SEQUENCE: 10
gagcgcagag agaagtcgat                                              20
```